US011730781B2

(12) United States Patent
O'Shea et al.

(10) Patent No.: US 11,730,781 B2

(45) Date of Patent: Aug. 22, 2023

(54) SYNTHETIC ADENOVIRUSES WITH TROPISM TO DAMAGED TISSUE FOR USE IN PROMOTING WOUND REPAIR AND TISSUE REGENERATION

(71) Applicant: Salk Institute for Biological Studies, La Jolla, CA (US)

(72) Inventors: Clodagh O'Shea, San Diego, CA (US); Colin Powers, San Diego, CA (US); Lei Zhang, La Jolla, CA (US)

(73) Assignee: Salk Institute for Biological Studies, La Jolla, CA (US)

(*) Notice: Subject to any disclaimer, the term of this patent is extended or adjusted under 35 U.S.C. 154(b) by 1266 days.

(21) Appl. No.: 15/945,079

(22) Filed: Apr. 4, 2018

(65) Prior Publication Data

US 2018/0221423 A1 Aug. 9, 2018

Related U.S. Application Data

(63) Continuation of application No. PCT/US2016/055579, filed on Oct. 5, 2016.

(60) Provisional application No. 62/237,410, filed on Oct. 5, 2015.

(51) Int. Cl.
*A61K 35/761* (2015.01)
*C12N 15/85* (2006.01)

(52) U.S. Cl.
CPC ............ *A61K 35/761* (2013.01); *C12N 15/85* (2013.01); *C12N 2710/10322* (2013.01); *C12N 2710/10332* (2013.01); *C12N 2710/10333* (2013.01); *C12N 2710/10341* (2013.01); *C12N 2710/10343* (2013.01); *C12N 2710/10345* (2013.01); *C12N 2810/6018* (2013.01)

(58) Field of Classification Search
None
See application file for complete search history.

(56) References Cited

U.S. PATENT DOCUMENTS

| | | | |
|---|---|---|---|
| 7,094,398 | B1 | 8/2006 | Lieber et al. |
| 9,187,733 | B2 | 11/2015 | O'Shea et al. |
| 9,217,160 | B2 | 12/2015 | O'Shea et al. |
| 9,885,090 | B2 | 2/2018 | O'Shea et al. |
| 9,913,866 | B2 | 3/2018 | O'Shea et al. |
| 2003/0170208 | A1 | 9/2003 | Clancy et al. |
| 2005/0136042 | A1 | 6/2005 | Betz et al. |
| 2009/0176260 | A1 | 7/2009 | Wu et al. |
| 2011/0111505 | A1 | 5/2011 | Moutsatsos et al. |
| 2012/0100107 | A1 | 4/2012 | Goldstein et al. |
| 2013/0231267 | A1 | 9/2013 | O'Shea et al. |
| 2013/0243729 | A1 | 9/2013 | O'Shea et al. |
| 2015/0005397 | A1 | 1/2015 | O'Shea et al. |
| 2015/0017127 | A1 | 1/2015 | O'Shea et al. |
| 2015/0374766 | A1 | 12/2015 | O'Shea et al. |
| 2017/0202893 | A1 | 7/2017 | O'Shea et al. |
| 2018/0355374 | A1 | 12/2018 | O'Shea et al. |
| 2018/0355379 | A1 | 12/2018 | O'Shea et al. |
| 2019/0314525 | A1 | 10/2019 | O'Shea et al. |

FOREIGN PATENT DOCUMENTS

| | | |
|---|---|---|
| WO | WO 2000/052186 | 9/2000 |
| WO | WO 2000/073478 | 12/2000 |
| WO | WO 2003/004661 | 1/2003 |
| WO | WO 2003/062400 | 7/2003 |
| WO | WO 2008/153742 | 12/2008 |
| WO | WO 2013/036791 | 3/2013 |
| WO | WO 2013/174910 | 11/2013 |
| WO | WO 2016/049201 | 3/2016 |
| WO | WO 2017/062511 | 4/2017 |

OTHER PUBLICATIONS

Alba et al. ("Alba"; Blood 2010, 116 (15): 2656-2664 (Year: 2010).*

Heldin et al. ("Heldin"; Physiological Reviews 1999, 79(4)1283-1316 (Year: 1999).*

Maruotti et al., J. Cell. Physiol. 2013, 228: 1428-1432 (Year: 2013).*

Weiss et al., Dev. Biol. 2013, 2:47-63 (Year: 2013).*

Koski et al., "Mutation of the Fiber Shaft Heparan Sulphate binding Site of a 5/3 Chimeric Adenovirus Reduces Liver Tropism," *PLoS ONE* 8(4):e60032, 2013.

Alba et al., "Identification of Coagulation Factor (F)X Binding Sites on the Adenovirus Serotype 5 Hexon: Effect of Mutagenesis on FX Interactions and Gene Transfer," *Blood.*, vol. 114:965-971, 2009.

Leja et al., "Double-Detargeted Oncolytic Adenovirus Shows Replication Arrest in Liver Cells and Retains Neuroendocrine Cell Killing Ability," *PLoS ONE*, vol. 5:e8916, 2010.

Stevenson et al., "Selective Targeting of Human Cells by a Chimeric Adenovirus Vector Containing a Modified Fiber Protein," *J. Virol.*, vol. 71:4782-4790, 1997.

Bennett et al., "Regulation of Osteoblastogenesis and Bone Mass by Wnt10b," *Proc. Natl. Acad. Sci. USA* , vol. 102:3324-3329, 2005.

Canalis et al., "Bone Morphogenetic Proteins, Their Antagonists, and the Skeleton," *Endoc. Rev.*, vol. 24:218-235, 2003.

Canalis et al., "Mechanisms of Anabolic Therapies for Osteoporosis," *N. Engl. J. Med.*, vol. 357:905-916, 2007.

Davison et al., "TPA: Human adenovirus type 11, complete genome," (GenBank Accession No. BK001453, deposited Oct. 24, 2003).

(Continued)

*Primary Examiner* — James D Schultz

(74) *Attorney, Agent, or Firm* — Klarquist Sparkman, LLP

(57) ABSTRACT

Synthetic adenoviruses having chimeric fiber proteins and liver detargeting mutations are described. The synthetic adenovirus vectors are capable of specifically infecting cells at wound sites or in regions of damaged tissue. The synthetic adenovirus vectors also are capable of expressing transgenes, such as wound healing factors, at sites of wounded or damaged tissue. Accordingly, the described vectors can be used to detect wounded or damaged tissue, and/or to promote wound healing and regeneration of damaged tissue, such as by expression of heterologous wound healing or tissue regeneration factors.

11 Claims, 13 Drawing Sheets

Specification includes a Sequence Listing.

(56) References Cited

OTHER PUBLICATIONS

Hou et al., "Osteoblast-specific gene expression after transplantation of marrow cells: Implications for skeletal gene therapy," *Proc Natl Acad Sci USA* 96:7294-7299, 1999.
International Search Report and Written Opinion for PCT/US2017/068652, dated Apr. 5, 2018 (15 pages).
Krishnan et al., "Regulation of Bone Mass by Wnt Signaling," *J. Clin. Invest.*, vol. 116:1202-1209, 2006.
NCBI Blast nucleotide alignment, https://blast.ncbi.nlm.nih.gov/Blast.cgi, pp. 1-17, Jan. 15, 2022.
Qiao et al., "Liver-specific microRNA-122 target sequences incorporated in AAV vectors efficiently inhibits transgene expression in the liver," *Gene Ther* 18:403-410, 2011.
Uetsuki et al., Human elongation factor EF-lalpha gene, complete CDS (GenBank Accession No. J04617, deposited Nov. 7, 1994).
Yu et al., "PTH Induces Differentiation of Mesenchymal Stem Cells by Enhancing Bmp Signaling," *J Bone Miner Res* 27(9):2001-2014, 2012.

* cited by examiner

Induce IRI by surgery on the left kidney 48 hours later

AdSyn-CO176 injection
10 fold of the volume used before 48 hours later

IVIS imaging and
Tissue section

Ventral Dorsal

SYNTHETIC ADENOVIRUSES WITH TROPISM TO DAMAGED TISSUE FOR USE IN PROMOTING WOUND REPAIR AND TISSUE REGENERATION

CROSS-REFERENCE TO RELATED APPLICATIONS

This application is a continuation of International Application No. PCT/US2016/055579, filed Oct. 5, 2016, published in English under PCT Article 21(2), which claims the benefit of U.S. Provisional Application No. 62/237,410, filed Oct. 5, 2015. The above-listed applications are herein incorporated by reference in their entirety.

FIELD

This disclosure concerns synthetic adenoviruses that home to sites of damaged tissue. This disclosure further concerns use of the synthetic adenoviruses to express diagnostic or therapeutic transgenes to detect damaged tissue and/or promote wound healing and tissue regeneration.

BACKGROUND

Proper wound healing and recovery from injuries is essential for human health. Failure to repair tissue can result in opportunistic infection, sepsis, irreparable loss of tissue function and pain. In addition, the chronic inflammation from the wound site also predisposes the tissue to cancer development (Coussens and Werb, *Nature* 420:860-867, 2002). In general, the wound repair process occurs in almost all tissues. Thus, the sequence of events that follows kidney damage, for example, is similar to a burn or gunshot wound, despite the different types of insult and the different organs affected. However, aberrant tissue repair (such as excessive fibrosis) will result in the dysfunction of the organ and even lifelong disability. Fibrosis is a process that is activated in response to injury to maintain the original tissue architecture and functional integrity (Schieppati and Remuzzi, *Kidney Int Suppl*, S7-S10, 2005). However, prolonged chronic stimuli may cause deregulation of normal processes and result in excess deposition of extracellular matrix (Hirschberg, *J Am Soc Nephrol* 16:9-11, 2005). Continuous deposition of extracellular matrix results in fibrous scars, leading to loss of function of the tissue. Thus, a need exists for a means to accelerate wound closure and promote regeneration of tissue function.

The identification of the reprogramming factors Oct4, Sox2, Klf4 and c-myc was an important scientific finding. However, the stable expression of these factors can give rise to cancer (Abad et al., *Nature* 502:340-345, 2013). Also, the ex vivo manipulation of a patient's cells is time consuming and inefficient. The epigenetic alterations in culture also preclude its functional utility in acute and chronic tissue repair. Another potential means for promoting wound repair is to utilize the key pathways in the wound healing process, such as the Wnt pathway. Wnt proteins are a family of 19 secreted glycoproteins that have critical roles in wound repair and healing. The inhibition or lack of Wnt signaling in a bone fracture prevents union of the injured bone (Secreto et al., *Curr Osteoporos Rep* 7:64-69, 2009). In skin lesions, a lack of Wnt results in permanent scarring (Lim and Nusse, *Cold Spring Harb Perspect Biol* 5, 2013). In myocardial infarctions, a lack of Wnt signaling worsens the symptoms and the result is myocardial rupture. Elevating Wnt at the time of injury can induce a fully functional limb in amputations of postmetamorphic frogs. Elevating Wnt in mammalian skin wounds also reduces scarring and results in a functional epidermis (Whyte et al., *Cold Spring Harb Perspect Biol* 4:a008078, 2012). However, the caveat is that unrestrained and constitutive Wnt signaling leads to cancer (Arwert et al., *Nat Rev Cancer* 12:170-180, 2012). Thus, a need exists for a vector system that specifically targets injured tissue and mediates transient expression of heterologous proteins. Thus, the identification of a non-replicating vector (such as a replication-defective adenovirus) that specifically homes and transduces cells at the site of injury would enable the transient regulated expression of diagnostic and/or therapeutic protein(s). Such a vector could be used to detect and/or treat a variety of human conditions where an aberrant repair process results in loss of tissue function and long term disability.

SUMMARY

Described herein are synthetic adenovirus vectors that specifically infect cells at wound sites or in regions of damaged tissue, where the vectors drive transient expression of transgenes. The synthetic adenoviruses encode one or multiple transgenes, such as transgenes encoding diagnostic probes (for example, fluorescent or enzymatic markers), tissue regeneration factors, wound healing proteins and/or repair factors.

Provided herein is a method of expressing at least one transgene in cells at the site of a wound or damaged tissue in a subject. In some embodiments, the method includes administering to the subject a synthetic adenovirus that comprises the transgene(s), a native or modified capsid that detargets the synthetic adenovirus from the liver, and a chimeric fiber protein that includes an adenovirus type 5 (Ad5) shaft domain and an adenovirus type 34 (Ad34) knob domain. In some examples, the transgene(s) is a reporter gene. In other examples, the transgene(s) encodes at least one factor that promotes wound repair or tissue regeneration. In some examples, the method further includes selecting a subject with a wound or damaged tissue.

Also provided herein is a method of promoting wound repair or tissue regeneration in a subject. In some embodiments, the method includes administering to the subject a synthetic adenovirus that comprises a transgene encoding at least one heterologous factor that promotes wound repair or tissue regeneration, a native or modified capsid that detargets the synthetic adenovirus from the liver, and a chimeric fiber protein that includes an Ad5 shaft domain and an Ad34 knob domain. In some examples, the method further includes selecting a subject with a wound or damaged tissue.

Further provided herein is a method of detecting a wound or damaged tissue in a subject. In some embodiments, the method includes administering to the subject a synthetic adenovirus that includes a reporter gene, a native or modified capsid that detargets the synthetic adenovirus from the liver, and a chimeric fiber protein that includes an Ad5 shaft domain and an Ad34 knob domain.

Synthetic adenovirus genomes comprising the nucleotide sequence of any one of SEQ ID NOs: 1-8, 10 and 11 are further provided by the present disclosure.

The foregoing and other objects and features of the disclosure will become more apparent from the following detailed description, which proceeds with reference to the accompanying figures.

BRIEF DESCRIPTION OF THE DRAWINGS

(FIG. 2A) The adenovirus AdSyn-CO171 (ΔE1-EF1α-[luc-GFP]-miR122, hexon E451Q; SEQ ID NO: 1), AdSyn-CO172 (ΔE1-EF1α-[luc-GFP]-miR122; fiber chimera Ad5/5/3, hexon E451Q; SEQ ID NO: 2), AdSyn-CO174 (ΔE1-EF1α-[Luc-GFP]-miR122; fiber chimera Ad5/5/11, hexon E451Q; SEQ ID NO: 4), AdSyn-CO176 (ΔE1-EF1α-[luc-GFP]-miR122; fiber chimera Ad5/5/34, hexon E451Q; SEQ ID NO: 6) were injected into FVB/NJ mice by tail vein. The mouse that received saline served as the control. The mouse that received AdSyn-CO171 was tagged by left ear clip. The mouse that received AdSyn-CO172 was tagged by left ear and left forehand clip. The mice that received AdSyn-CO174 were tagged by right ear and right forehand clip. The mice that received AdSyn-CO176 were tagged by both ears and both forehands clip. IVIS™ imaging was performed at 48 hours post injection. The exposure time was 1 minute. The luciferase signals from the wound sites are indicated with a rectangle. (FIG. 2B) Prior to wounding, AdSyn-CO176 was injected into the FVB/NJ mouse by tail vein. IVIS™ imaging was performed at 72 hours post injection. Mice were then cut at both ears and both forehands and IVIS™ imaging was performed 72 hours post clip (6 days after injection). The exposure time was 1 minute. Luciferase signals from the wound sites are indicated.

(FIG. 4A) Flow chart of the experiment. Surgery was performed on the left kidney of mice to induce IRI damage. Forty-eight hours post-surgery, a 10-fold higher dose of AdSyn-CO176 (compared to the experiment shown in FIGS. 3A-3B) was injected into mice by tail vein injection. IVIS™ imaging was performed 48 hours post-injection and both kidneys were separated and sectioned to observe GFP signal. (FIG. 4B) IVIS™ image of an infected mouse showing that expression of AdSyn-CO176 concentrated at the damaged kidney part.

FIG. 7A) and creatinine (FIG. 7B).

(FIG. 8A) Relative luciferase signal in the liver and spleen following injection with AdSyn-CO171. (FIG. 8B) Relative luciferase signal in the liver following injection of either AdSyn-CO338 or AdySyn-CO339. (FIG. 8C) Relative luciferase signal in the spleen following infection of AdSyn-CO338 or AdySyn-CO339.

SEQUENCE LISTING

Figure 1:
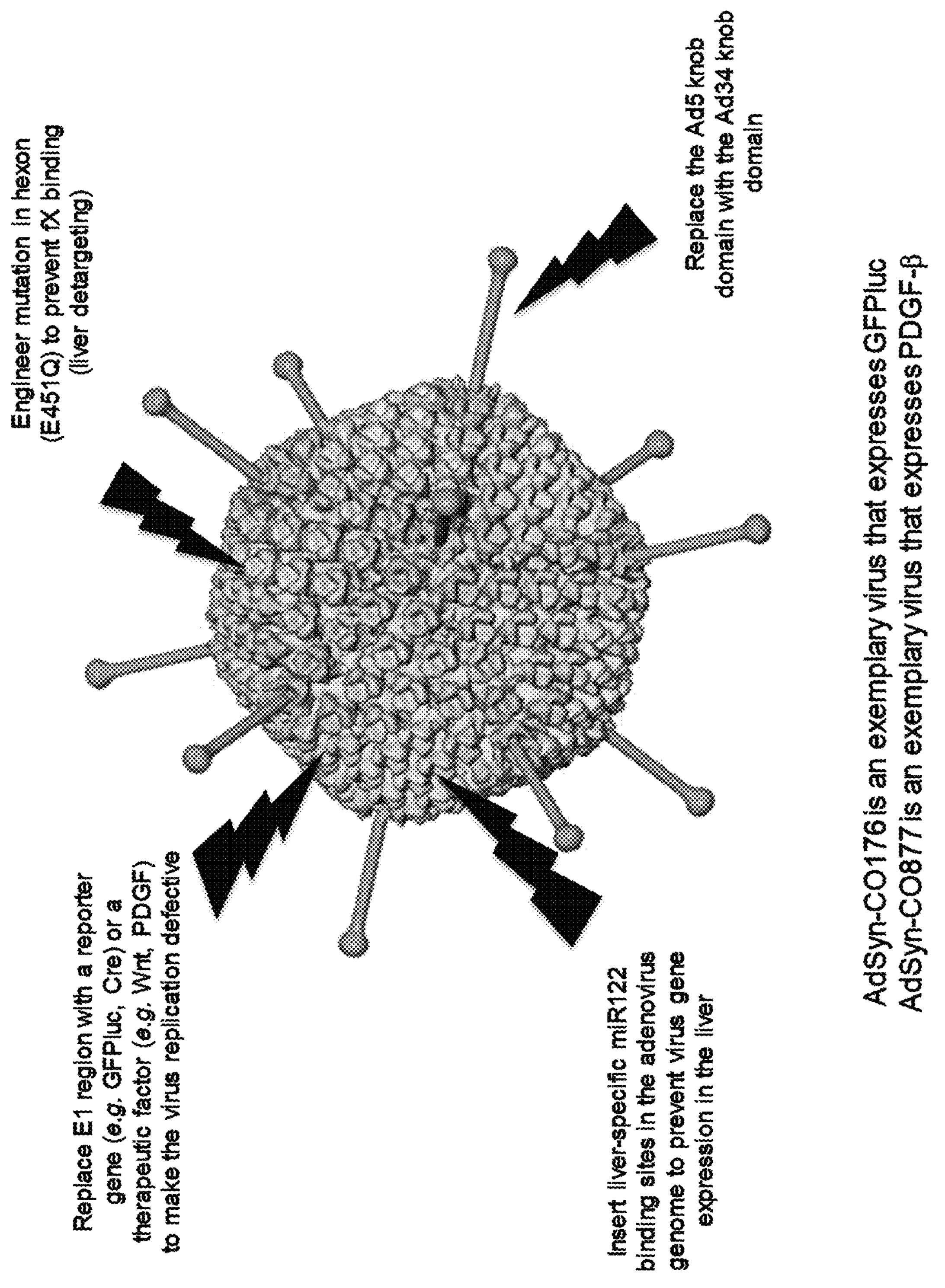
FIG. 1 is a schematic showing modifications introduced into exemplary synthetic adenoviruses disclosed herein. A replication defective virus is engineered by replacement of the E1 region with a reporter gene or a therapeutic factor. The hexon protein is mutated to prevent binding of the adenovirus capsid to factor X (fX), thereby detargeting the virus from the liver (Bradshaw et al., *Blood* 114(5):965-971, 2009). Binding sites for the liver-specific miR122 are inserted to prevent virus gene expression in the liver (Leja et al., *PLoS ONE* 5(1):e8916, 2010). The Ad5 knob domain is replaced with the Ad34 knob domain. AdSyn-CO176 (SEQ ID NO: 6) and AdSyn-CO877 (SEQ ID NO: 10) are exemplary synthetic viruses comprising these modifications.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Mar. 29, 2018, 499 KB, which is incorporated by reference herein. In the accompanying sequence listing:

SEQ ID NO: 1 is the nucleotide sequence of synthetic adenovirus AdSyn-CO171.

SEQ ID NO: 2 is the nucleotide sequence of synthetic adenovirus AdSyn-CO172.

SEQ ID NO: 3 is the nucleotide sequence of synthetic adenovirus AdSyn-CO173.

SEQ ID NO: 4 is the nucleotide sequence of synthetic adenovirus AdSyn-CO174.

SEQ ID NO: 5 is the nucleotide sequence of synthetic adenovirus AdSyn-CO175.

SEQ ID NO: 6 is the nucleotide sequence of synthetic adenovirus AdSyn-CO176.

SEQ ID NO: 7 is the nucleotide sequence of synthetic adenovirus AdSyn-CO199.

SEQ ID NO: 8 is the amino acid sequence of Ad5 hexon.

SEQ ID NO: 9 is the amino acid sequence of Ad5 hexon E451Q.

SEQ ID NO: 10 is the nucleotide sequence of synthetic adenovirus AdSyn-CO877.

SEQ ID NO: 11 is the nucleotide sequence of synthetic adenovirus AdSyn-CO338.

DETAILED DESCRIPTION

I. Abbreviations

Ad adenovirus
BUN blood urea nitrogen
CAR coxsackie adenovirus receptor
GFP green fluorescent protein
IRI ischemia-reperfusion injury
miR microRNA
PDGF platelet-derived growth factor
UTR untranslated region
WT wild-type II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adenovirus: A non-enveloped virus with a linear, double-stranded DNA genome and an icosahedral capsid. There are currently 68 known serotypes of human adenovirus, which are divided into seven species (species A, B, C, D, E, F and G). Different serotypes of adenovirus are associated with different types of disease, with some serotypes causing respiratory disease (primarily species B and C), conjunctivitis (species B and D) and/or gastroenteritis (species F and G).

Administration: To provide or give a subject an agent, such as a therapeutic agent (e.g. a recombinant virus), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes. In some examples, the recombinant adenoviruses disclosed herein are administered directly to a wound site, for example on the skin.

Chimeric: Composed of at least two parts having different origins. In the context of the present disclosure, a "chimeric adenovirus" is an adenovirus having genetic material and/or proteins derived from at least two different serotypes (such as from Ad5 and a second serotype of adenovirus). In this context, a "capsid-swapped" adenovirus refers to a chimeric adenovirus in which the capsid proteins are derived from one serotype of adenovirus and the remaining proteins are derived from another adenovirus serotype. Similarly, a "chimeric fiber" is a fiber protein having amino acid sequence derived from at least two different serotypes of adenovirus. For example, a chimeric fiber can be composed of a fiber shaft from Ad5 and a fiber knob from a second serotype of adenovirus.

Contacting: Placement in direct physical association; includes both in solid and liquid form.

Degenerate variant: In the context of the present disclosure, a "degenerate variant" refers to a polynucleotide encoding a peptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detargeted: In the context of the present disclosure, a "detargeted" adenovirus is a recombinant or synthetic adenovirus comprising one or more modifications that alter tropism of the virus such that is no longer infects, or no longer substantially infects, a particular cell or tissue type. In some embodiments, the recombinant or synthetic adenovirus comprises a capsid mutation, such as a mutation in the hexon protein (for example, E451Q). In some embodiments, the recombinant or synthetic adenovirus comprises a native capsid from an adenovirus that naturally does not infect, or does not substantially infect, a particular cell or tissue type. In some embodiments herein, the recombinant or synthetic adenovirus is liver detargeted and/or spleen detargeted.

E1A: The adenovirus early region 1A (E1A) gene and polypeptides expressed from the gene. The E1A protein plays a role in viral genome replication by driving cells into the cell cycle. As used herein, the term "E1A protein" refers to the proteins expressed from the E1A gene and the term includes E1A proteins produced by any adenovirus serotype.

Fiber: The adenovirus fiber protein is a trimeric protein that mediates binding to cell surface receptors. The fiber protein is comprised of a long N-terminal shaft and globular C-terminal knob.

Fusion protein: A protein containing amino acid sequence from at least two different (heterologous) proteins or peptides. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis.

Heterologous: A heterologous protein or gene refers to a protein or gene derived from a different source or species.

Hexon: A major adenovirus capsid protein. An exemplary hexon sequence from Ad5 is set forth herein as SEQ ID NO: 8. A mutant hexon sequence comprising an E451Q substitution is set forth herein as SEQ ID NO: 9.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

MicroRNA (miRNA or miR): A single-stranded RNA molecule that regulates gene expression in plants, animals and viruses. A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs). MicroRNAs modulate gene expression by promoting cleavage of target mRNAs or by blocking translation of the cellular transcript. In the context of the present disclosure, a “liver-specific microRNA” is a microRNA that is preferentially expressed in the liver, such as a microRNA that is expressed only in the liver, or a microRNA that is expressed significantly more in the liver as compared to other organs or tissue types. In some embodiments, the microRNA is miR-122.

Modification: A change in the sequence of a nucleic acid or protein sequence. For example, amino acid sequence modifications include, for example, substitutions, insertions and deletions, or combinations thereof. Insertions include amino and/or carboxyl terminal fusions as well as intrasequence insertions of single or multiple amino acid residues. Deletions are characterized by the removal of one or more amino acid residues from the protein sequence. In some embodiments herein, the modification (such as a substitution, insertion or deletion) results in a change in function, such as a reduction or enhancement of a particular activity of a protein. As used herein, “Δ” or “delta” refer to a deletion. Substitutional modifications are those in which at least one residue has been removed and a different residue inserted in its place. Amino acid substitutions are typically of single residues, but can occur at a number of different locations at once. Substitutions, deletions, insertions or any combination thereof may be combined to arrive at a final mutant sequence. These modifications can be prepared by modification of nucleotides in the DNA encoding the protein, thereby producing DNA encoding the modification. Techniques for making insertion, deletion and substitution mutations at predetermined sites in DNA having a known sequence are well known in the art. A “modified” protein, nucleic acid or virus is one that has one or more modifications as outlined above.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents (e.g. a synthetic virus disclosed herein).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide, peptide or protein: A polymer in which the monomers are amino acid residues which are joined together through amide bonds. When the amino acids are alpha-amino acids, either the L-optical isomer or the D-optical isomer can be used. The terms “polypeptide,” “peptide” and “protein” are used interchangeably herein. These terms apply to amino acid polymers in which one or more amino acid residue is an artificial chemical mimetic of a corresponding naturally occurring amino acid, as well as to naturally occurring amino acid polymers and non-naturally occurring amino acid polymers. The term “residue” or “amino acid residue” includes reference to an amino acid that is incorporated into a protein, polypeptide, or peptide.

A conservative substitution in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription. A "constitutive promoter" is a promoter that is continuously active and is not subject to regulation by external signals or molecules. In contrast, the activity of an "inducible promoter" is regulated by an external signal or molecule (for example, a transcription factor or tetracycline). A "tissue-specific promoter" is a promoter that is substantially active only in a particular tissue or tissues.

Protein IX (pIX): A minor component of the adenovirus capsid that associates with the hexon protein Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule, protein or virus is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids, proteins and viruses that have been altered solely by addition, substitution, or deletion of a portion of the natural nucleic acid molecule, protein or virus.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Subject: Living multi-cellular vertebrate organisms, a category that includes human and non-human mammals, such as veterinary subjects, for example mice, dogs, cats, rabbits, cows, horses, sheep, and pigs.

Synthetic: Produced by artificial means in a laboratory, for example a synthetic nucleic acid or protein can be chemically synthesized in a laboratory.

Therapeutic agent: A chemical compound, small molecule, recombinant virus or other composition, such as an antisense compound, antibody, peptide or nucleic acid molecule capable of inducing a desired therapeutic or prophylactic effect when properly administered to a subject.

Therapeutically effective amount: A quantity of a specified pharmaceutical or therapeutic agent (e.g. a recombinant virus) sufficient to achieve a desired effect in a subject, or in a cell, being treated with the agent. The effective amount of the agent can be dependent on several factors, including, but not limited to the subject or cells being treated, and the manner of administration of the therapeutic composition.

Tissue damage: Refers to any damage or injury to a tissue that may result from, for example, a physical injury, or a disease or pathological condition. In some cases, the tissue damage is damage caused by ischemia, ischemia/reperfusion, cirrhosis, or abnormal fibrosis.

Tissue regeneration: In the context of the present disclosure, "tissue regeneration" refers to the growth of new tissue or to the healing of damaged tissue.

Transgene: A gene that has been inserted into the genome of a different organism (such as a virus). Transgenes can also be referred to as heterologous genes.

Uexon: An open reading frame located on the 1 strand (leftward transcription) between the early E3 region and the fiber gene (Tollefson et al., *J Virol* 81(23):12918-12926).

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

Wound: An injury or damage to living tissue.

Wound repair: The process of replacing damaged or missing cellular structures or tissue layers. Wound repair (or wound healing) is characterized by the steps of hemostasis (blood clotting), inflammation, proliferation (growth of new tissues) and remodeling.

III. Overview of Several Embodiments

Adenovirus (Ad) is a natural multi-gene expression vehicle. Certain coding regions of the virus (E1, E3 and E4) are either not necessary for replication in culture or can be complemented with available cell lines. Therefore, each of these regions can be replaced with non-viral genes to drive the expression of multiple therapeutic gene products from a single virus. Adenovirus genomes do not integrate into human cell genomes and are lost upon cell division and nuclear envelope breakdown. There are 68 different human adenovirus serotypes, each of which as different properties. Ad5 has been the predominant Ad vector used in basic research, gene therapy and oncolytic virus therapy. However, Ad5 has a limited tropism and only infects epithelial cells that have the CAR receptor for viral uptake. Furthermore, when injected intravenously, Ad5 binds to blood factors that cause it to be sequestered in the liver where it can trigger potentially limiting inflammation and toxicity. To overcome these issues, the present disclosure provides synthetic adenoviruses with genomic modifications in the E1 region and capsid modules that prevent uptake and expression in the liver, and allow for targeting specifically to the sites of wounds and tissue damage when injected intravenously.

Disclosed herein are synthetic adenoviruses comprising a chimeric fiber protein that includes an Ad5 shaft domain and an Ad34 knob domain. The disclosed viruses also include a native or modified capsid that detargets the synthetic adenovirus from the liver. The synthetic adenoviruses are capable of specifically infecting wound sites and regions of damaged or injured tissue. It is disclosed herein that the synthetic adenovirus vectors that specifically infect cells at wound sites or in regions of damaged tissue are capable of expressing heterologous proteins in these cells. Synthetic adenoviruses expressing reporter genes can be used, for example, to enable early detection of a wound site or damaged tissue, thereby allowing for appropriate treatment decisions. Synthetic adenoviruses expressing key regulators of wound repair or tissue regeneration can be used to promote wound repair and/or boost tissue regeneration in organs such as the kidney, heart, liver, lung and skin, for example to restore tissue homeostasis, reduce fibrosis or scarring, and enhance regenerative capacity without the increased risk of off-target effects in other tissues (such as in the liver) or of cellular transformation.

Provided herein is a method of expressing at least one transgene (such as at least 2, at least 3, at least 4 or at least 5 transgenes) at the site of a wound or damaged tissue in a subject. In some embodiments, the method includes administering to the subject a synthetic adenovirus comprising the transgene(s); a native or modified capsid that detargets the synthetic adenovirus from the liver; and a chimeric fiber protein comprising an Ad5 shaft domain and an Ad34 knob domain, thereby expressing the at least one transgene at the site of the wound or damaged tissue. In some examples, the at least one transgene encodes at least one factor (such as at least 2, at least 3, at least 4 or at least 5 factors) that promotes wound repair or tissue regeneration. In some examples, the method further includes the step of detecting expression of the at least one transgene at the site of the wound or damaged tissue.

Also provided herein is a method of promoting wound repair or tissue regeneration in a subject. In some embodiments, the method includes administering to the subject a synthetic adenovirus comprising a transgene encoding at least one heterologous factor that promotes wound repair or tissue regeneration; a native or modified capsid that detargets the synthetic adenovirus from the liver; and a chimeric fiber protein comprising an Ad5 shaft domain and an Ad34 knob domain, thereby promoting wound repair or tissue regeneration in the subject.

In some embodiments of the method disclosed herein, the method further includes selecting a subject with a wound or damaged tissue. In some embodiments, the method further includes measuring wound repair or tissue regeneration, or detecting an increase in wound repair or tissue regeneration.

In some embodiments, the wound is a cutaneous wound. In particular examples, the cutaneous wound comprises an incision, a laceration, an abrasion, a puncture wound, a closed wound, a burn, an infected lesion, a surgical site, an ulcer, a scar, a keloid, a blister, sepsis, stroke, myocardial infarction, or any combination thereof.

In some embodiments, the tissue is damaged as a result of an injury, disease or pathological condition. In some examples, the tissue damage or injury is an ischemic injury, an ischemia/reperfusion injury, a microvascular injury, inflammation, abnormal fibrosis, cirrhosis, or any combination thereof. In some examples, the damaged tissue is kidney, heart, liver or lung tissue.

In some embodiments, the synthetic adenovirus comprises a modified capsid that detargets the synthetic adenovirus from the liver. In some examples, the modified capsid includes one or more modifications that detarget the virus from the liver. In some examples, the synthetic adenovirus comprises a modified hexon protein. In one non-limiting examples, the modified hexon protein comprises an E451Q mutation, such as the hexon protein of SEQ ID NO: 9. In another example, the modified hexon protein comprises hypervariable regions from a different adenovirus serotype.

In other embodiments, the synthetic adenovirus comprises a native capsid that detargets the synthetic adenovirus from the liver. In some examples, the native capsid is an Ad11, Ad34 or Ad35 capsid.

In some embodiments, the synthetic adenovirus further comprises one or more binding sites for a liver-specific microRNA. In some examples, the liver-specific microRNA is miR-122, miR-30 or miR-192. In particular examples, the one or more (such as 1, 2, 3 or 4) miR binding sites are in the 3'UTR of the adenovirus E1 region.

In some embodiments, the synthetic adenovirus further comprises one or more binding sites for a spleen-specific microRNA. In some examples, the spleen-specific microRNA is miR142-3p. In particular examples, the one or more (such as 1, 2, 3 or 4) miR binding sites are in the 3'UTR of the adenovirus E1 region.

Also provided herein is a method of detecting a wound or damaged tissue in a subject. In some embodiments, the method includes administering to the subject a synthetic adenovirus comprising a reporter gene; a native or modified capsid that detargets the synthetic adenovirus from the liver; and a chimeric fiber protein comprising an Ad5 shaft domain and an Ad34 knob domain.

In some embodiments of the methods disclosed herein, the synthetic adenovirus encodes at least one reporter gene (such as at least 2, at least 3, at least 4 or at least 5 report genes) to detect a wound site or damaged tissue. In specific non-limiting examples, the at least one reporter gene comprises a fluorophore, such as luciferase, GFP, yellow fluorescent protein (YFP), cyan fluorescent protein (CFP), red fluorescent protein (RFP), blue fluorescent protein (BFP), and/or orange fluorescent protein (for example, mOrange), a soluble secreted factor, or a MRI/PET/CT probe.

In some embodiments, the synthetic adenovirus encodes at least one factor that promotes wound repair. In some examples, the factor(s) that promotes wound repair is a member of the Wnt signaling pathway or the TGF-β signaling pathway. In specific non-limiting examples, the at least one factor that promote wound repair is selected from the group consisting of Wnt1, Wnt2, Wnt2b, Wnt3, Wnt3a, Wnt4, Wnt5a, Wnt5b, Wnt6, Wnt7a, Wnt8a, Wnt8b, Wnt9a, Wnt9b, Wnt10a, Wnt10b, Wnt11, Wnt16, TGF-β1, TGF-β2, TGF-β3, PDGF-α, PDGF-β, PDGF-c, PDGF-d, and TNF-α. In one non-limiting examples, the factor is PDGF-β.

In some embodiments, the synthetic adenovirus encodes at least one factor that promotes kidney tissue regeneration. In some examples, the at least one factor that promotes kidney tissue regeneration is selected from the group consisting of Wt1, Pax2, Foxc1, Foxd1, Bmp4, Sall1, Fgf7, Gdnf, Notch2, Sox and progranulin (PGRN).

In some embodiments, the synthetic adenovirus encodes at least one factor that promotes heart tissue regeneration. In some examples, the at least one factor that promotes heart tissue regeneration is selected from the group consisting of Mef2c, Tbx20, Hand2, Foxh1 and Bop.

In some embodiments, the synthetic adenovirus encodes at least one factor that promotes liver tissue regeneration. In some examples, the at least one factor that promotes liver tissue regeneration is selected from the group consisting of Hex, Gata4, Gata6, Tbx3, Cebp-α, Hnf1-α, Hnf1-β, Foxa1, Foxa2, Foxa3, Hnf4-α and Hnf6.

In some embodiments, the synthetic adenovirus encodes at least one factor that promotes lung tissue regeneration. In some examples, the at least one factor that promotes lung tissue regeneration is selected from the group consisting of stem cell factor (SCF), Hnf3-β, Shh, Nkx2.1, Foxf1, Gli, FGF-10, GATA and VEGF.

In some embodiments, the synthetic adenovirus encodes at least one factor that promotes pancreatic tissue regeneration. In some examples, the at least one factor that promotes pancreatic tissue regeneration is selected from the group consisting of Glul, Lgmn, Reg3α, Ngn3, Pdx1 and Mafa.

In some embodiments, expression of the at least one heterologous factor that promotes wound repair or tissue regeneration is regulated by a tissue-specific promoter. In some examples, the tissue-specific promoter is active in kidney, heart, lung, liver or pancreas tissue. In particular non-limiting examples the pancreas-specific promoter comprises Pdx1; the liver-specific promoter comprises albumin or α1-antitrypsin; the heart-specific promoter comprises MLC-2v; the lung-specific promoter comprises surfactant protein A, B or C; or the kidney-specific promoter comprises Sglt2, nephrin, and kidney-specific cadherin.

In some embodiments of the methods disclosed herein, the synthetic adenovirus is generated from an Ad5 vector genome. In other embodiments, the synthetic adenovirus is generated from an Ad2 vector genome.

In alternative embodiments of the methods disclosed herein, the synthetic adenovirus comprises a chimeric fiber protein that includes an Ad2 shaft domain (instead of an Ad5 shaft domain) and an Ad34 knob domain.

Further provided herein are synthetic adenovirus genomes that include the nucleotide sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 10 or SEQ ID NO: 11.

IV. Synthetic Adenoviruses

The Adsembly, AdSLICr and RapAD technologies enable the modular design and production of adenoviruses with unique capabilities (see PCT Publication Nos. WO2012/024351 and WO2013/138505, which are herein incorporated by reference). The ability to design custom viruses with novel functions and properties opens up the potential to expand the utility of adenovirus as a vehicle to deliver therapeutic proteins by persuading the host to produce proteins in situ. This provides the unique capability to use human proteins that are difficult to manufacture for therapeutic purposes, and enable flexible delivery of almost any protein to diseased tissues.

The specific modifications disclosed herein are described with reference to the adenovirus 5 (Ad5) genome sequence, but may be used with any adenovirus serotype. Adenovirus is a natural multi-gene expression vehicle. The E1, E3, and E4 regions are either not necessary for replication in culture or can be complemented with available cell lines. Each of these regions has independent promoter elements that can be replaced with cellular promoters if necessary to drive the expression of multiple gene products via alternative splicing.

As disclosed herein, to create Ad5 expression vectors for in vivo use and gene delivery, the E1A/E1 genes were deleted and replaced with at least one transgene. In some embodiments, the transgene is an EF1α driven luciferase-GFP fusion.

The synthetic adenoviruses disclosed herein may further include modifications that detarget the virus from the liver. Ad5 hexon can bind to Factor X in the blood, which can lead to its absorption by Kuppfer cells in the liver that prevent systemic dissemination and limiting inflammation. To overcome this, synthetic adenoviruses were engineered to include additional genomic modifications in the E1 and core modules that prevent uptake and expression in the liver, as described further below.

A. Ad34 Fiber and Chimeric Fiber Proteins for Retargeting

While the fiber proteins of Ad5 and many other serotypes have been shown to bind to the coxsackie adenovirus receptor (CAR) for cellular attachment, other serotypes have been shown to use CD46 (Gaggar et al., *Nat Med* 9:1408-1412, 2003), desmoglein 2 (Wang et al., *Nat Med* 17:96-104, 2011), sialic acid (Nilsson et al., *Nat Med* 17:105-109, 2011), or others (Arnberg, *Trends Pharmacol Sci* 33:442-448, 2012). The receptor usage of many serotypes has not been thoroughly examined and CD46 is not thought to be expressed in mature mice. Since the globular knob at the C-terminus of the fiber protein is typically responsible for receptor binding, chimeras were created by replacing the Ad5 fiber knob with that from either Ad3, Ad9, Ad11, Ad12, or Ad34 (see Example 1 below). Each virus was created with the same E1 module containing an E1A/E1B deletion and a luciferase-GFP fusion driven by an EF1α promoter. The panel was used to transduce the H9 stem cell line and luciferase expression was measured. Compared to Ad5 fibers, significantly higher luciferase-GFP expression was observed in almost all cells when using chimeras with either Ad3, Ad9, Ad12 or Ad34. Conversely, luciferase-GFP expression was almost universally lower in cells transduced with the Ad11 fiber chimera. These data demonstrate the ability to combine modified parts from other serotypes in order to improve Ad5-based vectors. In this case allowing for rapid assembly of viruses that are optimized for entry into specific cell types.

B. Liver Detargeting Modifications

Natural adenovirus type 5 vectors will only infect the lungs (via inhalation) or liver (via intravenous administration). Ad5 hexon binds to Factor X in the blood, which leads its absorption by Kuppfer cells in the liver, preventing systemic dissemination and inducing virus-limiting inflammation. To overcome this and enable intravenous delivery of viruses that could travel to the sites of wounds/injuries systemically, synthetic adenoviruses were engineered to include additional genomic modifications in the E1 and core modules that prevent uptake and expression in the liver.

To prevent virus uptake and sequestration in the liver through Ad5 hexon binding to Factor X, viruses were engineered with an additional mutation in hexon (E451Q) that prevents liver uptake. For example, AdSyn-CO171 does not accumulate in the liver and instead is able to target other organs, such as the spleen and lymph nodes. Thus, in some embodiments herein, the synthetic adenovirus comprises a modified hexon protein with an E451Q substitution.

To prevent off-target expression in the liver, viruses were engineered to include binding sites in the 3' untranslated region (UTR) of the E1 region for microRNAs that are specifically expressed in the liver. In particular embodiments, miR122 was selected as the liver-specific microRNA as its expression and binding sites are conserved in both human and mouse liver cells. In some examples, two microRNA binding sites for liver-specific miR122 were inserted in the 3'UTR of E1A to prevent any residual virus uptake in the liver inducing viral gene expression and cellular inflammatory responses.

It is disclosed herein that a synthetic adenovirus with the miR-122 binding site and hexon mutation does not accumulate in the liver and instead is able to target other organs, such as the spleen and lymph nodes (see Example 1). In some embodiments, the one or more binding sites for the liver-specific microRNA are located in the 3'-UTR of E1A. In some examples, the liver-specific microRNA is miR-122, miR-30 or miR-192.

Other mutations to the adenovirus hexon gene are contemplated herein to prevent adenovirus accumulation in the liver. For example, a synthetic adenovirus could be detargeted from the liver by replacing the nine hypervariable regions of hexon with those from different serotypes.

In some examples, the synthetic adenovirus comprises a hexon protein comprising or consisting of the amino acid sequence of SEQ ID NO: 8 or SEQ ID NO: 9.

```
Ad5 hexon
                                            (SEQ ID NO: 8)
MATPSMMPQWSYMHISGQDASEYLSPGLVQFARATETYFSLNNKFRNP
TVAPTHDVTTDRSQRLTLRFIPVDREDTAYSYKARFTLAVGDNRVLDM
ASTYFDIRGVLDRGPTFKPYSGTAYNALAPKGAPNPCEWDEAATALEI
NLEEEDDDNEDEVDEQAEQQKTHVFGQAPYSGINITKEGIQIGVEGQT
PKYADKTFQPEPQIGESQWYETEINHAAGRVLKKTTPMKPCYGSYAKP
TNENGGQGILVKQQNGKLESQVEMQFFSTTEATAGNGDNLTPKVVLYS
EDVDIETPDTHISYMPTIKEGNSRELMGQQSMPNRPNYIAFRDNFIGL
MYYNSTGNMGVLAGQASQLNAVVDLQDRNTELSYQLLLDSIGDRTRYF
```

-continued

```
SMWNQAVDSYDPDVRIIENHGTEDELPNYCFPLGGVINTETLTKVKPK
TGQENGWEKDATEFSDKNEIRVGNNFAMEINLNANLWRNFLYSNIALY
LPDKLKYSPSNVKISDNPNTYDYMNKRVVAPGLVDCYINLGARWSLDY
MDNVNPFNHHRNAGLRYRSMLLGNGRYVPFHIQVPQKFFAIKNLLLLP
GSYTYEWNFRKDVNMVLQSSLGNDLRVDGASIKFDSICLYATFFPMAH
NTASTLEAMLRNDTNDQSFNDYLSAANMLYPIPANATNVPISIPSRNW
AAFRGWAFTRLKTKETPSLGSGYDPYYTYSGSIPYLDGTFYLNHTFKK
VAITFDSSVSWPGNDRLLTPNEFEIKRSVDGEGYNVAQCNMTKDWFLV
QMLANYNIGYQGFYIPESYKDRMYSFFRNFQPMSRQVVDDTKYKDYQQ
VGILHQHNNSGFVGYLAPTMREGQAYPANFPYPLIGKTAVDSITQKKF
LCDRTLWRIPFSSNFMSMGALTDLGQNLLYANSAHALDMTFEVDPMDE
PTLLYVLFEVFDVVRVHRPHRGVIETVYLRTPFSAGNATT

Ad5 hexon E451Q
                                            (SEQ ID NO: 9)
MATPSMMPQWSYMHISGQDASEYLSPGLVQFARATETYFSLNNKFRNP
TVAPTHDVTTDRSQRLTLRFIPVDREDTAYSYKARFTLAVGDNRVLDM
ASTYFDIRGVLDRGPTFKPYSGTAYNALAPKGAPNPCEWDEAATALEI
NLEEEDDDNEDEVDEQAEQQKTHVFGQAPYSGINITKEGIQIGVEGQT
PKYADKTFQPEPQIGESQWYETEINHAAGRVLKKTTPMKPCYGSYAKP
TNENGGQGILVKQQNGKLESQVEMQFFSTTEATAGNGDNLTPKVVLYS
EDVDIETPDTHISYMPTIKEGNSRELMGQQSMPNRPNYIAFRDNFIGL
MYYNSTGNMGVLAGQASQLNAVVDLQDRNTELSYQLLLDSIGDRTRYF
SMWNQAVDSYDPDVRIIENHGTEDELPNYCFPLGGVINTETLTKVKPK
TGQENGWEKDATEFSDKNQIRVGNNFAMEINLNANLWRNFLYSNIALY
LPDKLKYSPSNVKISDNPNTYDYMNKRVVAPGLVDCYINLGARWSLDY
MDNVNPFNHHRNAGLRYRSMLLGNGRYVPFHIQVPQKFFAIKNLLLLP
GSYTYEWNFRKDVNMVLQSSLGNDLRVDGASIKFDSICLYATFFPMAH
NTASTLEAMLRNDTNDQSFNDYLSAANMLYPIPANATNVPISIPSRNW
AAFRGWAFTRLKTKETPSLGSGYDPYYTYSGSIPYLDGTFYLNHTFKK
VAITFDSSVSWPGNDRLLTPNEFEIKRSVDGEGYNVAQCNMTKDWFLV
QMLANYNIGYQGFYIPESYKDRMYSFFRNFQPMSRQVVDDTKYKDYQQ
VGILHQHNNSGFVGYLAPTMREGQAYPANFPYPLIGKTAVDSITQKKF
LCDRTLWRIPFSSNFMSMGALTDLGQNLLYANSAHALDMTFEVDPMDE
PTLLYVLFEVFDVVRVHRPHRGVIETVYLRTPFSAGNATT
(the E451Q substitution is shown in bold
underline)
```

C. Capsid Swaps for Evading Neutralizing Antibodies

The majority of the human population already has antibodies that recognize Ad5, the serotype most frequently used in research and therapeutic applications. Moreover, once a particular adenovirus serotype is used in a patient, new antibodies that recognize the viral capsid will be generated, making repeated administration of the same vector problematic. Therefore, the present disclosure further contemplates exploiting natural adenovirus modularity to create chimeric viruses capable of evading existing neutralizing antibodies. For example, the synthetic adenoviruses disclosed herein may further have complete 'capsid' module swaps (almost 60% of genome), which render them 'invisible' to pre-existing antibodies and enables repeated inoculations.

In some embodiments, the E1, E3 and E4 regions of the genome are derived from a first adenovirus serotype and the E2B, L1, L2, L3, E2A and L4 regions of the genome are derived from a second adenovirus serotype, such as Ad34. In some examples, the E1 region of the first adenovirus serotype is modified to encode a pIX protein from the second adenovirus serotype; and/or the E3 region of the first adenovirus serotype is modified to encode Uexon and fiber proteins from the second adenovirus serotype. In particular examples, the first adenovirus serotype is Ad5 and the second adenovirus serotype is Ad34.

D. Expression of Transgenes for Research and Therapeutic Applications

It is disclosed herein that synthetic adenoviruses comprising a chimeric fiber protein having an Ad34 knob domain and liver detargeting mutations is capable of specifically infecting sites of wounded or damaged tissue. It is further disclosed that the synthetic adenoviruses are capable of expressing transgenes in cells of wounds/injured tissue. In one example, the transgene is a reporter, such as a luciferase-GFP reporter that enables detection of virus expression. The present disclosure contemplates synthetic adenoviruses encoding reporter genes to detect the wound sites and/or damaged tissue. The present disclosure further contemplates transgenes encoding factors that promote wound repair and/or tissue regeneration. Such synthetic vectors could be used for a variety of therapeutic applications.

The present disclosure provides synthetic adenoviruses encoding reporter genes to detect wound sites and/or damaged tissue. Early detection and treatment of a wound or tissue damage is desirable in order to prevent or limit potentially severe consequences of a wound, particularly sepsis. Sepsis is a heightened systemic immune response state and the eleventh leading cause of death (Murphy et al., *Natl Vital Stat Rep* 61:1-117, 2013). In some embodiments, the synthetic adenoviruses encode on or more reporter genes selected from luciferase, GFP, yellow fluorescent protein (YFP), cyan fluorescent protein (CFP), red fluorescent protein (RFP), blue fluorescent protein (BFP) and orange fluorescent protein (such as mOrange).

The major signaling pathways involved in cutaneous wound repair have been investigated, including, for example, the Wnt and TGF-β pathways (Bielefeld et al., *Cell Mol Life Sci* 70: 2059-2081, 2013). The synthetic adenoviruses disclosed herein are capable of specifically infecting wound sites. In some embodiments, the synthetic adenoviruses encode at least one factor involved in wound repair, such as a member of the Wnt or TGF-β pathway. In some examples, the at least one factor includes one or more of (such as at least 2, at least 3, at least 4, or at least 5 of) Wnt1, Wnt2, Wnt2b, Wnt3, Wnt3a, Wnt4, Wnt5a, Wnt5b, Wnt6, Wnt7a, Wnt8a, Wnt8b, Wnt9a, Wnt9b, Wnt10a, Wnt10b, Wnt11, Wnt16 TGF-β1, TGF-β2, TGF-β3, PDGF-α, PDGF-β, PDGF-c, PDCF-d, and TNF-α.

In other embodiments, the factors involved in wound repair may include growth factors, cytokines, therapeutic proteins, hormones, peptide fragments of hormones, inhibitors of cytokines, peptide growth and differentiation factors, interleukins, chemokines, interferons, colony stimulating factors and angiogenic factors. In some examples, the at least one factor involved in wound repair includes, but is not limited to, a member of the TGF-β superfamily, such as one of the five TGF-β isoforms, bone morphogenetic proteins (BMP), or latent TGF-β binding proteins (LTBP); keratinocyte growth factor (KGF); hepatocyte growth factor (HGF); platelet derived growth factor (PDGF); insulin-like growth factor (IGF); the basic fibroblast growth factors (FGF-1, FGF-2 etc.), vascular endothelial growth factor (VEGF); Factor VIII and Factor IX; erythropoietin (EPO); tissue plasminogen activator (TPA); and activins and inhibins. In some examples, the at least one factor involved in wound repair is a hormone, such as growth hormone (GH) or parathyroid hormone (PTH). The at least one factor involved in wound repair may also include extracellular proteins, such as extracellular matrix proteins, for example collagen, laminin, and fibronectin. In other examples, the at least one factor involved in wound repair includes cell adhesion molecules (for example, integrins, selectins, Ig family members, such as N-CAM and L1, and cadherins); cytokine signaling receptors, such as the type I and type II TGF-β receptors and the FGF receptor; and non-signaling co-receptors such as betaglycan and syndecan. In yet other examples, the at least one factor involved in wound repair includes cytoskeletal proteins, such as talin and vinculin; cytokine binding proteins, such as the family of latent TGF-β binding proteins; and nuclear trans-acting proteins, such as transcription factors and enhancing factors.

Although damaged tissues share a similar repair process after almost any destructive stimulus, tissue specific growth factors, especially the genes that play key roles in tissue development, may play a role in recovery from the injury and avoid fibrosis. In some embodiments, the synthetic adenovirus encodes at least one factor for promoting tissue regeneration or healing of damaged kidney tissue. In some examples, the at least one factor is selected from Wt1, Pax2, Foxc1, Foxd1, Bmp4, Sall1, Fgf7, Gdnf, Notch2 and Sox9 (Vainio and Lin, *Nat Rev Genet* 3:533-543, 2002).

The present disclosure also contemplates the use of the disclosed synthetic adenoviruses for promoting tissue regeneration/repair following myocardial infarction, cirrhosis of the liver, fibrosis of the lung and fibrosis of the pancreas. Myocardial infarction can lead to the formation of scar tissue, ultimately resulting in congestive heart failure. Congestive heart failure accounts for more than 100,000 deaths each year in the United States. Cirrhosis of the liver and fibrosis of the lungs are also life-threatening conditions (2012 NHLBI Morbidity and Mortality Chart Book). Fibrosis in the pancreas is caused by alcohol consumption, tobacco use, genetic mutations or autoimmune destruction. The necrosis/apoptosis, inflammation or duct obstruction in the processes of fibrosis result in exocrine and endocrine insufficiency, and ultimately diabetes.

In some embodiments, the synthetic adenovirus disclosed herein encodes at least one factor for promoting heart tissue regeneration or healing of damaged heart tissue. In some examples, the at least one factor is selected from Mef2c, Tbx20, Hand2, Foxh1 and Bop (Chen and Fishman, *Trends Genet* 16:383-388, 2000).

In some embodiments, the synthetic adenovirus disclosed herein encodes at least one factor for promoting liver tissue regeneration or healing of damaged liver tissue. In some examples, the at least one factor is selected from Hex, Gata4, Gata6, Tbx3, Cebp-α, Hnf1-α, Hnf1-β, Foxa1, Foxa2, Foxa3, Hnf4-α and Hnf6 (Gordillo et al., *Development* 142:2094-2108, 2015).

In some embodiments, the synthetic adenovirus disclosed herein encodes at least one factor for promoting lung tissue regeneration or healing of damaged lung tissue. In some examples, the at least one factor is selected from stem cell factor (SCF), Hnf3-β, Shh, Nkx2.1, Foxf1, Gli, FGF-10, GATA and VEGF (Kumar et al., *Adv Clin Chem* 40:261-316, 2005).

In some embodiments, the synthetic adenovirus disclosed herein encodes at least one factor for promoting pancreatic tissue regeneration or healing of damaged pancreatic tissue. In some examples, the at least one factor is selected from Glul, Lgmn, Reg3a, Ngn3, Pdx1 and Mafa (Choi et al., *Bio Chem* 391:1019-1029, 2010; Zhou et al., *Nature* 455:627-632, 2008).

In some embodiments, the expression cassette/transgene(s) is inserted into and replace the E1 and/or E3 and/or E4 region(s). Appropriate transgene insertion sites are well known in the art (see, for example, PCT Publication No. WO2012/024351).

The transgene (or nucleic acid encoding the factor that promotes wound repair and/or tissue regeneration) is operably linked to a promoter. In some embodiments, the promoter is a heterologous promoter. In some examples, the promoter is the EF1α promoter. The selection of promoter is within the capabilities of one of skill in the art. In some cases, the promoter is an inducible promoter or a tissue-specific promoter. For instances in which a tissue-specific promoter is used to regulate expression of the transgene, exemplary promoters include, but are not limited to, Pdx1 (pancreas), albumin (liver), al-antitrypsin (liver), MLC-2v (heart), surfactant proteins A, B or C (lung), Sglt2 (kidney), nephrin (kidney) and kidney-specific cadherin (kidney).

In some cases a single promoter is used to regulate expression of multiple genes, which can be achieved by use of an internal ribosomal entry site (IRES) or 2A peptide.

V. Pharmaceutical Compositions and Administration Thereof

Provided herein are compositions comprising a synthetic adenovirus (or one or more nucleic acids or vectors encoding the synthetic adenovirus). The compositions are, optionally, suitable for formulation and administration in vitro or in vivo. Optionally, the compositions comprise one or more of the provided agents and a pharmaceutically acceptable carrier. Suitable carriers and their formulations are described in *Remington: The Science and Practice of Pharmacy,* $22^{nd}$ *Edition*, Loyd V. Allen et al., editors, Pharmaceutical Press (2012). Pharmaceutically acceptable carriers include materials that are not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

The synthetic viruses (or one or more nucleic acids or vectors encoding the synthetic adenovirus) are administered in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, intratumoral or inhalation routes. The administration may be local or systemic, and in some examples directly to a wound site. The compositions can be administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Thus, the compositions are administered in a number of ways depending on whether local or systemic treatment is desired, and on the area to be treated.

In some embodiments, the compositions for administration will include a synthetic adenovirus (or synthetic genome) as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Pharmaceutical formulations, particularly, of the synthetic viruses can be prepared by mixing the synthetic adenovirus (or one or more nucleic acids encoding the synthetic adenovirus) having the desired degree of purity with optional pharmaceutically acceptable carriers, excipients or stabilizers. Such formulations can be lyophilized formulations or aqueous solutions.

Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives, low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The synthetic adenovirus (or one or more nucleic acids encoding the synthetic adenovirus) can be formulated at any appropriate concentration of infectious units.

Formulations suitable for oral administration can consist of (a) liquid solutions, such as an effective amount of the synthetic adenovirus suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The synthetic adenovirus (or one or more nucleic acids encoding the synthetic adenovirus), alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the provided methods, compositions can be administered, for example, by intravenous infusion, orally, topically, intraperitoneally, intravesically intratumorally, or intrathecally. Parenteral administration, intratumoral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced or infected by adenovirus or transfected with nucleic acids for ex vivo therapy can also be administered intravenously or parenterally as described above.

The pharmaceutical preparation is preferably in unit dosage form. In such form the preparation is subdivided into unit doses containing appropriate quantities of the active component. Thus, the pharmaceutical compositions can be administered in a variety of unit dosage forms depending upon the method of administration. For example, unit dosage forms suitable for oral administration include, but are not limited to, powder, tablets, pills, capsules and lozenges.

In some embodiments, the compositions include at least two different synthetic adenoviruses, such as synthetic adenoviruses that encode different transgenes. In some examples, the composition includes two, three, four, five or six different synthetic adenoviruses.

In therapeutic applications, synthetic adenoviruses or compositions thereof are administered to a subject in a therapeutically effective amount or dose. Amounts effective for this use will depend upon the severity of the disease and the general state of the patient's health. Single or multiple administrations of the compositions may be administered depending on the dosage and frequency as required and tolerated by the patient. A "patient" or "subject" includes both humans and other animals, particularly mammals. Thus, the methods are applicable to both human therapy and veterinary applications.

An effective amount of a synthetic adenovirus is determined on an individual basis and is based, at least in part, on the particular synthetic adenovirus used; the individual's size, age, gender and general health. For example, for treatment of a human, at least $10^3$ plaque forming units (PFU) of a synthetic virus is used, such as at least $10^4$, at least $10^5$, at least $10^6$, at least $10^7$, at least $10^8$, at least $10^9$, at least $10^{10}$, at least $10^{11}$, or at least $10^{12}$ PFU, for example approximately $10^3$ to $10^{12}$ PFU of a synthetic virus is used, depending on the type, size and number of proliferating cells or neoplasms present. The effective amount can be from about 1.0 pfu/kg body weight to about $10^{15}$ pfu/kg body weight (e.g., from about $10^2$ pfu/kg body weight to about $10^{13}$ pfu/kg body weight). A synthetic adenovirus is administered in a single dose or in multiple doses (e.g., two, three, four, six, or more doses). Multiple doses can be administered concurrently or consecutively (e.g., over a period of days or weeks).

In some embodiments, the provided methods include administering to the subject one or more additional therapeutic agents, such as one or more agents that promote wound healing or tissue regeneration.

The following examples are provided to illustrate certain particular features and/or embodiments. These examples should not be construed to limit the disclosure to the particular features or embodiments described.

EXAMPLES

Using genome assembly technologies and structure based design, a library of synthetic adenovirus vectors that express GFP-luciferase and have multiple different combinations of capsid protein modifications were generated. To prevent liver uptake and limit inflammation, viral and transgene expression cassettes were engineered with binding sites for liver specific microRNAs and hexon modifications that prevent binding to factor X and uptake through toll-like receptors in Kupffer cells. These modifications prevented synthetic Ad5 vector sequestration in the liver. The detargeted Ad5 viruses were used as a genomic platform to screen for novel in vivo tropisms by swapping regions of the Ad5 fiber knob and shaft with those of other human Ad serotypes. These viruses were screened in vivo using luciferase bioluminescence and IVIS imaging.

Example 1: Synthetic Adenoviruses Expressing Chimeric Fiber Proteins and Liver Detargeting Modifications This example describes synthetic adenoviruses expressing chimeric fiber proteins and liver detargeting modifications to direct infection to specific cell types.

While the fiber proteins of Ad5 and many other serotypes have been shown to bind to CAR for cellular attachment, other serotypes have been shown to use CD46 (Gaggar et al., *Nat Med* 9:1408-1412, 2003), desmoglein 2 (Wang et al., *Nat Med* 17:96-104, 2011), sialic acid (Nilsson et al., *Nat Med* 17:105-109, 2011), or others (Arnberg, *Trends Pharmacol Sci* 33:442-448, 2012). The receptor usage of many serotypes has not been thoroughly examined and CD46 is not thought to be expressed in mature mice. Since Adsembly/AdSLIC (see PCT Publication No. WO 2012/024351, incorporated herein by reference) allows for the rapid creation of chimeric viruses, an initial panel of six fiber chimeric viruses was generated in order to examine the alternate cellular targeting capabilities of various serotypes. Since the globular knob at the C-terminus of the fiber protein is typically responsible for receptor binding, chimeras were created by replacing the Ad5 fiber knob with fiber knob from Ad3, Ad9, Ad11, Ad12, or Ad34 (Table 1). Each virus was created with the same E1 module containing an E1A/E1B deletion and a luciferase-GFP fusion driven by an EF1α promoter. The panel was used to transduce the H9 stem cell line and luciferase expression measured. Compared to Ad5 fibers, significantly higher luciferase-GFP expression was observed in almost all cells when using chimeras with either Ad3, Ad9, Ad12 or Ad34. Conversely, luciferase-GFP expression was almost universally lower in cells transduced with the Ad11 fiber chimera. These data demonstrate a powerful use for being able to combine modified parts from other serotypes in order to improve Ad5-based vectors and optimize synthetic viruses for entry into specific cell types.

The synthetic viruses listed in Table 1 also include liver detargeting modifications. Natural adenovirus type 5 vectors will only infect the lungs (via inhalation) or liver (via intravenous administration). Ad5 hexon binds to Factor X in the blood, which leads to its absorption by Kuppfer cells in the liver, preventing systemic dissemination and inducing limited inflammation. To overcome this and enable intravenous delivery of viruses that can travel to sites of wounds/injuries systemically, the synthetic adenoviruses were engineered to include additional genomic modifications in the E1 and core regions that prevent uptake and expression in the liver. These viruses include binding sites in the 3'UTR of the E1 expression module for a microRNA that is specifically expressed in the liver (miR-122) and an E451Q mutation in hexon.

To evaluate the effect of the liver detargeting modifications on adenovirus tropism, AdSyn-CO171 (with the liver detargeting modifications) and AdSyn-CO199 (a control virus) were injected into the tail vain of FVB/NJ mice. IVIS™ imaging was performed 72 hours after the injection to detect expression of luciferase. In contrast to control virus AdSyn-CO199, liver detargeted virus AdSyn-CO171 did not accumulate in the liver and instead was able to target other organs, including the spleen and lymph nodes.

TABLE 1

Adenoviruses with Chimeric Fiber Proteins and Liver Detargeting Modifications

| Virus Name | SEQ ID NO: | E1 | L3 | E3 | E4 |
|---|---|---|---|---|---|
| AdSyn-CO171 | 1 | ΔE1 + EF1α-luciferase-miR122 | hexon E451Q | wt | wt |
| AdSyn-CO172 | 2 | ΔE1 + EF1α-luciferase-miR122 | hexon E451Q | Ad3 knob Ad5 shaft fiber chimera | wt |
| AdSyn-CO173 | 3 | ΔE1 + EF1α-luciferase-miR122 | hexon E451Q | Ad9 knob Ad5 shaft fiber chimera | wt |
| AdSyn-CO174 | 4 | ΔE1 + EF1α-luciferase-miR122 | hexon E451Q | Ad11 knob Ad5 shaft fiber chimera | wt |
| AdSyn-CO175 | 5 | ΔE1 + EF1α-luciferase-miR122 | hexon E451Q | Ad12 knob Ad5 shaft fiber chimera | wt |
| AdSyn-CO176 | 6 | ΔE1 + EF1α-luciferase-miR122 | hexon E451Q | Ad34 knob Ad5 shaft fiber chimera | wt |
| AdSyn-CO199 | 7 | ΔE1 + EF1α-luciferase-miR122 | wt | wt | wt |

Example 2: Acute Skin/Ear and Limb Wounding Models

Figure 2A:
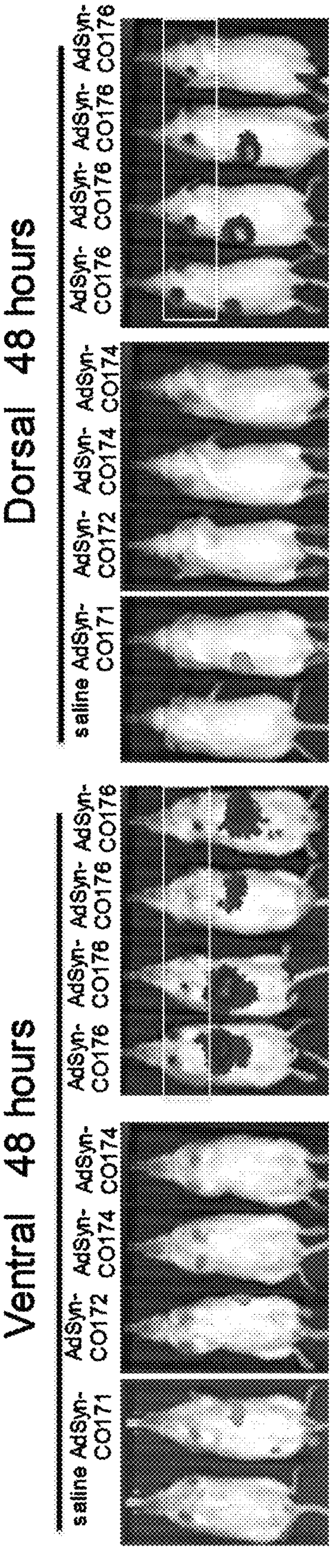
FIGS. 2A-2B: A synthetic adenovirus with the fiber knob domain of Ad34 exhibits tropism to wound sites.
Figure 2B:
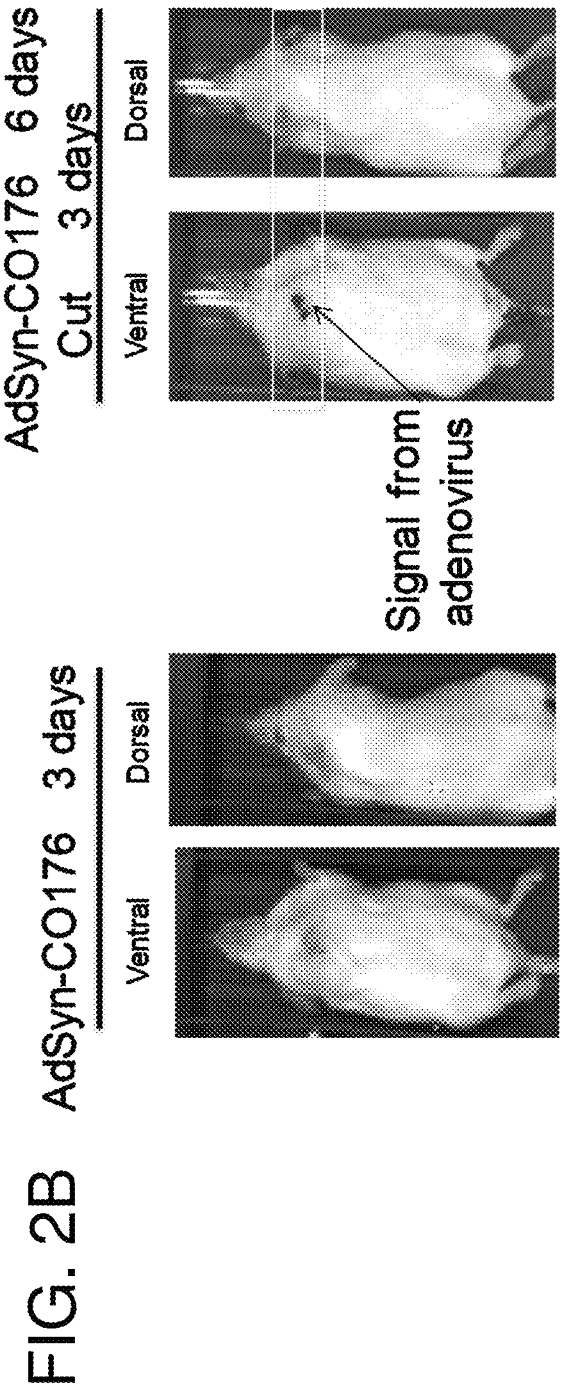

To identify synthetic viruses that travel to the sites of skin wounds, synthetic adenoviruses AdSyn-CO171 (WT fiber), AdSyn-CO172 (Ad3 fiber knob), AdSyn-CO174 (Ad11 fiber knob) or AdSyn-CO176 (Ad34 fiber knob) were injected into FVB/NJ mice by tail vein injection. At the same time, the ears and forehands of the mice were cut. By detection of luciferase (IVIS imaging) and GFP (fluorescence imaging), it was determined that synthetic adenovirus AdSyn-CO176, with the fiber knob of adenovirus type 34, transduces cells at the wound sites specifically, while injection of other synthetic adenoviruses, including AdSyn-CO171, AdSyn-CO172 and AdSyn-CO174, resulted in no luciferase activity at the wound parts (FIG. 2A). The detection of GFP by tissue section also showed the same result. In particular, only the forehands were cut in this experiment and signal could only be detected from the forehands, not the hindhands, which indicates that the signal represents the specific infection in the wound sites on the forehands. In addition, chimeric adenovirus AdSyn-CO176 did not travel to the ears and forehands if no damage was present in those tissue. Furthermore, even 3 days after the injection, the induction of cutaneous damage (via the cut) led to expression of luciferase on the ears and forehands (FIG. 2B). This result demonstrates that the specific infection of AdSyn-CO176 was driven by the injury. During subsequent observation, it was found that the luciferase signals from other tissues, mainly from liver and spleen, were silenced within one week. In contrast, the signals from wound sites lasted for three weeks. This result indicates that the synthetic adenovirus with Ad34 fiber knob exhibits prolonged transgene expression and is not silenced, which are ideal features for wound repair.

Example 3: Post Wounding Transduction and Site Specific Delivery to Wounded Tissue Cutaneous wound repair is characterized by three overlapping stages, termed the (1) hemostasis and inflammation, (2) proliferation, and (3) remodeling stages (Bielefeld et al., *Cell Mol Life Sci* 70:2059-2081, 2013). The hemostasis/inflammation phase lasts up to 48 hours. The proliferation stage lasts about 2 to 10 days and the process of remodeling lasts for a year or longer (Gurtner et al., *Nature* 453:314-321, 2008). To determine if the delivery of synthetic adenovirus vectors can infect cells at the site of a wound several days after injury, as opposed to prior to or at time of injury, ear clipping was performed 48 hours prior to administering synthetic adenovirus vectors (AdSyn-CO171, AdSyn-CO174 and AdSyn-CO176). Adenovirus type 11 (AdSyn-CO174) and type 34 (AdSyn-CO176) both belong to species B and subspecies B1 so they were expected to have similar target tissues. Luciferase detection showed that the synthetic adenovirus with Ad34 knob/Ad5 shaft chimeric fiber (AdSyn-CO176) still expressed specifically at wound sites. But other adenoviruses, including the chimeric adenovirus with Ad11 fiber knob/Ad5 fiber shaft (AdSyn-CO174), gave no signal at the wound site. This result indicates that the chimeric adenovirus with a fiber knob from type 34 can also infect the wound sites at the later phase after the injury.

Example 4: Acute Kidney Damage Model

The observation of the specific expression of the synthetic adenovirus with the fiber knob domain of type 34 cutaneous skin lesion and bone digit clips prompted the investigation of whether the synthetic adenovirus can infect additional internal tissues damaged through alternative mechanisms. To explore this issue, the renal ischemia-reperfusion injury (IRI) model was established. IRI has been most widely used as a model to study the pathobiology of acute kidney injury, which is associated with diverse clinical conditions including trauma, sepsis, toxicity, and cardiac arrest (Himmelfarb and Ikizler, *Kidney Int* 71:971-976, 2007). Depending on the severity of the ischemic insult, acute IRI can either resolve with regeneration of damaged tubules, or it can progress to chronic kidney disease with interstitial fibrosis (Burne-Taney et al., *Kidney Int* 67:1002-1009, 2005). In the model used herein, moderate ischemic injury (25 minutes) results in a regenerative response and resolution of injury.

Figure 3A:
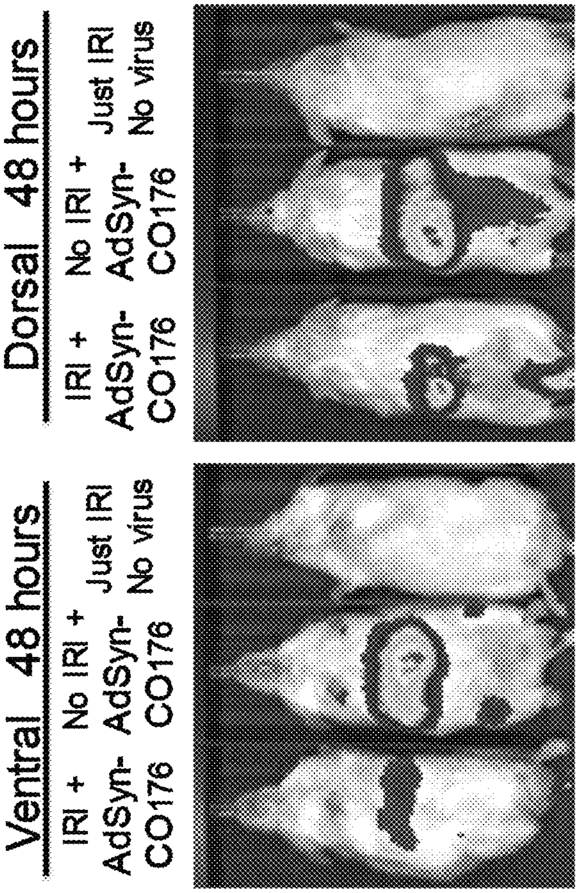
FIGS. 3A-3B: The specific infection of AdSyn-CO176 in the damaged kidney. FVB/NJ mice were induced with ischemia-reperfusion injury in one kidney by surgical operation. The chimeric adenovirus AdSyn-CO176 was injected into mice 24 hours later. IVIS™ imaging was performed at 2 days (FIG. 3A) and 7 Days (FIG. 3B) post injection. The exposure time was 1 minute.
Figure 3B:
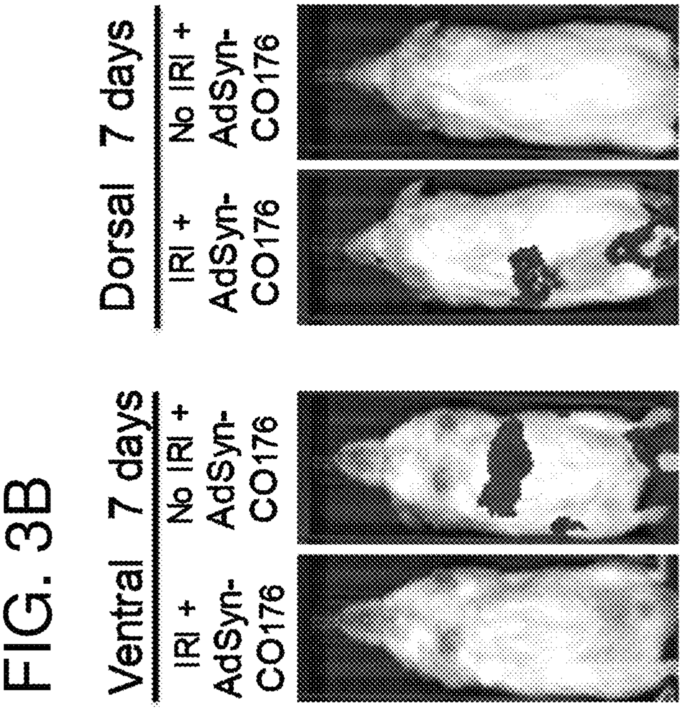
Figures 4A, 4B:
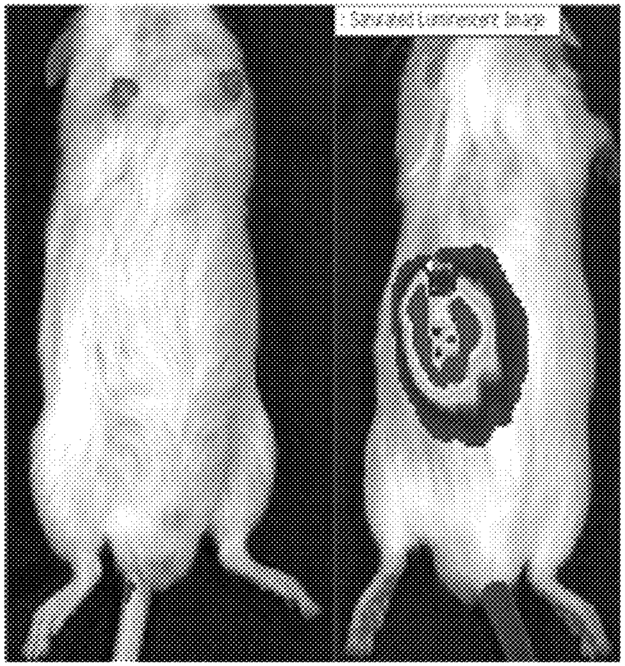
FIGS. 4A-4B: A higher dose injection of AdSyn-CO176 leads to specific expression of adenovirus in the IRI damaged kidney.

Mice were injected with chimeric adenovirus AdSyn-CO176 by tail vein 24 hours after the induction of the injury. The expression of luciferase was detected at the damaged kidney side 48 hours after the injection. The kidney of an infected mouse without damage gave no signal of the luciferase. In addition, uninfected mice in which damage was induced at the same time as for infected mice also gave no signal (FIG. 3A). On day 7, expression of the adenovirus in liver and spleen was silenced, but expression in the damaged kidney remained (FIG. 3B). The detection of GFP by tissue section also supported this result. Interestingly, for the mouse that didn't get the surgery, luciferase expression was limited to the liver and spleen. However, when the damage was induced at the kidney, AdSyn-CO176 infected the damaged kidney and exhibited reduced uptake by the liver. This phenomenon prompted a study to determine whether a more concentrated signal could be obtained if more virus is injected. Therefore, a second experiment was performed in which mice received a 10-fold higher dose of AdSyn-CO176 than mice received for the prior study. IRI surgery was performed on the left kidney of the mice to induce IRI damage. Forty-eight hours post-surgery, the higher dose of AdSyn-CO176 was injected into the mice by tail vein injection. IVIS™ imaging was performed 48 hours post-injection. Both kidneys were then separated and sectioned to observe GFP signal (FIG. 4A). An IVIS™ image of the mice showed that expression of AdSyn-CO176 concentrated at the damaged kidney, with reduced accumulation in the liver and spleen (FIG. 4B). Sections from normal kidney showed no GFP signal. The sections from IRI damaged kidney showed a strong GFP signal, indicating that AdSyn-CO176 is specifically expressed at the site of damaged tissue. Collectively, these findings reveal that a synthetic adenovirus, having a chimeric Ad5 shaft/Ad34 knob fiber, has the ability to infect the IRI kidney specifically.

Example 5: Wild-Type Ad34 does not Exhibit Tropism to Wound Sites

Figure 5A:
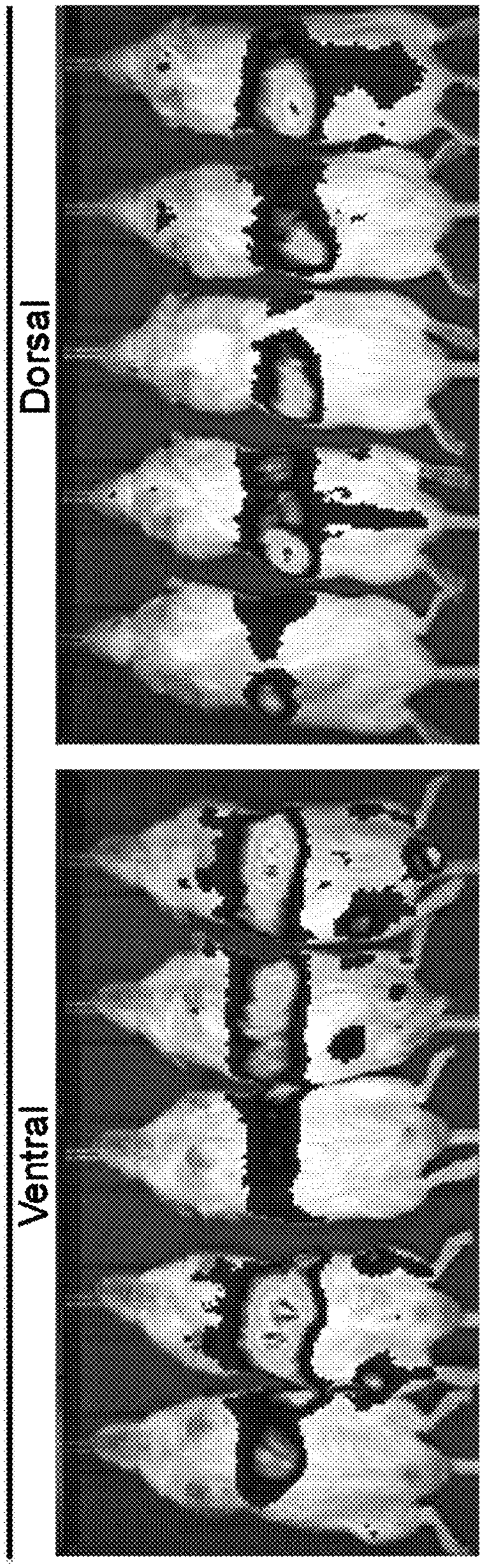
FIGS. 5A-5C: Wild-type Ad34 does not exhibit tropism to wound sites. Synthetic virus AdSyn-CO721 was generated by replacing the genes of the E1 region of wild-type Ad34 with the reporter EF1α-[luc-GFP]-miR122. FVB/NJ mice were injected by tail vein with AdSyn-CO171 (FIG. 5A), AdSyn-CO176 (FIG. 5B) or AdSyn-CO721 (FIG. 5C). Both ears of the mice were clipped at the same time as virus injection. IVIS™ imaging was performed at 48 hours post injection. The exposure time was 1 minute.
Figure 5B:
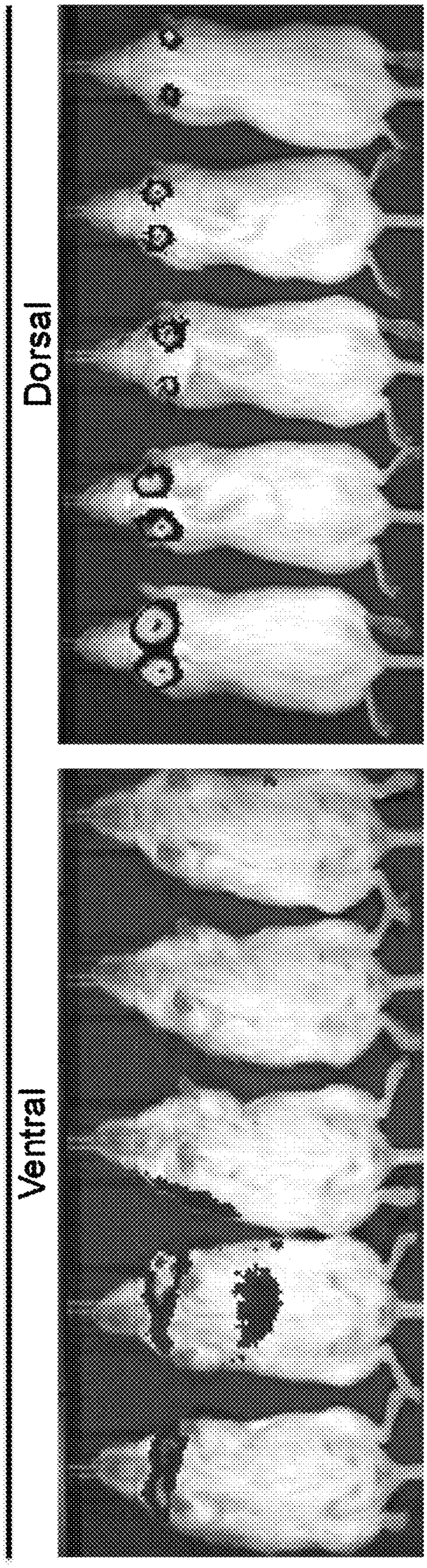
Figure 5C:
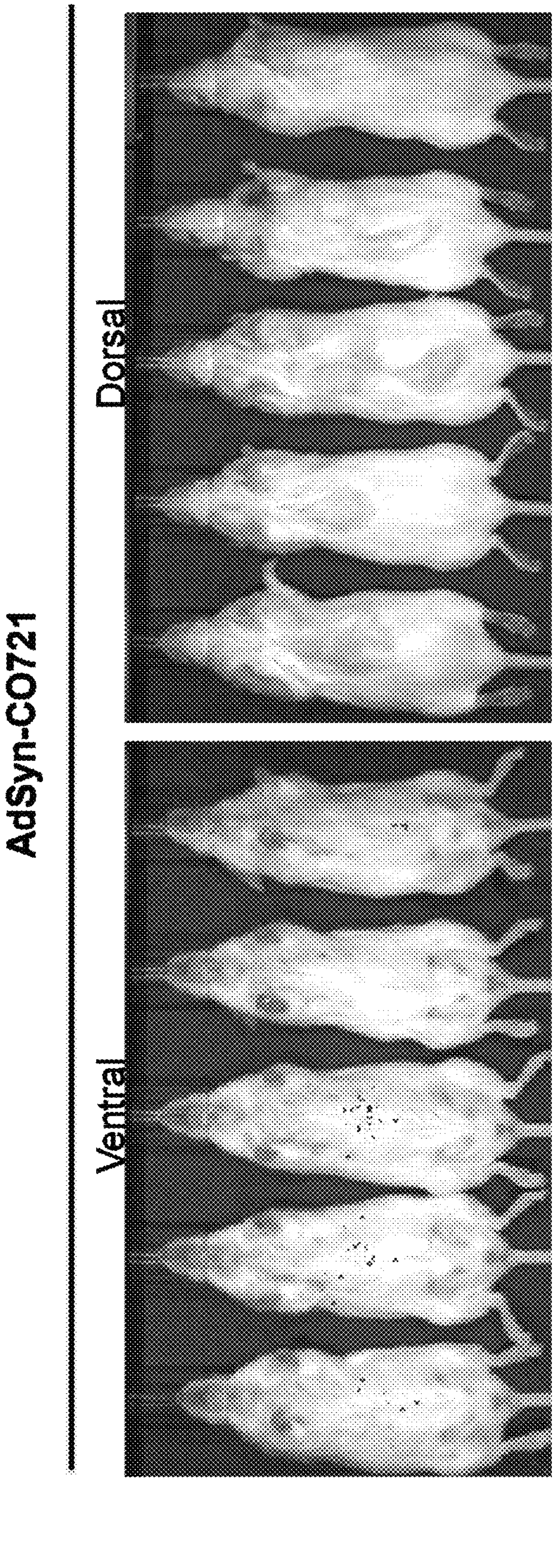

The Examples above demonstrated that a synthetic adenovirus comprising the knob domain of Ad34 was capable of homing to sites of wounded tissue. To evaluate whether wild-type Ad34 also is capable of tracking to the wound, a synthetic reporter virus based on wild-type Ad34 was engineered. AdSyn-CO721 was generated by replacing the genes of the E1 region of wild-type Ad34 with the reporter EF1α-[luc-GFP]-miR122. AdSyn-CO721 contains no other modifications. FVB/NJ mice were injected by tail vein with AdSyn-CO171, AdSyn-CO176 or AdSyn-CO721. Both ears of the mice were clipped at the same time as virus injection. IVIS™ imaging was performed at 48 hours post injection. The results are shown in FIGS. 5A-5C. As expected, AdSyn-CO176 infected the wound sites, while AdSyn-CO171 did not. The Ad34 virus (AdSyn-CO721) gave no specific luciferase signal following intravenous injection, which is consistent with the published literature. These results demonstrated that wild-type Ad34 does not exhibit tropism to wounded tissue.

Example 6: Synthetic Adenovirus Encoding PDGF-β in a Renal Ischemia-Reperfusion Injury (IRI) Model The renal ischemia-reperfusion injury (IRI) model was used as an example to determine whether synthetic adenovirus that specifically homes to damaged tissue could deliver a wound healing factor to promote tissue repair. Platelet-derived growth factor-β (PDGF-β) was selected as the wound healing factor because this growth factor has been previously reported to be important in the wound healing process in other models of tissue damage. It has also been previously disclosed that a synthetic adenovirus encoding PDGF-β was capable of healing damaged ear tissue when injected directly into an ischemic rabbit ear (Liechty et al., *J Invest Dermatol* 113:375-383, 1999). However, this virus is not capable of specifically infecting wound sites after systemic administration and was thus injected directly into the injured tissue. As disclosed in the Examples above, synthetic adenovirus AdSyn-CO176 is capable of specifically infecting sites of tissue injury and can thus be used to target damaged tissue following intravenous administration.

For the following study, two additional synthetic adenoviruses were generated:

(1) AdSyn-CO876 is a modified version of AdSyn-CO171 (which is a liver detargeted vector that does not target wounded tissues) that expresses PDGF-β; and (2) AdSyn-CO877 (SEQ ID NO: 10) is a modified version of AdSyn-CO176 (which is a liver detargeted vectors that transduces s wounded tissues) that expresses PDGF-β.

Figure 7A:
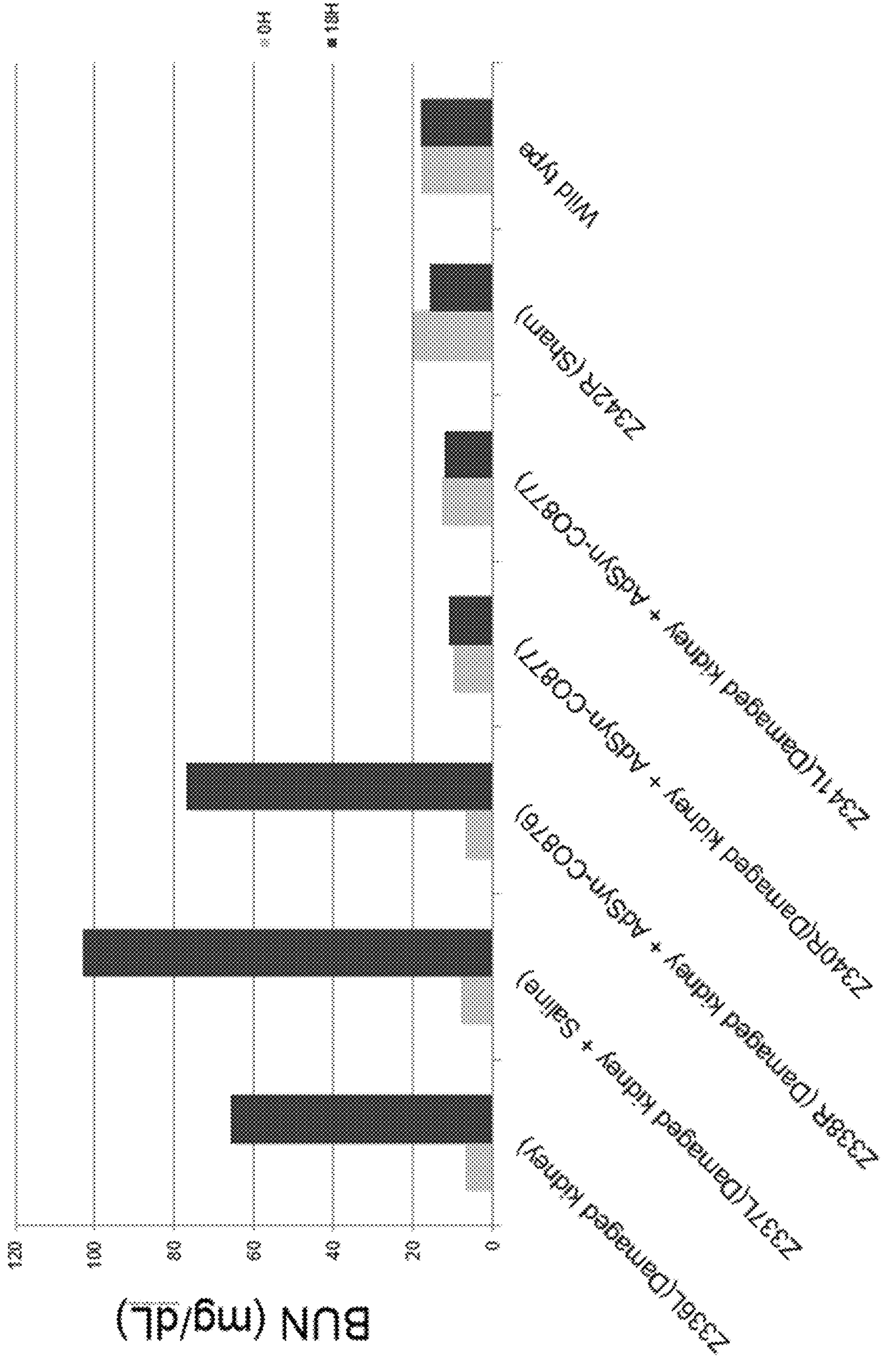
FIGS. 7A-7B: Administration of a wound-targeting synthetic adenovirus encoding PDFG-β promotes recovery from kidney damage in an ischemia-reperfusion injury (IRI) mouse model. Ischemia-reperfusion injury was induced in both kidneys by clamping the renal pedicles for 30 minutes. Mice were then immediately injected intravenously via the tail vein with 200 μl saline (Z337L), $10^9$ particles of non-wound targeting virus AdSyn-CO876 (Z338R) or $10^9$ particles of wound-targeting virus AdSyn-CO877 (Z340R and Z341L). Controls included a mouse with induced kidney damage that received no injection (Z336L), a sham-operated mouse (same surgical procedure except the clamp was not applied) that received no injection (Z342R), and a mouse with no kidney damage that did not receive an injection (Wild type). Blood was collected at the time of injection (0 h) and after 18 hours to measure blood urea nitrogen (BUN.
Figure 7B:
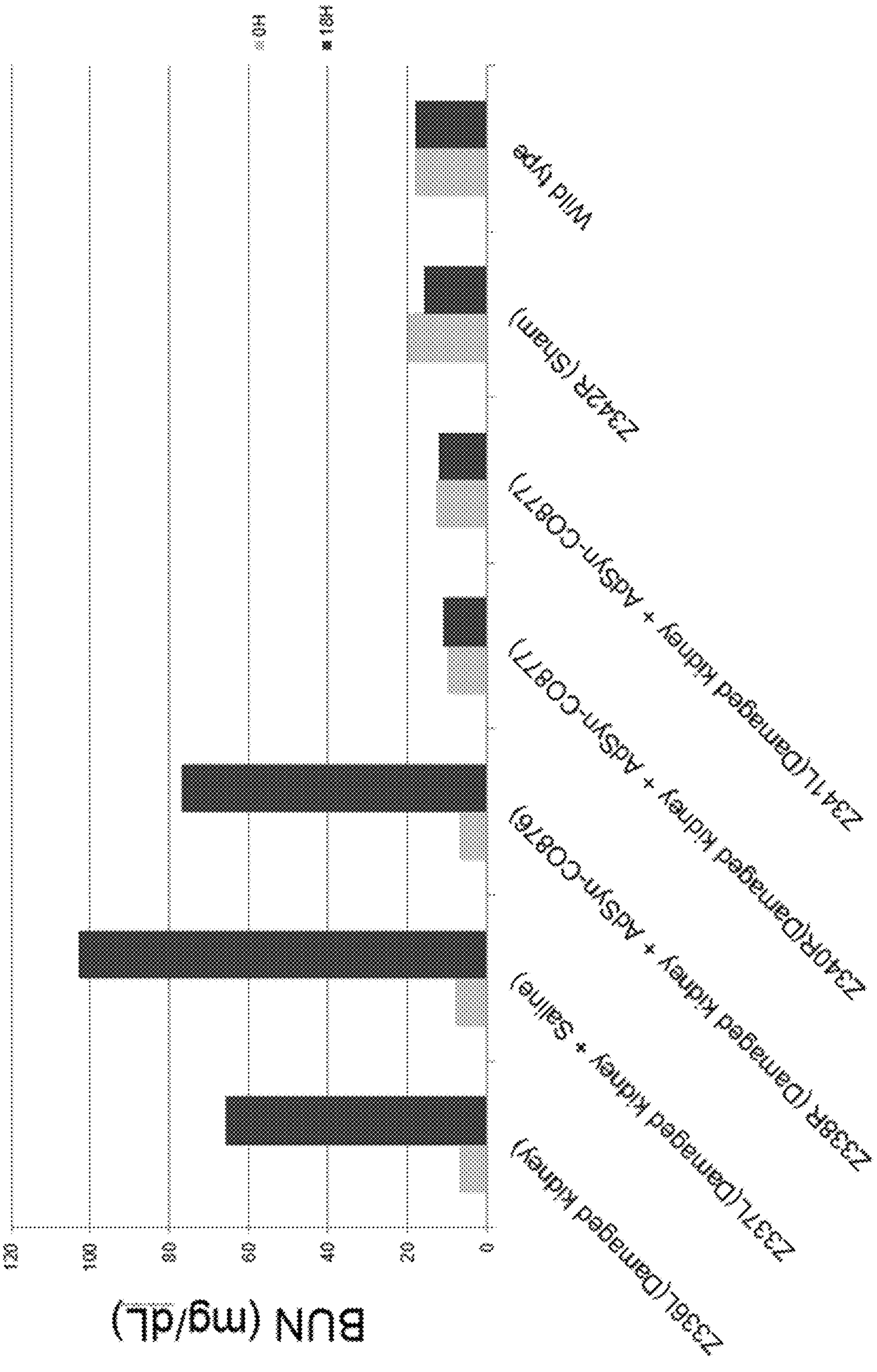

To evaluate these viruses in the renal IRI model, ischemia-reperfusion injury was induced in both kidneys by clamping the renal pedicles for 30 minutes. Mice were then immediately injected intravenously via the tail vein with 200 μl saline, $10^9$ virus particles of AdSyn-CO876 or $10^9$ virus particles of AdSyn-CO877. Controls included a mouse with induced kidney damage that received no injection, a sham-operated mouse (same surgical procedure except the clamp was not applied) that received no infection, and a mouse with no kidney damage that did not receive an injection. Blood was collected at the time of injection (0 h) and after 18 hours to measure blood urea nitrogen (BUN) and creatinine. The results are shown in FIG. 7A (BUN) and FIG. 7B (creatinine).

IRI mice that did not receive any therapeutic treatment showed elevated BUN and creatinine levels, consistent with the induction of kidney damage. Treatment of IRI mice with AdSyn-CO876 did not reduce serum BUN and creatinine levels. This is consistent with the fact that a liver detargeted Ad5 vector with a wild-type Ad5 shaft (based on AdSyn-CO171) is unable to home to damaged tissue. In contrast, treatment of IRI mice with AdSyn-CO877 led to a significant reduction in serum BUN and creatinine levels. This demonstrates that AdSyn-CO877 (based on AdSyn-CO176) can home to damaged tissue and deliver a wound repair factor capable of healing the damaged kidney.

These results demonstrate that liver detargeted, synthetic adenoviruses expressing a chimeric Ad34 knob/Ad5 shaft fiber protein (such as AdSyn-CO176 or AdSyn-CO877) can be used as therapeutic viruses for the treatment of damaged or wounded tissues.

Example 7: Synthetic Adenovirus Encoding PDGF-β in a Scratch Wound Model

Fibroblasts are critical in supporting normal wound healing involved in key processes, such as breaking down the fibrin clot, creating new extra cellular matrix (ECM), supporting other cells associated with effective wound healing, and contracting the wound. In order to test whether AdSyn-CO877 could accelerate the wound healing process in vitro, a Scratch Wound assay was performed with human fibroblast cells using the INCUCYTE™ Cell Migration Kit (Essen Bioscience). This system allows for the analysis of the therapeutic effects of different agents on the migration and/or invasion potential of the cell type being assayed.

To perform this study, human fetal lung fibroblasts (IMR-90) were plated in 96-well ImageLock plates (Essen Bioscience) and cultured for 18 hours to nearly 100% confluence. The INCUCYTE™ 96-pin WoundMaker was then used to create a scratch wound in each well of the 96-well plate. Cells were then either left untreated or were immediately infected with AdSyn-CO877 at an MOI of 1. The INCUCYTE™ Cell Migration Analysis software module was used to assess cell migration and wound healing according to the following metrics:

Wound Confluence (%): A report of the confluence of cells within the wound region, given as the percentage of the wound region area occupied by cells.

Relative Wound Density (%): Relies on measuring the spatial cell density in the wound area relative to the spatial cell density outside of the wound area at every time point.

Figure 6A:
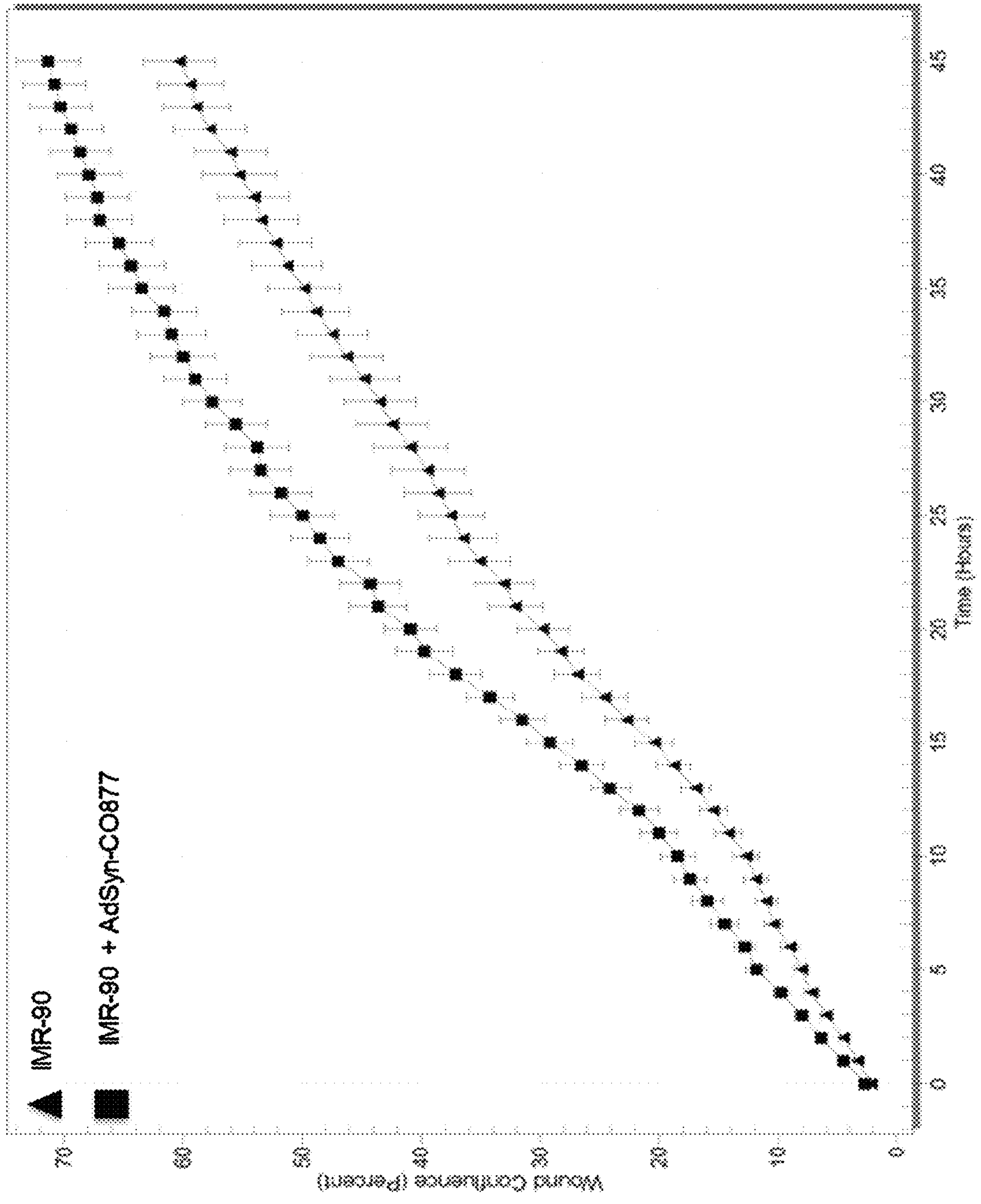
FIGS. 6A-6B: Synthetic adenovirus encoding PDFG-β promotes wound healing in a scratch wound model. Human fetal lung fibroblasts (IMR-90) were plated in 96-well plates and cultured for 18 hours to nearly 100% confluence. The INCUCYTE™ 96-pin WoundMaker was used to create a scratch wound in each well of the 96-well plate. Cells were either left untreated or were immediately infected with AdSyn-CO877 (expressing PDFG-β) at an MOI of 1. Cell migration and wound healing were evaluated by measuring wound confluence (FIG. 6A) and relative wound density (FIG. 6B).
Figure 6B:
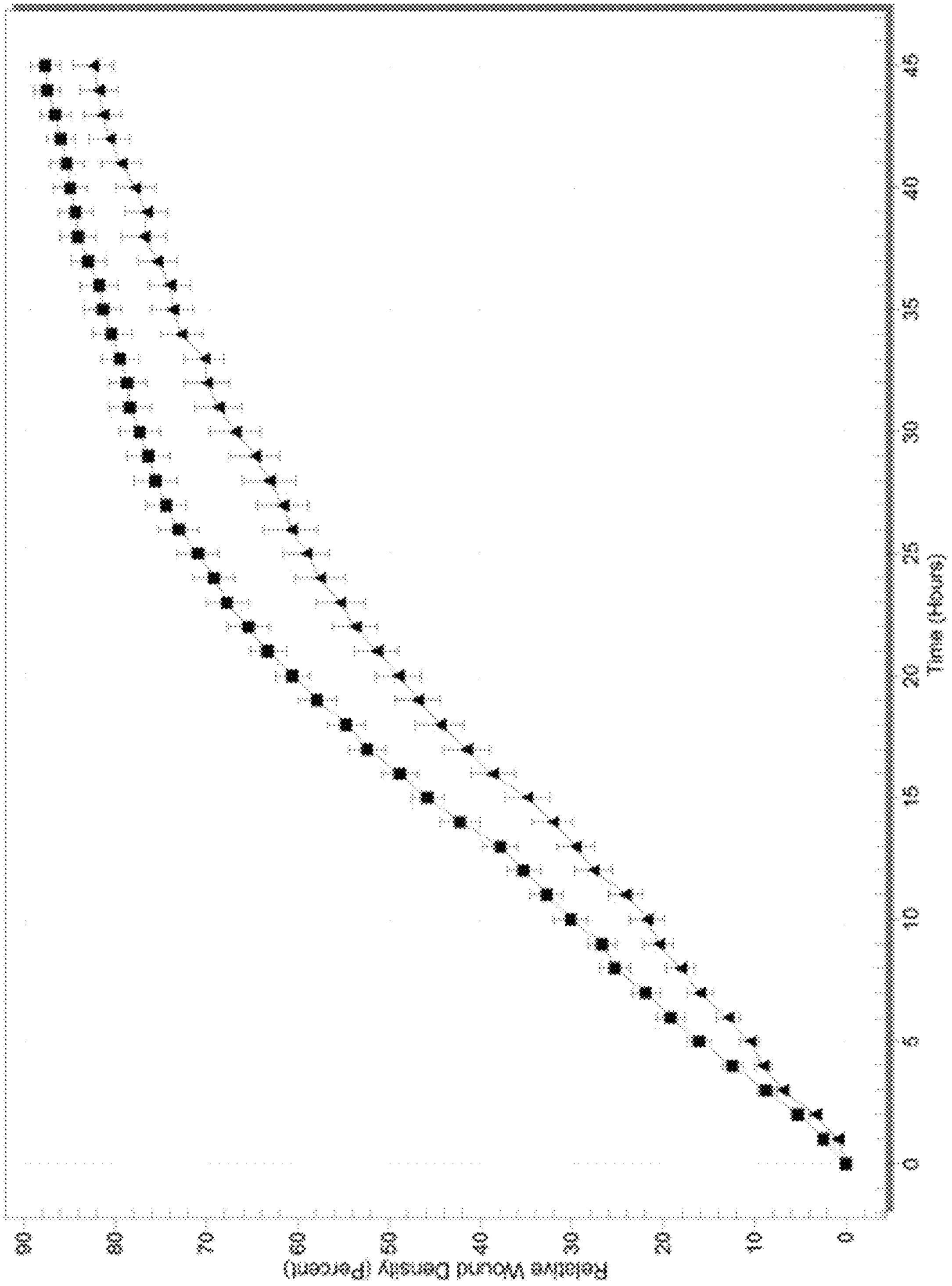

FIG. 6A and FIG. 6B show wound confluence and relative wound density, respectively, of scratch wounded IMR-90 cells left untreated or infected with AdSyn-CO877. The results demonstrate that cultures infected with AdSyn-CO877 (encoding the wound healing factor PDGF-3) heal more quickly than untreated cultures.

Figure 8A:
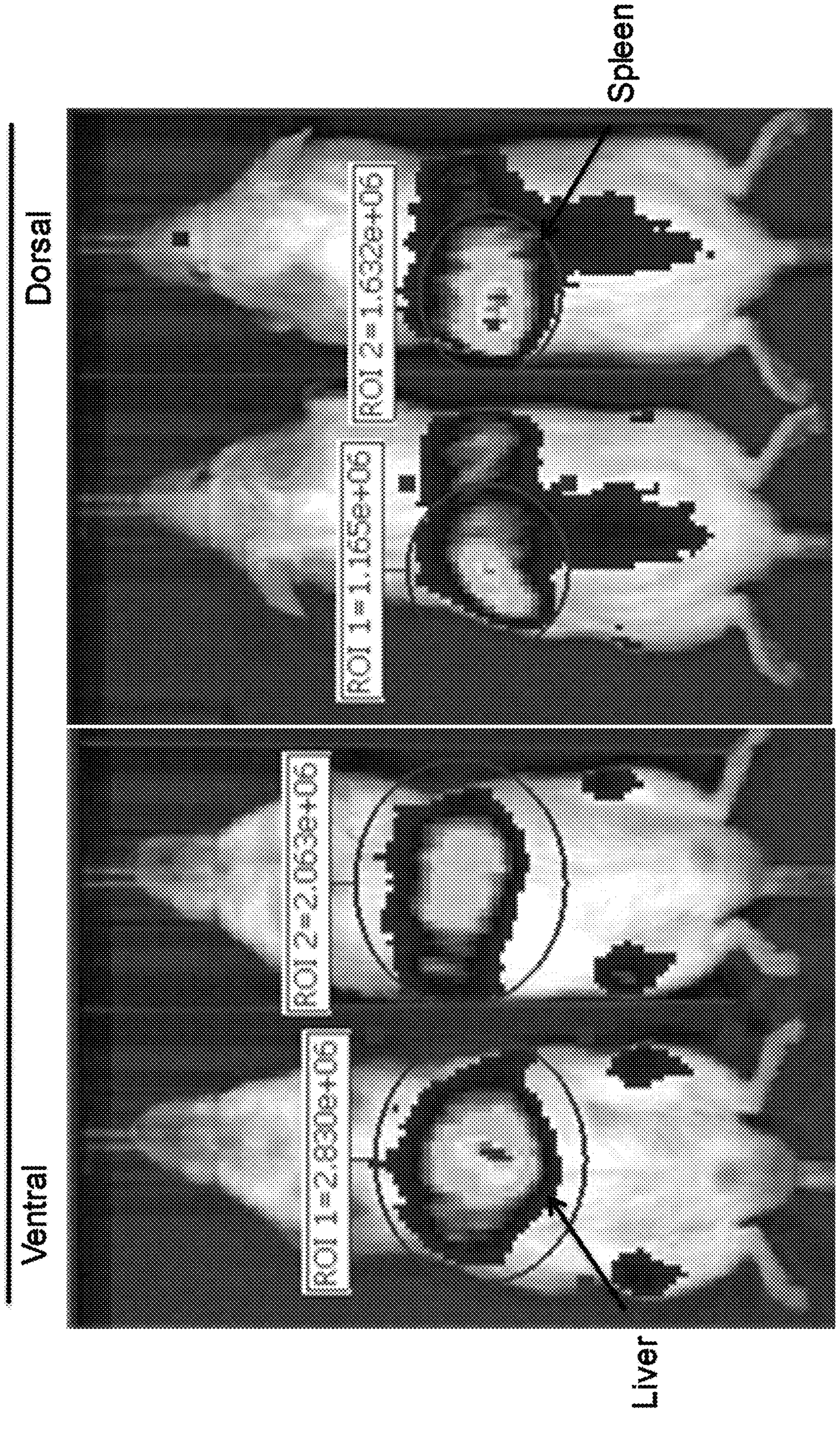
FIGS. 8A-8C: Spleen-specific miR142-3p silences virus expression in the spleen. A synthetic virus (AdSyn-CO338) containing four miR142-3p binding sites in the 3' UTR of E1A was generated to test whether miR142-3p can silence virus expression in the spleen. AdSyn-CO171 (ΔE1-EF1α-[luc-GFP]-miR122, hexon E451Q), AdSyn-CO338 (ΔE1-EF1α-[luc-GFP]-miR142-3p, hexon E451Q, ΔE3A/E3B) and AdSyn-CO339 (ΔE1-EF1α-[luc-GFP], hexon E451Q, ΔE3A/E3B) were injected into the tail vein of mice and luciferase expression was detected after 48 hours by IVIS™ imaging. The exposure time was 1 minute.
Figure 8B:
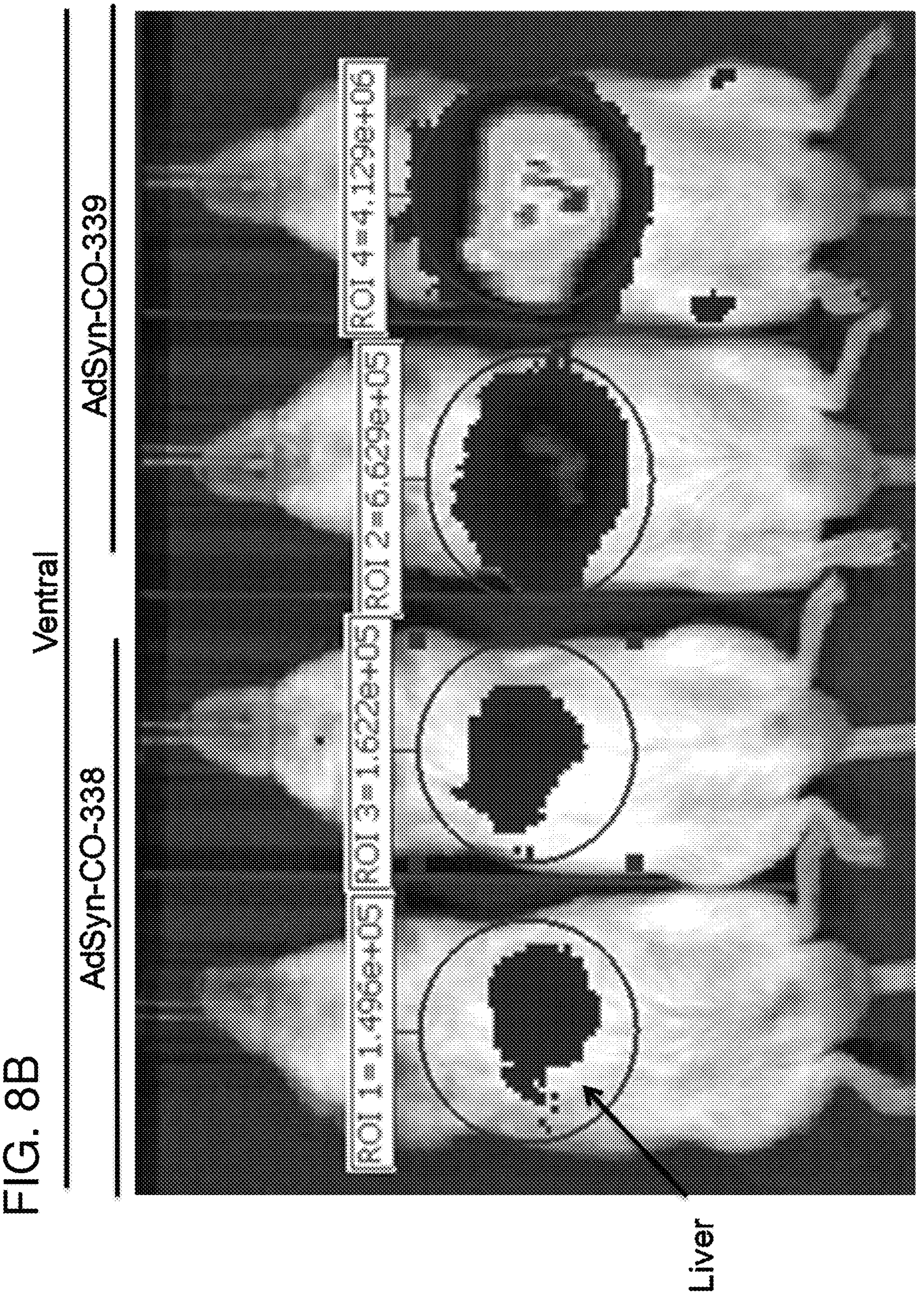
Figure 8C:
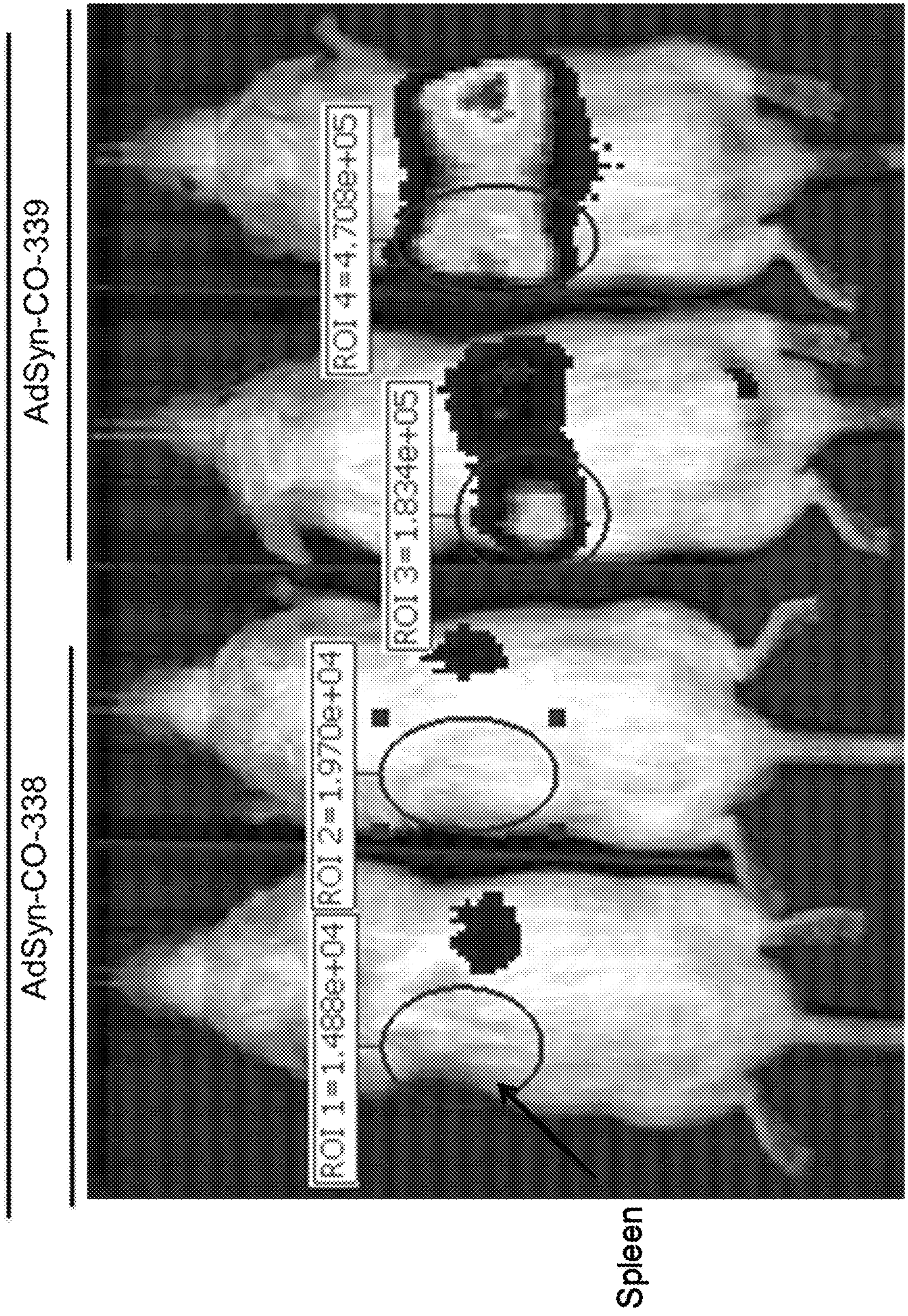

Example 8: Spleen-Specific miR142-3p Silences Virus Expression in the Spleen A synthetic virus (AdSyn-CO338) containing four miR142-3p binding sites in the 3' UTR of E1A was generated to test whether miR142-3p can silence virus expression in the spleen. AdSyn-CO171 (ΔE1-EF1α-[Luc-GFP]-miR122, hexon E451Q; SEQ ID NO: 1), AdSyn-CO338 (ΔE1-EF1α-[luc-GFP]-miR142-3p, hexon E451Q, ΔE3A/E3B; SEQ ID NO: 11) and AdSyn-CO339 (ΔE1-EF1α-[luc-GFP], hexon E451Q, ΔE3A/E3B) were injected into the tail vein of mice and luciferase expression was detected after 48 hours by IVIS™ imaging. The results are shown in FIGS. 8A-8C. In mice injected with AdSyn-CO171, significant luciferase signal was detected in both the liver and spleen (FIG. 8A). Luciferase signal was also detected in the liver of mice injected with either AdSyn-CO338 or AdSyn-CO339 (FIG. 8B). However, luciferase signal in the spleen of mice injected with AdSyn-CO338 was at least 10-fold lower than in mice injected with AdSyn-CO339 or AdSyn-CO171 (FIG. 8C). These results demonstrate that miR142-3p can silence virus expression in the spleen. Luciferase expression in the liver of mice injected with AdSyn-CO338 was also lower than either AdSyn-CO339 or AdSyn-CO171, indicating that miR14203p also has some effect on reducing virus expression in the liver.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

The invention claimed is:

1. A method of promoting wound repair or tissue regeneration in a subject, comprising administering to the subject a synthetic adenovirus comprising:

a transgene encoding platelet-derived growth factor-β (PDGF-β), transforming growth factor (TGF)-β1, or TGF-β2;

a modified hexon protein comprising an E451Q mutation, numbered with reference to SEQ ID NO: 8; and a chimeric fiber protein comprising an adenovirus type 5 (Ad5) shaft domain and an adenovirus type 34 (Ad34) knob domain.

2. The method of claim 1, further comprising selecting a subject with a wound or damaged tissue.

3. The method of claim 2, wherein:

the wound is a cutaneous wound; or the damaged tissue is kidney, heart, liver or lung tissue.

4. The method of claim 1, wherein the synthetic adenovirus further comprises one or more binding sites for a liver-specific microRNA.

5. The method of claim 4, wherein the liver-specific microRNA is miR-122.

6. The method of claim 4, wherein the one or more binding sites are in the 3'UTR of the adenovirus E1 region.

7. The method of claim 1, wherein the transgene encodes PDGF-β.

8. The method of claim 1, wherein the synthetic adenovirus further comprises a deletion of the E1 region.

9. A method of promoting wound repair or tissue regeneration in a subject, comprising administering to the subject a synthetic adenovirus comprising:

a transgene encoding platelet-derived growth factor-β (PDGF-β);

a modified hexon protein comprising an E451Q mutation, numbered with reference to SEQ ID NO: 8;

a deletion of the E1 region;

one or more binding sites for liver-specific microRNA (miR)-122; and a chimeric fiber protein comprising an adenovirus type 5 (Ad5) shaft domain and an adenovirus type 34 (Ad34) knob domain.

10. The method of claim 9, wherein the synthetic adenovirus further comprises a reporter gene.

11. The method of claim 1, wherein the synthetic adenovirus further comprises a reporter gene.

* * * * *

SEQUENCE LISTING

```
<160> NUMBER OF SEQ ID NOS: 11

<210> SEQ ID NO 1
<211> LENGTH: 36913
<212> TYPE: DNA
<213> ORGANISM: Artificial Sequence
<220> FEATURE:
<223> OTHER INFORMATION: Synthetic adenovirus construct (AdSyn-CO171)

<400> SEQUENCE: 1

catcatcaat aatatacctt attttggatt gaagccaata tgataatgag ggggtggagt      60

ttgtgacgtg gcgcggggcg tgggaacggg gcgggtgacg tagtagtgtg gcggaagtgt     120

gatgttgcaa gtgtggcgga acacatgtaa gcgacggatg tggcaaaagt gacgtttttg     180

gtgtgcgccg gtgtacacag gaagtgacaa ttttcgcgcg gttttaggcg gatgttgtag     240

taaatttggg cgtaaccgag taagatttgg ccattttcgc gggaaaactg aataagagga     300

agtgaaatct gaataatttt gtgttactca tagcgcgtaa tatttgtcta gggccgcggg     360

gactttgacc gtttacgtgg agactcgccc aggtgttttt ctcaggtgtt ttccgcgttc     420

cgggtcaaag ttggcgtttt attattaaac cgtattaccg ccatgcattt aatggagtgc     480

ctcgtgaggc tccggtgccc gtcagtgggc agagcgcaca tcgcccacag tccccgagaa     540

gttgggggga ggggtcggca attgaaccgg tgcctagaga aggtggcgcg gggtaaactg     600

ggaaagtgat gtcgtgtact ggctccgcct ttttcccgag ggtgggggag aaccgtatat     660

aagtgcagta gtcgccgtga acgttctttt tcgcaacggg tttgccgcca gaacacaggt     720

aagtgccgtg tgtggttccc gcgggcctgg cctctttacg ggttatggcc cttgcgtgcc     780

ttgaattact tccacctggc tgcagtacgt gattcttgat cccgagcttc gggttggaag     840

tgggtgggag agttcgaggc cttgcgctta aggagcccct tcgcctcgtg cttgagttga     900

ggcctggcct gggcgctggg gccgccgcgt gcgaatctgg tggcaccttc gcgcctgtct     960
```

-continued

```
cgctgctttc gataagtctc tagccattta aaatttttga tgacctgctg cgacgctttt   1020
tttctggcaa gatagtcttg taaatgcggg ccaagatctg cacactggta tttcggtttt   1080
tggggccgcg ggcggcgacg gggcccgtgc gtcccagcgc acatgttcgg cgaggcgggg   1140
cctgcgagcg cggccaccga gaatcggacg ggggtagtct caagctggcc ggcctgctct   1200
ggtgcctggc ctcgcgccgc cgtgtatcgc cccgccctgg gcggcaaggc tggcccggtc   1260
ggcaccagtt gcgtgagcgg aaagatggcc gcttcccggc cctgctgcag ggagctcaaa   1320
atggaggacg cggcgctcgg gagagcgggc gggtgagtca cccacacaaa ggaaaagggc   1380
ctttccgtcc tcagccgtcg cttcatgtga ctccacggag taccgggcgc cgtccaggca   1440
cctcgattag ttctcgagct tttggagtac gtcgtcttta ggttgggggg aggggtttta   1500
tgcgatggag tttccccaca ctgagtgggt ggagactgaa gttaggccag cttggcactt   1560
gatgtaattc tccttggaat ttgccctttt tgagtttgga tcttggttca ttctcaagcc   1620
tcagacagtg gttcaaagtt tttttcttcc atttcaggtg tcgtgacgct agcgctaccg   1680
gactcagatc tcgagctcaa gcttcgaatt ctgcagtcga cggtaccgga tccatggaag   1740
acgccaaaaa cataaagaaa ggcccggcgc cattctatcc gctggaagat ggaaccgctg   1800
gagagcaact gcataaggct atgaagagat acgccctggt tcctggaaca attgctttta   1860
cagatgcaca tatcgaggtg gacatcactt acgctgagta cttcgaaatg tccgttcggt   1920
tggcagaagc tatgaaacga tatgggctga atacaaatca cagaatcgtc gtatgcagtg   1980
aaaactctct tcaattcttt atgccggtgt tgggcgcgtt atttatcgga gttgcagttg   2040
cgcccgcgaa cgacatttat aatgaacgtg aattgctcaa cagtatgggc atttcgcagc   2100
ctaccgtggt gttcgtttcc aaaaaggggt tgcaaaaaat tttgaacgtg caaaaaaagc   2160
tcccaatcat ccaaaaaatt attatcatgg attctaaaac ggattaccag ggatttcagt   2220
cgatgtacac gttcgtcaca tctcatctac ctcccggttt taatgaatac gattttgtgc   2280
cagagtcctt cgatagggac aagacaattg cactgatcat gaactcctct ggatctactg   2340
gtctgcctaa aggtgtcgct ctgcctcata gaactgcctg cgtgagattc tcgcatgcca   2400
gagatcctat ttttggcaat caaatcattc cggatactgc gattttaagt gttgttccat   2460
tccatcacgg ttttggaatg tttactacac tcggatattt gatatgtgga tttcgagtcg   2520
tcttaatgta tagatttgaa gaagagctgt ttctgaggag ccttcaggat tacaagattc   2580
aaagtgcgct gctggtgcca accctattct ccttcttcgc caaaagcact ctgattgaca   2640
aatacgattt atctaattta cacgaaattg cttctggtgg cgctcccctc tctaaggaag   2700
tcggggaagc ggttgccaag aggttccatc tgccaggtat caggcaagga tatgggctca   2760
ctgagactac atcagctatt ctgattacac ccgaggggga tgataaaccg ggcgcggtcg   2820
gtaaagttgt tccatttttt gaagcgaagg ttgtggatct ggataccggg aaaacgctgg   2880
gcgttaatca aagaggcgaa ctgtgtgtga gaggtcctat gattatgtcc ggttatgtaa   2940
acaatccgga agcgaccaac gccttgattg acaaggatgg atggctacat tctggagaca   3000
tagcttactg ggacgaagac gaacacttct tcatcgttga ccgcctgaag tctctgatta   3060
agtacaaagg ctatcaggtg gctcccgctg aattggaatc catcttgctc caacacccca   3120
acatcttcga cgcaggtgtc gcaggtcttc ccgacgatga cgccggtgaa cttcccgccg   3180
ccgttgttgt tttggagcac ggaaagacga tgacggaaaa agagatcgtg gattacgtcg   3240
ccagtcaagt aacaaccgcg aaaaagttgc gcggaggagt tgtgtttgtg gacgaagtac   3300
```

-continued

```
cgaaaggtct taccggaaaa ctcgacgcaa gaaaaatcag agagatcctc ataaaggcca   3360
agaagggcgg aaagatcgcc gtggcagccg cagccaccat ggtgagcaag ggcgaggagc   3420
tgttcaccgg ggtggtgccc atcctggtcg agctggacgg cgacgtaaac ggccacaagt   3480
tcagcgtgtc cggcgagggc gagggcgatg ccacctacgg caagctgacc ctgaagttca   3540
tctgcaccac cggcaagctg cccgtgccct ggcccaccct cgtgaccacc ctgacctacg   3600
gcgtgcagtg cttcagccgc taccccgacc acatgaagca gcacgacttc ttcaagtccg   3660
ccatgcccga aggctacgtc caggagcgca ccatcttctt caaggacgac ggcaactaca   3720
agacccgcgc cgaggtgaag ttcgagggcg acaccctggt gaaccgcatc gagctgaagg   3780
gcatcgactt caaggaggac ggcaacatcc tggggcacaa gctggagtac aactacaaca   3840
gccacaacgt ctatatcatg gccgacaagc agaagaacgg catcaaggtg aacttcaaga   3900
tccgccacaa catcgaggac ggcagcgtgc agctcgccga ccactaccag cagaacaccc   3960
ccatcggcga cggccccgtg ctgctgcccg acaaccacta cctgagcacc cagtccgccc   4020
tgagcaaaga ccccaacgag aagcgcgatc acatggtcct gctggagttc gtgaccgccg   4080
ccgggatcac tctcggcatg gacgagctgt acaagtaaag cgactctaga tcataatcag   4140
ccataccaa acaccattgt cacactccaa tcgattcaaa caccattgtc acactccaac   4200
atttgtagag gttttacttg ctttaaaaaa cctcccacac ctccccctga acctgaaaca   4260
taaaatgaat gcaattgttg ttgttaactt gtttattgca gcttataatg gttacaaata   4320
aagcaatagc atcacaaatt tcacaaataa agcatttttt tcactgcatt ctagttgtgg   4380
tttgtccaaa ctcatcaatg taagtttaaa cggcgcgcct gaaatgtgtg ggcgtggctt   4440
aagggtggga aagaatatat aaggtggggg tcttatgtag ttttgtatct gttttgcagc   4500
agccgccgcc gccatgagca ccaactcgtt tgatggaagc attgtgagct catatttgac   4560
aacgcgcatg cccccatggg ccggggtgcg tcagaatgtg atgggctcca gcattgatgg   4620
tcgccccgtc ctgcccgcaa actctactac cttgacctac gagaccgtgt ctggaacgcc   4680
gttggagact gcagcctccg ccgccgcttc agccgctgca gccaccgccc gcgggattgt   4740
gactgacttt gctttcctga gcccgcttgc aagcagtgca gcttcccgtt catccgcccg   4800
cgatgacaag ttgacggctc ttttggcaca attggattct ttgacccggg aacttaatgt   4860
cgtttctcag cagctgttgg atctgcgcca gcaggtttct gccctgaagg cttcctcccc   4920
tcccaatgcg gtttaaaaca caacttttct atacaaagtt gtaaataaaa aaccagactc   4980
tgtttggatt tggatcaagc taagtgtctt gctgtcttta tttaggggtt ttgcgcgcgc   5040
ggtaggcccg ggaccagcgg tctcggtcgt tgagggtcct gtgtattttt tccaggacgt   5100
ggtaaaggtg actctggatg ttcagataca tgggcataag cccgtctctg gggtggaggt   5160
agcaccactg cagagcttca tgctgcgggg tggtgttgta gatgatccag tcgtagcagg   5220
agcgctgggc gtggtgccta aaaatgtctt tcagtagcaa gctgattgcc aggggcaggc   5280
ccttggtgta agtgtttaca aagcggttaa gctgggatgg gtgcatacgt ggggatatga   5340
gatgcatctt ggactgtatt tttaggttgg ctatgttccc agccatatcc ctccggggat   5400
tcatgttgtg cagaaccacc agcacagtgt atccggtgca cttgggaaat ttgtcatgta   5460
gcttagaagg aaatgcgtgg aagaacttgg agacgccctt gtgacctcca agattttcca   5520
tgcattcgtc cataatgatg gcaatgggcc cacgggcggc ggcctgggcg aagatatttc   5580
tgggatcact aacgtcatag ttgtgttcca ggatgagatc gtcataggcc atttttacaa   5640
agcgcgggcg gagggtgcca gactgcggta taatggttcc atccggccca ggggcgtagt   5700
```

-continued

```
taccctcaca gatttgcatt tcccacgctt tgagttcaga tggggggatc atgtctacct   5760
gcggggcgat gaagaaaacg gtttccgggg taggggagat cagctgggaa gaaagcaggt   5820
tcctgagcag ctgcgactta ccgcagccgg tgggcccgta aatcacacct attaccggct   5880
gcaactggta gttaagagag ctgcagctgc cgtcatccct gagcaggggg gccacttcgt   5940
taagcatgtc cctgactcgc atgttttccc tgaccaaatc cgccagaagg cgctcgccgc   6000
ccagcgatag cagttcttgc aaggaagcaa agtttttcaa cggtttgaga ccgtccgccg   6060
taggcatgct tttgagcgtt tgaccaagca gttccaggcg gtcccacagc tcggtcacct   6120
gctctacggc atctcgatcc agcatatctc ctcgtttcgc gggttggggc ggctttcgct   6180
gtacggcagt agtcggtgct cgtccagacg ggccagggtc atgtctttcc acgggcgcag   6240
ggtcctcgtc agcgtagtct gggtcacggt gaaggggtgc gctccgggct gcgcgctggc   6300
cagggtgcgc ttgaggctgg tcctgctggt gctgaagcgc tgccggtctt cgccctgcgc   6360
gtcggccagg tagcatttga ccatggtgtc atagtccagc ccctccgcgg cgtggccctt   6420
ggcgcgcagc ttgcccttgg aggaggcgcc gcacgagggg cagtgcagac ttttgagggc   6480
gtagagcttg ggcgcgagaa ataccgattc cggggagtag gcatccgcgc cgcaggcccc   6540
gcagacggtc tcgcattcca cgagccaggt gagctctggc cgttcggggt caaaaaccag   6600
gtttccccca tgctttttga tgcgtttctt acctctggtt tccatgagcc ggtgtccacg   6660
ctcggtgacg aaaaggctgt ccgtgtcccc gtatacagac ttgagaggcc tgtcctcgag   6720
cggtgttccg cggtcctcct cgtatagaaa ctcggaccac tctgagacaa aggctcgcgt   6780
ccaggccagc acgaaggagg ctaagtggga ggggtagcgg tcgttgtcca ctagggggtc   6840
cactcgctcc agggtgtgaa gacacatgtc gccctcttcg gcatcaagga aggtgattgg   6900
tttgtaggtg taggccacgt gaccgggtgt tcctgaaggg gggctataaa agggggtggg   6960
ggcgcgttcg tcctcactct cttccgcatc gctgtctgcg agggccagct gttggggtga   7020
gtactccctc tgaaaagcgg gcatgacttc tgcgctaaga ttgtcagttt ccaaaaacga   7080
ggaggatttg atattcacct ggcccgcggt gatgcctttg agggtggccg catccatctg   7140
gtcagaaaag acaatctttt tgttgtcaag cttggtggca aacgacccgt agagggcgtt   7200
ggacagcaac ttggcgatgg agcgcagggt ttggtttttg tcgcgatcgg cgcgctcctt   7260
ggccgcgatg tttagctgca cgtattcgcg cgcaacgcac cgccattcgg gaaagacggt   7320
ggtgcgctcg tcgggcacca ggtgcacgcg ccaaccgcgg ttgtgcaggg tgacaaggtc   7380
aacgctggtg gctacctctc cgcgtaggcg ctcgttggtc cagcagaggc ggccgccctt   7440
gcgcgagcag aatggcggta gggggtctag ctgcgtctcg tccgggggt  ctgcgtccac   7500
ggtaaagacc ccgggcagca ggcgcgcgtc gaagtagtct atcttgcatc cttgcaagtc   7560
tagcgcctgc tgccatgcgc gggcggcaag cgcgcgctcg tatgggttga gtgggggacc   7620
ccatggcatg gggtgggtga gcgcggaggc gtacatgccg caaatgtcgt aaacgtagag   7680
gggctctctg agtattccaa gatatgtagg gtagcatctt ccaccgcgga tgctggcgcg   7740
cacgtaatcg tatagttcgt gcgagggagc gaggaggtcg ggaccgaggt tgctacgggc   7800
gggctgctct gctcggaaga ctatctgcct gaagatggca tgtgagttgg atgatatggt   7860
tggacgctgg aagacgttga agctggcgtc tgtgagacct accgcgtcac gcacgaagga   7920
ggcgtaggag tcgcgcagct tgttgaccag ctcggcggtg acctgcacgt ctagggcgca   7980
gtagtccagg gtttccttga tgatgtcata cttatcctgt cccttttttt tccacagctc   8040
```

```
gcggttgagg acaaactctt cgcggtcttt ccagtactct tggatcggaa acccgtcggc   8100
ctccgaacgg taagagccta gcatgtagaa ctggttgacg gcctggtagg cgcagcatcc   8160
cttttctacg ggtagcgcgt atgcctgcgc ggccttccgg agcgaggtgt gggtgagcgc   8220
aaaggtgtcc ctgaccatga ctttgaggta ctggtatttg aagtcagtgt cgtcgcatcc   8280
gccctgctcc cagagcaaaa agtccgtgcg ctttttggaa cgcggatttg gcagggcgaa   8340
ggtgacatcg ttgaagagta tctttcccgc gcgaggcata aagttgcgtg tgatgcggaa   8400
gggtcccggc acctcggaac ggttgttaat tacctgggcg gcgagcacga tctcgtcaaa   8460
gccgttgatg ttgtggccca caatgtaaag ttccaagaag cgcgggatgc ccttgatgga   8520
aggcaatttt ttaagttcct cgtaggtgag ctcttcaggg gagctgagcc cgtgctctga   8580
aagggcccag tctgcaagat gagggttgga agcgacgaat gagctccaca ggtcacgggc   8640
cattagcatt tgcaggtggt cgcgaaaggt cctaaactgg cgacctatgg ccattttttc   8700
tggggtgatg cagtagaagg taagcgggtc ttgttcccag cggtcccatc caaggttcgc   8760
ggctaggtct cgcgcggcag tcactagagg ctcatctccg ccgaacttca tgaccagcat   8820
gaagggcacg agctgcttcc caaaggcccc catccaagta taggtctcta catcgtaggt   8880
gacaaagaga cgctcggtgc gaggatgcga gccgatcggg aagaactgga tctcccgcca   8940
ccaattggag gagtggctat tgatgtggtg aaagtagaag tccctgcgac gggccgaaca   9000
ctcgtgctgg cttttgtaaa aacgtgcgca gtactggcag cggtgcacgg gctgtacatc   9060
ctgcacgagg ttgacctgac gaccgcgcac aaggaagcag agtgggaatt tgagcccctc   9120
gcctggcggg tttggctggt ggtcttctac ttcggctgct tgtccttgac cgtctggctg   9180
ctcgagggga gttacggtgg atcggaccac cacgccgcgc gagcccaaag tccagatgtc   9240
cgcgcgcggc ggtcggagct tgatgacaac atcgcgcaga tgggagctgt ccatggtctg   9300
gagctcccgc ggcgtcaggt caggcgggag ctcctgcagg tttacctcgc atagacgggt   9360
cagggcgcgg gctagatcca ggtgatacct aatttccagg ggctggttgg tggcggcgtc   9420
gatggcttgc aagaggccgc atccccgcgg cgcgactacg gtaccgcgcg gcgggcggtg   9480
ggccgcgggg gtgtccttgg atgatgcatc taaaagcggt gacgcgggcg agcccccgga   9540
ggtagggggg gctccggacc cgccgggaga gggggcaggg gcacgtcggc gccgcgcgcg   9600
ggcaggagct ggtgctgcgc gcgtaggttg ctggcgaacg cgacgacgcg gcggttgatc   9660
tcctgaatct ggcgcctctg cgtgaagacg acgggcccgg tgagcttgaa cctgaaagag   9720
agttcgacag aatcaatttc ggtgtcgttg acggcggcct ggcgcaaaat ctcctgcacg   9780
tctcctgagt tgtcttgata ggcgatctcg gccatgaact gctcgatctc ttcctcctgg   9840
agatctccgc gtccggctcg ctccacggtg gcggcgaggt cgttggaaat gcgggccatg   9900
agctgcgaga aggcgttgag gcctccctcg ttccagacgc ggctgtagac cacgcccccct  9960
tcggcatcgc gggcgcgcat gaccacctgc gcgagattga gctccacgtg ccgggcgaag  10020
acggcgtagt ttcgcaggcg ctgaaagagg tagttgaggg tggtggcggt gtgttctgcc  10080
acgaagaagt acataaccca gcgtcgcaac gtggattcgt tgatatcccc caaggcctca  10140
aggcgctcca tggcctcgta gaagtccacg gcgaagttga aaaactggga gttgcgcgcc  10200
gacacggtta actcctcctc cagaagacgg atgagctcgg cgacagtgtc gcgcacctcg  10260
cgctcaaagg ctacaggggc ctcttcttct tcttcaatct cctcttccat aagggcctcc  10320
ccttcttctt cttctggcgg cggtggggga gggggacac ggcggcgacg acggcgcacc  10380
gggaggcggt cgacaaagcg ctcgatcatc tccccgcggc gacggcgcat ggtctcggtg  10440
```

```
acggcgcggc cgttctcgcg ggggcgcagt tggaagacgc cgcccgtcat gtcccggtta  10500
tgggttggcg gggggctgcc atgcggcagg gatacggcgc taacgatgca tctcaacaat  10560
tgttgtgtag gtactccgcc gccgagggac ctgagcgagt ccgcatcgac cggatcggaa  10620
aacctctcga gaaaggcgtc taaccagtca cagtcgcaag gtaggctgag caccgtggcg  10680
ggcggcagcg ggcggcggtc ggggttgttt ctggcggagg tgctgctgat gatgtaatta  10740
aagtaggcgg tcttgagacg gcggatggtc gacagaagca ccatgtcctt gggtccggcc  10800
tgctgaatgc gcaggcggtc ggccatgccc caggcttcgt tttgacatcg gcgcaggtct  10860
ttgtagtagt cttgcatgag cctttctacc ggcacttctt cttctccttc ctcttgtcct  10920
gcatctcttg catctatcgc tgcggcggcg gcggagtttg gccgtaggtg gcgccctctt  10980
cctcccatgc gtgtgacccc gaagcccctc atcggctgaa gcagggctag gtcggcgaca  11040
acgcgctcgg ctaatatggc ctgctgcacc tgcgtgaggg tagactggaa gtcatccatg  11100
tccacaaagc ggtggtatgc gcccgtgttg atggtgtaag tgcagttggc cataacggac  11160
cagttaacgg tctggtgacc cggctgcgag agctcggtgt acctgagacg cgagtaagcc  11220
ctcgagtcaa atacgtagtc gttgcaagtc cgcaccaggt actggtatcc caccaaaaag  11280
tgcggcggcg gctggcggta gaggggccag cgtagggtgg ccggggctcc gggggcgaga  11340
tcttccaaca taaggcgatg atatccgtag atgtacctgg acatccaggt gatgccggcg  11400
gcggtggtgg aggcgcgcgg aaagtcgcgg acgcggttcc agatgttgcg cagcggcaaa  11460
aagtgctcca tggtcgggac gctctggccg gtcaggcgcg cgcaatcgtt gacgctctag  11520
accgtgcaaa aggagagcct gtaagcgggc actcttccgt ggtctggtgg ataaattcgc  11580
aagggtatca tggcggacga ccggggttcg agccccgtat ccggccgtcc gccgtgatcc  11640
atgcggttac cgcccgcgtg tcgaacccag gtgtgcgacg tcagacaacg ggggagtgct  11700
ccttttggct tccttccagg cgcggcggct gctgcgctag ctttttggc cactggccgc  11760
gcgcagcgta agcggttagg ctggaaagcg aaagcattaa gtggctcgct ccctgtagcc  11820
ggagggttat tttccaaggg ttgagtcgcg ggacccccgg ttcgagtctc ggaccggccg  11880
gactgcggcg aacgggggtt tgcctccccg tcatgcaaga ccccgcttgc aaattcctcc  11940
ggaaacaggg acgagcccct tttttgcttt tcccagatgc atccggtgct gcggcagatg  12000
cgccccccctc ctcagcagcg gcaagagcaa gagcagcggc agacatgcag ggcaccctcc  12060
cctcctccta ccgcgtcagg aggggcgaca tccgcggttg acgcggcagc agatggtgat  12120
tacgaacccc cgcggcgccg ggcccggcac tacctggact tggaggaggg cgagggcctg  12180
gcgcggctag gagcgccctc tcctgagcgg cacccaaggg tgcagctgaa gcgtgatacg  12240
cgtgaggcgt acgtgccgcg gcagaacctg tttcgcgacc gcgagggaga ggagcccgag  12300
gagatgcggg atcgaaagtt ccacgcaggg cgcgagctgc ggcatggcct gaatcgcgag  12360
cggttgctgc gcgaggagga ctttgagccc gacgcgcgaa ccgggattag tcccgcgcgc  12420
gcacacgtgg cggccgccga cctggtaacc gcatacgagc agacggtgaa ccaggagatt  12480
aactttcaaa aaagctttaa caaccacgtg cgtacgcttg tggcgcgcga ggaggtggct  12540
ataggactga tgcatctgtg ggactttgta agcgcgctgg agcaaaaccc aaatagcaag  12600
ccgctcatgg cgcagctgtt ccttatagtg cagcacagca gggacaacga ggcattcagg  12660
gatgcgctgc taaacatagt agagcccgag ggccgctggc tgctcgattt gataaacatc  12720
ctgcagagca tagtggtgca ggagcgcagc ttgagcctgg ctgacaaggt ggccgccatc  12780
```

-continued

```
aactattcca tgcttagcct gggcaagttt tacgcccgca agatatacca taccccttac  12840
gttcccatag acaaggaggt aaagatcgag ggttctaca tgcgcatggc gctgaaggtg  12900
cttaccttga gcgacgacct gggcgtttat cgcaacgagc gcatccacaa ggccgtgagc  12960
gtgagccggc ggcgcgagct cagcgaccgc gagctgatgc acagcctgca aagggccctg  13020
gctggcacgg gcagcggcga tagagaggcc gagtcctact ttgacgcggg cgctgacctg  13080
cgctgggccc caagccgacg cgccctggag gcagctgggg ccggacctgg gctggcggtg  13140
gcacccgcgc gcgctggcaa cgtcggcggc gtggaggaat atgacgagga cgatgagtac  13200
gagccagagg acggcgagta ctaagcggtg atgtttctga tcagatgatg caagacgcaa  13260
cggacccggc ggtgcgggcg gcgctgcaga gccagccgtc cggccttaac tccacggacg  13320
actggcgcca ggtcatggac cgcatcatgt cgctgactgc gcgcaatcct gacgcgttcc  13380
ggcagcagcc gcaggccaac cggctctccg caattctgga agcggtggtc ccggcgcgcg  13440
caaaccccac gcacgagaag gtgctggcga tcgtaaacgc gctggccgaa aacagggcca  13500
tccggcccga cgaggccggc ctggtctacg acgcgctgct tcagcgcgtg gctcgttaca  13560
acagcggcaa cgtgcagacc aacctggacc ggctggtggg ggatgtgcgc gaggccgtgg  13620
cgcagcgtga gcgcgcgcag cagcagggca acctgggctc catggttgca ctaaacgcct  13680
tcctgagtac acagcccgcc aacgtgccgc ggggacagga ggactacacc aactttgtga  13740
gcgcactgcg gctaatggtg actgagacac cgcaaagtga ggtgtaccag tctgggccag  13800
actatttttt ccagaccagt agacaaggcc tgcagaccgt aaacctgagc caggctttca  13860
aaaacttgca ggggctgtgg ggggtgcggg ctcccacagg cgaccgcgcg accgtgtcta  13920
gcttgctgac gcccaactcg cgcctgttgc tgctgctaat agcgcccttc acggacagtg  13980
gcagcgtgtc ccgggacaca tacctaggtc acttgctgac actgtaccgc gaggccatag  14040
gtcaggcgca tgtggacgag catactttcc aggagattac aagtgtcagc cgcgcgctgg  14100
ggcaggagga cacgggcagc ctggaggcaa ccctaaacta cctgctgacc aaccggcggc  14160
agaagatccc ctcgttgcac agtttaaaca gcgaggagga gcgcattttg cgctacgtgc  14220
agcagagcgt gagccttaac ctgatgcgcg acggggtaac gcccagcgtg gcgctggaca  14280
tgaccgcgcg caacatggaa ccgggcatgt atgcctcaaa ccggccgttt atcaaccgcc  14340
taatggacta cttgcatcgc gcggccgccg tgaaccccga gtatttcacc aatgccatct  14400
tgaacccgca ctggctaccg ccccctggtt tctacaccgg gggattcgag gtgcccgagg  14460
gtaacgatgg attcctctgg gacgacatag acgacagcgt gttttccccg caaccgcaga  14520
ccctgctaga gttgcaacag cgcgagcagg cagaggcggc gctgcgaaag gaaagcttcc  14580
gcaggccaag cagcttgtcc gatctaggcg ctgcggcccc gcggtcagat gctagtagcc  14640
catttccaag cttgataggg tctcttacca gcactcgcac cacccgcccg cgcctgctgg  14700
gcgaggagga gtacctaaac aactcgctgc tgcagccgca gcgcgaaaaa aacctgcctc  14760
cggcatttcc caacaacggg atagagagcc tagtggacaa gatgagtaga tggaagacgt  14820
acgcgcagga gcacagggac gtgccaggcc cgcgcccgcc cacccgtcgt caaaggcacg  14880
accgtcagcg gggtctggtg tgggaggacg atgactcggc agacgacagc agcgtcctgg  14940
atttgggagg gagtggcaac ccgtttgcgc accttcgccc caggctgggg agaatgtttt  15000
aaaaaaaaaa aaaaagcatg atgcaaaata aaaaactcac caaggccatg gcaccgagcg  15060
ttggttttct tgtattcccc ttagtatgcg gcgcgcggcg atgtatgagg aaggtcctcc  15120
tccctcctac gagagtgtgg tgagcgcggc gccagtggcg gcggcgctgg gttctccctt  15180
```

-continued

```
cgatgctccc ctggacccgc cgtttgtgcc tccgcggtac ctgcggccta ccggggggag  15240
aaacagcatc cgttactctg agttggcacc cctattcgac accacccgtg tgtacctggt  15300
ggacaacaag tcaacggatg tggcatccct gaactaccag aacgaccaca gcaactttct  15360
gaccacggtc attcaaaaca atgactacag cccgggggag gcaagcacac agaccatcaa  15420
tcttgacgac cggtcgcact ggggcggcga cctgaaaacc atcctgcata ccaacatgcc  15480
aaatgtgaac gagttcatgt ttaccaataa gtttaaggcg cgggtgatgg tgtcgcgctt  15540
gcctactaag gacaatcagg tggagctgaa atacgagtgg gtggagttca cgctgcccga  15600
gggcaactac tccgagacca tgaccataga ccttatgaac aacgcgatcg tggagcacta  15660
cttgaaagtg ggcagacaga acggggttct ggaaagcgac atcggggtaa agtttgacac  15720
ccgcaacttc agactggggt ttgaccccgt cactggtctt gtcatgcctg ggtatatac  15780
aaacgaagcc ttccatccag acatcatttt gctgccagga tgcggggtgg acttcaccca  15840
cagccgcctg agcaacttgt tgggcatccg caagcggcaa cccttccagg agggctttag  15900
gatcacctac gatgatctgg agggtggtaa cattcccgca ctgttggatg tggacgccta  15960
ccaggcgagc ttgaaagatg acaccgaaca gggcgggggt ggcgcaggcg gcagcaacag  16020
cagtggcagc ggcgcggaag agaactccaa cgcggcagcc gcggcaatgc agccggtgga  16080
ggacatgaac gatcatgcca ttcgcggcga cacctttgcc acacgggctg aggagaagcg  16140
cgctgaggcc gaagcagcgg ccgaagctgc cgcccccgct gcgcaacccg aggtcgagaa  16200
gcctcagaag aaaccggtga tcaaacccct gacagaggac agcaagaaac gcagttacaa  16260
cctaataagc aatgacagca ccttcaccca gtaccgcagc tggtaccttg catacaacta  16320
cggcgaccct cagaccggaa tccgctcatg gaccctgctt tgcactcctg acgtaacctg  16380
cggctcggag caggtctact ggtcgttgcc agacatgatg caagaccccg tgaccttccg  16440
ctccacgcgc cagatcagca actttccggt ggtgggcgcc gagctgttgc ccgtgcactc  16500
caagagcttc tacaacgacc aggccgtcta ctcccaactc atccgccagt ttacctctct  16560
gacccacgtg ttcaatcgct ttcccgagaa ccagattttg gcgcgcccgc cagcccccac  16620
catcaccacc gtcagtgaaa acgttcctgc tctcacagat cacgggacgc taccgctgcg  16680
caacagcatc ggaggagtcc agcgagtgac cattactgac gccagacgcc gcacctgccc  16740
ctacgtttac aaggccctgg gcatagtctc gccgcgcgtc ctatcgagcc gcactttttg  16800
agcaagcatg tccatcctta tatcgcccag caataacaca ggctggggcc tgcgcttccc  16860
aagcaagatg tttggcgggg ccaagaagcg ctccgaccaa cacccagtgc gcgtgcgcgg  16920
gcactaccgc gcgccctggg gcgcgcacaa acgcggccgc actgggcgca ccaccgtcga  16980
tgacgccatc gacgcggtgg tggaggaggc gcgcaactac acgcccacgc cgccaccagt  17040
gtccacagtg gacgcggcca ttcagaccgt ggtgcgcgga gcccggcgct atgctaaaat  17100
gaagagacgg cggaggcgcg tagcacgtcg ccaccgccgc cgacccggca ctgccgccca  17160
acgcgcggcg gcggccctgc ttaaccgcgc acgtcgcacc ggccgacggg cggccatgcg  17220
ggccgctcga aggctggccg cgggtattgt cactgtgccc cccaggtcca ggcgacgagc  17280
ggccgccgca gcagccgcgg ccattagtgc tatgactcag ggtcgcaggg gcaacgtgta  17340
ttgggtgcgc gactcggtta gcggcctgcg cgtgcccgtg cgcacccgcc ccccgcgcaa  17400
ctagattgca agaaaaaact acttagactc gtactgttgt atgtatccag cggcggcggc  17460
gcgcaacgaa gctatgtcca agcgcaaaat caaagaagag atgctccagg tcatcgcgcc  17520
```

-continued

```
ggagatctat ggccccccga agaaggaaga gcaggattac aagccccgaa agctaaagcg  17580
ggtcaaaaag aaaaagaaag atgatgatga tgaacttgac gacgaggtgg aactgctgca  17640
cgctaccgcg cccaggcgac gggtacagtg gaaaggtcga cgcgtaaaac gtgttttgcg  17700
acccggcacc accgtagtct ttacgcccgg tgagcgctcc acccgcacct acaagcgcgt  17760
gtatgatgag gtgtacggcg acgaggacct gcttgagcag gccaacgagc gcctcgggga  17820
gtttgcctac ggaaagcggc ataaggacat gctggcgttg ccgctggacg agggcaaccc  17880
aacacctagc ctaaagcccg taacactgca gcaggtgctg cccgcgcttg caccgtccga  17940
agaaaagcgc ggcctaaagc gcgagtctgg tgacttggca cccaccgtgc agctgatggt  18000
acccaagcgc cagcgactgg aagatgtctt ggaaaaaatg accgtggaac ctgggctgga  18060
gcccgaggtc cgcgtgcggc caatcaagca ggtggcgccg ggactgggcg tgcagaccgt  18120
ggacgttcag atacccacta ccagtagcac cagtattgcc accgccacag agggcatgga  18180
gacacaaacg tccccggttg cctcagcggt ggcggatgcc gcggtgcagg cggtcgctgc  18240
ggccgcgtcc aagacctcta cggaggtgca aacggacccg tggatgtttc gcgtttcagc  18300
cccccggcgc ccgcgccgtt cgaggaagta cggcgccgcc agcgcgctac tgcccgaata  18360
tgccctacat ccttccattg cgcctacccc cggctatcgt ggctacacct accgccccag  18420
aagacgagca actacccgac gccgaaccac cactggaacc cgccgccgcc gtcgccgtcg  18480
ccagcccgtg ctggccccga tttccgtgcg cagggtggct cgcgaaggag gcaggaccct  18540
ggtgctgcca acagcgcgct accaccccag catcgtttaa aagccggtct ttgtggttct  18600
tgcagatatg gccctcacct gccgcctccg tttcccggtg ccgggattcc gaggaagaat  18660
gcaccgtagg aggggcatgg ccggccacgg cctgacgggc ggcatgcgtc gtgcgcacca  18720
ccggcggcgg cgcgcgtcgc accgtcgcat gcgcggcggt atcctgcccc tccttattcc  18780
actgatcgcc gcggcgattg gcgccgtgcc cggaattgca tccgtggcct tgcaggcgca  18840
gagacactga ttaaaaacaa gttgcatgtg gaaaaatcaa aataaaaagt ctggactctc  18900
acgctcgctt ggtcctgtaa ctattttgta gaatggaaga catcaacttt gcgtctctgg  18960
ccccgcgaca cggctcgcgc ccgttcatgg gaaactggca agatatcggc accagcaata  19020
tgagcggtgg cgccttcagc tggggctcgc tgtggagcgg cattaaaaat ttcggttcca  19080
ccgttaagaa ctatggcagc aaggcctgga acagcagcac aggccagatg ctgagggata  19140
agttgaaaga gcaaaatttc caacaaaagg tggtagatgg cctggcctct ggcattagcg  19200
gggtggtgga cctggccaac caggcagtgc aaaataagat taacagtaag cttgatcccc  19260
gccctcccgt agaggagcct ccaccggccg tggagacagt gtctccagag gggcgtggcg  19320
aaaagcgtcc gcgccccgac agggaagaaa ctctggtgac gcaaatagac gagcctccct  19380
cgtacgagga ggcactaaag caaggcctgc ccaccacccg tcccatcgcg cccatggcta  19440
ccggagtgct gggccagcac acacccgtaa cgctggacct gcctcccccc gccgacaccc  19500
agcagaaacc tgtgctgcca ggcccgaccg ccgttgttgt aacccgtcct agccgcgcgt  19560
ccctgcgccg cgccgccagc ggtccgcgat cgttgcggcc cgtagccagt ggcaactggc  19620
aaagcacact gaacagcatc gtgggtctgg gggtgcaatc cctgaagcgc cgacgatgct  19680
tctgaatagc taacgtgtcg tatgtgtgtc atgtatgcgt ccatgtcgcc gccagaggag  19740
ctgctgagcc gccgcgcgcc cgctttccaa gatggctacc ccttcgatga tgccgcagtg  19800
gtcttacatg cacatctcgg gccaggacgc ctcggagtac ctgagccccg ggctggtgca  19860
gtttgcccgc gccaccgaga cgtacttcag cctgaataac aagtttagaa accccacggt  19920
```

ggcgcctacg cacgacgtga ccacagaccg gtcccagcgt ttgacgctgc ggttcatccc 19980
tgtggaccgt gaggatactg cgtactcgta caaggcgcgg ttcaccctag ctgtgggtga 20040
taaccgtgtg ctggacatgg cttccacgta ctttgacatc cgcggcgtgc tggacagggg 20100
ccctactttt aagccctact ctggcactgc ctacaacgcc ctggctccca agggtgcccc 20160
aaatccttgc gaatgggatg aagctgctac tgctcttgaa ataaacctag aagaagagga 20220
cgatgacaac gaagacgaag tagacgagca agctgagcag caaaaaactc acgtatttgg 20280
gcaggcgcct tattctggta taaatattac aaaggagggt attcaaatag gtgtcgaagg 20340
tcaaacacct aaatatgccg ataaaacatt tcaacctgaa cctcaaatag gagaatctca 20400
gtggtacgaa actgaaatta atcatgcagc tgggagagtc cttaaaaaga ctaccccaat 20460
gaaaccatgt tacggttcat atgcaaaacc cacaaatgaa aatggagggc aaggcattct 20520
tgtaaagcaa caaaatggaa agctagaaag tcaagtggaa atgcaatttt tctcaactac 20580
tgaggcgacc gcaggcaatg gtgataactt gactcctaaa gtggtattgt acagtgaaga 20640
tgtagatata gaaaccccag acactcatat ttcttacatg cccactatta aggaaggtaa 20700
ctcacgagaa ctaatgggcc aacaatctat gcccaacagg cctaattaca ttgcttttag 20760
ggacaatttt attggtctaa tgtattacaa cagcacgggt aatatgggtg ttctggcggg 20820
ccaagcatcg cagttgaatg ctgttgtaga tttgcaagac agaaacacag agctttcata 20880
ccagcttttg cttgattcca ttggtgatag aaccaggtac ttttctatgt ggaatcaggc 20940
tgttgacagc tatgatccag atgttagaat tattgaaaat catggaactg aagatgaact 21000
tccaaattac tgctttccac tgggaggtgt gattaataca gagactctta ccaaggtaaa 21060
acctaaaaca ggtcaggaaa atggatggga aaaagatgct acagaatttt cagataaaaa 21120
tcaaataaga gttggaaata attttgccat ggaaatcaat ctaaatgcca acctgtggag 21180
aaatttcctg tactccaaca tagcgctgta tttgcccgac aagctaaagt acagtccttc 21240
caacgtaaaa atttctgata acccaaacac ctacgactac atgaacaagc gagtggtggc 21300
tcccgggtta gtggactgct acattaacct tggagcacgc tggtcccttg actatatgga 21360
caacgtcaac ccatttaacc accaccgcaa tgctggcctg cgctaccgct caatgttgct 21420
gggcaatggt cgctatgtgc ccttccacat ccaggtgcct cagaagttct ttgccattaa 21480
aaacctcctt ctcctgccgg gctcatacac ctacgagtgg aacttcagga aggatgttaa 21540
catggttctg cagagctccc taggaaatga cctaagggtt gacggagcca gcattaagtt 21600
tgatagcatt tgcctttacg ccaccttctt ccccatggcc cacaacaccg cctccacgct 21660
tgaggccatg cttagaaacg acaccaacga ccagtccttt aacgactatc tctccgccgc 21720
caacatgctc taccctatac ccgccaacgc taccaacgtg cccatatcca tcccctcccg 21780
caactgggcg gctttccgcg gctgggcctt cacgcgcctt aagactaagg aaaccccatc 21840
actgggctcg ggctacgacc cttattacac ctactctggc tctataccct acctagatgg 21900
aacctttttac ctcaaccaca cctttaagaa ggtggccatt acctttgact cttctgtcag 21960
ctggcctggc aatgaccgcc tgcttacccc caacgagttt gaaattaagc gctcagttga 22020
cggggagggt tacaacgttg cccagtgtaa catgaccaaa gactggttcc tggtacaaat 22080
gctagctaac tacaacattg gctaccaggg cttctatatc ccagagagct acaaggaccg 22140
catgtactcc ttctttagaa acttccagcc catgagccgt caggtggtgg atgatactaa 22200
atacaaggac taccaacagg tgggcatcct acaccaacac aacaactctg gatttgttgg 22260

-continued

```
ctaccttgcc cccaccatgc gcgaaggaca ggcctaccct gctaacttcc cctatccgct  22320
tataggcaag accgcagttg acagcattac ccagaaaaag tttctttgcg atcgcaccct  22380
ttggcgcatc ccattctcca gtaactttat gtccatgggc gcactcacag acctgggcca  22440
aaaccttctc tacgccaact ccgcccacgc gctagacatg acttttgagg tggatcccat  22500
ggacgagccc acccttcttt atgttttgtt tgaagtcttt gacgtggtcc gtgtgcaccg  22560
gccgcaccgc ggcgtcatcg aaaccgtgta cctgcgcacg cccttctcgg ccggcaacgc  22620
cacaacataa agaagcaagc aacatcaaca acagctgccg ccatgggctc cagtgagcag  22680
gaactgaaag ccattgtcaa agatcttggt tgtgggccat attttttggg cacctatgac  22740
aagcgctttc caggctttgt ttctccacac aagctcgcct gcgccatagt caatacggcc  22800
ggtcgcgaga ctgggggcgt acactggatg gcctttgcct ggaacccgca ctcaaaaaca  22860
tgctacctct ttgagccctt tggcttttct gaccagcgac tcaagcaggt ttaccagttt  22920
gagtacgagt cactcctgcg ccgtagcgcc attgcttctt cccccgaccg ctgtataacg  22980
ctggaaaagt ccacccaaag cgtacagggg cccaactcgg ccgcctgtgg actattctgc  23040
tgcatgtttc tccacgcctt tgccaactgg ccccaaactc ccatggatca caaccccacc  23100
atgaacctta ttaccggggt acccaactcc atgctcaaca gtccccaggt acagcccacc  23160
ctgcgtcgca accaggaaca gctctacagc ttcctggagc gccactcgcc ctacttccgc  23220
agccacagtg cgcagattag gagcgccact tctttttgtc acttgaaaaa catgtaaaaa  23280
taatgtacta gagacacttt caataaaggc aaatgctttt atttgtacac tctcgggtga  23340
ttatttaccc ccacccttgc cgtctgcgcc gtttaaaaat caaaggggtt ctgccgcgca  23400
tcgctatgcg ccactggcag ggacacgttg cgatactggt gtttagtgct ccacttaaac  23460
tcaggcacaa ccatccgcgg cagctcggtg aagttttcac tccacaggct gcgcaccatc  23520
accaacgcgt ttagcaggtc gggcgccgat atcttgaagt cgcagttggg gcctccgccc  23580
tgcgcgcgcg agttgcgata cacagggttg cagcactgga acactatcag cgccgggtgg  23640
tgcacgctgg ccagcacgct cttgtcggag atcagatccg cgtccaggtc ctccgcgttg  23700
ctcagggcga acggagtcaa ctttggtagc tgccttccca aaaagggcgc gtgcccaggc  23760
tttgagttgc actcgcaccg tagtggcatc aaaaggtgac cgtgcccggt ctgggcgtta  23820
ggatacagcg cctgcataaa agccttgatc tgcttaaaag ccacctgagc ctttgcgcct  23880
tcagagaaga acatgccgca agacttgccg gaaaactgat tggccggaca ggccgcgtcg  23940
tgcacgcagc accttgcgtc ggtgttggag atctgcacca catttcggcc ccaccggttc  24000
ttcacgatct tggccttgct agactgctcc ttcagcgcgc gctgcccgtt ttcgctcgtc  24060
acatccattt caatcacgtg ctccttattt atcataatgc ttccgtgtag acacttaagc  24120
tcgccttcga tctcagcgca gcggtgcagc cacaacgcgc agcccgtggg ctcgtgatgc  24180
ttgtaggtca cctctgcaaa cgactgcagg tacgcctgca ggaatcgccc catcatcgtc  24240
acaaaggtct tgttgctggt gaaggtcagc tgcaacccgc ggtgctcctc gttcagccag  24300
gtcttgcata cggccgccag agcttccact tggtcaggca gtagtttgaa gttcgccttt  24360
agatcgttat ccacgtggta cttgtccatc agcgcgcgcg cagcctccat gcccttctcc  24420
cacgcagaca cgatcggcac actcagcggg ttcatcaccg taatttcact ttccgcttcg  24480
ctgggctctt cctcttcctc ttgcgtccgc ataccacgcg ccactgggtc gtcttcattc  24540
agccgccgca ctgtgcgctt acctcctttg ccatgcttga ttagcaccgg tgggttgctg  24600
aaacccacca tttgtagcgc cacatcttct ctttcttcct cgctgtccac gattacctct  24660
```

```
ggtgatggcg ggcgctcggg cttgggagaa gggcgcttct ttttcttctt gggcgcaatg  24720
gccaaatccg ccgccgaggt cgatggccgc gggctgggtg tgcgcggcac cagcgcgtct  24780
tgtgatgagt cttcctcgtc ctcggactcg atacgccgcc tcatccgctt ttttgggggc  24840
gcccggggag gcggcggcga cggggacggg gacgacacgt cctccatggt tgggggacgt  24900
cgcgccgcac cgcgtccgcg ctcgggggtg gtttcgcgct gctcctcttc ccgactggcc  24960
atttccttct cctataggca gaaaaagatc atggagtcag tcgagaagaa ggacagccta  25020
accgcccccct ctgagttcgc caccaccgcc tccaccgatg ccgccaacgc gcctaccacc  25080
ttccccgtcg aggcaccccc gcttgaggag gaggaagtga ttatcgagca ggacccaggt  25140
tttgtaagcg aagacgacga ggaccgctca gtaccaacag aggataaaaa gcaagaccag  25200
gacaacgcag aggcaaacga ggaacaagtc gggcgggggg acgaaaggca tggcgactac  25260
ctagatgtgg gagacgacgt gctgttgaag catctgcagc gccagtgcgc cattatctgc  25320
gacgcgttgc aagagcgcag cgatgtgccc ctcgccatag cggatgtcag ccttgcctac  25380
gaacgccacc tattctcacc gcgcgtaccc cccaaacgcc aagaaaacgg cacatgcgag  25440
cccaacccgc gcctcaactt ctaccccgta tttgccgtgc cagaggtgct tgccacctat  25500
cacatctttt tccaaaactg caagataccc ctatcctgcc gtgccaaccg cagccgagcg  25560
gacaagcagc tggccttgcg gcagggcgct gtcatacctg atatcgcctc gctcaacgaa  25620
gtgccaaaaa tctttgaggg tcttggacgc gacgagaagc gcgcggcaaa cgctctgcaa  25680
caggaaaaca gcgaaaatga aagtcactct ggagtgttgg tggaactcga gggtgacaac  25740
gcgcgcctag ccgtactaaa acgcagcatc gaggtcaccc actttgccta cccggcactt  25800
aacctacccc ccaaggtcat gagcacagtc atgagtgagc tgatcgtgcg ccgtgcgcag  25860
cccctggaga gggatgcaaa tttgcaagaa caaacagagg agggcctacc cgcagttggc  25920
gacgagcagc tagcgcgctg gcttcaaacg cgcgagcctg ccgacttgga ggagcgacgc  25980
aaactaatga tggccgcagt gctcgttacc gtggagcttg agtgcatgca gcggttcttt  26040
gctgacccgg agatgcagcg caagctagag gaaacattgc actacacctt tcgacagggc  26100
tacgtacgcc aggcctgcaa gatctccaac gtggagctct gcaacctggt ctcctacctt  26160
ggaattttgc acgaaaaccg ccttgggcaa aacgtgcttc attccacgct caagggcgag  26220
gcgcgccgcg actacgtccg cgactgcgtt tacttatttc tatgctacac ctggcagacg  26280
gccatgggcg tttggcagca gtgcttggag gagtgcaacc tcaaggagct gcagaaactg  26340
ctaaagcaaa acttgaagga cctatggacg gccttcaacg agcgctccgt ggccgcgcac  26400
ctggcggaca tcattttccc cgaacgcctg cttaaaaccc tgcaacaggg tctgccagac  26460
ttcaccagtc aaagcatgtt gcagaacttt aggaacttta tcctagagcg ctcaggaatc  26520
ttgcccgcca cctgctgtgc acttcctagc gactttgtgc ccattaagta ccgcgaatgc  26580
cctccgccgc tttggggcca ctgctacctt ctgcagctag ccaactacct tgcctaccac  26640
tctgacataa tggaagacgt gagcggtgac ggtctactgg agtgtcactg tcgctgcaac  26700
ctatgcaccc cgcaccgctc cctggtttgc aattcgcagc tgcttaacga aagtcaaatt  26760
atcggtacct ttgagctgca gggtccctcg cctgacgaaa agtccgcggc tccggggttg  26820
aaactcactc cggggctgtg gacgtcggct taccttcgca aatttgtacc tgaggactac  26880
cacgcccacg agattaggtt ctacgaagac caatcccgcc cgccaaatgc ggagcttacc  26940
gcctgcgtca ttacccaggg ccacattctt ggccaattgc aagccatcaa caaagcccgc  27000
```

```
caagagtttc tgctacgaaa gggacggggg gtttacttgg acccccagtc cggcgaggag  27060
ctcaacccaa tccccccgcc gccgcagccc tatcagcagc agccgcgggc ccttgcttcc  27120
caggatggca cccaaaaaga agctgcagct gccgccgcca cccacggacg aggaggaata  27180
ctgggacagt caggcagagg aggttttgga cgaggaggag gaggacatga tggaagactg  27240
ggagagccta gacgaggaag cttccgaggt cgaagaggtg tcagacgaaa caccgtcacc  27300
ctcggtcgca ttcccctcgc cggcgcccca gaaatcggca accggttcca gcatggctac  27360
aacctccgct cctcaggcgc cgccggcact gcccgttcgc cgacccaacc gtagatggga  27420
caccactgga accagggccg gtaagtccaa gcagccgccg ccgttagccc aagagcaaca  27480
acagcgccaa ggctaccgct catggcgcgg gcacaagaac gccatagttg cttgcttgca  27540
agactgtggg ggcaacatct ccttcgcccg ccgctttctt ctctaccatc acggcgtggc  27600
cttcccccgt aacatcctgc attactaccg tcatctctac agcccatact gcaccggcgg  27660
cagcggcagc ggcagcaaca gcagcggcca cacagaagca aaggcgaccg gatagcaaga  27720
ctctgacaaa gcccaagaaa tccacagcgg cggcagcagc aggaggagga gcgctgcgtc  27780
tggcgcccaa cgaacccgta tcgacccgcg agcttagaaa caggattttt cccactctgt  27840
atgctatatt tcaacagagc aggggccaag aacaagagct gaaaataaaa aacaggtctc  27900
tgcgatccct cacccgcagc tgcctgtatc acaaaagcga agatcagctt cggcgcacgc  27960
tggaagacgc ggaggctctc ttcagtaaat actgcgcgct gactcttaag gactagtttc  28020
gcgccctttc tcaaatttaa gcgcgaaaac tacgtcatct ccagcggcca cacccggcgc  28080
cagcacctgt cgtcagcgcc atttcaactt tgtatacaaa agttgtgatg agcaaggaaa  28140
ttcccacgcc ctacatgtgg agttaccagc cacaaatggg acttgcggct ggagctgccc  28200
aagactactc aacccgaata aactacatga gcgcgggacc ccacatgata tcccgggtca  28260
acggaatacg cgcccaccga aaccgaattc tcctggaaca ggcggctatt accaccacac  28320
ctcgtaataa ccttaatccc cgtagttggc ccgctgccct ggtgtaccag gaaagtcccg  28380
ctcccaccac tgtggtactt cccagagacg cccaggccga agttcagatg actaactcag  28440
gggcgcagct tgcgggcggc tttcgtcaca gggtgcggtc gcccgggcag ggtataactc  28500
acctgacaat cagagggcga ggtattcagc tcaacgacga gtcggtgagc tcctcgcttg  28560
gtctccgtcc ggacgggaca tttcagatcg gcggcgccgg ccgctcttca ttcacgcctc  28620
gtcaggcaat cctaactctg cagacctcgt cctctgagcc gcgctctgga ggcattggaa  28680
ctctgcaatt tattgaggag tttgtgccat cggtctactt taacccctte tcgggacctc  28740
ccggccacta tccggatcaa tttattccta actttgacgc ggtaaaggac tcggcggacg  28800
gctacgactg aatgttaagt ggagaggcag agcaactgcg cctgaaacac ctggtccact  28860
gtcgccgcca caagtgcttt gcccgcgact ccggtgagtt ttgctacttt gaattgcccg  28920
aggatcatat cgagggcccg gcgcacggcg tccggcttac cgcccaggga gagcttgccc  28980
gtagcctgat tcgggagttt acccagcgcc ccctgctagt tgagcgggac aggggaccct  29040
gtgttctcac tgtgatttgc aactgtccta accctggatt acatcaagat ctttgttgcc  29100
atctctgtgc tgagtataat aaatacagaa attaaaatat actggggctc ctatcgccat  29160
cctgtaaacg ccaccgtctt cacccgccca agcaaaccaa ggcgaacctt acctggtact  29220
tttaacatct ctccctctgt gatttacaac agtttcaacc cagacggagt gagtctacga  29280
gagaacctct ccgagctcag ctactccatc agaaaaaaca ccaccctcct tacctgccgg  29340
gaacgtacga gtgcgtcacc ggccgctgca ccacacctac cgcctgaccg taaaccagac  29400
```

```
tttttccgga cagacctcaa taactctgtt taccagaaca ggaggtgagc ttagaaaacc  29460
cttagggtat taggccaaag gcgcagctac tgtggggttt atgaacaatt caagcaactc  29520
tacgggctat tctaattcag gtttctctag aatcggggtt ggggttattc tctgtcttgt  29580
gattctcttt attcttatac taacgcttct ctgcctaagg ctcgccgcct gctgtgtgca  29640
catttgcatt tattgtcagc tttttaaacg ctggggtcgc cacccaagat gattaggtac  29700
ataatcctag gtttactcac ccttgcgtca gcccacggta ccacccaaaa ggtggatttt  29760
aaggagccag cctgtaatgt tacattcgca gctgaagcta atgagtgcac cactcttata  29820
aaatgcacca cagaacatga aaagctgctt attcgccaca aaaacaaaat tggcaagtat  29880
gctgtttatg ctatttggca gccaggtgac actacagagt ataatgttac agttttccag  29940
ggtaaaagtc ataaaacttt tatgtatact tttccatttt atgaaatgtg cgacattacc  30000
atgtacatga gcaaacagta taagttgtgg cccccacaaa attgtgtgga aaacactggc  30060
actttctgct gcactgctat gctaattaca gtgctcgctt tggtctgtac cctactctat  30120
attaaataca aaagcagacg cagctttatt gaggaaaaga aaatgcctta atttactaag  30180
ttacaaagct aatgtcacca ctaactgctt tactcgctgc ttgcaaaaca aattcaaaaa  30240
gttagcatta taattagaat aggatttaaa ccccccggtc atttcctgct caataccatt  30300
cccctgaaca attgactcta tgtgggatat gctccagcgc tacaaccttg aagtcaggct  30360
tcctggatgt cagcatctga ctttggccag cacctgtccc gcggatttgt tccagtccaa  30420
ctacagcgac ccaccctaac agagatgacc aacacaacca acgcggccgc cgctaccgga  30480
cttacatcta ccacaaatac accccaagtt tctgcctttg tcaataactg ggataacttg  30540
ggcatgtggt ggttctccat agcgcttatg tttgtatgcc ttattattat gtggctcatc  30600
tgctgcctaa agcgcaaacg cgcccgacca cccatctata gtcccatcat tgtgctacac  30660
ccaaacaatg atggaatcca tagattggac ggactgaaac acatgttctt ttctcttaca  30720
gtatgattaa atgagacatg attcctcgag tttttatatt actgaccctt gttgcgcttt  30780
tttgtgcgtg ctccacattg gctgcggttt ctcacatcga agtagactgc attccagcct  30840
tcacagtcta tttgctttac ggatttgtca ccctcacgct catctgcagc ctcatcactg  30900
tggtcatcgc ctttatccag tgcattgact gggtctgtgt gcgctttgca tatctcagac  30960
accatcccca gtacagggac aggactatag ctgagcttct tagaattctt taattatgaa  31020
atttactgtg acttttctgc tgattatttg caccctatct gcgttttgtt ccccgacctc  31080
caagcctcaa agacatatat catgcagatt cactcgtata tggaatattc caagttgcta  31140
caatgaaaaa agcgatcttt ccgaagcctg gttatatgca atcatctctg ttatggtgtt  31200
ctgcagtacc atcttagccc tagctatata tccctacctt gacattggct ggaacgcaat  31260
agatgccatg aaccacccaa ctttccccgc gcccgctatg cttccactgc aacaagttgt  31320
tgccggcggc tttgtcccag ccaatcagcc tcgcccacct tctcccaccc ccactgaaat  31380
cagctacttt aatctaacag gaggagatga ctgacaccct agatctagaa atggacggaa  31440
ttattacaga gcagcgcctg ctagaaagac gcagggcagc ggccgagcaa cagcgcatga  31500
atcaagagct ccaagacatg gttaacttgc accagtgcaa aaggggtatc ttttgtctgg  31560
taaagcaggc caaagtcacc tacgacagta ataccaccgg acaccgcctt agctacaagt  31620
tgccaaccaa gcgtcagaaa ttggtggtca tggtgggaga aaagcccatt accataactc  31680
agcactcggt agaaaccgaa ggctgcattc actcaccttg tcaaggacct gaggatctct  31740
```

-continued gcacccttat taagaccctg tgcggtctca aagatcttat tccctttaac taataaaaaa 31800
aaataataaa gcatcactta cttaaaatca gttagcaaat ttctgtccag tttattcagc 31860
agcacctcct tgccctcctc ccagctctgg tattgcagct tcctcctggc tgcaaacttt 31920
ctccacaatc taaatggaat gtcagtttcc tcctgttcct gtccatccgc acccactatc 31980
ttcatgttgt tgcagatgaa gcgcgcaaga ccgtctgaag ataccttcaa ccccgtgtat 32040
ccatatgaca cggaaaccgg tcctccaact gtgccttttc ttactcctcc ctttgtatcc 32100
cccaatgggt ttcaagagag tcccccctggg gtactctctt tgcgcctatc cgaacctcta 32160
gttacctcca atggcatgct tgcgctcaaa atgggcaacg gcctctctct ggacgaggcc 32220
ggcaacctta cctcccaaaa tgtaaccact gtgagcccac ctctcaaaaa aaccaagtca 32280
aacataaacc tggaaatatc tgcacccctc acagttacct cagaagccct aactgtggct 32340
gccgccgcac ctctaatggt cgcgggcaac acactcacca tgcaatcaca ggccccgcta 32400
accgtgcacg actccaaact tagcattgcc acccaaggac ccctcacagt gtcagaagga 32460
aagctagccc tgcaaacatc aggcccccctc accaccaccg atagcagtac ccttactatc 32520
actgcctcac cccctctaac tactgccact ggtagcttgg gcattgactt gaaagagccc 32580
atttatacac aaaatggaaa actaggacta aagtacgggg ctcctttgca tgtaacagac 32640
gacctaaaca ctttgaccgt agcaactggt ccaggtgtga ctattaataa tacttccttg 32700
caaactaaag ttactggagc cttgggtttt gattcacaag gcaatatgca acttaatgta 32760
gcaggaggac taaggattga ttctcaaaac agacgcctta tacttgatgt tagttatccg 32820
tttgatgctc aaaaccaact aaatctaaga ctaggacagg gccctctttt tataaactca 32880
gcccacaact tggatattaa ctacaacaaa ggcctttact tgtttacagc ttcaaacaat 32940
tccaaaaagc ttgaggttaa cctaagcact gccaaggggt tgatgtttga cgctacagcc 33000
atagccatta atgcaggaga tggcttgaa tttggttcac ctaatgcacc aaacacaaat 33060
cccctcaaaa caaaaattgg ccatggccta gaatttgatt caaacaaggc tatggttcct 33120
aaactaggaa ctggccttag ttttgacagc acaggtgcca ttacagtagg aaacaaaaat 33180
aatgataagc taactttgtg gaccacacca gctccatctc ctaactgtag actaaatgca 33240
gagaaagatg ctaaactcac tttggtctta acaaaatgtg gcagtcaaat acttgctaca 33300
gtttcagttt tggctgttaa aggcagtttg gctccaatat ctggaacagt tcaaagtgct 33360
catcttatta taagatttga cgaaaatgga gtgctactaa acaattcctt cctggaccca 33420
gaatattgga actttagaaa tggagatctt actgaaggca cagcctatac aaacgctgtt 33480
ggatttatgc ctaacctatc agcttatcca aaatctcacg gtaaaactgc caaaagtaac 33540
attgtcagtc aagtttactt aaacggagac aaaactaaac ctgtaacact aaccattaca 33600
ctaaacggta cacaggaaac aggagacaca actccaagtg catactctat gtcattttca 33660
tgggactggt ctggccacaa ctacattaat gaaatatttg ccacatcctc ttacactttt 33720
tcatacattg cccaagaata aagaatcgtt tgtgttatgt ttcaacgtgt ttatttttca 33780
attgcagaaa atttcaagtc atttttcatt cagtagtata gccccaccac cacatagctt 33840
atacagatca ccgtacctca actttgtata ataaagttgt aatcaaactc acagaaccct 33900
agtattcaac ctgccacctc cctcccaaca cacagagtac acagtccttt ctccccggct 33960
ggccttaaaa agcatcatat catgggtaac agacatattc ttaggtgtta tattccacac 34020
ggtttcctgt cgagccaaac gctcatcagt gatattaata aactccccgg gcagctcact 34080
taagttcatg tcgctgtcca gctgctgagc cacaggctgc tgtccaactt gcggttgctt 34140

-continued

```
aacgggcggc gaaggagaag tccacgccta catgggggta gagtcataat cgtgcatcag  34200
gatagggcgg tggtgctgca gcagcgcgcg aataaactgc tgccgccgcc gctccgtcct  34260
gcaggaatac aacatggcag tggtctcctc agcgatgatt cgcaccgccc gcagcataag  34320
gcgccttgtc ctccgggcac agcagcgcac cctgatctca cttaaatcag cacagtaact  34380
gcagcacagc accacaatat tgttcaaaat cccacagtgc aaggcgctgt atccaaagct  34440
catggcgggg accacagaac ccacgtggcc atcataccac aagcgcaggt agattaagtg  34500
gcgacccctc ataaacacgc tggacataaa cattacctct tttggcatgt tgtaattcac  34560
cacctcccgg taccatataa acctctgatt aaacatggcg ccatccacca ccatcctaaa  34620
ccagctggcc aaaacctgcc cgccggctat acactgcagg gaaccgggac tggaacaatg  34680
acagtggaga gcccaggact cgtaaccatg gatcatcatg ctcgtcatga tatcaatgtt  34740
ggcacaacac aggcacacgt gcatacactt cctcaggatt acaagctcct cccgcgttag  34800
aaccatatcc cagggaacaa cccattcctg aatcagcgta aatcccacac tgcagggaag  34860
acctcgcacg taactcacgt tgtgcattgt caaagtgtta cattcgggca gcagcggatg  34920
atcctccagt atggtagcgc gggtttctgt ctcaaaagga ggtagacgat ccctactgta  34980
cggagtgcgc cgagacaacc gagatcgtgt tggtcgtagt gtcatgccaa atggaacgcc  35040
ggacgtagtc atatttcctg aagcaaaacc aggtgcgggc gtgacaaaca gatctgcgtc  35100
tccggtctcg ccgcttagat cgctctgtgt agtagttgta gtatatccac tctctcaaag  35160
catccaggcg ccccctggct tcgggttcta tgtaaactcc ttcatgcgcc gctgccctga  35220
taacatccac caccgcagaa taagccacac ccagccaacc tacacattcg ttctgcgagt  35280
cacacacggg aggagcggga agagctggaa gaaccatgtt ttttttttta ttccaaaaga  35340
ttatccaaaa cctcaaaatg aagatctatt aagtgaacgc gctcccctcc ggtggcgtgg  35400
tcaaactcta cagccaaaga acagataatg gcatttgtaa gatgttgcac aatggcttcc  35460
aaaaggcaaa cggccctcac gtccaagtgg acgtaaaggc taaacccttc agggtgaatc  35520
tcctctataa acattccagc accttcaacc atgcccaaat aattctcatc tcgccacctt  35580
ctcaatatat ctctaagcaa atcccgaata ttaagtccgg ccattgtaaa aatctgctcc  35640
agagcgccct ccaccttcag cctcaagcag cgaatcatga ttgcaaaaat tcaggttcct  35700
cacagacctg tataagattc aaaagcggaa cattaacaaa aataccgcga tcccgtaggt  35760
cccttcgcag ggccagctga acataatcgt gcaggtctgc acggaccagc gcggccactt  35820
ccccgccagg aaccatgaca aaagaaccca cactgattat gacacgcata ctcggagcta  35880
tgctaaccag cgtagccccg atgtaagctt gttgcatggg cggcgatata aaatgcaagg  35940
tgctgctcaa aaaatcaggc aaagcctcgc gcaaaaaaga aagcacatcg tagtcatgct  36000
catgcagata aaggcaggta agctccggaa ccaccacaga aaaagacacc atttttctct  36060
caaacatgtc tgcgggtttc tgcataaaca caaaataaaa taacaaaaaa acatttaaac  36120
attagaagcc tgtcttacaa caggaaaaac aacccttata agcataagac ggactacggc  36180
catgccggcg tgaccgtaaa aaaactggtc accgtgatta aaaagcacca ccgacagctc  36240
ctcggtcatg tccggagtca taatgtaaga ctcggtaaac acatcaggtt gattcacatc  36300
ggtcagtgct aaaaagcgac cgaaatagcc cgggggaata catacccgca ggcgtagaga  36360
caacattaca gcccccatag gaggtataac aaaattaata ggagagaaaa acacataaac  36420
acctgaaaaa ccctcctgcc taggcaaaat agcaccctcc cgctccagaa caacatacag  36480
```

```
cgcttccaca gcggcagcca taacagtcag ccttaccagt aaaaaagaaa acctattaaa  36540

aaaacaccac tcgacacggc accagctcaa tcagtcacag tgtaaaaaag ggccaagtgc  36600

agagcgagta tatataggac taaaaaatga cgtaacggtt aaagtccaca aaaaacaccc  36660

agaaaaccgc acgcgaacct acgcccagaa acgaaagcca aaaaacccac aacttcctca  36720

aatcgtcact tccgttttcc cacgttacgt cacttcccat tttaagaaaa ctacaattcc  36780

caacacatac aagttactcc gccctaaaac ctacgtcacc cgccccgttc ccacgccccg  36840

cgccacgtca caaactccac cccctcatta tcatattggc ttcaatccaa aataaggtat  36900

attattgatg atg                                                     36913
```

<210> SEQ ID NO 2
<211> LENGTH: 36934
<212> TYPE: DNA
<213> ORGANISM: Artificial Sequence
<220> FEATURE:
<223> OTHER INFORMATION: Synthetic adenovirus construct (AdSyn-CO172)

<400> SEQUENCE: 2

```
catcatcaat aatatacctt attttggatt gaagccaata tgataatgag gggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tatttgtcta gggccgcggg    360

gactttgacc gtttacgtgg agactcgccc aggtgttttt ctcaggtgtt ttccgcgttc    420

cgggtcaaag ttggcgtttt attattaaac cgtattaccg ccatgcattt aatggagtgc    480

ctcgtgaggc tccggtgccc gtcagtgggc agagcgcaca tcgcccacag tccccgagaa    540

gttgggggga ggggtcggca attgaaccgg tgcctagaga aggtggcgcg gggtaaactg    600

ggaaagtgat gtcgtgtact ggctccgcct ttttcccgag ggtgggggag aaccgtatat    660

aagtgcagta gtcgccgtga acgttctttt tcgcaacggg tttgccgcca gaacacaggt    720

aagtgccgtg tgtggttccc gcgggcctgg cctctttacg ggttatggcc cttgcgtgcc    780

ttgaattact tccacctggc tgcagtacgt gattcttgat cccgagcttc gggttggaag    840

tgggtgggag agttcgaggc cttgcgctta aggagcccct tcgcctcgtg cttgagttga    900

ggcctggcct gggcgctggg gccgccgcgt gcgaatctgg tggcaccttc gcgcctgtct    960

cgctgctttc gataagtctc tagccattta aaatttttga tgacctgctg cgacgctttt   1020

tttctggcaa gatagtcttg taaatgcggg ccaagatctg cacactggta tttcggtttt   1080

tggggccgcg ggcggcgacg gggcccgtgc gtcccagcgc acatgttcgg cgaggcgggg   1140

cctgcgagcg cggccaccga gaatcggacg gggtagtct caagctggcc ggcctgctct    1200

ggtgcctggc ctcgcgccgc cgtgtatcgc cccgccctgg gcggcaaggc tggcccggtc   1260

ggcaccagtt gcgtgagcgg aaagatggcc gcttcccggc cctgctgcag ggagctcaaa   1320

atggaggacg cggcgctcgg gagagcgggc gggtgagtca cccacacaaa ggaaaagggc   1380

ctttccgtcc tcagccgtcg cttcatgtga ctccacggag taccgggcgc cgtccaggca   1440

cctcgattag ttctcgagct tttggagtac gtcgtcttta ggttgggggg aggggtttta   1500

tgcgatggag tttccccaca ctgagtgggt ggagactgaa gttaggccag cttggcactt   1560

gatgtaattc tccttggaat ttgccctttt tgagtttgga tcttggttca ttctcaagcc   1620
```

-continued

```
tcagacagtg gttcaaagtt tttttcttcc atttcaggtg tcgtgacgct agcgctaccg   1680
gactcagatc tcgagctcaa gcttcgaatt ctgcagtcga cggtaccgga tccatggaag   1740
acgccaaaaa cataaagaaa ggcccggcgc cattctatcc gctggaagat ggaaccgctg   1800
gagagcaact gcataaggct atgaagagat acgccctggt tcctggaaca attgctttta   1860
cagatgcaca tatcgaggtg gacatcactt acgctgagta cttcgaaatg tccgttcggt   1920
tggcagaagc tatgaaacga tatgggctga atacaaatca cagaatcgtc gtatgcagtg   1980
aaaactctct tcaattcttt atgccggtgt tgggcgcgtt atttatcgga gttgcagttg   2040
cgcccgcgaa cgacatttat aatgaacgtg aattgctcaa cagtatgggc atttcgcagc   2100
ctaccgtggt gttcgtttcc aaaaaggggt tgcaaaaaat tttgaacgtg caaaaaaagc   2160
tcccaatcat ccaaaaaatt attatcatgg attctaaaac ggattaccag ggatttcagt   2220
cgatgtacac gttcgtcaca tctcatctac ctcccggttt taatgaatac gattttgtgc   2280
cagagtcctt cgatagggac aagacaattg cactgatcat gaactcctct ggatctactg   2340
gtctgcctaa aggtgtcgct ctgcctcata gaactgcctg cgtgagattc tcgcatgcca   2400
gagatcctat ttttggcaat caaatcattc cggatactgc gattttaagt gttgttccat   2460
tccatcacgg ttttggaatg tttactacac tcggatattt gatatgtgga tttcgagtcg   2520
tcttaatgta tagatttgaa gaagagctgt ttctgaggag ccttcaggat tacaagattc   2580
aaagtgcgct gctggtgcca accctattct ccttcttcgc caaaagcact ctgattgaca   2640
aatacgattt atctaattta cacgaaattg cttctggtgg cgctcccctc tctaaggaag   2700
tcggggaagc ggttgccaag aggttccatc tgccaggtat caggcaagga tatgggctca   2760
ctgagactac atcagctatt ctgattacac ccgaggggga tgataaaccg ggcgcggtcg   2820
gtaaagttgt tccatttttt gaagcgaagg ttgtggatct ggataccggg aaaacgctgg   2880
gcgttaatca aagaggcgaa ctgtgtgtga gaggtcctat gattatgtcc ggttatgtaa   2940
acaatccgga agcgaccaac gccttgattg acaaggatgg atggctacat tctggagaca   3000
tagcttactg ggacgaagac gaacacttct tcatcgttga ccgcctgaag tctctgatta   3060
agtacaaagg ctatcaggtg gctcccgctg aattggaatc catcttgctc caacacccca   3120
acatcttcga cgcaggtgtc gcaggtcttc ccgacgatga cgccggtgaa cttcccgccg   3180
ccgttgttgt tttggagcac ggaaagacga tgacggaaaa agagatcgtg gattacgtcg   3240
ccagtcaagt aacaaccgcg aaaaagttgc gcggaggagt tgtgtttgtg gacgaagtac   3300
cgaaaggtct taccggaaaa ctcgacgcaa gaaaaatcag agagatcctc ataaaggcca   3360
agaagggcgg aaagatcgcc gtggcagccg cagccaccat ggtgagcaag ggcgaggagc   3420
tgttcaccgg ggtggtgccc atcctggtcg agctggacgg cgacgtaaac ggccacaagt   3480
tcagcgtgtc cggcgagggc gagggcgatg ccacctacgg caagctgacc ctgaagttca   3540
tctgcaccac cggcaagctg cccgtgccct ggcccaccct cgtgaccacc ctgacctacg   3600
gcgtgcagtg cttcagccgc taccccgacc acatgaagca gcacgacttc ttcaagtccg   3660
ccatgcccga aggctacgtc caggagcgca ccatcttctt caaggacgac ggcaactaca   3720
agacccgcgc cgaggtgaag ttcgagggcg acaccctggt gaaccgcatc gagctgaagg   3780
gcatcgactt caaggaggac ggcaacatcc tggggcacaa gctggagtac aactacaaca   3840
gccacaacgt ctatatcatg gccgacaagc agaagaacgg catcaaggtg aacttcaaga   3900
tccgccacaa catcgaggac ggcagcgtgc agctcgccga ccactaccag cagaacaccc   3960
```

-continued

```
ccatcggcga cggccccgtg ctgctgcccg acaaccacta cctgagcacc cagtccgccc   4020
tgagcaaaga ccccaacgag aagcgcgatc acatggtcct gctggagttc gtgaccgccg   4080
ccgggatcac tctcggcatg gacgagctgt acaagtaaag cgactctaga tcataatcag   4140
ccataccaa acaccattgt cacactccaa tcgattcaaa caccattgtc acactccaac   4200
atttgtagag gttttacttg ctttaaaaaa cctcccacac ctccccctga acctgaaaca   4260
taaaatgaat gcaattgttg ttgttaactt gtttattgca gcttataatg gttacaaata   4320
aagcaatagc atcacaaatt tcacaaataa agcatttttt tcactgcatt ctagttgtgg   4380
tttgtccaaa ctcatcaatg taagtttaaa cggcgcgcct gaaatgtgtg ggcgtggctt   4440
aagggtggga aagaatatat aaggtggggg tcttatgtag ttttgtatct gttttgcagc   4500
agccgccgcc gccatgagca ccaactcgtt tgatggaagc attgtgagct catatttgac   4560
aacgcgcatg cccccatggg ccggggtgcg tcagaatgtg atgggctcca gcattgatgg   4620
tcgccccgtc ctgcccgcaa actctactac cttgacctac gagaccgtgt ctggaacgcc   4680
gttggagact gcagcctccg ccgccgcttc agccgctgca gccaccgccc gcgggattgt   4740
gactgacttt gctttcctga gcccgcttgc aagcagtgca gcttcccgtt catccgcccg   4800
cgatgacaag ttgacggctc ttttggcaca attggattct ttgacccggg aacttaatgt   4860
cgtttctcag cagctgttgg atctgcgcca gcaggtttct gccctgaagg cttcctcccc   4920
tcccaatgcg gtttaaaaca caacttttct atacaaagtt gtaaataaaa aaccagactc   4980
tgtttggatt tggatcaagc taagtgtctt gctgtcttta tttaggggtt ttgcgcgcgc   5040
ggtaggcccg ggaccagcgg tctcggtcgt tgagggtcct gtgtattttt tccaggacgt   5100
ggtaaaggtg actctggatg ttcagataca tgggcataag cccgtctctg gggtggaggt   5160
agcaccactg cagagcttca tgctgcgggg tggtgttgta gatgatccag tcgtagcagg   5220
agcgctgggc gtggtgccta aaaatgtctt tcagtagcaa gctgattgcc aggggcaggc   5280
ccttggtgta agtgtttaca aagcggttaa gctgggatgg gtgcatacgt ggggatatga   5340
gatgcatctt ggactgtatt tttaggttgg ctatgttccc agccatatcc ctccggggat   5400
tcatgttgtg cagaaccacc agcacagtgt atccggtgca cttgggaaat ttgtcatgta   5460
gcttagaagg aaatgcgtgg aagaacttgg agacgccctt gtgacctcca agattttcca   5520
tgcattcgtc cataatgatg gcaatgggcc cacgggcggc ggcctgggcg aagatatttc   5580
tgggatcact aacgtcatag ttgtgttcca ggatgagatc gtcataggcc atttttacaa   5640
agcgcgggcg gagggtgcca gactgcggta taatggttcc atccggccca ggggcgtagt   5700
taccctcaca gatttgcatt tcccacgctt tgagttcaga tgggggggatc atgtctacct   5760
gcggggcgat gaagaaaacg gtttccgggg taggggagat cagctgggaa gaaagcaggt   5820
tcctgagcag ctgcgactta ccgcagccgg tgggcccgta aatcacacct attaccggct   5880
gcaactggta gttaagagag ctgcagctgc cgtcatccct gagcaggggg gccacttcgt   5940
taagcatgtc cctgactcgc atgttttccc tgaccaaatc cgccagaagg cgctcgccgc   6000
ccagcgatag cagttcttgc aaggaagcaa agtttttcaa cggtttgaga ccgtccgccg   6060
taggcatgct tttgagcgtt tgaccaagca gttccaggcg gtcccacagc tcggtcacct   6120
gctctacggc atctcgatcc agcatatctc ctcgtttcgc gggttggggc ggctttcgct   6180
gtacggcagt agtcggtgct cgtccagacg ggccagggtc atgtctttcc acgggcgcag   6240
ggtcctcgtc agcgtagtct gggtcacggt gaaggggtgc gctccgggct gcgcgctggc   6300
cagggtgcgc ttgaggctgg tcctgctggt gctgaagcgc tgccggtctt cgccctgcgc   6360
```

gtcggccagg tagcatttga ccatggtgtc atagtccagc ccctccgcgg cgtggccctt 6420
ggcgcgcagc ttgcccttgg aggaggcgcc gcacgagggg cagtgcagac ttttgagggc 6480
gtagagcttg ggcgcgagaa ataccgattc cggggagtag gcatccgcgc cgcaggcccc 6540
gcagacggtc tcgcattcca cgagccaggt gagctctggc cgttcggggt caaaaaccag 6600
gtttccccca tgctttttga tgcgtttctt acctctggtt tccatgagcc ggtgtccacg 6660
ctcggtgacg aaaaggctgt ccgtgtcccc gtatacagac ttgagaggcc tgtcctcgag 6720
cggtgttccg cggtcctcct cgtatagaaa ctcggaccac tctgagacaa aggctcgcgt 6780
ccaggccagc acgaaggagg ctaagtggga ggggtagcgg tcgttgtcca ctagggggtc 6840
cactcgctcc agggtgtgaa gacacatgtc gccctcttcg gcatcaagga aggtgattgg 6900
tttgtaggtg taggccacgt gaccgggtgt tcctgaaggg gggctataaa agggggtggg 6960
ggcgcgttcg tcctcactct cttccgcatc gctgtctgcg agggccagct gttggggtga 7020
gtactccctc tgaaaagcgg gcatgacttc tgcgctaaga ttgtcagttt ccaaaaacga 7080
ggaggatttg atattcacct ggcccgcggt gatgcctttg agggtggccg catccatctg 7140
gtcagaaaag acaatctttt tgttgtcaag cttggtggca aacgacccgt agagggcgtt 7200
ggacagcaac ttggcgatgg agcgcagggt ttggtttttg tcgcgatcgg cgcgctcctt 7260
ggccgcgatg tttagctgca cgtattcgcg cgcaacgcac cgccattcgg gaaagacggt 7320
ggtgcgctcg tcgggcacca ggtgcacgcg ccaaccgcgg ttgtgcaggg tgacaaggtc 7380
aacgctggtg gctacctctc cgcgtaggcg ctcgttggtc cagcagaggc ggccgccctt 7440
gcgcgagcag aatggcggta gggggtctag ctgcgtctcg tccggggggt ctgcgtccac 7500
ggtaaagacc ccgggcagca ggcgcgcgtc gaagtagtct atcttgcatc cttgcaagtc 7560
tagcgcctgc tgccatgcgc gggcggcaag cgcgcgctcg tatgggttga gtgggggacc 7620
ccatggcatg gggtgggtga gcgcggaggc gtacatgccg caaatgtcgt aaacgtagag 7680
gggctctctg agtattccaa gatatgtagg gtagcatctt ccaccgcgga tgctggcgcg 7740
cacgtaatcg tatagttcgt gcgagggagc gaggaggtcg ggaccgaggt tgctacgggc 7800
gggctgctct gctcggaaga ctatctgcct gaagatggca tgtgagttgg atgatatggt 7860
tggacgctgg aagacgttga agctggcgtc tgtgagacct accgcgtcac gcacgaagga 7920
ggcgtaggag tcgcgcagct tgttgaccag ctcggcggtg acctgcacgt ctagggcgca 7980
gtagtccagg gtttccttga tgatgtcata cttatcctgt cccttttttt tccacagctc 8040
gcggttgagg acaaactctt cgcggtcttt ccagtactct tggatcggaa acccgtcggc 8100
ctccgaacgg taagagccta gcatgtagaa ctggttgacg gcctggtagg cgcagcatcc 8160
cttttctacg ggtagcgcgt atgcctgcgc ggccttccgg agcgaggtgt gggtgagcgc 8220
aaaggtgtcc ctgaccatga ctttgaggta ctggtatttg aagtcagtgt cgtcgcatcc 8280
gccctgctcc cagagcaaaa agtccgtgcg ctttttggaa cgcggatttg gcagggcgaa 8340
ggtgacatcg ttgaagagta tctttcccgc gcgaggcata aagttgcgtg tgatgcggaa 8400
gggtcccggc acctcggaac ggttgttaat tacctgggcg gcgagcacga tctcgtcaaa 8460
gccgttgatg ttgtggccca caatgtaaag ttccaagaag cgcgggatgc ccttgatgga 8520
aggcaatttt ttaagttcct cgtaggtgag ctcttcaggg gagctgagcc cgtgctctga 8580
aagggcccag tctgcaagat gagggttgga agcgacgaat gagctccaca ggtcacgggc 8640
cattagcatt tgcaggtggt cgcgaaaggt cctaaactgg cgacctatgg ccattttttc 8700

-continued

```
tggggtgatg cagtagaagg taagcgggtc ttgttcccag cggtcccatc caaggttcgc   8760
ggctaggtct cgcgcggcag tcactagagg ctcatctccg ccgaacttca tgaccagcat   8820
gaagggcacg agctgcttcc caaaggcccc catccaagta taggtctcta catcgtaggt   8880
gacaaagaga cgctcggtgc gaggatgcga gccgatcggg aagaactgga tctcccgcca   8940
ccaattggag gagtggctat tgatgtggtg aaagtagaag tccctgcgac gggccgaaca   9000
ctcgtgctgg cttttgtaaa aacgtgcgca gtactggcag cggtgcacgg gctgtacatc   9060
ctgcacgagg ttgacctgac gaccgcgcac aaggaagcag agtgggaatt tgagcccctc   9120
gcctggcggg tttggctggt ggtcttctac ttcggctgct tgtccttgac cgtctggctg   9180
ctcgagggga gttacggtgg atcggaccac cacgccgcgc gagcccaaag tccagatgtc   9240
cgcgcgcggc ggtcggagct tgatgacaac atcgcgcaga tgggagctgt ccatggtctg   9300
gagctcccgc ggcgtcaggt caggcgggag ctcctgcagg tttacctcgc atagacgggt   9360
cagggcgcgg gctagatcca ggtgatacct aatttccagg ggctggttgg tggcggcgtc   9420
gatggcttgc aagaggccgc atccccgcgg cgcgactacg gtaccgcgcg gcgggcggtg   9480
ggccgcgggg gtgtccttgg atgatgcatc taaaagcggt gacgcgggcg agcccccgga   9540
ggtagggggg gctccggacc cgccgggaga gggggcaggg gcacgtcggc gccgcgcgcg   9600
ggcaggagct ggtgctgcgc gcgtaggttg ctggcgaacg cgacgacgcg gcggttgatc   9660
tcctgaatct ggcgcctctg cgtgaagacg acgggcccgg tgagcttgaa cctgaaagag   9720
agttcgacag aatcaatttc ggtgtcgttg acggcggcct ggcgcaaaat ctcctgcacg   9780
tctcctgagt tgtcttgata ggcgatctcg gccatgaact gctcgatctc ttcctcctgg   9840
agatctccgc gtccggctcg ctccacggtg gcggcgaggt cgttggaaat gcgggccatg   9900
agctgcgaga aggcgttgag gcctccctcg ttccagacgc ggctgtagac cacgccccct   9960
tcggcatcgc gggcgcgcat gaccacctgc gcgagattga gctccacgtg ccgggcgaag  10020
acggcgtagt ttcgcaggcg ctgaaagagg tagttgaggg tggtggcggt gtgttctgcc  10080
acgaagaagt acataaccca gcgtcgcaac gtggattcgt tgatatcccc caaggcctca  10140
aggcgctcca tggcctcgta gaagtccacg gcgaagttga aaaactggga gttgcgcgcc  10200
gacacggtta actcctcctc cagaagacgg atgagctcgg cgacagtgtc gcgcacctcg  10260
cgctcaaagg ctacaggggc ctcttcttct tcttcaatct cctcttccat aagggcctcc  10320
ccttcttctt cttctggcgg cggtggggga ggggggacac ggcggcgacg acggcgcacc  10380
gggaggcggt cgacaaagcg ctcgatcatc tccccgcggc gacggcgcat ggtctcggtg  10440
acggcgcggc cgttctcgcg gggggcgcagt tggaagacgc cgcccgtcat gtcccggtta  10500
tgggttggcg gggggctgcc atgcggcagg gatacggcgc taacgatgca tctcaacaat  10560
tgttgtgtag gtactccgcc gccgagggac ctgagcgagt ccgcatcgac cggatcggaa  10620
aacctctcga gaaaggcgtc taaccagtca cagtcgcaag gtaggctgag caccgtggcg  10680
ggcggcagcg ggcggcggtc ggggttgttt ctggcggagg tgctgctgat gatgtaatta  10740
aagtaggcgg tcttgagacg gcggatggtc gacagaagca ccatgtcctt gggtccggcc  10800
tgctgaatgc gcaggcggtc ggccatgccc caggcttcgt tttgacatcg gcgcaggtct  10860
ttgtagtagt cttgcatgag cctttctacc ggcacttctt cttctccttc ctcttgtcct  10920
gcatctcttg catctatcgc tgcggcggcg gcggagtttg gccgtaggtg gcgccctctt  10980
cctcccatgc gtgtgacccc gaagcccctc atcggctgaa gcagggctag gtcggcgaca  11040
acgcgctcgg ctaatatggc ctgctgcacc tgcgtgaggg tagactggaa gtcatccatg  11100
```

-continued

```
tccacaaagc ggtggtatgc gcccgtgttg atggtgtaag tgcagttggc cataacggac  11160
cagttaacgg tctggtgacc cggctgcgag agctcggtgt acctgagacg cgagtaagcc  11220
ctcgagtcaa atacgtagtc gttgcaagtc cgcaccaggt actggtatcc caccaaaaag  11280
tgcggcggcg gctggcggta gaggggccag cgtagggtgg ccggggctcc gggggcgaga  11340
tcttccaaca taaggcgatg atatccgtag atgtacctgg acatccaggt gatgccggcg  11400
gcggtggtgg aggcgcgcgg aaagtcgcgg acgcggttcc agatgttgcg cagcggcaaa  11460
aagtgctcca tggtcgggac gctctggccg gtcaggcgcg cgcaatcgtt gacgctctag  11520
accgtgcaaa aggagagcct gtaagcgggc actcttccgt ggtctggtgg ataaattcgc  11580
aagggtatca tggcggacga ccggggttcg agccccgtat ccggccgtcc gccgtgatcc  11640
atgcggttac cgcccgcgtg tcgaacccag gtgtgcgacg tcagacaacg ggggagtgct  11700
ccttttggct tccttccagg cgcggcggct gctgcgctag ctttttggc cactggccgc  11760
gcgcagcgta agcggttagg ctggaaagcg aaagcattaa gtggctcgct ccctgtagcc  11820
ggagggttat tttccaaggg ttgagtcgcg ggacccccgg ttcgagtctc ggaccggccg  11880
gactgcggcg aacgggggtt tgcctccccg tcatgcaaga ccccgcttgc aaattcctcc  11940
ggaaacaggg acgagcccct tttttgcttt tcccagatgc atccggtgct gcggcagatg  12000
cgcccccctc ctcagcagcg gcaagagcaa gagcagcggc agacatgcag ggcaccctcc  12060
cctcctccta ccgcgtcagg aggggcgaca tccgcggttg acgcggcagc agatggtgat  12120
tacgaacccc cgcggcgccg ggcccggcac tacctggact tggaggaggg cgagggcctg  12180
gcgcggctag gagcgccctc tcctgagcgg cacccaaggg tgcagctgaa gcgtgatacg  12240
cgtgaggcgt acgtgccgcg gcagaacctg tttcgcgacc gcgagggaga ggagcccgag  12300
gagatgcggg atcgaaagtt ccacgcaggg cgcgagctgc ggcatggcct gaatcgcgag  12360
cggttgctgc gcgaggagga ctttgagccc gacgcgcgaa ccgggattag tcccgcgcgc  12420
gcacacgtgg cggccgccga cctggtaacc gcatacgagc agacggtgaa ccaggagatt  12480
aactttcaaa aaagctttaa caaccacgtg cgtacgcttg tggcgcgcga ggaggtggct  12540
ataggactga tgcatctgtg ggactttgta agcgcgctgg agcaaaaccc aaatagcaag  12600
ccgctcatgg cgcagctgtt ccttatagtg cagcacagca gggacaacga ggcattcagg  12660
gatgcgctgc taaacatagt agagcccgag ggccgctggc tgctcgattt gataaacatc  12720
ctgcagagca tagtggtgca ggagcgcagc ttgagcctgg ctgacaaggt ggccgccatc  12780
aactattcca tgcttagcct gggcaagttt tacgcccgca agatatacca taccccttac  12840
gttcccatag acaaggaggt aaagatcgag gggttctaca tgcgcatggc gctgaaggtg  12900
cttaccttga gcgacgacct gggcgtttat cgcaacgagc gcatccacaa ggccgtgagc  12960
gtgagccggc ggcgcgagct cagcgaccgc gagctgatgc acagcctgca aagggccctg  13020
gctggcacgg gcagcggcga tagagaggcc gagtcctact ttgacgcggg cgctgacctg  13080
cgctgggccc caagccgacg cgccctggag gcagctgggg ccggacctgg gctggcggtg  13140
gcacccgcgc gcgctggcaa cgtcggcggc gtggaggaat atgacgagga cgatgagtac  13200
gagccagagg acggcgagta ctaagcggtg atgtttctga tcagatgatg caagacgcaa  13260
cggacccggc ggtgcgggcg gcgctgcaga gccagccgtc cggccttaac tccacggacg  13320
actggcgcca ggtcatggac cgcatcatgt cgctgactgc gcgcaatcct gacgcgttcc  13380
ggcagcagcc gcaggccaac cggctctccg caattctgga agcggtggtc ccggcgcgcg  13440
```

-continued

```
caaaccccac gcacgagaag gtgctggcga tcgtaaacgc gctggccgaa aacagggcca  13500
tccggcccga cgaggccggc ctggtctacg acgcgctgct tcagcgcgtg gctcgttaca  13560
acagcggcaa cgtgcagacc aacctggacc ggctggtggg ggatgtgcgc gaggccgtgg  13620
cgcagcgtga gcgcgcgcag cagcagggca acctgggctc catggttgca ctaaacgcct  13680
tcctgagtac acagcccgcc aacgtgccgc ggggacagga ggactacacc aactttgtga  13740
gcgcactgcg gctaatggtg actgagacac cgcaaagtga ggtgtaccag tctgggccag  13800
actatttttt ccagaccagt agacaaggcc tgcagaccgt aaacctgagc caggctttca  13860
aaaacttgca ggggctgtgg ggggtgcggg ctcccacagg cgaccgcgcg accgtgtcta  13920
gcttgctgac gcccaactcg cgcctgttgc tgctgctaat agcgcccttc acggacagtg  13980
gcagcgtgtc ccgggacaca tacctaggtc acttgctgac actgtaccgc gaggccatag  14040
gtcaggcgca tgtggacgag catactttcc aggagattac aagtgtcagc cgcgcgctgg  14100
ggcaggagga cacgggcagc ctggaggcaa ccctaaacta cctgctgacc aaccggcggc  14160
agaagatccc ctcgttgcac agtttaaaca gcgaggagga gcgcattttg cgctacgtgc  14220
agcagagcgt gagccttaac ctgatgcgcg acggggtaac gcccagcgtg gcgctggaca  14280
tgaccgcgcg caacatggaa ccgggcatgt atgcctcaaa ccggccgttt atcaaccgcc  14340
taatggacta cttgcatcgc gcggccgccg tgaaccccga gtatttcacc aatgccatct  14400
tgaacccgca ctggctaccg ccccctggtt tctacaccgg gggattcgag gtgcccgagg  14460
gtaacgatgg attcctctgg gacgacatag acgacagcgt gttttccccg caaccgcaga  14520
ccctgctaga gttgcaacag cgcgagcagg cagaggcggc gctgcgaaag gaaagcttcc  14580
gcaggccaag cagcttgtcc gatctaggcg ctgcggcccc gcggtcagat gctagtagcc  14640
catttccaag cttgataggg tctcttacca gcactcgcac cacccgcccg cgcctgctgg  14700
gcgaggagga gtacctaaac aactcgctgc tgcagccgca gcgcgaaaaa aacctgcctc  14760
cggcatttcc caacaacggg atagagagcc tagtggacaa gatgagtaga tggaagacgt  14820
acgcgcagga gcacagggac gtgccaggcc cgcgcccgcc cacccgtcgt caaaggcacg  14880
accgtcagcg gggtctggtg tgggaggacg atgactcggc agacgacagc agcgtcctgg  14940
atttgggagg gagtggcaac ccgtttgcgc accttcgccc caggctgggg agaatgtttt  15000
aaaaaaaaaa aaaaagcatg atgcaaaata aaaaactcac caaggccatg gcaccgagcg  15060
ttggttttct tgtattcccc ttagtatgcg gcgcgcggcg atgtatgagg aaggtcctcc  15120
tccctcctac gagagtgtgg tgagcgcggc gccagtggcg gcggcgctgg gttctccctt  15180
cgatgctccc ctggacccgc cgtttgtgcc tccgcggtac ctgcggccta ccggggggag  15240
aaacagcatc cgttactctg agttggcacc cctattcgac accacccgtg tgtacctggt  15300
ggacaacaag tcaacggatg tggcatccct gaactaccag aacgaccaca gcaactttct  15360
gaccacggtc attcaaaaca atgactacag cccgggggag gcaagcacac agaccatcaa  15420
tcttgacgac cggtcgcact ggggcggcga cctgaaaacc atcctgcata ccaacatgcc  15480
aaatgtgaac gagttcatgt ttaccaataa gtttaaggcg cgggtgatgg tgtcgcgctt  15540
gcctactaag gacaatcagg tggagctgaa atacgagtgg gtggagttca cgctgcccga  15600
gggcaactac tccgagacca tgaccataga ccttatgaac aacgcgatcg tggagcacta  15660
cttgaaagtg ggcagacaga acggggttct ggaaagcgac atcggggtaa agtttgacac  15720
ccgcaacttc agactggggt ttgaccccgt cactggtctt gtcatgcctg ggtatatac  15780
aaacgaagcc ttccatccag acatcatttt gctgccagga tgcggggtgg acttcaccca  15840
```

-continued

```
cagccgcctg agcaacttgt tgggcatccg caagcggcaa cccttccagg agggctttag  15900
gatcacctac gatgatctgg agggtggtaa cattcccgca ctgttggatg tggacgccta  15960
ccaggcgagc ttgaaagatg acaccgaaca gggcgggggt ggcgcaggcg gcagcaacag  16020
cagtggcagc ggcgcggaag agaactccaa cgcggcagcc gcggcaatgc agccggtgga  16080
ggacatgaac gatcatgcca ttcgcggcga cacctttgcc acacgggctg aggagaagcg  16140
cgctgaggcc gaagcagcgg ccgaagctgc cgcccccgct gcgcaacccg aggtcgagaa  16200
gcctcagaag aaaccggtga tcaaacccct gacagaggac agcaagaaac gcagttacaa  16260
cctaataagc aatgacagca ccttcaccca gtaccgcagc tggtaccttg catacaacta  16320
cggcgaccct cagaccggaa tccgctcatg gaccctgctt tgcactcctg acgtaacctg  16380
cggctcggag caggtctact ggtcgttgcc agacatgatg caagaccccg tgaccttccg  16440
ctccacgcgc cagatcagca actttccggt ggtgggcgcc gagctgttgc ccgtgcactc  16500
caagagcttc tacaacgacc aggccgtcta ctcccaactc atccgccagt ttacctctct  16560
gacccacgtg ttcaatcgct ttcccgagaa ccagattttg gcgcgcccgc cagcccccac  16620
catcaccacc gtcagtgaaa acgttcctgc tctcacagat cacgggacgc taccgctgcg  16680
caacagcatc ggaggagtcc agcgagtgac cattactgac gccagacgcc gcacctgccc  16740
ctacgtttac aaggccctgg gcatagtctc gccgcgcgtc ctatcgagcc gcactttttg  16800
agcaagcatg tccatcctta tatcgcccag caataacaca ggctggggcc tgcgcttccc  16860
aagcaagatg tttggcgggg ccaagaagcg ctccgaccaa cacccagtgc gcgtgcgcgg  16920
gcactaccgc gcgccctggg gcgcgcacaa acgcggccgc actgggcgca ccaccgtcga  16980
tgacgccatc gacgcggtgg tggaggaggc gcgcaactac acgcccacgc cgccaccagt  17040
gtccacagtg gacgcggcca ttcagaccgt ggtgcgcgga gcccggcgct atgctaaaat  17100
gaagagacgg cggaggcgcg tagcacgtcg ccaccgccgc cgacccggca ctgccgccca  17160
acgcgcggcg gcggccctgc ttaaccgcgc acgtcgcacc ggccgacggg cggccatgcg  17220
ggccgctcga aggctggccg cgggtattgt cactgtgccc cccaggtcca ggcgacgagc  17280
ggccgccgca gcagccgcgg ccattagtgc tatgactcag ggtcgcaggg gcaacgtgta  17340
ttgggtgcgc gactcggtta gcggcctgcg cgtgcccgtg cgcacccgcc ccccgcgcaa  17400
ctagattgca agaaaaaact acttagactc gtactgttgt atgtatccag cggcggcggc  17460
gcgcaacgaa gctatgtcca agcgcaaaat caaagaagag atgctccagg tcatcgcgcc  17520
ggagatctat ggcccccga agaaggaaga gcaggattac aagccccgaa agctaaagcg  17580
ggtcaaaaag aaaaagaaag atgatgatga tgaacttgac gacgaggtgg aactgctgca  17640
cgctaccgcg cccaggcgac gggtacagtg gaaaggtcga cgcgtaaaac gtgttttgcg  17700
acccggcacc accgtagtct ttacgcccgg tgagcgctcc acccgcacct acaagcgcgt  17760
gtatgatgag gtgtacggcg acgaggacct gcttgagcag gccaacgagc gcctcgggga  17820
gtttgcctac ggaaagcggc ataaggacat gctggcgttg ccgctggacg agggcaaccc  17880
aacacctagc ctaaagcccg taacactgca gcaggtgctg cccgcgcttg caccgtccga  17940
agaaaagcgc ggcctaaagc gcgagtctgg tgacttggca cccaccgtgc agctgatggt  18000
acccaagcgc cagcgactgg aagatgtctt ggaaaaaatg accgtggaac ctgggctgga  18060
gcccgaggtc cgcgtgcggc caatcaagca ggtggcgccg ggactgggcg tgcagaccgt  18120
ggacgttcag atacccacta ccagtagcac cagtattgcc accgccacag agggcatgga  18180
```

gacacaaacg tccccggttg cctcagcggt ggcggatgcc gcggtgcagg cggtcgctgc 18240
ggccgcgtcc aagacctcta cggaggtgca aacggacccg tggatgtttc gcgtttcagc 18300
cccccggcgc ccgcgccgtt cgaggaagta cggcgccgcc agcgcgctac tgcccgaata 18360
tgccctacat ccttccattg cgcctacccc cggctatcgt ggctacacct accgccccag 18420
aagacgagca actacccgac gccgaaccac cactggaacc cgccgccgcc gtcgccgtcg 18480
ccagcccgtg ctggccccga tttccgtgcg cagggtggct cgcgaaggag gcaggaccct 18540
ggtgctgcca acagcgcgct accaccccag catcgtttaa aagccggtct ttgtggttct 18600
tgcagatatg gccctcacct gccgcctccg tttcccggtg ccgggattcc gaggaagaat 18660
gcaccgtagg aggggcatgg ccggccacgg cctgacgggc ggcatgcgtc gtgcgcacca 18720
ccggcggcgg cgcgcgtcgc accgtcgcat gcgcggcggt atcctgcccc tccttattcc 18780
actgatcgcc gcggcgattg gcgccgtgcc cggaattgca tccgtggcct tgcaggcgca 18840
gagacactga ttaaaaacaa gttgcatgtg gaaaaatcaa aataaaaagt ctggactctc 18900
acgctcgctt ggtcctgtaa ctattttgta gaatggaaga catcaacttt gcgtctctgg 18960
ccccgcgaca cggctcgcgc ccgttcatgg gaaactggca agatatcggc accagcaata 19020
tgagcggtgg cgccttcagc tggggctcgc tgtggagcgg cattaaaaat ttcggttcca 19080
ccgttaagaa ctatggcagc aaggcctgga acagcagcac aggccagatg ctgagggata 19140
agttgaaaga gcaaaatttc caacaaaagg tggtagatgg cctggcctct ggcattagcg 19200
gggtggtgga cctggccaac caggcagtgc aaaataagat taacagtaag cttgatcccc 19260
gccctcccgt agaggagcct ccaccggccg tggagacagt gtctccagag gggcgtggcg 19320
aaaagcgtcc gcgccccgac agggaagaaa ctctggtgac gcaaatagac gagcctccct 19380
cgtacgagga ggcactaaag caaggcctgc ccaccacccg tcccatcgcg cccatggcta 19440
ccggagtgct gggccagcac acacccgtaa cgctggacct gcctcccccc gccgacaccc 19500
agcagaaacc tgtgctgcca ggcccgaccg ccgttgttgt aacccgtcct agccgcgcgt 19560
ccctgcgccg cgccgccagc ggtccgcgat cgttgcggcc cgtagccagt ggcaactggc 19620
aaagcacact gaacagcatc gtgggtctgg gggtgcaatc cctgaagcgc cgacgatgct 19680
tctgaatagc taacgtgtcg tatgtgtgtc atgtatgcgt ccatgtcgcc gccagaggag 19740
ctgctgagcc gccgcgcgcc cgctttccaa gatggctacc ccttcgatga tgccgcagtg 19800
gtcttacatg cacatctcgg gccaggacgc ctcggagtac ctgagccccg ggctggtgca 19860
gtttgcccgc gccaccgaga cgtacttcag cctgaataac aagtttagaa accccacggt 19920
ggcgcctacg cacgacgtga ccacagaccg gtcccagcgt ttgacgctgc ggttcatccc 19980
tgtggaccgt gaggatactg cgtactcgta caaggcgcgg ttcaccctag ctgtgggtga 20040
taaccgtgtg ctggacatgg cttccacgta ctttgacatc cgcggcgtgc tggacagggg 20100
ccctactttt aagccctact ctggcactgc ctacaacgcc ctggctccca agggtgcccc 20160
aaatccttgc gaatgggatg aagctgctac tgctcttgaa ataaacctag aagaagagga 20220
cgatgacaac gaagacgaag tagacgagca agctgagcag caaaaaactc acgtatttgg 20280
gcaggcgcct tattctggta taaatattac aaaggagggt attcaaatag gtgtcgaagg 20340
tcaaacacct aaatatgccg ataaaacatt tcaacctgaa cctcaaatag gagaatctca 20400
gtggtacgaa actgaaatta atcatgcagc tgggagagtc cttaaaaaga ctaccccaat 20460
gaaaccatgt tacggttcat atgcaaaacc cacaaatgaa aatggagggc aaggcattct 20520
tgtaaagcaa caaaatggaa agctagaaag tcaagtggaa atgcaatttt tctcaactac 20580

```
tgaggcgacc gcaggcaatg gtgataactt gactcctaaa gtggtattgt acagtgaaga  20640
tgtagatata gaaaccccag acactcatat ttcttacatg cccactatta aggaaggtaa  20700
ctcacgagaa ctaatgggcc aacaatctat gcccaacagg cctaattaca ttgcttttag  20760
ggacaatttt attggtctaa tgtattacaa cagcacgggt aatatgggtg ttctggcggg  20820
ccaagcatcg cagttgaatg ctgttgtaga tttgcaagac agaaacacag agctttcata  20880
ccagcttttg cttgattcca ttggtgatag aaccaggtac ttttctatgt ggaatcaggc  20940
tgttgacagc tatgatccag atgttagaat tattgaaaat catggaactg aagatgaact  21000
tccaaattac tgctttccac tgggaggtgt gattaataca gagactctta ccaaggtaaa  21060
acctaaaaca ggtcaggaaa atggatggga aaaagatgct acagaatttt cagataaaaa  21120
tcaaataaga gttggaaata attttgccat ggaaatcaat ctaaatgcca acctgtggag  21180
aaatttcctg tactccaaca tagcgctgta tttgcccgac aagctaaagt acagtccttc  21240
caacgtaaaa atttctgata acccaaacac ctacgactac atgaacaagc gagtggtggc  21300
tcccgggtta gtggactgct acattaacct tggagcacgc tggtcccttg actatatgga  21360
caacgtcaac ccatttaacc accaccgcaa tgctggcctg cgctaccgct caatgttgct  21420
gggcaatggt cgctatgtgc ccttccacat ccaggtgcct cagaagttct ttgccattaa  21480
aaacctcctt ctcctgccgg gctcatacac ctacgagtgg aacttcagga aggatgttaa  21540
catggttctg cagagctccc taggaaatga cctaagggtt gacggagcca gcattaagtt  21600
tgatagcatt tgcctttacg ccaccttctt ccccatggcc cacaacaccg cctccacgct  21660
tgaggccatg cttagaaacg acaccaacga ccagtccttt aacgactatc tctccgccgc  21720
caacatgctc taccctatac ccgccaacgc taccaacgtg cccatatcca tcccctcccg  21780
caactgggcg gctttccgcg gctgggcctt cacgcgcctt aagactaagg aaaccccatc  21840
actgggctcg ggctacgacc cttattacac ctactctggc tctataccct acctagatgg  21900
aacctttttac ctcaaccaca cctttaagaa ggtggccatt acctttgact cttctgtcag  21960
ctggcctggc aatgaccgcc tgcttacccc caacgagttt gaaattaagc gctcagttga  22020
cggggagggt tacaacgttg cccagtgtaa catgaccaaa gactggttcc tggtacaaat  22080
gctagctaac tacaacattg gctaccaggg cttctatatc ccagagagct acaaggaccg  22140
catgtactcc ttctttagaa acttccagcc catgagccgt caggtggtgg atgatactaa  22200
atacaaggac taccaacagg tgggcatcct acaccaacac aacaactctg gatttgttgg  22260
ctaccttgcc cccaccatgc gcgaaggaca ggcctaccct gctaacttcc cctatccgct  22320
tataggcaag accgcagttg acagcattac ccagaaaaag tttctttgcg atcgcaccct  22380
ttggcgcatc ccattctcca gtaactttat gtccatgggc gcactcacag acctgggcca  22440
aaaccttctc tacgccaact ccgcccacgc gctagacatg acttttgagg tggatcccat  22500
ggacgagccc acccttcttt atgttttgtt tgaagtcttt gacgtggtcc gtgtgcaccg  22560
gccgcaccgc ggcgtcatcg aaaccgtgta cctgcgcacg cccttctcgg ccggcaacgc  22620
cacaacataa agaagcaagc aacatcaaca acagctgccg ccatgggctc cagtgagcag  22680
gaactgaaag ccattgtcaa agatcttggt tgtgggccat atttttttggg cacctatgac  22740
aagcgctttc caggctttgt ttctccacac aagctcgcct gcgccatagt caatacggcc  22800
ggtcgcgaga ctgggggcgt acactggatg gcctttgcct ggaacccgca ctcaaaaaca  22860
tgctacctct ttgagccctt tggcttttct gaccagcgac tcaagcaggt ttaccagttt  22920
```

```
gagtacgagt cactcctgcg ccgtagcgcc attgcttctt cccccgaccg ctgtataacg  22980
ctggaaaagt ccacccaaag cgtacagggg cccaactcgg ccgcctgtgg actattctgc  23040
tgcatgtttc tccacgcctt tgccaactgg ccccaaactc ccatggatca caaccccacc  23100
atgaacctta ttaccggggt acccaactcc atgctcaaca gtccccaggt acagcccacc  23160
ctgcgtcgca accaggaaca gctctacagc ttcctggagc gccactcgcc ctacttccgc  23220
agccacagtg cgcagattag gagcgccact tctttttgtc acttgaaaaa catgtaaaaa  23280
taatgtacta gagacacttt caataaaggc aaatgctttt atttgtacac tctcgggtga  23340
ttatttaccc ccacccttgc cgtctgcgcc gtttaaaaat caaaggggtt ctgccgcgca  23400
tcgctatgcg ccactggcag ggacacgttg cgatactggt gtttagtgct ccacttaaac  23460
tcaggcacaa ccatccgcgg cagctcggtg aagttttcac tccacaggct gcgcaccatc  23520
accaacgcgt ttagcaggtc gggcgccgat atcttgaagt cgcagttggg gcctccgccc  23580
tgcgcgcgcg agttgcgata cacagggttg cagcactgga acactatcag cgccgggtgg  23640
tgcacgctgg ccagcacgct cttgtcggag atcagatccg cgtccaggtc ctccgcgttg  23700
ctcagggcga acggagtcaa ctttggtagc tgccttccca aaaagggcgc gtgcccaggc  23760
tttgagttgc actcgcaccg tagtggcatc aaaaggtgac cgtgcccggt ctgggcgtta  23820
ggatacagcg cctgcataaa agccttgatc tgcttaaaag ccacctgagc ctttgcgcct  23880
tcagagaaga acatgccgca agacttgccg gaaaactgat tggccggaca ggccgcgtcg  23940
tgcacgcagc accttgcgtc ggtgttggag atctgcacca catttcggcc ccaccggttc  24000
ttcacgatct tggccttgct agactgctcc ttcagcgcgc gctgcccgtt ttcgctcgtc  24060
acatccattt caatcacgtg ctccttattt atcataatgc ttccgtgtag acacttaagc  24120
tcgccttcga tctcagcgca gcggtgcagc cacaacgcgc agcccgtggg ctcgtgatgc  24180
ttgtaggtca cctctgcaaa cgactgcagg tacgcctgca ggaatcgccc catcatcgtc  24240
acaaaggtct tgttgctggt gaaggtcagc tgcaacccgc ggtgctcctc gttcagccag  24300
gtcttgcata cggccgccag agcttccact tggtcaggca gtagtttgaa gttcgccttt  24360
agatcgttat ccacgtggta cttgtccatc agcgcgcgcg cagcctccat gcccttctcc  24420
cacgcagaca cgatcggcac actcagcggg ttcatcaccg taatttcact ttccgcttcg  24480
ctgggctctt cctcttcctc ttgcgtccgc ataccacgcg ccactgggtc gtcttcattc  24540
agccgccgca ctgtgcgctt acctcctttg ccatgcttga ttagcaccgg tgggttgctg  24600
aaacccacca tttgtagcgc cacatcttct ctttcttcct cgctgtccac gattacctct  24660
ggtgatggcg ggcgctcggg cttgggagaa gggcgcttct tttcttcttt gggcgcaatg  24720
gccaaatccg ccgccgaggt cgatggccgc gggctgggtg tgcgcggcac cagcgcgtct  24780
tgtgatgagt cttcctcgtc ctcggactcg atacgccgcc tcatccgctt ttttgggggc  24840
gcccggggag gcggcggcga cggggacggg gacgacacgt cctccatggt tgggggacgt  24900
cgcgccgcac cgcgtccgcg ctcgggggtg gtttcgcgct gctcctcttc ccgactggcc  24960
atttccttct cctataggca gaaaaagatc atggagtcag tcgagaagaa ggacagccta  25020
accgcccccct ctgagttcgc caccaccgcc tccaccgatg ccgccaacgc gcctaccacc  25080
ttccccgtcg aggcaccccc gcttgaggag gaggaagtga ttatcgagca ggacccaggt  25140
tttgtaagcg aagacgacga ggaccgctca gtaccaacag aggataaaaa gcaagaccag  25200
gacaacgcag aggcaaacga ggaacaagtc gggcgggggg acgaaaggca tggcgactac  25260
ctagatgtgg gagacgacgt gctgttgaag catctgcagc gccagtgcgc cattatctgc  25320
```

```
gacgcgttgc aagagcgcag cgatgtgccc ctcgccatag cggatgtcag ccttgcctac  25380
gaacgccacc tattctcacc gcgcgtaccc cccaaacgcc aagaaaacgg cacatgcgag  25440
cccaacccgc gcctcaactt ctaccccgta tttgccgtgc cagaggtgct tgccacctat  25500
cacatctttt tccaaaactg caagataccc ctatcctgcc gtgccaaccg cagccgagcg  25560
gacaagcagc tggccttgcg gcagggcgct gtcatacctg atatcgcctc gctcaacgaa  25620
gtgccaaaaa tctttgaggg tcttggacgc gacgagaagc gcgcggcaaa cgctctgcaa  25680
caggaaaaca gcgaaaatga aagtcactct ggagtgttgg tggaactcga gggtgacaac  25740
gcgcgcctag ccgtactaaa acgcagcatc gaggtcaccc actttgccta cccggcactt  25800
aacctacccc ccaaggtcat gagcacagtc atgagtgagc tgatcgtgcg ccgtgcgcag  25860
cccctggaga gggatgcaaa tttgcaagaa caaacagagg agggcctacc cgcagttggc  25920
gacgagcagc tagcgcgctg gcttcaaacg cgcgagcctg ccgacttgga ggagcgacgc  25980
aaactaatga tggccgcagt gctcgttacc gtggagcttg agtgcatgca gcggttcttt  26040
gctgacccgg agatgcagcg caagctagag gaaacattgc actacacctt tcgacagggc  26100
tacgtacgcc aggcctgcaa gatctccaac gtggagctct gcaacctggt ctcctacctt  26160
ggaattttgc acgaaaaccg ccttgggcaa aacgtgcttc attccacgct caagggcgag  26220
gcgcgccgcg actacgtccg cgactgcgtt tacttatttc tatgctacac ctggcagacg  26280
gccatgggcg tttggcagca gtgcttggag gagtgcaacc tcaaggagct gcagaaactg  26340
ctaaagcaaa acttgaagga cctatggacg gccttcaacg agcgctccgt ggccgcgcac  26400
ctggcggaca tcattttccc cgaacgcctg cttaaaaccc tgcaacaggg tctgccagac  26460
ttcaccagtc aaagcatgtt gcagaacttt aggaacttta tcctagagcg ctcaggaatc  26520
ttgcccgcca cctgctgtgc acttcctagc gactttgtgc ccattaagta ccgcgaatgc  26580
cctccgccgc tttggggcca ctgctacctt ctgcagctag ccaactacct tgcctaccac  26640
tctgacataa tggaagacgt gagcggtgac ggtctactgg agtgtcactg tcgctgcaac  26700
ctatgcaccc cgcaccgctc cctggtttgc aattcgcagc tgcttaacga aagtcaaatt  26760
atcggtacct ttgagctgca gggtccctcg cctgacgaaa agtccgcggc tccggggttg  26820
aaactcactc cggggctgtg gacgtcggct taccttcgca aatttgtacc tgaggactac  26880
cacgcccacg agattaggtt ctacgaagac caatcccgcc cgccaaatgc ggagcttacc  26940
gcctgcgtca ttacccaggg ccacattctt ggccaattgc aagccatcaa caaagcccgc  27000
caagagtttc tgctacgaaa gggacggggg gtttacttgg acccccagtc cggcgaggag  27060
ctcaacccaa tcccccgcc gccgcagccc tatcagcagc agccgcgggc ccttgcttcc  27120
caggatggca cccaaaaaga agctgcagct gccgccgcca cccacggacg aggaggaata  27180
ctgggacagt caggcagagg aggttttgga cgaggaggag gaggacatga tggaagactg  27240
ggagagccta gacgaggaag cttccgaggt cgaagaggtg tcagacgaaa caccgtcacc  27300
ctcggtcgca ttcccctcgc cggcgcccca gaaatcggca accggttcca gcatggctac  27360
aacctccgct cctcaggcgc cgccggcact gcccgttcgc cgacccaacc gtagatggga  27420
caccactgga accagggccg gtaagtccaa gcagccgccg ccgttagccc aagagcaaca  27480
acagcgccaa ggctaccgct catggcgcgg gcacaagaac gccatagttg cttgcttgca  27540
agactgtggg ggcaacatct ccttcgcccg ccgctttctt ctctaccatc acggcgtggc  27600
cttcccccgt aacatcctgc attactaccg tcatctctac agcccatact gcaccggcgg  27660
```

cagcggcagc ggcagcaaca gcagcggcca cacagaagca aaggcgaccg gatagcaaga 27720
ctctgacaaa gcccaagaaa tccacagcgg cggcagcagc aggaggagga gcgctgcgtc 27780
tggcgcccaa cgaacccgta tcgacccgcg agcttagaaa caggattttt cccactctgt 27840
atgctatatt tcaacagagc aggggccaag aacaagagct gaaaataaaa aacaggtctc 27900
tgcgatccct cacccgcagc tgcctgtatc acaaaagcga agatcagctt cggcgcacgc 27960
tggaagacgc ggaggctctc ttcagtaaat actgcgcgct gactcttaag gactagtttc 28020
gcgccctttc tcaaatttaa gcgcgaaaac tacgtcatct ccagcggcca cacccggcgc 28080
cagcacctgt cgtcagcgcc atttcaactt tgtatacaaa agttgtgatg agcaaggaaa 28140
ttcccacgcc ctacatgtgg agttaccagc cacaaatggg acttgcggct ggagctgccc 28200
aagactactc aacccgaata aactacatga gcgcgggacc ccacatgata tcccgggtca 28260
acggaatacg cgcccaccga aaccgaattc tcctggaaca ggcggctatt accaccacac 28320
ctcgtaataa ccttaatccc cgtagttggc ccgctgccct ggtgtaccag gaaagtcccg 28380
ctcccaccac tgtggtactt cccagagacg cccaggccga agttcagatg actaactcag 28440
gggcgcagct tgcgggcggc tttcgtcaca gggtgcggtc gcccgggcag ggtataactc 28500
acctgacaat cagagggcga ggtattcagc tcaacgacga gtcggtgagc tcctcgcttg 28560
gtctccgtcc ggacgggaca tttcagatcg gcggcgccgg ccgctcttca ttcacgcctc 28620
gtcaggcaat cctaactctg cagacctcgt cctctgagcc gcgctctgga ggcattggaa 28680
ctctgcaatt tattgaggag tttgtgccat cggtctactt taaccccttc tcgggacctc 28740
ccggccacta tccggatcaa tttattccta actttgacgc ggtaaaggac tcggcggacg 28800
gctacgactg aatgttaagt ggagaggcag agcaactgcg cctgaaacac ctggtccact 28860
gtcgccgcca caagtgcttt gcccgcgact ccggtgagtt ttgctacttt gaattgcccg 28920
aggatcatat cgagggcccg gcgcacggcg tccggcttac cgcccaggga gagcttgccc 28980
gtagcctgat tcgggagttt acccagcgcc ccctgctagt tgagcgggac aggggaccct 29040
gtgttctcac tgtgatttgc aactgtccta accctggatt acatcaagat ctttgttgcc 29100
atctctgtgc tgagtataat aaatacagaa attaaaatat actggggctc ctatcgccat 29160
cctgtaaacg ccaccgtctt cacccgccca agcaaaccaa ggcgaacctt acctggtact 29220
tttaacatct ctccctctgt gatttacaac agtttcaacc cagacggagt gagtctacga 29280
gagaacctct ccgagctcag ctactccatc agaaaaaaca ccaccctcct tacctgccgg 29340
gaacgtacga gtgcgtcacc ggccgctgca ccacacctac cgcctgaccg taaaccagac 29400
tttttccgga cagacctcaa taactctgtt taccagaaca ggaggtgagc ttagaaaacc 29460
cttagggtat taggccaaag gcgcagctac tgtggggttt atgaacaatt caagcaactc 29520
tacgggctat tctaattcag gtttctctag aatcggggtt ggggttattc tctgtcttgt 29580
gattctcttt attcttatac taacgcttct ctgcctaagg ctcgccgcct gctgtgtgca 29640
catttgcatt tattgtcagc tttttaaacg ctggggtcgc cacccaagat gattaggtac 29700
ataatcctag gtttactcac ccttgcgtca gcccacggta ccacccaaaa ggtggatttt 29760
aaggagccag cctgtaatgt tacattcgca gctgaagcta atgagtgcac cactcttata 29820
aaatgcacca cagaacatga aaagctgctt attcgccaca aaaacaaaat tggcaagtat 29880
gctgtttatg ctatttggca gccaggtgac actacagagt ataatgttac agttttccag 29940
ggtaaaagtc ataaaacttt tatgtatact tttccatttt atgaaatgtg cgacattacc 30000
atgtacatga gcaaacagta taagttgtgg cccccacaaa attgtgtgga aaacactggc 30060
actttctgct gcactgctat gctaattaca gtgctcgctt tggtctgtac cctactctat 30120
attaaataca aaagcagacg cagctttatt gaggaaaaga aaatgcctta atttactaag 30180
ttacaaagct aatgtcacca ctaactgctt tactcgctgc ttgcaaaaca aattcaaaaa 30240
gttagcatta taattagaat aggatttaaa ccccccggtc atttcctgct caataccatt 30300
cccctgaaca attgactcta tgtgggatat gctccagcgc tacaaccttg aagtcaggct 30360
tcctggatgt cagcatctga ctttggccag cacctgtccc gcggatttgt tccagtccaa 30420
ctacagcgac ccaccctaac agagatgacc aacacaacca acgcggccgc cgctaccgga 30480
cttacatcta ccacaaatac accccaagtt tctgcctttg tcaataactg ggataacttg 30540
ggcatgtggt ggttctccat agcgcttatg tttgtatgcc ttattattat gtggctcatc 30600
tgctgcctaa agcgcaaacg cgcccgacca cccatctata gtcccatcat tgtgctacac 30660
ccaaacaatg atggaatcca tagattggac ggactgaaac acatgttctt ttctcttaca 30720
gtatgattaa atgagacatg attcctcgag tttttatatt actgaccctt gttgcgcttt 30780
tttgtgcgtg ctccacattg gctgcggttt ctcacatcga agtagactgc attccagcct 30840
tcacagtcta tttgctttac ggatttgtca ccctcacgct catctgcagc ctcatcactg 30900
tggtcatcgc ctttatccag tgcattgact gggtctgtgt gcgctttgca tatctcagac 30960
accatcccca gtacagggac aggactatag ctgagcttct tagaattctt taattatgaa 31020
atttactgtg acttttctgc tgattatttg caccctatct gcgttttgtt ccccgacctc 31080
caagcctcaa agacatatat catgcagatt cactcgtata tggaatattc caagttgcta 31140
caatgaaaaa agcgatcttt ccgaagcctg gttatatgca atcatctctg ttatggtgtt 31200
ctgcagtacc atcttagccc tagctatata tccctacctt gacattggct ggaacgcaat 31260
agatgccatg aaccacccaa ctttccccgc gcccgctatg cttccactgc aacaagttgt 31320
tgccggcggc tttgtcccag ccaatcagcc tcgcccacct tctcccaccc ccactgaaat 31380
cagctacttt aatctaacag gaggagatga ctgacaccct agatctagaa atggacggaa 31440
ttattacaga gcagcgcctg ctagaaagac gcagggcagc ggccgagcaa cagcgcatga 31500
atcaagagct ccaagacatg gttaacttgc accagtgcaa aaggggtatc ttttgtctgg 31560
taaagcaggc caaagtcacc tacgacagta ataccaccgg acaccgcctt agctacaagt 31620
tgccaaccaa gcgtcagaaa ttggtggtca tggtgggaga aaagcccatt accataactc 31680
agcactcggt agaaaccgaa ggctgcattc actcaccttg tcaaggacct gaggatctct 31740
gcacccttat taagaccctg tgcggtctca aagatcttat tccctttaac taataaaaaa 31800
aaataataaa gcatcactta cttaaaatca gttagcaaat ttctgtccag tttattcagc 31860
agcacctcct tgccctcctc ccagctctgg tattgcagct tcctcctggc tgcaaacttt 31920
ctccacaatc taaatggaat gtcagtttcc tcctgttcct gtccatccgc acccactatc 31980
ttcatgttgt tgcagatgaa gcgcgcaaga ccgtctgaag ataccttcaa ccccgtgtat 32040
ccatatgaca cggaaaccgg tcctccaact gtgccttttc ttactcctcc ctttgtatcc 32100
cccaatgggt ttcaagagag tccccctggg gtactctctt tgcgcctatc cgaacctcta 32160
gttacctcca atggcatgct tgcgctcaaa atgggcaacg gcctctctct ggacgaggcc 32220
ggcaacctta cctcccaaaa tgtaaccact gtgagcccac ctctcaaaaa aaccaagtca 32280
aacataaacc tggaaatatc tgcacccctc acagttacct cagaagccct aactgtggct 32340
gccgccgcac ctctaatggt cgcgggcaac acactcacca tgcaatcaca ggccccgcta 32400

-continued

```
accgtgcacg actccaaact tagcattgcc acccaaggac ccctcacagt gtcagaagga  32460
aagctagccc tgcaaacatc aggccccctc accaccaccg atagcagtac ccttactatc  32520
actgcctcac cccctctaac tactgccact ggtagcttgg gcattgactt gaaagagccc  32580
atttatacac aaaatggaaa actaggacta aagtacgggg ctcctttgca tgtaacagac  32640
gacctaaaca ctttgaccgt agcaactggt ccaggtgtga ctattaataa tacttccttg  32700
caaactaaag ttactggagc cttgggtttt gattcacaag gcaatatgca acttaatgta  32760
gcaggaggac taaggattga ttctcaaaac agacgcctta tacttgatgt tagttatccg  32820
tttgatgctc aaaaccaact aaatctaaga ctaggacagg gccctctttt tataaactca  32880
gcccacaact tggatattaa ctacaacaaa ggcctttact tgtttacagc ttcaaacaat  32940
tccaaaaagc ttgaggttaa cctaagcact gccaaggggt tgatgtttga cgctacagcc  33000
atagccatta atgcaggaga tgggcttgaa tttggttcac ctaatgcacc aaacacaaat  33060
cccctcaaaa caaaaattgg ccatggccta gaatttgatt caaacaaggc tatggttcct  33120
aaactaggaa ctggccttag ttttgacagc acaggtgcca ttacagtagg aaacaaaaat  33180
aatgataagc taactttatg gacaggtcca aaaccagaag ccaactgcat aattgaatac  33240
gggaaacaaa acccagatag caaactaact ttaatccttg taaaaaatgg aggaattgtt  33300
aatggatatg taacgctaat gggagcctca gactacgtta acaccttatt taaaaacaaa  33360
aatgtctcca ttaatgtaga actatacttt gatgccactg gtcatatatt accagactca  33420
tcttctctta aaacagatct agaactaaaa tacaagcaaa ccgctgactt tagtgcaaga  33480
ggttttatgc caagtactac agcgtatcca tttgtccttc ctaatgcggg aacacataat  33540
gaaaattata tttttggtca atgctactac aaagcaagcg atggtgccct tttccgttg  33600
gaagttactg ttatgcttaa taaacgcctg ccagatagtc gcacatccta tgttatgact  33660
tttttatggt ccttgaatgc tggtctagct ccagaaacta ctcaggcaac cctcataacc  33720
tccccattta ccttttccta tattagagaa gatgactaat aaagaatcgt ttgtgttatg  33780
tttcaacgtg tttatttttc aattgcagaa aatttcaagt catttttcat tcagtagtat  33840
agccccacca ccacatagct tatacagatc accgtacctc aactttgtat aataaagttg  33900
taatcaaact cacagaaccc tagtattcaa cctgccacct ccctcccaac acacagagta  33960
cacagtcctt tctccccggc tggccttaaa aagcatcata tcatgggtaa cagacatatt  34020
cttaggtgtt atattccaca cggtttcctg tcgagccaaa cgctcatcag tgatattaat  34080
aaactccccg ggcagctcac ttaagttcat gtcgctgtcc agctgctgag ccacaggctg  34140
ctgtccaact tgcggttgct taacgggcgg cgaaggagaa gtccacgcct acatgggggt  34200
agagtcataa tcgtgcatca ggatagggcg gtggtgctgc agcagcgcgc gaataaactg  34260
ctgccgccgc cgctccgtcc tgcaggaata caacatggca gtggtctcct cagcgatgat  34320
tcgcaccgcc cgcagcataa ggcgccttgt cctccgggca cagcagcgca ccctgatctc  34380
acttaaatca gcacagtaac tgcagcacag caccacaata ttgttcaaaa tcccacagtg  34440
caaggcgctg tatccaaagc tcatggcggg gaccacagaa cccacgtggc catcatacca  34500
caagcgcagg tagattaagt ggcgacccct cataaacacg ctggacataa acattacctc  34560
ttttggcatg ttgtaattca ccacctcccg gtaccatata aacctctgat taaacatggc  34620
gccatccacc accatcctaa accagctggc caaaacctgc ccgccggcta tacactgcag  34680
ggaaccggga ctggaacaat gacagtggag agcccaggac tcgtaaccat ggatcatcat  34740
gctcgtcatg atatcaatgt tggcacaaca caggcacacg tgcatacact tcctcaggat  34800
```

tacaagctcc tcccgcgtta gaaccatatc ccagggaaca acccattcct gaatcagcgt 34860
aaatcccaca ctgcagggaa gacctcgcac gtaactcacg ttgtgcattg tcaaagtgtt 34920
acattcgggc agcagcggat gatcctccag tatggtagcg cgggtttctg tctcaaaagg 34980
aggtagacga tccctactgt acggagtgcg ccgagacaac cgagatcgtg ttggtcgtag 35040
tgtcatgcca aatggaacgc cggacgtagt catatttcct gaagcaaaac caggtgcggg 35100
cgtgacaaac agatctgcgt ctccggtctc gccgcttaga tcgctctgtg tagtagttgt 35160
agtatatcca ctctctcaaa gcatccaggc gccccctggc ttcgggttct atgtaaactc 35220
cttcatgcgc cgctgccctg ataacatcca ccaccgcaga ataagccaca cccagccaac 35280
ctacacattc gttctgcgag tcacacacgg gaggagcggg aagagctgga agaaccatgt 35340
ttttttttt attccaaaag attatccaaa acctcaaaat gaagatctat taagtgaacg 35400
cgctcccctc cggtggcgtg gtcaaactct acagccaaag aacagataat ggcatttgta 35460
agatgttgca caatggcttc caaaaggcaa acggccctca cgtccaagtg gacgtaaagg 35520
ctaaaccctt cagggtgaat ctcctctata aacattccag caccttcaac catgcccaaa 35580
taattctcat ctcgccacct tctcaatata tctctaagca aatcccgaat attaagtccg 35640
gccattgtaa aaatctgctc cagagcgccc tccaccttca gcctcaagca gcgaatcatg 35700
attgcaaaaa ttcaggttcc tcacagacct gtataagatt caaaagcgga acattaacaa 35760
aaataccgcg atcccgtagg tcccttcgca gggccagctg aacataatcg tgcaggtctg 35820
cacggaccag cgcggccact tccccgccag gaaccatgac aaaagaaccc acactgatta 35880
tgacacgcat actcggagct atgctaacca gcgtagcccc gatgtaagct tgttgcatgg 35940
gcggcgatat aaaatgcaag gtgctgctca aaaaatcagg caaagcctcg cgcaaaaaag 36000
aaagcacatc gtagtcatgc tcatgcagat aaaggcaggt aagctccgga accaccacag 36060
aaaaagacac catttttctc tcaaacatgt ctgcgggttt ctgcataaac acaaaataaa 36120
ataacaaaaa aacatttaaa cattagaagc ctgtcttaca acaggaaaaa caacccttat 36180
aagcataaga cggactacgg ccatgccggc gtgaccgtaa aaaaactggt caccgtgatt 36240
aaaaagcacc accgacagct cctcggtcat gtccggagtc ataatgtaag actcggtaaa 36300
cacatcaggt tgattcacat cggtcagtgc taaaaagcga ccgaaatagc ccgggggaat 36360
acatacccgc aggcgtagag acaacattac agcccccata ggaggtataa caaaattaat 36420
aggagagaaa aacacataaa cacctgaaaa accctcctgc ctaggcaaaa tagcaccctc 36480
ccgctccaga acaacataca gcgcttccac agcggcagcc ataacagtca gccttaccag 36540
taaaaaagaa aacctattaa aaaaacacca ctcgacacgg caccagctca atcagtcaca 36600
gtgtaaaaaa gggccaagtg cagagcgagt atatatagga ctaaaaaatg acgtaacggt 36660
taaagtccac aaaaaacacc cagaaaaccg cacgcgaacc tacgcccaga aacgaaagcc 36720
aaaaaaccca caacttcctc aaatcgtcac ttccgttttc ccacgttacg tcacttccca 36780
ttttaagaaa actacaattc ccaacacata caagttactc cgccctaaaa cctacgtcac 36840
ccgccccgtt cccacgcccc gcgccacgtc acaaactcca ccccctcatt atcatattgg 36900
cttcaatcca aaataaggta tattattgat gatg 36934

<210> SEQ ID NO 3
<211> LENGTH: 36916
<212> TYPE: DNA
<213> ORGANISM: Artificial Sequence
<220> FEATURE:

-continued

<223> OTHER INFORMATION: Synthetic adenovirus construct (AdSyn-CO173)

<400> SEQUENCE: 3

```
catcatcaat aatatacctt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattaaac cgtattaccg ccatgcattt aatggagtgc    480
ctcgtgaggc tccggtgccc gtcagtgggc agagcgcaca tcgcccacag tccccgagaa    540
gttgggggga ggggtcggca attgaaccgg tgcctagaga aggtggcgcg gggtaaactg    600
ggaaagtgat gtcgtgtact ggctccgcct ttttcccgag ggtgggggag aaccgtatat    660
aagtgcagta gtcgccgtga acgttctttt tcgcaacggg tttgccgcca gaacacaggt    720
aagtgccgtg tgtggttccc gcgggcctgg cctctttacg ggttatggcc cttgcgtgcc    780
ttgaattact tccacctggc tgcagtacgt gattcttgat cccgagcttc gggttggaag    840
tgggtgggag agttcgaggc cttgcgctta aggagcccct tcgcctcgtg cttgagttga    900
ggcctggcct gggcgctggg gccgccgcgt gcgaatctgg tggcaccttc gcgcctgtct    960
cgctgctttc gataagtctc tagccattta aaatttttga tgacctgctg cgacgctttt   1020
tttctggcaa gatagtcttg taaatgcggg ccaagatctg cacactggta tttcggtttt   1080
tggggccgcg ggcggcgacg gggcccgtgc gtcccagcgc acatgttcgg cgaggcgggg   1140
cctgcgagcg cggccaccga gaatcggacg ggggtagtct caagctggcc ggcctgctct   1200
ggtgcctggc ctcgcgccgc cgtgtatcgc cccgccctgg gcggcaaggc tggcccggtc   1260
ggcaccagtt gcgtgagcgg aaagatggcc gcttcccggc cctgctgcag ggagctcaaa   1320
atggaggacg cggcgctcgg gagagcgggc gggtgagtca cccacacaaa ggaaaagggc   1380
ctttccgtcc tcagccgtcg cttcatgtga ctccacggag taccgggcgc cgtccaggca   1440
cctcgattag ttctcgagct tttggagtac gtcgtcttta ggttgggggg aggggtttta   1500
tgcgatggag tttccccaca ctgagtgggt ggagactgaa gttaggccag cttggcactt   1560
gatgtaattc tccttggaat ttgccctttt tgagtttgga tcttggttca ttctcaagcc   1620
tcagacagtg gttcaaagtt tttttcttcc atttcaggtg tcgtgacgct agcgctaccg   1680
gactcagatc tcgagctcaa gcttcgaatt ctgcagtcga cggtaccgga tccatggaag   1740
acgccaaaaa cataaagaaa ggcccggcgc cattctatcc gctggaagat ggaaccgctg   1800
gagagcaact gcataaggct atgaagagat acgccctggt tcctggaaca attgctttta   1860
cagatgcaca tatcgaggtg gacatcactt acgctgagta cttcgaaatg tccgttcggt   1920
tggcagaagc tatgaaacga tatgggctga atacaaatca cagaatcgtc gtatgcagtg   1980
aaaactctct tcaattcttt atgccggtgt tgggcgcgtt atttatcgga gttgcagttg   2040
cgcccgcgaa cgacatttat aatgaacgtg aattgctcaa cagtatgggc atttcgcagc   2100
ctaccgtggt gttcgtttcc aaaaaggggt tgcaaaaaat tttgaacgtg caaaaaaagc   2160
tcccaatcat ccaaaaaatt attatcatgg attctaaaac ggattaccag ggatttcagt   2220
cgatgtacac gttcgtcaca tctcatctac ctcccggttt taatgaatac gattttgtgc   2280
```

-continued

```
cagagtcctt cgatagggac aagacaattg cactgatcat gaactcctct ggatctactg   2340
gtctgcctaa aggtgtcgct ctgcctcata gaactgcctg cgtgagattc tcgcatgcca   2400
gagatcctat ttttggcaat caaatcattc cggatactgc gattttaagt gttgttccat   2460
tccatcacgg ttttggaatg tttactacac tcggatattt gatatgtgga tttcgagtcg   2520
tcttaatgta tagatttgaa gaagagctgt ttctgaggag ccttcaggat tacaagattc   2580
aaagtgcgct gctggtgcca accctattct ccttcttcgc caaaagcact ctgattgaca   2640
aatacgattt atctaattta cacgaaattg cttctggtgg cgctcccctc tctaaggaag   2700
tcggggaagc ggttgccaag aggttccatc tgccaggtat caggcaagga tatgggctca   2760
ctgagactac atcagctatt ctgattacac ccgaggggga tgataaaccg ggcgcggtcg   2820
gtaaagttgt tccatttttt gaagcgaagg ttgtggatct ggataccggg aaaacgctgg   2880
gcgttaatca aagaggcgaa ctgtgtgtga gaggtcctat gattatgtcc ggttatgtaa   2940
acaatccgga agcgaccaac gccttgattg acaaggatgg atggctacat tctggagaca   3000
tagcttactg ggacgaagac gaacacttct tcatcgttga ccgcctgaag tctctgatta   3060
agtacaaagg ctatcaggtg gctcccgctg aattggaatc catcttgctc caacacccca   3120
acatcttcga cgcaggtgtc gcaggtcttc ccgacgatga cgccggtgaa cttcccgccg   3180
ccgttgttgt tttggagcac ggaaagacga tgacggaaaa agagatcgtg gattacgtcg   3240
ccagtcaagt aacaaccgcg aaaaagttgc gcggaggagt tgtgtttgtg gacgaagtac   3300
cgaaaggtct taccggaaaa ctcgacgcaa gaaaaatcag agagatcctc ataaaggcca   3360
agaagggcgg aaagatcgcc gtggcagccg cagccaccat ggtgagcaag ggcgaggagc   3420
tgttcaccgg ggtggtgccc atcctggtcg agctggacgg cgacgtaaac ggccacaagt   3480
tcagcgtgtc cggcgagggc gagggcgatg ccacctacgg caagctgacc ctgaagttca   3540
tctgcaccac cggcaagctg cccgtgccct ggcccaccct cgtgaccacc ctgacctacg   3600
gcgtgcagtg cttcagccgc taccccgacc acatgaagca gcacgacttc ttcaagtccg   3660
ccatgcccga aggctacgtc caggagcgca ccatcttctt caaggacgac ggcaactaca   3720
agacccgcgc cgaggtgaag ttcgagggcg acaccctggt gaaccgcatc gagctgaagg   3780
gcatcgactt caaggaggac ggcaacatcc tggggcacaa gctggagtac aactacaaca   3840
gccacaacgt ctatatcatg gccgacaagc agaagaacgg catcaaggtg aacttcaaga   3900
tccgccacaa catcgaggac ggcagcgtgc agctcgccga ccactaccag cagaacaccc   3960
ccatcggcga cggccccgtg ctgctgcccg acaaccacta cctgagcacc cagtccgccc   4020
tgagcaaaga ccccaacgag aagcgcgatc acatggtcct gctggagttc gtgaccgccg   4080
ccgggatcac tctcggcatg gacgagctgt acaagtaaag cgactctaga tcataatcag   4140
ccataccaca acaccattgt cacactccaa tcgattcaaa caccattgtc acactccaac   4200
atttgtagag gttttacttg ctttaaaaaa cctcccacac ctccccctga acctgaaaca   4260
taaaatgaat gcaattgttg ttgttaactt gtttattgca gcttataatg gttacaaata   4320
aagcaatagc atcacaaatt tcacaaataa agcatttttt tcactgcatt ctagttgtgg   4380
tttgtccaaa ctcatcaatg taagtttaaa cggcgcgcct gaaatgtgtg ggcgtggctt   4440
aagggtggga aagaatatat aaggtggggg tcttatgtag ttttgtatct gttttgcagc   4500
agccgccgcc gccatgagca ccaactcgtt tgatggaagc attgtgagct catatttgac   4560
aacgcgcatg cccccatggg ccggggtgcg tcagaatgtg atgggctcca gcattgatgg   4620
```

-continued

```
tcgccccgtc ctgcccgcaa actctactac cttgacctac gagaccgtgt ctggaacgcc   4680
gttggagact gcagcctccg ccgccgcttc agccgctgca gccaccgccc gcgggattgt   4740
gactgacttt gctttcctga gcccgcttgc aagcagtgca gcttcccgtt catccgcccg   4800
cgatgacaag ttgacggctc ttttggcaca attggattct ttgacccggg aacttaatgt   4860
cgtttctcag cagctgttgg atctgcgcca gcaggtttct gccctgaagg cttcctcccc   4920
tcccaatgcg gtttaaaaca caacttttct atacaaagtt gtaaataaaa aaccagactc   4980
tgtttggatt tggatcaagc taagtgtctt gctgtcttta tttaggggtt ttgcgcgcgc   5040
ggtaggcccg ggaccagcgg tctcggtcgt tgagggtcct gtgtattttt tccaggacgt   5100
ggtaaaggtg actctggatg ttcagataca tgggcataag cccgtctctg gggtggaggt   5160
agcaccactg cagagcttca tgctgcgggg tggtgttgta gatgatccag tcgtagcagg   5220
agcgctgggc gtggtgccta aaaatgtctt tcagtagcaa gctgattgcc aggggcaggc   5280
ccttggtgta agtgtttaca aagcggttaa gctgggatgg gtgcatacgt ggggatatga   5340
gatgcatctt ggactgtatt tttaggttgg ctatgttccc agccatatcc ctccggggat   5400
tcatgttgtg cagaaccacc agcacagtgt atccggtgca cttgggaaat ttgtcatgta   5460
gcttagaagg aaatgcgtgg aagaacttgg agacgccctt gtgacctcca agattttcca   5520
tgcattcgtc cataatgatg gcaatgggcc cacgggcggc ggcctgggcg aagatatttc   5580
tgggatcact aacgtcatag ttgtgttcca ggatgagatc gtcataggcc atttttacaa   5640
agcgcgggcg gagggtgcca gactgcggta taatggttcc atccggccca ggggcgtagt   5700
taccctcaca gatttgcatt tcccacgctt tgagttcaga tgggggggatc atgtctacct   5760
gcggggcgat gaagaaaacg gtttccgggg taggggagat cagctgggaa gaaagcaggt   5820
tcctgagcag ctgcgactta ccgcagccgg tgggcccgta aatcacacct attaccggct   5880
gcaactggta gttaagagag ctgcagctgc cgtcatccct gagcaggggg gccacttcgt   5940
taagcatgtc cctgactcgc atgttttccc tgaccaaatc cgccagaagg cgctcgccgc   6000
ccagcgatag cagttcttgc aaggaagcaa agtttttcaa cggtttgaga ccgtccgccg   6060
taggcatgct tttgagcgtt tgaccaagca gttccaggcg gtcccacagc tcggtcacct   6120
gctctacggc atctcgatcc agcatatctc ctcgtttcgc gggttggggc ggctttcgct   6180
gtacggcagt agtcggtgct cgtccagacg ggccagggtc atgtctttcc acgggcgcag   6240
ggtcctcgtc agcgtagtct gggtcacggt gaaggggtgc gctccgggct gcgcgctggc   6300
cagggtgcgc ttgaggctgg tcctgctggt gctgaagcgc tgccggtctt cgccctgcgc   6360
gtcggccagg tagcatttga ccatggtgtc atagtccagc ccctccgcgg cgtggccctt   6420
ggcgcgcagc ttgcccttgg aggaggcgcc gcacgagggg cagtgcagac ttttgagggc   6480
gtagagcttg ggcgcgagaa ataccgattc cggggagtag gcatccgcgc cgcaggcccc   6540
gcagacggtc tcgcattcca cgagccaggt gagctctggc cgttcggggt caaaaaccag   6600
gtttccccca tgctttttga tgcgtttctt acctctggtt tccatgagcc ggtgtccacg   6660
ctcggtgacg aaaaggctgt ccgtgtcccc gtatacagac ttgagaggcc tgtcctcgag   6720
cggtgttccg cggtcctcct cgtatagaaa ctcggaccac tctgagacaa aggctcgcgt   6780
ccaggccagc acgaaggagg ctaagtggga ggggtagcgg tcgttgtcca ctagggggtc   6840
cactcgctcc agggtgtgaa gacacatgtc gccctcttcg gcatcaagga aggtgattgg   6900
tttgtaggtg taggccacgt gaccgggtgt tcctgaaggg gggctataaa agggggtggg   6960
ggcgcgttcg tcctcactct cttccgcatc gctgtctgcg agggccagct gttggggtga   7020
```

-continued

```
gtactccctc tgaaaagcgg gcatgacttc tgcgctaaga ttgtcagttt ccaaaaacga   7080
ggaggatttg atattcacct ggcccgcggt gatgcctttg agggtggccg catccatctg   7140
gtcagaaaag acaatctttt tgttgtcaag cttggtggca aacgacccgt agagggcgtt   7200
ggacagcaac ttggcgatgg agcgcagggt ttggtttttg tcgcgatcgg cgcgctcctt   7260
ggccgcgatg tttagctgca cgtattcgcg cgcaacgcac cgccattcgg gaaagacggt   7320
ggtgcgctcg tcgggcacca ggtgcacgcg ccaaccgcgg ttgtgcaggg tgacaaggtc   7380
aacgctggtg gctacctctc cgcgtaggcg ctcgttggtc cagcagaggc ggccgccctt   7440
gcgcgagcag aatggcggta gggggtctag ctgcgtctcg tccggggggt ctgcgtccac   7500
ggtaaagacc ccgggcagca ggcgcgcgtc gaagtagtct atcttgcatc cttgcaagtc   7560
tagcgcctgc tgccatgcgc gggcggcaag cgcgcgctcg tatgggttga gtgggggacc   7620
ccatggcatg gggtgggtga gcgcggaggc gtacatgccg caaatgtcgt aaacgtagag   7680
gggctctctg agtattccaa gatatgtagg gtagcatctt ccaccgcgga tgctggcgcg   7740
cacgtaatcg tatagttcgt gcgagggagc gaggaggtcg ggaccgaggt tgctacgggc   7800
gggctgctct gctcggaaga ctatctgcct gaagatggca tgtgagttgg atgatatggt   7860
tggacgctgg aagacgttga agctggcgtc tgtgagacct accgcgtcac gcacgaagga   7920
ggcgtaggag tcgcgcagct tgttgaccag ctcggcggtg acctgcacgt ctagggcgca   7980
gtagtccagg gtttccttga tgatgtcata cttatcctgt cccttttttt tccacagctc   8040
gcggttgagg acaaactctt cgcggtcttt ccagtactct tggatcggaa acccgtcggc   8100
ctccgaacgg taagagccta gcatgtagaa ctggttgacg gcctggtagg cgcagcatcc   8160
cttttctacg ggtagcgcgt atgcctgcgc ggccttccgg agcgaggtgt gggtgagcgc   8220
aaaggtgtcc ctgaccatga ctttgaggta ctggtatttg aagtcagtgt cgtcgcatcc   8280
gccctgctcc cagagcaaaa agtccgtgcg ctttttggaa cgcggatttg gcagggcgaa   8340
ggtgacatcg ttgaagagta tctttcccgc gcgaggcata aagttgcgtg tgatgcggaa   8400
gggtcccggc acctcggaac ggttgttaat tacctgggcg gcgagcacga tctcgtcaaa   8460
gccgttgatg ttgtggccca caatgtaaag ttccaagaag cgcgggatgc ccttgatgga   8520
aggcaatttt ttaagttcct cgtaggtgag ctcttcaggg gagctgagcc cgtgctctga   8580
aagggcccag tctgcaagat gagggttgga agcgacgaat gagctccaca ggtcacgggc   8640
cattagcatt tgcaggtggt cgcgaaaggt cctaaactgg cgacctatgg ccattttttc   8700
tggggtgatg cagtagaagg taagcgggtc ttgttcccag cggtcccatc caaggttcgc   8760
ggctaggtct cgcgcggcag tcactagagg ctcatctccg ccgaacttca tgaccagcat   8820
gaagggcacg agctgcttcc caaaggcccc catccaagta taggtctcta catcgtaggt   8880
gacaaagaga cgctcggtgc gaggatgcga gccgatcggg aagaactgga tctcccgcca   8940
ccaattggag gagtggctat tgatgtggtg aaagtagaag tccctgcgac gggccgaaca   9000
ctcgtgctgg cttttgtaaa aacgtgcgca gtactggcag cggtgcacgg gctgtacatc   9060
ctgcacgagg ttgacctgac gaccgcgcac aaggaagcag agtgggaatt tgagcccctc   9120
gcctggcggg tttggctggt ggtcttctac ttcggctgct tgtccttgac cgtctggctg   9180
ctcgagggga gttacggtgg atcggaccac cacgccgcgc gagcccaaag tccagatgtc   9240
cgcgcgcggc ggtcggagct tgatgacaac atcgcgcaga tgggagctgt ccatggtctg   9300
gagctcccgc ggcgtcaggt caggcgggag ctcctgcagg tttacctcgc atagacgggt   9360
```

-continued

```
cagggcgcgg gctagatcca ggtgatacct aatttccagg ggctggttgg tggcggcgtc   9420
gatggcttgc aagaggccgc atccccgcgg cgcgactacg gtaccgcgcg gcgggcggtg   9480
ggccgcgggg gtgtccttgg atgatgcatc taaaagcggt gacgcgggcg agcccccgga   9540
ggtagggggg gctccggacc cgccgggaga gggggcaggg gcacgtcggc gccgcgcgcg   9600
ggcaggagct ggtgctgcgc gcgtaggttg ctggcgaacg cgacgacgcg gcggttgatc   9660
tcctgaatct ggcgcctctg cgtgaagacg acgggcccgg tgagcttgaa cctgaaagag   9720
agttcgacag aatcaatttc ggtgtcgttg acggcggcct ggcgcaaaat ctcctgcacg   9780
tctcctgagt tgtcttgata ggcgatctcg gccatgaact gctcgatctc ttcctcctgg   9840
agatctccgc gtccggctcg ctccacggtg gcggcgaggt cgttggaaat gcgggccatg   9900
agctgcgaga aggcgttgag gcctccctcg ttccagacgc ggctgtagac cacgcccccct  9960
tcggcatcgc gggcgcgcat gaccacctgc gcgagattga gctccacgtg ccgggcgaag  10020
acggcgtagt ttcgcaggcg ctgaaagagg tagttgaggg tggtggcggt gtgttctgcc  10080
acgaagaagt acataaccca gcgtcgcaac gtggattcgt tgatatcccc caaggcctca  10140
aggcgctcca tggcctcgta gaagtccacg gcgaagttga aaaactggga gttgcgcgcc  10200
gacacggtta actcctcctc cagaagacgg atgagctcgg cgacagtgtc gcgcacctcg  10260
cgctcaaagg ctacaggggc ctcttcttct tcttcaatct cctcttccat aagggcctcc  10320
ccttcttctt cttctggcgg cggtggggga gggggggacac ggcggcgacg acggcgcacc  10380
gggaggcggt cgacaaagcg ctcgatcatc tccccgcggc gacggcgcat ggtctcggtg  10440
acggcgcggc cgttctcgcg gggcgcagt tggaagacgc cgcccgtcat gtcccggtta  10500
tgggttggcg gggggctgcc atgcggcagg gatacggcgc taacgatgca tctcaacaat  10560
tgttgtgtag gtactccgcc gccgagggac ctgagcgagt ccgcatcgac cggatcggaa  10620
aacctctcga gaaaggcgtc taaccagtca cagtcgcaag gtaggctgag caccgtggcg  10680
ggcggcagcg ggcggcggtc ggggttgttt ctggcggagg tgctgctgat gatgtaatta  10740
aagtaggcgg tcttgagacg gcggatggtc gacagaagca ccatgtcctt gggtccggcc  10800
tgctgaatgc gcaggcggtc ggccatgccc caggcttcgt tttgacatcg gcgcaggtct  10860
ttgtagtagt cttgcatgag cctttctacc ggcacttctt cttctccttc ctcttgtcct  10920
gcatctcttg catctatcgc tgcggcggcg gcggagtttg gccgtaggtg gcgccctctt  10980
cctcccatgc gtgtgacccc gaagcccctc atcggctgaa gcagggctag gtcggcgaca  11040
acgcgctcgg ctaatatggc ctgctgcacc tgcgtgaggg tagactggaa gtcatccatg  11100
tccacaaagc ggtggtatgc gcccgtgttg atggtgtaag tgcagttggc cataacggac  11160
cagttaacgg tctggtgacc cggctgcgag agctcggtgt acctgagacg cgagtaagcc  11220
ctcgagtcaa atacgtagtc gttgcaagtc cgcaccaggt actggtatcc caccaaaaag  11280
tgcggcggcg gctggcggta gaggggccag cgtagggtgg ccggggctcc gggggcgaga  11340
tcttccaaca taaggcgatg atatccgtag atgtacctgg acatccaggt gatgccggcg  11400
gcggtggtgg aggcgcgcgg aaagtcgcgg acgcggttcc agatgttgcg cagcggcaaa  11460
aagtgctcca tggtcgggac gctctggccg gtcaggcgcg cgcaatcgtt gacgctctag  11520
accgtgcaaa aggagagcct gtaagcgggc actcttccgt ggtctggtgg ataaattcgc  11580
aagggtatca tggcggacga ccggggttcg agccccgtat ccggccgtcc gccgtgatcc  11640
atgcggttac cgcccgcgtg tcgaacccag gtgtgcgacg tcagacaacg gggagtgct  11700
ccttttggct tccttccagg cgcggcggct gctgcgctag ctttttggc cactggccgc  11760
```

-continued

```
gcgcagcgta agcggttagg ctggaaagcg aaagcattaa gtggctcgct ccctgtagcc  11820
ggagggttat tttccaaggg ttgagtcgcg ggacccccgg ttcgagtctc ggaccggccg  11880
gactgcggcg aacgggggtt tgcctccccg tcatgcaaga ccccgcttgc aaattcctcc  11940
ggaaacaggg acgagcccct tttttgcttt tcccagatgc atccggtgct gcggcagatg  12000
cgcccccctc ctcagcagcg gcaagagcaa gagcagcggc agacatgcag ggcaccctcc  12060
cctcctccta ccgcgtcagg aggggcgaca tccgcggttg acgcggcagc agatggtgat  12120
tacgaacccc cgcggcgccg ggcccggcac tacctggact tggaggaggg cgagggcctg  12180
gcgcggctag gagcgccctc tcctgagcgg cacccaaggg tgcagctgaa gcgtgatacg  12240
cgtgaggcgt acgtgccgcg gcagaacctg tttcgcgacc gcgagggaga ggagcccgag  12300
gagatgcggg atcgaaagtt ccacgcaggg cgcgagctgc ggcatggcct gaatcgcgag  12360
cggttgctgc gcgaggagga ctttgagccc gacgcgcgaa ccgggattag tcccgcgcgc  12420
gcacacgtgg cggccgccga cctggtaacc gcatacgagc agacggtgaa ccaggagatt  12480
aactttcaaa aaagctttaa caaccacgtg cgtacgcttg tggcgcgcga ggaggtggct  12540
ataggactga tgcatctgtg ggactttgta agcgcgctgg agcaaaaccc aaatagcaag  12600
ccgctcatgg cgcagctgtt ccttatagtg cagcacagca gggacaacga ggcattcagg  12660
gatgcgctgc taaacatagt agagcccgag ggccgctggc tgctcgattt gataaacatc  12720
ctgcagagca tagtggtgca ggagcgcagc ttgagcctgg ctgacaaggt ggccgccatc  12780
aactattcca tgcttagcct gggcaagttt tacgcccgca agatatacca taccccttac  12840
gttcccatag acaaggaggt aaagatcgag gggttctaca tgcgcatggc gctgaaggtg  12900
cttaccttga gcgacgacct gggcgtttat cgcaacgagc gcatccacaa ggccgtgagc  12960
gtgagccggc ggcgcgagct cagcgaccgc gagctgatgc acagcctgca aagggccctg  13020
gctggcacgg gcagcggcga tagagaggcc gagtcctact ttgacgcggg cgctgacctg  13080
cgctgggccc caagccgacg cgccctggag gcagctgggg ccggacctgg gctggcggtg  13140
gcacccgcgc gcgctggcaa cgtcggcggc gtggaggaat atgacgagga cgatgagtac  13200
gagccagagg acggcgagta ctaagcggtg atgtttctga tcagatgatg caagacgcaa  13260
cggacccggc ggtgcgggcg gcgctgcaga gccagccgtc cggccttaac tccacggacg  13320
actggcgcca ggtcatggac cgcatcatgt cgctgactgc gcgcaatcct gacgcgttcc  13380
ggcagcagcc gcaggccaac cggctctccg caattctgga agcggtggtc ccggcgcgcg  13440
caaaccccac gcacgagaag gtgctggcga tcgtaaacgc gctggccgaa aacagggcca  13500
tccggcccga cgaggccggc ctggtctacg acgcgctgct tcagcgcgtg gctcgttaca  13560
acagcggcaa cgtgcagacc aacctggacc ggctggtggg ggatgtgcgc gaggccgtgg  13620
cgcagcgtga gcgcgcgcag cagcagggca acctgggctc catggttgca ctaaacgcct  13680
tcctgagtac acagcccgcc aacgtgccgc ggggacagga ggactacacc aactttgtga  13740
gcgcactgcg gctaatggtg actgagacac cgcaaagtga ggtgtaccag tctgggccag  13800
actatttttt ccagaccagt agacaaggcc tgcagaccgt aaacctgagc caggctttca  13860
aaaacttgca ggggctgtgg ggggtgcggg ctcccacagg cgaccgcgcg accgtgtcta  13920
gcttgctgac gcccaactcg cgcctgttgc tgctgctaat agcgcccttc acggacagtg  13980
gcagcgtgtc ccgggacaca tacctaggtc acttgctgac actgtaccgc gaggccatag  14040
gtcaggcgca tgtggacgag catactttcc aggagattac aagtgtcagc cgcgcgctgg  14100
```

```
ggcaggagga cacgggcagc ctggaggcaa ccctaaacta cctgctgacc aaccggcggc  14160
agaagatccc ctcgttgcac agtttaaaca gcgaggagga gcgcattttg cgctacgtgc  14220
agcagagcgt gagccttaac ctgatgcgcg acggggtaac gcccagcgtg gcgctggaca  14280
tgaccgcgcg caacatggaa ccgggcatgt atgcctcaaa ccggccgttt atcaaccgcc  14340
taatggacta cttgcatcgc gcggccgccg tgaaccccga gtatttcacc aatgccatct  14400
tgaacccgca ctggctaccg ccccctggtt tctacaccgg gggattcgag gtgcccgagg  14460
gtaacgatgg attcctctgg gacgacatag acgacagcgt gttttccccg caaccgcaga  14520
ccctgctaga gttgcaacag cgcgagcagg cagaggcggc gctgcgaaag gaaagcttcc  14580
gcaggccaag cagcttgtcc gatctaggcg ctgcggcccc gcggtcagat gctagtagcc  14640
catttccaag cttgataggg tctcttacca gcactcgcac cacccgcccg cgcctgctgg  14700
gcgaggagga gtacctaaac aactcgctgc tgcagccgca gcgcgaaaaa aacctgcctc  14760
cggcatttcc caacaacggg atagagagcc tagtggacaa gatgagtaga tggaagacgt  14820
acgcgcagga gcacagggac gtgccaggcc cgcgcccgcc cacccgtcgt caaaggcacg  14880
accgtcagcg gggtctggtg tgggaggacg atgactcggc agacgacagc agcgtcctgg  14940
atttgggagg gagtggcaac ccgtttgcgc accttcgccc caggctgggg agaatgtttt  15000
aaaaaaaaaa aaaaagcatg atgcaaaata aaaaactcac caaggccatg gcaccgagcg  15060
ttggttttct tgtattcccc ttagtatgcg gcgcgcggcg atgtatgagg aaggtcctcc  15120
tccctcctac gagagtgtgg tgagcgcggc gccagtggcg gcggcgctgg gttctccctt  15180
cgatgctccc ctggacccgc cgtttgtgcc tccgcggtac ctgcggccta ccggggggag  15240
aaacagcatc cgttactctg agttggcacc cctattcgac accacccgtg tgtacctggt  15300
ggacaacaag tcaacggatg tggcatccct gaactaccag aacgaccaca gcaactttct  15360
gaccacggtc attcaaaaca atgactacag cccgggggag gcaagcacac agaccatcaa  15420
tcttgacgac cggtcgcact ggggcggcga cctgaaaacc atcctgcata ccaacatgcc  15480
aaatgtgaac gagttcatgt ttaccaataa gtttaaggcg cgggtgatgg tgtcgcgctt  15540
gcctactaag gacaatcagg tggagctgaa atacgagtgg gtggagttca cgctgcccga  15600
gggcaactac tccgagacca tgaccataga ccttatgaac aacgcgatcg tggagcacta  15660
cttgaaagtg ggcagacaga acggggttct ggaaagcgac atcggggtaa agtttgacac  15720
ccgcaacttc agactggggt ttgaccccgt cactggtctt gtcatgcctg ggtatatac   15780
aaacgaagcc ttccatccag acatcatttt gctgccagga tgcggggtgg acttcaccca  15840
cagccgcctg agcaacttgt tgggcatccg caagcggcaa cccttccagg agggctttag  15900
gatcacctac gatgatctgg agggtggtaa cattcccgca ctgttggatg tggacgccta  15960
ccaggcgagc ttgaaagatg acaccgaaca gggcgggggt ggcgcaggcg gcagcaacag  16020
cagtggcagc ggcgcggaag agaactccaa cgcggcagcc gcggcaatgc agccggtgga  16080
ggacatgaac gatcatgcca ttcgcggcga cacctttgcc acacgggctg aggagaagcg  16140
cgctgaggcc gaagcagcgg ccgaagctgc cgcccccgct gcgcaacccg aggtcgagaa  16200
gcctcagaag aaaccggtga tcaaacccct gacagaggac agcaagaaac gcagttacaa  16260
cctaataagc aatgacagca ccttcaccca gtaccgcagc tggtaccttg catacaacta  16320
cggcgaccct cagaccggaa tccgctcatg gaccctgctt tgcactcctg acgtaacctg  16380
cggctcggag caggtctact ggtcgttgcc agacatgatg caagaccccg tgaccttccg  16440
ctccacgcgc cagatcagca actttccggt ggtgggcgcc gagctgttgc ccgtgcactc  16500
```

caagagcttc tacaacgacc aggccgtcta ctcccaactc atccgccagt ttacctctct 16560
gacccacgtg ttcaatcgct ttcccgagaa ccagattttg gcgcgcccgc cagcccccac 16620
catcaccacc gtcagtgaaa acgttcctgc tctcacagat cacgggacgc taccgctgcg 16680
caacagcatc ggaggagtcc agcgagtgac cattactgac gccagacgcc gcacctgccc 16740
ctacgtttac aaggccctgg gcatagtctc gccgcgcgtc ctatcgagcc gcactttttg 16800
agcaagcatg tccatcctta tatcgcccag caataacaca ggctggggcc tgcgcttccc 16860
aagcaagatg tttggcgggg ccaagaagcg ctccgaccaa cacccagtgc gcgtgcgcgg 16920
gcactaccgc gcgccctggg gcgcgcacaa acgcggccgc actgggcgca ccaccgtcga 16980
tgacgccatc gacgcggtgg tggaggaggc gcgcaactac acgcccacgc cgccaccagt 17040
gtccacagtg gacgcggcca ttcagaccgt ggtgcgcgga gcccggcgct atgctaaaat 17100
gaagagacgg cggaggcgcg tagcacgtcg ccaccgccgc cgacccggca ctgccgccca 17160
acgcgcggcg gcggccctgc ttaaccgcgc acgtcgcacc ggccgacggg cggccatgcg 17220
ggccgctcga aggctggccg cgggtattgt cactgtgccc cccaggtcca ggcgacgagc 17280
ggccgccgca gcagccgcgg ccattagtgc tatgactcag ggtcgcaggg gcaacgtgta 17340
ttgggtgcgc gactcggtta gcggcctgcg cgtgcccgtg cgcacccgcc ccccgcgcaa 17400
ctagattgca agaaaaaact acttagactc gtactgttgt atgtatccag cggcggcggc 17460
gcgcaacgaa gctatgtcca agcgcaaaat caaagaagag atgctccagg tcatcgcgcc 17520
ggagatctat ggcccccga agaaggaaga gcaggattac aagccccgaa agctaaagcg 17580
ggtcaaaaag aaaaagaaag atgatgatga tgaacttgac gacgaggtgg aactgctgca 17640
cgctaccgcg cccaggcgac gggtacagtg gaaaggtcga cgcgtaaaac gtgttttgcg 17700
acccggcacc accgtagtct ttacgcccgg tgagcgctcc acccgcacct acaagcgcgt 17760
gtatgatgag gtgtacggcg acgaggacct gcttgagcag gccaacgagc gcctcgggga 17820
gtttgcctac ggaaagcggc ataaggacat gctggcgttg ccgctggacg agggcaaccc 17880
aacacctagc ctaaagcccg taacactgca gcaggtgctg cccgcgcttg caccgtccga 17940
agaaaagcgc ggcctaaagc gcgagtctgg tgacttggca cccaccgtgc agctgatggt 18000
acccaagcgc cagcgactgg aagatgtctt ggaaaaaatg accgtggaac ctgggctgga 18060
gcccgaggtc cgcgtgcggc caatcaagca ggtggcgccg ggactgggcg tgcagaccgt 18120
ggacgttcag atacccacta ccagtagcac cagtattgcc accgccacag agggcatgga 18180
gacacaaacg tccccggttg cctcagcggt ggcggatgcc gcggtgcagg cggtcgctgc 18240
ggccgcgtcc aagacctcta cggaggtgca aacggacccg tggatgtttc gcgtttcagc 18300
cccccggcgc ccgcgccgtt cgaggaagta cggcgccgcc agcgcgctac tgcccgaata 18360
tgccctacat ccttccattg cgcctacccc cggctatcgt ggctacacct accgccccag 18420
aagacgagca actacccgac gccgaaccac cactggaacc cgccgccgcc gtcgccgtcg 18480
ccagcccgtg ctggccccga tttccgtgcg cagggtggct cgcgaaggag gcaggaccct 18540
ggtgctgcca acagcgcgct accaccccag catcgtttaa aagccggtct ttgtggttct 18600
tgcagatatg gccctcacct gccgcctccg tttcccggtg ccgggattcc gaggaagaat 18660
gcaccgtagg aggggcatgg ccggccacgg cctgacgggc ggcatgcgtc gtgcgcacca 18720
ccggcggcgg cgcgcgtcgc accgtcgcat gcgcggcggt atcctgcccc tccttattcc 18780
actgatcgcc gcggcgattg gcgccgtgcc cggaattgca tccgtggcct tgcaggcgca 18840

-continued gagacactga ttaaaaacaa gttgcatgtg gaaaaatcaa aataaaaagt ctggactctc 18900
acgctcgctt ggtcctgtaa ctattttgta gaatggaaga catcaacttt gcgtctctgg 18960
ccccgcgaca cggctcgcgc ccgttcatgg gaaactggca agatatcggc accagcaata 19020
tgagcggtgg cgccttcagc tggggctcgc tgtggagcgg cattaaaaat ttcggttcca 19080
ccgttaagaa ctatggcagc aaggcctgga acagcagcac aggccagatg ctgagggata 19140
agttgaaaga gcaaaatttc caacaaaagg tggtagatgg cctggcctct ggcattagcg 19200
gggtggtgga cctggccaac caggcagtgc aaaataagat taacagtaag cttgatcccc 19260
gccctcccgt agaggagcct ccaccggccg tggagacagt gtctccagag ggcgtggcg 19320
aaaagcgtcc gcgccccgac agggaagaaa ctctggtgac gcaaatagac gagcctccct 19380
cgtacgagga ggcactaaag caaggcctgc ccaccacccg tcccatcgcg cccatggcta 19440
ccggagtgct gggccagcac acacccgtaa cgctggacct gcctcccccc gccgacaccc 19500
agcagaaacc tgtgctgcca ggcccgaccg ccgttgttgt aacccgtcct agccgcgcgt 19560
ccctgcgccg cgccgccagc ggtccgcgat cgttgcggcc cgtagccagt ggcaactggc 19620
aaagcacact gaacagcatc gtgggtctgg gggtgcaatc cctgaagcgc cgacgatgct 19680
tctgaatagc taacgtgtcg tatgtgtgtc atgtatgcgt ccatgtcgcc gccagaggag 19740
ctgctgagcc gccgcgcgcc cgctttccaa gatggctacc ccttcgatga tgccgcagtg 19800
gtcttacatg cacatctcgg gccaggacgc ctcggagtac ctgagccccg ggctggtgca 19860
gtttgcccgc gccaccgaga cgtacttcag cctgaataac aagtttagaa accccacggt 19920
ggcgcctacg cacgacgtga ccacagaccg gtcccagcgt ttgacgctgc ggttcatccc 19980
tgtggaccgt gaggatactg cgtactcgta caaggcgcgg ttcaccctag ctgtgggtga 20040
taaccgtgtg ctggacatgg cttccacgta ctttgacatc cgcggcgtgc tggacagggg 20100
ccctactttt aagccctact ctggcactgc ctacaacgcc ctggctccca agggtgcccc 20160
aaatccttgc gaatgggatg aagctgctac tgctcttgaa ataaacctag aagaagagga 20220
cgatgacaac gaagacgaag tagacgagca agctgagcag caaaaaactc acgtatttgg 20280
gcaggcgcct tattctggta taaatattac aaaggagggt attcaaatag gtgtcgaagg 20340
tcaaacacct aaatatgccg ataaaacatt tcaacctgaa cctcaaatag gagaatctca 20400
gtggtacgaa actgaaatta atcatgcagc tgggagagtc cttaaaaaga ctaccccaat 20460
gaaaccatgt tacggttcat atgcaaaacc cacaaatgaa aatggagggc aaggcattct 20520
tgtaaagcaa caaaatggaa agctagaaag tcaagtggaa atgcaatttt tctcaactac 20580
tgaggcgacc gcaggcaatg gtgataactt gactcctaaa gtggtattgt acagtgaaga 20640
tgtagatata gaaaccccag acactcatat ttcttacatg cccactatta aggaaggtaa 20700
ctcacgagaa ctaatgggcc aacaatctat gcccaacagg cctaattaca ttgcttttag 20760
ggacaatttt attggtctaa tgtattacaa cagcacgggt aatatgggtg ttctggcggg 20820
ccaagcatcg cagttgaatg ctgttgtaga tttgcaagac agaaacacag agctttcata 20880
ccagcttttg cttgattcca ttggtgatag aaccaggtac ttttctatgt ggaatcaggc 20940
tgttgacagc tatgatccag atgttagaat tattgaaaat catggaactg aagatgaact 21000
tccaaattac tgctttccac tgggaggtgt gattaataca gagactctta ccaaggtaaa 21060
acctaaaaca ggtcaggaaa atggatggga aaaagatgct acagaatttt cagataaaaa 21120
tcaaataaga gttggaaata attttgccat ggaaatcaat ctaaatgcca acctgtggag 21180
aaatttcctg tactccaaca tagcgctgta tttgcccgac aagctaaagt acagtccttc 21240

```
caacgtaaaa atttctgata acccaaacac ctacgactac atgaacaagc gagtggtggc  21300
tcccgggtta gtggactgct acattaacct tggagcacgc tggtcccttg actatatgga  21360
caacgtcaac ccatttaacc accaccgcaa tgctggcctg cgctaccgct caatgttgct  21420
gggcaatggt cgctatgtgc ccttccacat ccaggtgcct cagaagttct ttgccattaa  21480
aaacctcctt ctcctgccgg gctcatacac ctacgagtgg aacttcagga aggatgttaa  21540
catggttctg cagagctccc taggaaatga cctaagggtt gacggagcca gcattaagtt  21600
tgatagcatt tgcctttacg ccaccttctt ccccatggcc cacaacaccg cctccacgct  21660
tgaggccatg cttagaaacg acaccaacga ccagtccttt aacgactatc tctccgccgc  21720
caacatgctc taccctatac ccgccaacgc taccaacgtg cccatatcca tcccctcccg  21780
caactgggcg gctttccgcg gctgggcctt cacgcgcctt aagactaagg aaaccccatc  21840
actgggctcg ggctacgacc cttattacac ctactctggc tctataccct acctagatgg  21900
aacctttac ctcaaccaca cctttaagaa ggtggccatt acctttgact cttctgtcag  21960
ctggcctggc aatgaccgcc tgcttacccc caacgagttt gaaattaagc gctcagttga  22020
cggggagggt tacaacgttg cccagtgtaa catgaccaaa gactggttcc tggtacaaat  22080
gctagctaac tacaacattg gctaccaggg cttctatatc ccagagagct acaaggaccg  22140
catgtactcc ttctttagaa acttccagcc catgagccgt caggtggtgg atgatactaa  22200
atacaaggac taccaacagg tgggcatcct acaccaacac aacaactctg gatttgttgg  22260
ctaccttgcc cccaccatgc gcgaaggaca ggcctaccct gctaacttcc cctatccgct  22320
tataggcaag accgcagttg acagcattac ccagaaaaag tttctttgcg atcgcaccct  22380
ttggcgcatc ccattctcca gtaactttat gtccatgggc gcactcacag acctgggcca  22440
aaaccttctc tacgccaact ccgcccacgc gctagacatg acttttgagg tggatcccat  22500
ggacgagccc acccttcttt atgttttgtt tgaagtcttt gacgtggtcc gtgtgcaccg  22560
gccgcaccgc ggcgtcatcg aaaccgtgta cctgcgcacg cccttctcgg ccggcaacgc  22620
cacaacataa agaagcaagc aacatcaaca acagctgccg ccatgggctc cagtgagcag  22680
gaactgaaag ccattgtcaa agatcttggt tgtgggccat attttttggg cacctatgac  22740
aagcgctttc caggctttgt ttctccacac aagctcgcct gcgccatagt caatacggcc  22800
ggtcgcgaga ctgggggcgt acactggatg gcctttgcct ggaacccgca ctcaaaaaca  22860
tgctacctct ttgagccctt tggcttttct gaccagcgac tcaagcaggt ttaccagttt  22920
gagtacgagt cactcctgcg ccgtagcgcc attgcttctt cccccgaccg ctgtataacg  22980
ctggaaaagt ccacccaaag cgtacagggg cccaactcgg ccgcctgtgg actattctgc  23040
tgcatgtttc tccacgcctt tgccaactgg ccccaaactc ccatggatca caaccccacc  23100
atgaacctta ttaccggggt acccaactcc atgctcaaca gtccccaggt acagcccacc  23160
ctgcgtcgca accaggaaca gctctacagc ttcctggagc gccactcgcc ctacttccgc  23220
agccacagtg cgcagattag gagcgccact tctttttgtc acttgaaaaa catgtaaaaa  23280
taatgtacta gagacacttt caataaaggc aaatgctttt atttgtacac tctcgggtga  23340
ttatttaccc ccacccttgc cgtctgcgcc gtttaaaaat caaaggggtt ctgccgcgca  23400
tcgctatgcg ccactggcag ggacacgttg cgatactggt gtttagtgct ccacttaaac  23460
tcaggcacaa ccatccgcgg cagctcggtg aagttttcac tccacaggct gcgcaccatc  23520
accaacgcgt ttagcaggtc gggcgccgat atcttgaagt cgcagttggg gcctccgccc  23580
```

-continued tgcgcgcgcg agttgcgata cacagggttg cagcactgga acactatcag cgccgggtgg 23640
tgcacgctgg ccagcacgct cttgtcggag atcagatccg cgtccaggtc ctccgcgttg 23700
ctcagggcga acggagtcaa ctttggtagc tgccttccca aaaagggcgc gtgcccaggc 23760
tttgagttgc actcgcaccg tagtggcatc aaaaggtgac cgtgcccggt ctgggcgtta 23820
ggatacagcg cctgcataaa agccttgatc tgcttaaaag ccacctgagc ctttgcgcct 23880
tcagagaaga acatgccgca agacttgccg gaaaactgat tggccggaca ggccgcgtcg 23940
tgcacgcagc accttgcgtc ggtgttggag atctgcacca catttcggcc ccaccggttc 24000
ttcacgatct tggccttgct agactgctcc ttcagcgcgc gctgcccgtt ttcgctcgtc 24060
acatccattt caatcacgtg ctccttattt atcataatgc ttccgtgtag acacttaagc 24120
tcgccttcga tctcagcgca gcggtgcagc cacaacgcgc agcccgtggg ctcgtgatgc 24180
ttgtaggtca cctctgcaaa cgactgcagg tacgcctgca ggaatcgccc catcatcgtc 24240
acaaaggtct tgttgctggt gaaggtcagc tgcaacccgc ggtgctcctc gttcagccag 24300
gtcttgcata cggccgccag agcttccact tggtcaggca gtagtttgaa gttcgccttt 24360
agatcgttat ccacgtggta cttgtccatc agcgcgcgcg cagcctccat gcccttctcc 24420
cacgcagaca cgatcggcac actcagcggg ttcatcaccg taatttcact ttccgcttcg 24480
ctgggctctt cctcttcctc ttgcgtccgc ataccacgcg ccactgggtc gtcttcattc 24540
agccgccgca ctgtgcgctt acctcctttg ccatgcttga ttagcaccgg tgggttgctg 24600
aaacccacca tttgtagcgc cacatcttct ctttcttcct cgctgtccac gattacctct 24660
ggtgatggcg ggcgctcggg cttgggagaa gggcgcttct ttttcttctt gggcgcaatg 24720
gccaaatccg ccgccgaggt cgatggccgc gggctgggtg tgcgcggcac cagcgcgtct 24780
tgtgatgagt cttcctcgtc ctcggactcg atacgccgcc tcatccgctt ttttgggggc 24840
gcccggggag gcggcggcga cggggacggg gacgacacgt cctccatggt tgggggacgt 24900
cgcgccgcac cgcgtccgcg ctcgggggtg gtttcgcgct gctcctcttc ccgactggcc 24960
atttccttct cctataggca gaaaaagatc atggagtcag tcgagaagaa ggacagccta 25020 accgcccccct ctgagttcgc caccaccgcc tccaccgatg ccgccaacgc gcctaccacc 25080
ttccccgtcg aggcaccccc gcttgaggag gaggaagtga ttatcgagca ggacccaggt 25140
tttgtaagcg aagacgacga ggaccgctca gtaccaacag aggataaaaa gcaagaccag 25200
gacaacgcag aggcaaacga ggaacaagtc gggcgggggg acgaaaggca tggcgactac 25260
ctagatgtgg gagacgacgt gctgttgaag catctgcagc gccagtgcgc cattatctgc 25320
gacgcgttgc aagagcgcag cgatgtgccc ctcgccatag cggatgtcag ccttgcctac 25380
gaacgccacc tattctcacc gcgcgtaccc cccaaacgcc aagaaaacgg cacatgcgag 25440
cccaacccgc gcctcaactt ctaccccgta tttgccgtgc cagaggtgct tgccacctat 25500
cacatctttt tccaaaactg caagataccc ctatcctgcc gtgccaaccg cagccgagcg 25560
gacaagcagc tggccttgcg gcagggcgct gtcatacctg atatcgcctc gctcaacgaa 25620
gtgccaaaaa tctttgaggg tcttggacgc gacgagaagc gcgcggcaaa cgctctgcaa 25680
caggaaaaca gcgaaaatga aagtcactct ggagtgttgg tggaactcga gggtgacaac 25740
gcgcgcctag ccgtactaaa acgcagcatc gaggtcaccc actttgccta cccggcactt 25800
aacctacccc ccaaggtcat gagcacagtc atgagtgagc tgatcgtgcg ccgtgcgcag 25860
cccctggaga gggatgcaaa tttgcaagaa caaacagagg agggcctacc cgcagttggc 25920
gacgagcagc tagcgcgctg gcttcaaacg cgcgagcctg ccgacttgga ggagcgacgc 25980

-continued

```
aaactaatga tggccgcagt gctcgttacc gtggagcttg agtgcatgca gcggttcttt  26040
gctgacccgg agatgcagcg caagctagag gaaacattgc actacacctt tcgacagggc  26100
tacgtacgcc aggcctgcaa gatctccaac gtggagctct gcaacctggt ctcctacctt  26160
ggaattttgc acgaaaaccg ccttgggcaa aacgtgcttc attccacgct caagggcgag  26220
gcgcgccgcg actacgtccg cgactgcgtt tacttatttc tatgctacac ctggcagacg  26280
gccatgggcg tttggcagca gtgcttggag gagtgcaacc tcaaggagct gcagaaactg  26340
ctaaagcaaa acttgaagga cctatggacg gccttcaacg agcgctccgt ggccgcgcac  26400
ctggcggaca tcattttccc cgaacgcctg cttaaaaccc tgcaacaggg tctgccagac  26460
ttcaccagtc aaagcatgtt gcagaacttt aggaacttta tcctagagcg ctcaggaatc  26520
ttgcccgcca cctgctgtgc acttcctagc gactttgtgc ccattaagta ccgcgaatgc  26580
cctccgccgc tttggggcca ctgctacctt ctgcagctag ccaactacct tgcctaccac  26640
tctgacataa tggaagacgt gagcggtgac ggtctactgg agtgtcactg tcgctgcaac  26700
ctatgcaccc cgcaccgctc cctggtttgc aattcgcagc tgcttaacga aagtcaaatt  26760
atcggtacct ttgagctgca gggtccctcg cctgacgaaa agtccgcggc tccggggttg  26820
aaactcactc cggggctgtg gacgtcggct taccttcgca aatttgtacc tgaggactac  26880
cacgcccacg agattaggtt ctacgaagac caatcccgcc cgccaaatgc ggagcttacc  26940
gcctgcgtca ttacccaggg ccacattctt ggccaattgc aagccatcaa caaagcccgc  27000
caagagtttc tgctacgaaa gggacggggg gtttacttgg acccccagtc cggcgaggag  27060
ctcaacccaa tcccccgcc gccgcagccc tatcagcagc agccgcgggc ccttgcttcc  27120
caggatggca cccaaaaaga agctgcagct gccgccgcca cccacggacg aggaggaata  27180
ctgggacagt caggcagagg aggttttgga cgaggaggag gaggacatga tggaagactg  27240
ggagagccta gacgaggaag cttccgaggt cgaagaggtg tcagacgaaa caccgtcacc  27300
ctcggtcgca ttcccctcgc cggcgcccca gaaatcggca accggttcca gcatggctac  27360
aacctccgct cctcaggcgc cgccggcact gcccgttcgc cgacccaacc gtagatggga  27420
caccactgga accagggccg gtaagtccaa gcagccgccg ccgttagccc aagagcaaca  27480
acagcgccaa ggctaccgct catggcgcgg gcacaagaac gccatagttg cttgcttgca  27540
agactgtggg ggcaacatct ccttcgcccg ccgctttctt ctctaccatc acggcgtggc  27600
cttcccccgt aacatcctgc attactaccg tcatctctac agcccatact gcaccggcgg  27660
cagcggcagc ggcagcaaca gcagcggcca cacagaagca aaggcgaccg gatagcaaga  27720
ctctgacaaa gcccaagaaa tccacagcgg cggcagcagc aggaggagga gcgctgcgtc  27780
tggcgcccaa cgaacccgta tcgacccgcg agcttagaaa caggattttt cccactctgt  27840
atgctatatt tcaacagagc aggggccaag aacaagagct gaaaataaaa aacaggtctc  27900
tgcgatccct cacccgcagc tgcctgtatc acaaaagcga agatcagctt cggcgcacgc  27960
tggaagacgc ggaggctctc ttcagtaaat actgcgcgct gactcttaag gactagtttc  28020
gcgccctttc tcaaatttaa gcgcgaaaac tacgtcatct ccagcggcca cacccggcgc  28080
cagcacctgt cgtcagcgcc atttcaactt tgtatacaaa agttgtgatg agcaaggaaa  28140
ttcccacgcc ctacatgtgg agttaccagc cacaaatggg acttgcggct ggagctgccc  28200
aagactactc aacccgaata aactacatga gcgcgggacc ccacatgata tcccgggtca  28260
acggaatacg cgcccaccga aaccgaattc tcctggaaca ggcggctatt accaccacac  28320
```

-continued

```
ctcgtaataa ccttaatccc cgtagttggc ccgctgccct ggtgtaccag gaaagtcccg  28380
ctcccaccac tgtggtactt cccagagacg cccaggccga agttcagatg actaactcag  28440
gggcgcagct tgcgggcggc tttcgtcaca gggtgcggtc gcccgggcag ggtataactc  28500
acctgacaat cagagggcga ggtattcagc tcaacgacga gtcggtgagc tcctcgcttg  28560
gtctccgtcc ggacgggaca tttcagatcg gcggcgccgg ccgctcttca ttcacgcctc  28620
gtcaggcaat cctaactctg cagacctcgt cctctgagcc gcgctctgga ggcattggaa  28680
ctctgcaatt tattgaggag tttgtgccat cggtctactt taaccccttc tcgggacctc  28740
ccggccacta tccggatcaa tttattccta actttgacgc ggtaaaggac tcggcggacg  28800
gctacgactg aatgttaagt ggagaggcag agcaactgcg cctgaaacac ctggtccact  28860
gtcgccgcca caagtgcttt gcccgcgact ccggtgagtt ttgctacttt gaattgcccg  28920
aggatcatat cgagggcccg gcgcacggcg tccggcttac cgcccaggga gagcttgccc  28980
gtagcctgat tcgggagttt acccagcgcc ccctgctagt tgagcgggac aggggaccct  29040
gtgttctcac tgtgatttgc aactgtccta accctggatt acatcaagat ctttgttgcc  29100
atctctgtgc tgagtataat aaatacagaa attaaaatat actggggctc ctatcgccat  29160
cctgtaaacg ccaccgtctt cacccgccca agcaaaccaa ggcgaacctt acctggtact  29220
tttaacatct ctccctctgt gatttacaac agtttcaacc cagacggagt gagtctacga  29280
gagaacctct ccgagctcag ctactccatc agaaaaaaca ccaccctcct tacctgccgg  29340
gaacgtacga gtgcgtcacc ggccgctgca ccacacctac cgcctgaccg taaaccagac  29400
tttttccgga cagacctcaa taactctgtt taccagaaca ggaggtgagc ttagaaaacc  29460
cttagggtat taggccaaag gcgcagctac tgtggggttt atgaacaatt caagcaactc  29520
tacgggctat tctaattcag gtttctctag aatcggggtt ggggttattc tctgtcttgt  29580
gattctcttt attcttatac taacgcttct ctgcctaagg ctcgccgcct gctgtgtgca  29640
catttgcatt tattgtcagc tttttaaacg ctggggtcgc cacccaagat gattaggtac  29700
ataatcctag gtttactcac ccttgcgtca gcccacggta ccacccaaaa ggtggatttt  29760
aaggagccag cctgtaatgt tacattcgca gctgaagcta atgagtgcac cactcttata  29820
aaatgcacca cagaacatga aaagctgctt attcgccaca aaaacaaaat tggcaagtat  29880
gctgtttatg ctatttggca gccaggtgac actacagagt ataatgttac agttttccag  29940
ggtaaaagtc ataaaacttt tatgtatact tttccatttt atgaaatgtg cgacattacc  30000
atgtacatga gcaaacagta taagttgtgg cccccacaaa attgtgtgga aaacactggc  30060
actttctgct gcactgctat gctaattaca gtgctcgctt tggtctgtac cctactctat  30120
attaaataca aaagcagacg cagctttatt gaggaaaaga aaatgcctta atttactaag  30180
ttacaaagct aatgtcacca ctaactgctt tactcgctgc ttgcaaaaca aattcaaaaa  30240
gttagcatta taattagaat aggatttaaa ccccccggtc atttcctgct caataccatt  30300
cccctgaaca attgactcta tgtgggatat gctccagcgc tacaaccttg aagtcaggct  30360
tcctggatgt cagcatctga ctttggccag cacctgtccc gcggatttgt tccagtccaa  30420
ctacagcgac ccaccctaac agagatgacc aacacaacca acgcggccgc cgctaccgga  30480
cttacatcta ccacaaatac accccaagtt tctgcctttg tcaataactg ggataacttg  30540
ggcatgtggt ggttctccat agcgcttatg tttgtatgcc ttattattat gtggctcatc  30600
tgctgcctaa agcgcaaacg cgcccgacca cccatctata gtcccatcat tgtgctacac  30660
ccaaacaatg atggaatcca tagattggac ggactgaaac acatgttctt ttctcttaca  30720
```

```
gtatgattaa atgagacatg attcctcgag tttttatatt actgaccctt gttgcgcttt  30780
tttgtgcgtg ctccacattg gctgcggttt ctcacatcga agtagactgc attccagcct  30840
tcacagtcta tttgctttac ggatttgtca ccctcacgct catctgcagc ctcatcactg  30900
tggtcatcgc ctttatccag tgcattgact gggtctgtgt gcgctttgca tatctcagac  30960
accatcccca gtacagggac aggactatag ctgagcttct tagaattctt taattatgaa  31020
atttactgtg acttttctgc tgattatttg caccctatct gcgttttgtt ccccgacctc  31080
caagcctcaa agacatatat catgcagatt cactcgtata tggaatattc caagttgcta  31140
caatgaaaaa agcgatcttt ccgaagcctg gttatatgca atcatctctg ttatggtgtt  31200
ctgcagtacc atcttagccc tagctatata tccctacctt gacattggct ggaacgcaat  31260
agatgccatg aaccacccaa ctttccccgc gcccgctatg cttccactgc aacaagttgt  31320
tgccggcggc tttgtcccag ccaatcagcc tcgcccacct tctcccaccc ccactgaaat  31380
cagctacttt aatctaacag gaggagatga ctgacaccct agatctagaa atggacggaa  31440
ttattacaga gcagcgcctg ctagaaagac gcagggcagc ggccgagcaa cagcgcatga  31500
atcaagagct ccaagacatg gttaacttgc accagtgcaa aaggggtatc ttttgtctgg  31560
taaagcaggc caaagtcacc tacgacagta ataccaccgg acaccgcctt agctacaagt  31620
tgccaaccaa gcgtcagaaa ttggtggtca tggtgggaga aaagcccatt accataactc  31680
agcactcggt agaaaccgaa ggctgcattc actcaccttg tcaaggacct gaggatctct  31740
gcacccttat taagaccctg tgcggtctca aagatcttat tccctttaac taataaaaaa  31800
aaataataaa gcatcactta cttaaaatca gttagcaaat ttctgtccag tttattcagc  31860
agcacctcct tgccctcctc ccagctctgg tattgcagct tcctcctggc tgcaaacttt  31920
ctccacaatc taaatggaat gtcagtttcc tcctgttcct gtccatccgc acccactatc  31980
ttcatgttgt tgcagatgaa gcgcgcaaga ccgtctgaag ataccttcaa ccccgtgtat  32040
ccatatgaca cggaaaccgg tcctccaact gtgccttttc ttactcctcc ctttgtatcc  32100
cccaatgggt ttcaagagag tccccctggg gtactctctt tgcgcctatc cgaacctcta  32160
gttacctcca atggcatgct tgcgctcaaa atgggcaacg gcctctctct ggacgaggcc  32220
ggcaacctta cctcccaaaa tgtaaccact gtgagcccac ctctcaaaaa aaccaagtca  32280
aacataaacc tggaaatatc tgcacccctc acagttacct cagaagccct aactgtggct  32340
gccgccgcac ctctaatggt cgcgggcaac acactcacca tgcaatcaca ggccccgcta  32400
accgtgcacg actccaaact tagcattgcc acccaaggac ccctcacagt gtcagaagga  32460
aagctagccc tgcaaacatc aggccccctc accaccaccg atagcagtac ccttactatc  32520
actgcctcac cccctctaac tactgccact ggtagcttgg gcattgactt gaaagagccc  32580
atttatacac aaaatggaaa actaggacta aagtacgggg ctcctttgca tgtaacagac  32640
gacctaaaca ctttgaccgt agcaactggt ccaggtgtga ctattaataa tacttccttg  32700
caaactaaag ttactggagc cttgggtttt gattcacaag gcaatatgca acttaatgta  32760
gcaggaggac taaggattga ttctcaaaac agacgcctta tacttgatgt tagttatccg  32820
tttgatgctc aaaaccaact aaatctaaga ctaggacagg gccctctttt tataaactca  32880
gcccacaact tggatattaa ctacaacaaa ggcctttact tgtttacagc ttcaaacaat  32940
tccaaaaagc ttgaggttaa cctaagcact gccaaggggt tgatgtttga cgctacagcc  33000
atagccatta atgcaggaga tgggcttgaa tttggttcac ctaatgcacc aaacacaaat  33060
```

-continued

```
ccccctcaaaa caaaaattgg ccatggccta gaatttgatt caaacaaggc tatggttcct  33120
aaactaggaa ctggccttag ttttgacagc acaggtgcca ttacagtagg aaacaaaaat  33180
aatgataagc taactttatg gacaactcca gacacatctc caaattgcaa gattgatcaa  33240
gataaggact ctaagttaac tctggtcctt acaaagtgtg gaagtcaaat attggctaat  33300
gtgtcattaa ttgtcgtagc tggtaagtac aaaattatca ataacaatac tcaaccagct  33360
ctcaaaggat ttaccattaa attattgttt gatgaaaatg gagtacttat ggaatcttca  33420
aatcttggta aatcatattg gaactttaga aatgaaaatt caattatgtc aacagcttat  33480
gaaaaagcta ttggattcat gcctaatttg gtagcctatc caaaacctac cgctggctct  33540
aaaaaatatg caagagatat agtttatgga aacatctacc ttggtggaaa gccagatcaa  33600
ccagtaacca ttaaaactac ctttaatcag gaaactggat gtgaatattc tatcacattt  33660
gattttagtt gggccaagac ttatgtaaat gttgaatttg aaacaacctc ttttaccttt  33720
tcctatatcg cccaagaata ataaagaatc gtttgtgtta tgtttcaacg tgtttatttt  33780
tcaattgcag aaaatttcaa gtcatttttc attcagtagt atagccccac caccacatag  33840
cttatacaga tcaccgtacc tcaactttgt ataataaagt tgtaatcaaa ctcacagaac  33900
cctagtattc aacctgccac ctccctccca acacacagag tacacagtcc tttctccccg  33960
gctggcctta aaaagcatca tatcatgggt aacagacata ttcttaggtg ttatattcca  34020
cacggtttcc tgtcgagcca aacgctcatc agtgatatta ataaactccc cgggcagctc  34080
acttaagttc atgtcgctgt ccagctgctg agccacaggc tgctgtccaa cttgcggttg  34140
cttaacgggc ggcgaaggag aagtccacgc ctacatgggg gtagagtcat aatcgtgcat  34200
caggataggg cggtggtgct gcagcagcgc gcgaataaac tgctgccgcc gccgctccgt  34260
cctgcaggaa tacaacatgg cagtggtctc ctcagcgatg attcgcaccg cccgcagcat  34320
aaggcgcctt gtcctccggg cacagcagcg caccctgatc tcacttaaat cagcacagta  34380
actgcagcac agcaccacaa tattgttcaa aatcccacag tgcaaggcgc tgtatccaaa  34440
gctcatggcg gggaccacag aacccacgtg gccatcatac cacaagcgca ggtagattaa  34500
gtggcgaccc ctcataaaca cgctggacat aaacattacc tcttttggca tgttgtaatt  34560
caccacctcc cggtaccata taaacctctg attaaacatg gcgccatcca ccaccatcct  34620
aaaccagctg gccaaaacct gcccgccggc tatacactgc agggaaccgg gactggaaca  34680
atgacagtgg agagcccagg actcgtaacc atggatcatc atgctcgtca tgatatcaat  34740
gttggcacaa cacaggcaca cgtgcataca cttcctcagg attacaagct cctcccgcgt  34800
tagaaccata tcccagggaa caacccattc ctgaatcagc gtaaatccca cactgcaggg  34860
aagacctcgc acgtaactca cgttgtgcat tgtcaaagtg ttacattcgg gcagcagcgg  34920
atgatcctcc agtatggtag cgcgggtttc tgtctcaaaa ggaggtagac gatccctact  34980
gtacggagtg cgccgagaca accgagatcg tgttggtcgt agtgtcatgc caaatggaac  35040
gccggacgta gtcatatttc ctgaagcaaa accaggtgcg ggcgtgacaa acagatctgc  35100
gtctccggtc tcgccgctta gatcgctctg tgtagtagtt gtagtatatc cactctctca  35160
aagcatccag gcgcccccctg gcttcgggtt ctatgtaaac tccttcatgc gccgctgccc  35220
tgataacatc caccaccgca gaataagcca cacccagcca acctacacat tcgttctgcg  35280
agtcacacac gggaggagcg ggaagagctg gaagaaccat gtttttttt ttattccaaa  35340
agattatcca aaacctcaaa atgaagatct attaagtgaa cgcgctcccc tccggtggcg  35400
tggtcaaact ctacagccaa agaacagata atggcatttg taagatgttg cacaatggct  35460
```

tccaaaaggc aaacggccct cacgtccaag tggacgtaaa ggctaaaccc ttcagggtga 35520
atctcctcta taaacattcc agcaccttca accatgccca aataattctc atctcgccac 35580
cttctcaata tatctctaag caaatcccga atattaagtc cggccattgt aaaaatctgc 35640
tccagagcgc cctccacctt cagcctcaag cagcgaatca tgattgcaaa aattcaggtt 35700
cctcacagac ctgtataaga ttcaaaagcg gaacattaac aaaaataccg cgatcccgta 35760
ggtcccttcg cagggccagc tgaacataat cgtgcaggtc tgcacggacc agcgcggcca 35820
cttccccgcc aggaaccatg acaaaagaac ccacactgat tatgacacgc atactcggag 35880
ctatgctaac cagcgtagcc ccgatgtaag cttgttgcat gggcggcgat ataaaatgca 35940
aggtgctgct caaaaaatca ggcaaagcct cgcgcaaaaa agaaagcaca tcgtagtcat 36000
gctcatgcag ataaaggcag gtaagctccg gaaccaccac agaaaaagac accatttttc 36060
tctcaaacat gtctgcgggt ttctgcataa acacaaaata aaataacaaa aaaacattta 36120
aacattagaa gcctgtctta caacaggaaa aacaaccctt ataagcataa gacggactac 36180
ggccatgccg gcgtgaccgt aaaaaaactg gtcaccgtga ttaaaaagca ccaccgacag 36240
ctcctcggtc atgtccggag tcataatgta agactcggta aacacatcag gttgattcac 36300
atcggtcagt gctaaaaagc gaccgaaata gcccggggga atacataccc gcaggcgtag 36360
agacaacatt acagccccca taggaggtat aacaaaatta ataggagaga aaaacacata 36420
aacacctgaa aaaccctcct gcctaggcaa aatagcaccc tcccgctcca gaacaacata 36480
cagcgcttcc acagcggcag ccataacagt cagccttacc agtaaaaaag aaaacctatt 36540
aaaaaaacac cactcgacac ggcaccagct caatcagtca cagtgtaaaa aagggccaag 36600
tgcagagcga gtatatatag gactaaaaaa tgacgtaacg gttaaagtcc acaaaaaaca 36660
cccagaaaac cgcacgcgaa cctacgccca gaaacgaaag ccaaaaaacc cacaacttcc 36720
tcaaatcgtc acttccgttt tcccacgtta cgtcacttcc cattttaaga aaactacaat 36780
tcccaacaca tacaagttac tccgccctaa aacctacgtc acccgccccg ttcccacgcc 36840
ccgcgccacg tcacaaactc cacccccctca ttatcatatt ggcttcaatc caaaataagg 36900
tatattattg atgatg 36916

<210> SEQ ID NO 4
<211> LENGTH: 36949
<212> TYPE: DNA
<213> ORGANISM: Artificial Sequence
<220> FEATURE:
<223> OTHER INFORMATION: Synthetic adenovirus construct (AdSyn-CO174)

<400> SEQUENCE: 4
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattaaac cgtattaccg ccatgcattt aatggagtgc 480
ctcgtgaggc tccggtgccc gtcagtgggc agagcgcaca tcgcccacag tccccgagaa 540

-continued

```
gttgggggga ggggtcggca attgaaccgg tgcctagaga aggtggcgcg gggtaaactg    600
ggaaagtgat gtcgtgtact ggctccgcct ttttcccgag ggtgggggag aaccgtatat    660
aagtgcagta gtcgccgtga acgttctttt tcgcaacggg tttgccgcca gaacacaggt    720
aagtgccgtg tgtggttccc gcgggcctgg cctctttacg ggttatggcc cttgcgtgcc    780
ttgaattact tccacctggc tgcagtacgt gattcttgat cccgagcttc gggttggaag    840
tgggtgggag agttcgaggc cttgcgctta aggagcccct tcgcctcgtg cttgagttga    900
ggcctggcct gggcgctggg gccgccgcgt gcgaatctgg tggcaccttc gcgcctgtct    960
cgctgctttc gataagtctc tagccattta aaatttttga tgacctgctg cgacgctttt   1020
tttctggcaa gatagtcttg taaatgcggg ccaagatctg cacactggta tttcggtttt   1080
tggggccgcg ggcggcgacg gggcccgtgc gtcccagcgc acatgttcgg cgaggcgggg   1140
cctgcgagcg cggccaccga gaatcggacg ggggtagtct caagctggcc ggcctgctct   1200
ggtgcctggc ctcgcgccgc cgtgtatcgc cccgccctgg gcggcaaggc tggcccggtc   1260
ggcaccagtt gcgtgagcgg aaagatggcc gcttcccggc cctgctgcag ggagctcaaa   1320
atggaggacg cggcgctcgg gagagcgggc gggtgagtca cccacacaaa ggaaaagggc   1380
ctttccgtcc tcagccgtcg cttcatgtga ctccacggag taccgggcgc cgtccaggca   1440
cctcgattag ttctcgagct tttggagtac gtcgtcttta ggttgggggg aggggtttta   1500
tgcgatggag tttccccaca ctgagtgggt ggagactgaa gttaggccag cttggcactt   1560
gatgtaattc tccttggaat ttgccctttt tgagtttgga tcttggttca ttctcaagcc   1620
tcagacagtg gttcaaagtt tttttcttcc atttcaggtg tcgtgacgct agcgctaccg   1680
gactcagatc tcgagctcaa gcttcgaatt ctgcagtcga cggtaccgga tccatggaag   1740
acgccaaaaa cataaagaaa ggcccggcgc cattctatcc gctggaagat ggaaccgctg   1800
gagagcaact gcataaggct atgaagagat acgccctggt tcctggaaca attgctttta   1860
cagatgcaca tatcgaggtg gacatcactt acgctgagta cttcgaaatg tccgttcggt   1920
tggcagaagc tatgaaacga tatgggctga atacaaatca cagaatcgtc gtatgcagtg   1980
aaaactctct tcaattcttt atgccggtgt tgggcgcgtt atttatcgga gttgcagttg   2040
cgcccgcgaa cgacatttat aatgaacgtg aattgctcaa cagtatgggc atttcgcagc   2100
ctaccgtggt gttcgtttcc aaaaaggggt tgcaaaaaat tttgaacgtg caaaaaaagc   2160
tcccaatcat ccaaaaaatt attatcatgg attctaaaac ggattaccag ggatttcagt   2220
cgatgtacac gttcgtcaca tctcatctac ctcccggttt taatgaatac gattttgtgc   2280
cagagtcctt cgatagggac aagacaattg cactgatcat gaactcctct ggatctactg   2340
gtctgcctaa aggtgtcgct ctgcctcata gaactgcctg cgtgagattc tcgcatgcca   2400
gagatcctat ttttggcaat caaatcattc cggatactgc gattttaagt gttgttccat   2460
tccatcacgg ttttggaatg tttactacac tcggatattt gatatgtgga tttcgagtcg   2520
tcttaatgta tagatttgaa gaagagctgt ttctgaggag ccttcaggat tacaagattc   2580
aaagtgcgct gctggtgcca accctattct ccttcttcgc caaaagcact ctgattgaca   2640
aatacgattt atctaattta cacgaaattg cttctggtgg cgctcccctc tctaaggaag   2700
tcggggaagc ggttgccaag aggttccatc tgccaggtat caggcaagga tatgggctca   2760
ctgagactac atcagctatt ctgattacac ccgaggggga tgataaaccg ggcgcggtcg   2820
gtaaagttgt tccatttttt gaagcgaagg ttgtggatct ggataccggg aaaacgctgg   2880
gcgttaatca aagaggcgaa ctgtgtgtga gaggtcctat gattatgtcc ggttatgtaa   2940
```

acaatccgga agcgaccaac gccttgattg acaaggatgg atggctacat tctggagaca 3000
tagcttactg ggacgaagac gaacacttct tcatcgttga ccgcctgaag tctctgatta 3060
agtacaaagg ctatcaggtg gctcccgctg aattggaatc catcttgctc caacacccca 3120
acatcttcga cgcaggtgtc gcaggtcttc ccgacgatga cgccggtgaa cttcccgccg 3180
ccgttgttgt tttggagcac ggaaagacga tgacggaaaa agagatcgtg gattacgtcg 3240
ccagtcaagt aacaaccgcg aaaaagttgc gcggaggagt tgtgtttgtg gacgaagtac 3300
cgaaaggtct taccggaaaa ctcgacgcaa gaaaaatcag agagatcctc ataaaggcca 3360
agaagggcgg aaagatcgcc gtggcagccg cagccaccat ggtgagcaag ggcgaggagc 3420
tgttcaccgg ggtggtgccc atcctggtcg agctggacgg cgacgtaaac ggccacaagt 3480
tcagcgtgtc cggcgagggc gagggcgatg ccacctacgg caagctgacc ctgaagttca 3540
tctgcaccac cggcaagctg cccgtgccct ggcccaccct cgtgaccacc ctgacctacg 3600
gcgtgcagtg cttcagccgc taccccgacc acatgaagca gcacgacttc ttcaagtccg 3660
ccatgcccga aggctacgtc caggagcgca ccatcttctt caaggacgac ggcaactaca 3720
agacccgcgc cgaggtgaag ttcgagggcg acaccctggt gaaccgcatc gagctgaagg 3780
gcatcgactt caaggaggac ggcaacatcc tggggcacaa gctggagtac aactacaaca 3840
gccacaacgt ctatatcatg gccgacaagc agaagaacgg catcaaggtg aacttcaaga 3900
tccgccacaa catcgaggac ggcagcgtgc agctcgccga ccactaccag cagaacaccc 3960
ccatcggcga cggccccgtg ctgctgcccg acaaccacta cctgagcacc cagtccgccc 4020
tgagcaaaga ccccaacgag aagcgcgatc acatggtcct gctggagttc gtgaccgccg 4080
ccgggatcac tctcggcatg gacgagctgt acaagtaaag cgactctaga tcataatcag 4140
ccataccaca acaccattgt cacactccaa tcgattcaaa caccattgtc acactccaac 4200
atttgtagag gttttacttg ctttaaaaaa cctcccacac ctccccctga acctgaaaca 4260
taaaatgaat gcaattgttg ttgttaactt gtttattgca gcttataatg gttacaaata 4320
aagcaatagc atcacaaatt tcacaaataa agcatttttt tcactgcatt ctagttgtgg 4380
tttgtccaaa ctcatcaatg taagtttaaa cggcgcgcct gaaatgtgtg ggcgtggctt 4440
aagggtggga aagaatatat aaggtggggg tcttatgtag ttttgtatct gttttgcagc 4500
agccgccgcc gccatgagca ccaactcgtt tgatggaagc attgtgagct catatttgac 4560
aacgcgcatg cccccatggg ccggggtgcg tcagaatgtg atgggctcca gcattgatgg 4620
tcgccccgtc ctgcccgcaa actctactac cttgacctac gagaccgtgt ctggaacgcc 4680
gttggagact gcagcctccg ccgccgcttc agccgctgca gccaccgccc gcgggattgt 4740
gactgacttt gctttcctga gcccgcttgc aagcagtgca gcttcccgtt catccgcccg 4800
cgatgacaag ttgacggctc ttttggcaca attggattct ttgacccggg aacttaatgt 4860
cgtttctcag cagctgttgg atctgcgcca gcaggtttct gccctgaagg cttcctcccc 4920
tcccaatgcg gtttaaaaca caacttttct atacaaagtt gtaaataaaa aaccagactc 4980
tgtttggatt tggatcaagc taagtgtctt gctgtcttta tttaggggtt ttgcgcgcgc 5040
ggtaggcccg ggaccagcgg tctcggtcgt tgagggtcct gtgtattttt tccaggacgt 5100
ggtaaaggtg actctggatg ttcagataca tgggcataag cccgtctctg ggtggaggt 5160 agcaccactg cagagcttca tgctgcgggg tggtgttgta gatgatccag tcgtagcagg 5220
agcgctgggc gtggtgccta aaaatgtctt tcagtagcaa gctgattgcc aggggcaggc 5280

-continued ccttggtgta agtgtttaca aagcggttaa gctgggatgg gtgcatacgt ggggatatga 5340
gatgcatctt ggactgtatt tttaggttgg ctatgttccc agccatatcc ctccggggat 5400
tcatgttgtg cagaaccacc agcacagtgt atccggtgca cttgggaaat ttgtcatgta 5460
gcttagaagg aaatgcgtgg aagaacttgg agacgccctt gtgacctcca agattttcca 5520
tgcattcgtc cataatgatg gcaatgggcc cacgggcggc ggcctgggcg aagatatttc 5580
tgggatcact aacgtcatag ttgtgttcca ggatgagatc gtcataggcc atttttacaa 5640
agcgcgggcg gagggtgcca gactgcggta taatggttcc atccggccca ggggcgtagt 5700
taccctcaca gatttgcatt tcccacgctt tgagttcaga tgggggggatc atgtctacct 5760
gcggggcgat gaagaaaacg gtttccgggg taggggagat cagctgggaa gaaagcaggt 5820
tcctgagcag ctgcgactta ccgcagccgg tgggcccgta aatcacacct attaccggct 5880
gcaactggta gttaagagag ctgcagctgc cgtcatccct gagcaggggg gccacttcgt 5940
taagcatgtc cctgactcgc atgttttccc tgaccaaatc cgccagaagg cgctcgccgc 6000
ccagcgatag cagttcttgc aaggaagcaa agtttttcaa cggtttgaga ccgtccgccg 6060
taggcatgct tttgagcgtt tgaccaagca gttccaggcg gtcccacagc tcggtcacct 6120
gctctacggc atctcgatcc agcatatctc ctcgtttcgc gggttggggc ggctttcgct 6180
gtacggcagt agtcggtgct cgtccagacg ggccagggtc atgtctttcc acgggcgcag 6240
ggtcctcgtc agcgtagtct gggtcacggt gaaggggtgc gctccgggct gcgcgctggc 6300
cagggtgcgc ttgaggctgg tcctgctggt gctgaagcgc tgccggtctt cgccctgcgc 6360
gtcggccagg tagcatttga ccatggtgtc atagtccagc ccctccgcgg cgtggccctt 6420
ggcgcgcagc ttgcccttgg aggaggcgcc gcacgagggg cagtgcagac ttttgagggc 6480
gtagagcttg ggcgcgagaa ataccgattc cggggagtag gcatccgcgc cgcaggcccc 6540
gcagacggtc tcgcattcca cgagccaggt gagctctggc cgttcggggt caaaaaccag 6600
gtttccccca tgctttttga tgcgtttctt acctctggtt tccatgagcc ggtgtccacg 6660
ctcggtgacg aaaaggctgt ccgtgtcccc gtatacagac ttgagaggcc tgtcctcgag 6720
cggtgttccg cggtcctcct cgtatagaaa ctcggaccac tctgagacaa aggctcgcgt 6780
ccaggccagc acgaaggagg ctaagtggga ggggtagcgg tcgttgtcca ctagggggtc 6840
cactcgctcc agggtgtgaa gacacatgtc gccctcttcg gcatcaagga aggtgattgg 6900
tttgtaggtg taggccacgt gaccgggtgt tcctgaaggg gggctataaa agggggtggg 6960
ggcgcgttcg tcctcactct cttccgcatc gctgtctgcg agggccagct gttggggtga 7020
gtactccctc tgaaaagcgg gcatgacttc tgcgctaaga ttgtcagttt ccaaaaacga 7080
ggaggatttg atattcacct ggcccgcggt gatgcctttg agggtggccg catccatctg 7140
gtcagaaaag acaatctttt tgttgtcaag cttggtggca aacgacccgt agagggcgtt 7200
ggacagcaac ttggcgatgg agcgcagggt ttggtttttg tcgcgatcgg cgcgctcctt 7260
ggccgcgatg tttagctgca cgtattcgcg cgcaacgcac cgccattcgg gaaagacggt 7320
ggtgcgctcg tcgggcacca ggtgcacgcg ccaaccgcgg ttgtgcaggg tgacaaggtc 7380
aacgctggtg gctacctctc cgcgtaggcg ctcgttggtc cagcagaggc ggccgccctt 7440
gcgcgagcag aatggcggta gggggtctag ctgcgtctcg tccgggggggt ctgcgtccac 7500
ggtaaagacc ccgggcagca ggcgcgcgtc gaagtagtct atcttgcatc cttgcaagtc 7560
tagcgcctgc tgccatgcgc gggcggcaag cgcgcgctcg tatgggttga gtgggggacc 7620
ccatggcatg gggtgggtga gcgcggaggc gtacatgccg caaatgtcgt aaacgtagag 7680

-continued

```
gggctctctg agtattccaa gatatgtagg gtagcatctt ccaccgcgga tgctggcgcg   7740
cacgtaatcg tatagttcgt gcgagggagc gaggaggtcg ggaccgaggt tgctacgggc   7800
gggctgctct gctcggaaga ctatctgcct gaagatggca tgtgagttgg atgatatggt   7860
tggacgctgg aagacgttga agctggcgtc tgtgagacct accgcgtcac gcacgaagga   7920
ggcgtaggag tcgcgcagct tgttgaccag ctcggcggtg acctgcacgt ctagggcgca   7980
gtagtccagg gtttccttga tgatgtcata cttatcctgt ccctttttttt tccacagctc   8040
gcggttgagg acaaactctt cgcggtcttt ccagtactct tggatcggaa acccgtcggc   8100
ctccgaacgg taagagccta gcatgtagaa ctggttgacg gcctggtagg cgcagcatcc   8160
cttttctacg ggtagcgcgt atgcctgcgc ggccttccgg agcgaggtgt gggtgagcgc   8220
aaaggtgtcc ctgaccatga ctttgaggta ctggtatttg aagtcagtgt cgtcgcatcc   8280
gccctgctcc cagagcaaaa agtccgtgcg ctttttggaa cgcggatttg gcagggcgaa   8340
ggtgacatcg ttgaagagta tctttcccgc gcgaggcata aagttgcgtg tgatgcggaa   8400
gggtcccggc acctcggaac ggttgttaat tacctgggcg gcgagcacga tctcgtcaaa   8460
gccgttgatg ttgtggccca caatgtaaag ttccaagaag cgcgggatgc ccttgatgga   8520
aggcaatttt ttaagttcct cgtaggtgag ctcttcaggg gagctgagcc cgtgctctga   8580
aagggcccag tctgcaagat gagggttgga agcgacgaat gagctccaca ggtcacgggc   8640
cattagcatt tgcaggtggt cgcgaaaggt cctaaactgg cgacctatgg ccattttttc   8700
tggggtgatg cagtagaagg taagcgggtc ttgttcccag cggtcccatc caaggttcgc   8760
ggctaggtct cgcgcggcag tcactagagg ctcatctccg ccgaacttca tgaccagcat   8820
gaagggcacg agctgcttcc caaaggcccc catccaagta taggtctcta catcgtaggt   8880
gacaaagaga cgctcggtgc gaggatgcga gccgatcggg aagaactgga tctcccgcca   8940
ccaattggag gagtggctat tgatgtggtg aaagtagaag tccctgcgac gggccgaaca   9000
ctcgtgctgg cttttgtaaa aacgtgcgca gtactggcag cggtgcacgg gctgtacatc   9060
ctgcacgagg ttgacctgac gaccgcgcac aaggaagcag agtgggaatt tgagcccctc   9120
gcctggcggg tttggctggt ggtcttctac ttcggctgct tgtccttgac cgtctggctg   9180
ctcgagggga gttacggtgg atcggaccac cacgccgcgc gagcccaaag tccagatgtc   9240
cgcgcgcggc ggtcggagct tgatgacaac atcgcgcaga tgggagctgt ccatggtctg   9300
gagctcccgc ggcgtcaggt caggcgggag ctcctgcagg tttacctcgc atagacgggt   9360
cagggcgcgg gctagatcca ggtgatacct aatttccagg ggctggttgg tggcggcgtc   9420
gatggcttgc aagaggccgc atccccgcgg cgcgactacg gtaccgcgcg gcgggcggtg   9480
ggccgcgggg gtgtccttgg atgatgcatc taaaagcggt gacgcgggcg agcccccgga   9540
ggtagggggg gctccggacc cgccgggaga gggggcaggg gcacgtcggc gccgcgcgcg   9600
ggcaggagct ggtgctgcgc gcgtaggttg ctggcgaacg cgacgacgcg gcggttgatc   9660
tcctgaatct ggcgcctctg cgtgaagacg acgggcccgg tgagcttgaa cctgaaagag   9720
agttcgacag aatcaatttc ggtgtcgttg acggcggcct ggcgcaaaat ctcctgcacg   9780
tctcctgagt tgtcttgata ggcgatctcg gccatgaact gctcgatctc ttcctcctgg   9840
agatctccgc gtccggctcg ctccacggtg gcggcgaggt cgttggaaat gcgggccatg   9900
agctgcgaga aggcgttgag gcctccctcg ttccagacgc ggctgtagac cacgcccccct   9960
tcggcatcgc gggcgcgcat gaccacctgc gcgagattga gctccacgtg ccgggcgaag  10020
```

-continued

```
acggcgtagt ttcgcaggcg ctgaaagagg tagttgaggg tggtggcggt gtgttctgcc  10080
acgaagaagt acataaccca gcgtcgcaac gtggattcgt tgatatcccc caaggcctca  10140
aggcgctcca tggcctcgta gaagtccacg gcgaagttga aaaactggga gttgcgcgcc  10200
gacacggtta actcctcctc cagaagacgg atgagctcgg cgacagtgtc gcgcacctcg  10260
cgctcaaagg ctacaggggc ctcttcttct tcttcaatct cctcttccat aagggcctcc  10320
ccttcttctt cttctggcgg cggtggggga gggggggacac ggcggcgacg acggcgcacc  10380
gggaggcggt cgacaaagcg ctcgatcatc tccccgcggc gacggcgcat ggtctcggtg  10440
acggcgcggc cgttctcgcg gggcgcagt tggaagacgc cgcccgtcat gtcccggtta  10500
tgggttggcg gggggctgcc atgcggcagg gatacggcgc taacgatgca tctcaacaat  10560
tgttgtgtag gtactccgcc gccgagggac ctgagcgagt ccgcatcgac cggatcggaa  10620
aacctctcga gaaaggcgtc taaccagtca cagtcgcaag gtaggctgag caccgtggcg  10680
ggcggcagcg ggcggcggtc ggggttgttt ctggcggagg tgctgctgat gatgtaatta  10740
aagtaggcgg tcttgagacg gcggatggtc gacagaagca ccatgtcctt gggtccggcc  10800
tgctgaatgc gcaggcggtc ggccatgccc caggcttcgt tttgacatcg gcgcaggtct  10860
ttgtagtagt cttgcatgag cctttctacc ggcacttctt cttctccttc ctcttgtcct  10920
gcatctcttg catctatcgc tgcggcggcg gcggagtttg gccgtaggtg gcgccctctt  10980
cctcccatgc gtgtgacccc gaagcccctc atcggctgaa gcagggctag gtcggcgaca  11040
acgcgctcgg ctaatatggc ctgctgcacc tgcgtgaggg tagactggaa gtcatccatg  11100
tccacaaagc ggtggtatgc gcccgtgttg atggtgtaag tgcagttggc cataacggac  11160
cagttaacgg tctggtgacc cggctgcgag agctcggtgt acctgagacg cgagtaagcc  11220
ctcgagtcaa atacgtagtc gttgcaagtc cgcaccaggt actggtatcc caccaaaaag  11280
tgcggcggcg gctggcggta gaggggccag cgtagggtgg ccggggctcc gggggcgaga  11340
tcttccaaca taaggcgatg atatccgtag atgtacctgg acatccaggt gatgccggcg  11400
gcggtggtgg aggcgcgcgg aaagtcgcgg acgcggttcc agatgttgcg cagcggcaaa  11460
aagtgctcca tggtcgggac gctctggccg gtcaggcgcg cgcaatcgtt gacgctctag  11520
accgtgcaaa aggagagcct gtaagcgggc actcttccgt ggtctggtgg ataaattcgc  11580
aagggtatca tggcggacga ccggggttcg agccccgtat ccggccgtcc gccgtgatcc  11640
atgcggttac cgcccgcgtg tcgaacccag gtgtgcgacg tcagacaacg ggggagtgct  11700
ccttttggct tccttccagg cgcggcggct gctgcgctag ctttttggc cactggccgc  11760
gcgcagcgta agcggttagg ctggaaagcg aaagcattaa gtggctcgct ccctgtagcc  11820
ggagggttat tttccaaggg ttgagtcgcg ggacccccgg ttcgagtctc ggaccggccg  11880
gactgcggcg aacgggggtt tgcctccccg tcatgcaaga ccccgcttgc aaattcctcc  11940
ggaaacaggg acgagcccct tttttgcttt tcccagatgc atccggtgct gcggcagatg  12000
cgccccccctc ctcagcagcg gcaagagcaa gagcagcggc agacatgcag ggcaccctcc  12060
cctcctccta ccgcgtcagg aggggcgaca tccgcggttg acgcggcagc agatggtgat  12120
tacgaacccc cgcggcgccg ggcccggcac tacctggact tggaggaggg cgagggcctg  12180
gcgcggctag gagcgccctc tcctgagcgg cacccaaggg tgcagctgaa gcgtgatacg  12240
cgtgaggcgt acgtgccgcg gcagaacctg tttcgcgacc gcgagggaga ggagcccgag  12300
gagatgcggg atcgaaagtt ccacgcaggg cgcgagctgc ggcatggcct gaatcgcgag  12360
cggttgctgc gcgaggagga ctttgagccc gacgcgcgaa ccgggattag tcccgcgcgc  12420
```

-continued

```
gcacacgtgg cggccgccga cctggtaacc gcatacgagc agacggtgaa ccaggagatt  12480
aactttcaaa aaagctttaa caaccacgtg cgtacgcttg tggcgcgcga ggaggtggct  12540
ataggactga tgcatctgtg ggactttgta agcgcgctgg agcaaaaccc aaatagcaag  12600
ccgctcatgg cgcagctgtt ccttatagtg cagcacagca gggacaacga ggcattcagg  12660
gatgcgctgc taaacatagt agagcccgag ggccgctggc tgctcgattt gataaacatc  12720
ctgcagagca tagtggtgca ggagcgcagc ttgagcctgg ctgacaaggt ggccgccatc  12780
aactattcca tgcttagcct gggcaagttt tacgcccgca agatatacca taccccttac  12840
gttcccatag acaaggaggt aaagatcgag gggttctaca tgcgcatggc gctgaaggtg  12900
cttaccttga gcgacgacct gggcgtttat cgcaacgagc gcatccacaa ggccgtgagc  12960
gtgagccggc ggcgcgagct cagcgaccgc gagctgatgc acagcctgca aagggccctg  13020
gctggcacgg gcagcggcga tagagaggcc gagtcctact ttgacgcggg cgctgacctg  13080
cgctgggccc caagccgacg cgccctggag gcagctgggg ccggacctgg gctggcggtg  13140
gcacccgcgc gcgctggcaa cgtcggcggc gtggaggaat atgacgagga cgatgagtac  13200
gagccagagg acggcgagta ctaagcggtg atgtttctga tcagatgatg caagacgcaa  13260
cggacccggc ggtgcgggcg gcgctgcaga gccagccgtc cggccttaac tccacggacg  13320
actggcgcca ggtcatggac cgcatcatgt cgctgactgc gcgcaatcct gacgcgttcc  13380
ggcagcagcc gcaggccaac cggctctccg caattctgga agcggtggtc ccggcgcgcg  13440
caaaccccac gcacgagaag gtgctggcga tcgtaaacgc gctggccgaa aacagggcca  13500
tccggcccga cgaggccggc ctggtctacg acgcgctgct tcagcgcgtg gctcgttaca  13560
acagcggcaa cgtgcagacc aacctggacc ggctggtggg ggatgtgcgc gaggccgtgg  13620
cgcagcgtga gcgcgcgcag cagcagggca acctgggctc catggttgca ctaaacgcct  13680
tcctgagtac acagcccgcc aacgtgccgc ggggacagga ggactacacc aactttgtga  13740
gcgcactgcg gctaatggtg actgagacac cgcaaagtga ggtgtaccag tctgggccag  13800
actatttttt ccagaccagt agacaaggcc tgcagaccgt aaacctgagc caggctttca  13860
aaaacttgca ggggctgtgg ggggtgcggg ctcccacagg cgaccgcgcg accgtgtcta  13920
gcttgctgac gcccaactcg cgcctgttgc tgctgctaat agcgcccttc acggacagtg  13980
gcagcgtgtc ccgggacaca tacctaggtc acttgctgac actgtaccgc gaggccatag  14040
gtcaggcgca tgtggacgag catactttcc aggagattac aagtgtcagc cgcgcgctgg  14100
ggcaggagga cacgggcagc ctggaggcaa ccctaaacta cctgctgacc aaccggcggc  14160
agaagatccc ctcgttgcac agtttaaaca gcgaggagga gcgcattttg cgctacgtgc  14220
agcagagcgt gagccttaac ctgatgcgcg acggggtaac gcccagcgtg gcgctggaca  14280
tgaccgcgcg caacatggaa ccgggcatgt atgcctcaaa ccggccgttt atcaaccgcc  14340
taatggacta cttgcatcgc gcggccgccg tgaaccccga gtatttcacc aatgccatct  14400
tgaacccgca ctggctaccg ccccctggtt tctacaccgg gggattcgag gtgcccgagg  14460
gtaacgatgg attcctctgg gacgacatag acgacagcgt gttttccccg caaccgcaga  14520
ccctgctaga gttgcaacag cgcgagcagg cagaggcggc gctgcgaaag gaaagcttcc  14580
gcaggccaag cagcttgtcc gatctaggcg ctgcggcccc gcggtcagat gctagtagcc  14640
catttccaag cttgataggg tctcttacca gcactcgcac cacccgcccg cgcctgctgg  14700
gcgaggagga gtacctaaac aactcgctgc tgcagccgca gcgcgaaaaa aacctgcctc  14760
```

cggcatttcc caacaacggg atagagagcc tagtggacaa gatgagtaga tggaagacgt 14820
acgcgcagga gcacagggac gtgccaggcc cgcgcccgcc cacccgtcgt caaaggcacg 14880
accgtcagcg gggtctggtg tgggaggacg atgactcggc agacgacagc agcgtcctgg 14940
atttgggagg gagtggcaac ccgtttgcgc accttcgccc caggctgggg agaatgtttt 15000
aaaaaaaaaa aaaaagcatg atgcaaaata aaaaactcac caaggccatg gcaccgagcg 15060
ttggttttct tgtattcccc ttagtatgcg gcgcgcggcg atgtatgagg aaggtcctcc 15120
tccctcctac gagagtgtgg tgagcgcggc gccagtggcg gcggcgctgg gttctccctt 15180
cgatgctccc ctggacccgc cgtttgtgcc tccgcggtac ctgcggccta ccggggggag 15240
aaacagcatc cgttactctg agttggcacc cctattcgac accacccgtg tgtacctggt 15300
ggacaacaag tcaacggatg tggcatccct gaactaccag aacgaccaca gcaactttct 15360
gaccacggtc attcaaaaca atgactacag cccgggggag gcaagcacac agaccatcaa 15420
tcttgacgac cggtcgcact ggggcggcga cctgaaaacc atcctgcata ccaacatgcc 15480
aaatgtgaac gagttcatgt ttaccaataa gtttaaggcg cgggtgatgg tgtcgcgctt 15540
gcctactaag gacaatcagg tggagctgaa atacgagtgg gtggagttca cgctgcccga 15600
gggcaactac tccgagacca tgaccataga ccttatgaac aacgcgatcg tggagcacta 15660
cttgaaagtg ggcagacaga acggggttct ggaaagcgac atcggggtaa agtttgacac 15720
ccgcaacttc agactggggt ttgaccccgt cactggtctt gtcatgcctg ggtatatac 15780 aaacgaagcc ttccatccag acatcatttt gctgccagga tgcggggtgg acttcaccca 15840
cagccgcctg agcaacttgt tgggcatccg caagcggcaa cccttccagg agggctttag 15900
gatcacctac gatgatctgg agggtggtaa cattcccgca ctgttggatg tggacgccta 15960
ccaggcgagc ttgaaagatg acaccgaaca gggcgggggt ggcgcaggcg gcagcaacag 16020
cagtggcagc ggcgcggaag agaactccaa cgcggcagcc gcggcaatgc agccggtgga 16080
ggacatgaac gatcatgcca ttcgcggcga cacctttgcc acacgggctg aggagaagcg 16140
cgctgaggcc gaagcagcgg ccgaagctgc cgcccccgct gcgcaacccg aggtcgagaa 16200
gcctcagaag aaaccggtga tcaaacccct gacagaggac agcaagaaac gcagttacaa 16260
cctaataagc aatgacagca ccttcaccca gtaccgcagc tggtaccttg catacaacta 16320
cggcgaccct cagaccggaa tccgctcatg gaccctgctt tgcactcctg acgtaacctg 16380
cggctcggag caggtctact ggtcgttgcc agacatgatg caagaccccg tgaccttccg 16440
ctccacgcgc cagatcagca actttccggt ggtgggcgcc gagctgttgc ccgtgcactc 16500
caagagcttc tacaacgacc aggccgtcta ctcccaactc atccgccagt ttacctctct 16560
gacccacgtg ttcaatcgct ttcccgagaa ccagattttg gcgcgcccgc cagcccccac 16620
catcaccacc gtcagtgaaa acgttcctgc tctcacagat cacgggacgc taccgctgcg 16680
caacagcatc ggaggagtcc agcgagtgac cattactgac gccagacgcc gcacctgccc 16740
ctacgtttac aaggccctgg gcatagtctc gccgcgcgtc ctatcgagcc gcactttttg 16800
agcaagcatg tccatcctta tatcgcccag caataacaca ggctggggcc tgcgcttccc 16860
aagcaagatg tttggcgggg ccaagaagcg ctccgaccaa cacccagtgc gcgtgcgcgg 16920
gcactaccgc gcgccctggg gcgcgcacaa acgcggccgc actgggcgca ccaccgtcga 16980
tgacgccatc gacgcggtgg tggaggaggc gcgcaactac acgcccacgc cgccaccagt 17040
gtccacagtg gacgcggcca ttcagaccgt ggtgcgcgga gcccggcgct atgctaaaat 17100
gaagagacgg cggaggcgcg tagcacgtcg ccaccgccgc cgacccggca ctgccgccca 17160
acgcgcggcg gcggccctgc ttaaccgcgc acgtcgcacc ggccgacggg cggccatgcg 17220
ggccgctcga aggctggccg cgggtattgt cactgtgccc cccaggtcca ggcgacgagc 17280
ggccgccgca gcagccgcgg ccattagtgc tatgactcag ggtcgcaggg gcaacgtgta 17340
ttgggtgcgc gactcggtta gcggcctgcg cgtgcccgtg cgcacccgcc ccccgcgcaa 17400
ctagattgca agaaaaaact acttagactc gtactgttgt atgtatccag cggcggcggc 17460
gcgcaacgaa gctatgtcca agcgcaaaat caaagaagag atgctccagg tcatcgcgcc 17520
ggagatctat ggcccccega agaaggaaga gcaggattac aagccccgaa agctaaagcg 17580
ggtcaaaaag aaaaagaaag atgatgatga tgaacttgac gacgaggtgg aactgctgca 17640
cgctaccgcg cccaggcgac gggtacagtg gaaaggtcga cgcgtaaaac gtgttttgcg 17700
acccggcacc accgtagtct ttacgcccgg tgagcgctcc acccgcacct acaagcgcgt 17760
gtatgatgag gtgtacggcg acgaggacct gcttgagcag gccaacgagc gcctcgggga 17820
gtttgcctac ggaaagcggc ataaggacat gctggcgttg ccgctggacg agggcaaccc 17880
aacacctagc ctaaagcccg taacactgca gcaggtgctg cccgcgcttg caccgtccga 17940
agaaaagcgc ggcctaaagc gcgagtctgg tgacttggca cccaccgtgc agctgatggt 18000
acccaagcgc cagcgactgg aagatgtctt ggaaaaaatg accgtggaac ctgggctgga 18060
gcccgaggtc cgcgtgcggc caatcaagca ggtggcgccg ggactgggcg tgcagaccgt 18120
ggacgttcag atacccacta ccagtagcac cagtattgcc accgccacag agggcatgga 18180
gacacaaacg tccccggttg cctcagcggt ggcggatgcc gcggtgcagg cggtcgctgc 18240
ggccgcgtcc aagacctcta cggaggtgca aacggacccg tggatgtttc gcgtttcagc 18300
cccccggcgc ccgcgccgtt cgaggaagta cggcgccgcc agcgcgctac tgcccgaata 18360
tgccctacat ccttccattg cgcctacccc cggctatcgt ggctacacct accgccccag 18420
aagacgagca actacccgac gccgaaccac cactggaacc cgccgccgcc gtcgccgtcg 18480
ccagcccgtg ctggccccga tttccgtgcg cagggtggct cgcgaaggag gcaggaccct 18540
ggtgctgcca acagcgcgct accaccccag catcgtttaa aagccggtct ttgtggttct 18600
tgcagatatg gccctcacct gccgcctccg tttcccggtg ccgggattcc gaggaagaat 18660
gcaccgtagg aggggcatgg ccggccacgg cctgacgggc ggcatgcgtc gtgcgcacca 18720
ccggcggcgg cgcgcgtcgc accgtcgcat gcgcggcggt atcctgcccc tccttattcc 18780
actgatcgcc gcggcgattg gcgccgtgcc cggaattgca tccgtggcct tgcaggcgca 18840
gagacactga ttaaaaacaa gttgcatgtg gaaaaatcaa aataaaaagt ctggactctc 18900
acgctcgctt ggtcctgtaa ctattttgta gaatggaaga catcaacttt gcgtctctgg 18960
ccccgcgaca cggctcgcgc ccgttcatgg gaaactggca agatatcggc accagcaata 19020
tgagcggtgg cgccttcagc tggggctcgc tgtggagcgg cattaaaaat ttcggttcca 19080
ccgttaagaa ctatggcagc aaggcctgga acagcagcac aggccagatg ctgagggata 19140
agttgaaaga gcaaaatttc caacaaaagg tggtagatgg cctggcctct ggcattagcg 19200
gggtggtgga cctggccaac caggcagtgc aaaataagat taacagtaag cttgatcccc 19260
gccctcccgt agaggagcct ccaccggccg tggagacagt gtctccagag ggcgtggcg 19320 aaaagcgtcc gcgccccgac agggaagaaa ctctggtgac gcaaatagac gagcctccct 19380
cgtacgagga ggcactaaag caaggcctgc ccaccacccg tcccatcgcg cccatggcta 19440
ccggagtgct gggccagcac acacccgtaa cgctggacct gcctcccccc gccgacaccc 19500

-continued

```
agcagaaacc tgtgctgcca ggcccgaccg ccgttgttgt aacccgtcct agccgcgcgt  19560
ccctgcgccg cgccgccagc ggtccgcgat cgttgcggcc cgtagccagt ggcaactggc  19620
aaagcacact gaacagcatc gtgggtctgg gggtgcaatc cctgaagcgc cgacgatgct  19680
tctgaatagc taacgtgtcg tatgtgtgtc atgtatgcgt ccatgtcgcc gccagaggag  19740
ctgctgagcc gccgcgcgcc cgctttccaa gatggctacc ccttcgatga tgccgcagtg  19800
gtcttacatg cacatctcgg gccaggacgc ctcggagtac ctgagccccg ggctggtgca  19860
gtttgcccgc gccaccgaga cgtacttcag cctgaataac aagtttagaa accccacggt  19920
ggcgcctacg cacgacgtga ccacagaccg gtcccagcgt ttgacgctgc ggttcatccc  19980
tgtggaccgt gaggatactg cgtactcgta caaggcgcgg ttcaccctag ctgtgggtga  20040
taaccgtgtg ctggacatgg cttccacgta ctttgacatc cgcggcgtgc tggacagggg  20100
ccctactttt aagccctact ctggcactgc ctacaacgcc ctggctccca agggtgcccc  20160
aaatccttgc gaatgggatg aagctgctac tgctcttgaa ataaacctag aagaagagga  20220
cgatgacaac gaagacgaag tagacgagca agctgagcag caaaaaactc acgtatttgg  20280
gcaggcgcct tattctggta taaatattac aaaggagggt attcaaatag gtgtcgaagg  20340
tcaaacacct aaatatgccg ataaaacatt tcaacctgaa cctcaaatag gagaatctca  20400
gtggtacgaa actgaaatta atcatgcagc tgggagagtc cttaaaaaga ctaccccaat  20460
gaaaccatgt tacggttcat atgcaaaacc cacaaatgaa aatggagggc aaggcattct  20520
tgtaaagcaa caaaatggaa agctagaaag tcaagtggaa atgcaatttt tctcaactac  20580
tgaggcgacc gcaggcaatg gtgataactt gactcctaaa gtggtattgt acagtgaaga  20640
tgtagatata gaaaccccag acactcatat ttcttacatg cccactatta aggaaggtaa  20700
ctcacgagaa ctaatgggcc aacaatctat gcccaacagg cctaattaca ttgcttttag  20760
ggacaatttt attggtctaa tgtattacaa cagcacgggt aatatgggtg ttctggcggg  20820
ccaagcatcg cagttgaatg ctgttgtaga tttgcaagac agaaacacag agctttcata  20880
ccagcttttg cttgattcca ttggtgatag aaccaggtac ttttctatgt ggaatcaggc  20940
tgttgacagc tatgatccag atgttagaat tattgaaaat catggaactg aagatgaact  21000
tccaaattac tgctttccac tgggaggtgt gattaataca gagactctta ccaaggtaaa  21060
acctaaaaca ggtcaggaaa atggatggga aaaagatgct acagaatttt cagataaaaa  21120
tcaaataaga gttggaaata attttgccat ggaaatcaat ctaaatgcca acctgtggag  21180
aaatttcctg tactccaaca tagcgctgta tttgcccgac aagctaaagt acagtccttc  21240
caacgtaaaa atttctgata acccaaacac ctacgactac atgaacaagc gagtggtggc  21300
tcccgggtta gtggactgct acattaacct tggagcacgc tggtcccttg actatatgga  21360
caacgtcaac ccatttaacc accaccgcaa tgctggcctg cgctaccgct caatgttgct  21420
gggcaatggt cgctatgtgc ccttccacat ccaggtgcct cagaagttct ttgccattaa  21480
aaacctcctt ctcctgccgg gctcatacac ctacgagtgg aacttcagga aggatgttaa  21540
catggttctg cagagctccc taggaaatga cctaagggtt gacggagcca gcattaagtt  21600
tgatagcatt tgcctttacg ccaccttctt ccccatggcc cacaacaccg cctccacgct  21660
tgaggccatg cttagaaacg acaccaacga ccagtccttt aacgactatc tctccgccgc  21720
caacatgctc taccctatac ccgccaacgc taccaacgtg cccatatcca tcccctcccg  21780
caactgggcg gctttccgcg gctgggcctt cacgcgcctt aagactaagg aaaccccatc  21840
actgggctcg ggctacgacc cttattacac ctactctggc tctataccct acctagatgg  21900
```

```
aacctttac ctcaaccaca cctttaagaa ggtggccatt acctttgact cttctgtcag  21960
ctggcctggc aatgaccgcc tgcttacccc caacgagttt gaaattaagc gctcagttga  22020
cggggagggt tacaacgttg cccagtgtaa catgaccaaa gactggttcc tggtacaaat  22080
gctagctaac tacaacattg gctaccaggg cttctatatc ccagagagct acaaggaccg  22140
catgtactcc ttctttagaa acttccagcc catgagccgt caggtggtgg atgatactaa  22200
atacaaggac taccaacagg tgggcatcct acaccaacac aacaactctg gatttgttgg  22260
ctaccttgcc cccaccatgc gcgaaggaca ggcctaccct gctaacttcc cctatccgct  22320
tataggcaag accgcagttg acagcattac ccagaaaaag tttctttgcg atcgcaccct  22380
ttggcgcatc ccattctcca gtaactttat gtccatgggc gcactcacag acctgggcca  22440
aaaccttctc tacgccaact ccgcccacgc gctagacatg acttttgagg tggatcccat  22500
ggacgagccc acccttcttt atgttttgtt tgaagtcttt gacgtggtcc gtgtgcaccg  22560
gccgcaccgc ggcgtcatcg aaaccgtgta cctgcgcacg cccttctcgg ccggcaacgc  22620
cacaacataa agaagcaagc aacatcaaca acagctgccg ccatgggctc cagtgagcag  22680
gaactgaaag ccattgtcaa agatcttggt tgtgggccat atttttttggg cacctatgac  22740
aagcgctttc caggctttgt ttctccacac aagctcgcct gcgccatagt caatacggcc  22800
ggtcgcgaga ctgggggcgt acactggatg gcctttgcct ggaacccgca ctcaaaaaca  22860
tgctacctct ttgagccctt tggcttttct gaccagcgac tcaagcaggt ttaccagttt  22920
gagtacgagt cactcctgcg ccgtagcgcc attgcttctt cccccgaccg ctgtataacg  22980
ctggaaaagt ccacccaaag cgtacagggg cccaactcgg ccgcctgtgg actattctgc  23040
tgcatgtttc tccacgcctt tgccaactgg ccccaaactc ccatggatca caacccccacc  23100
atgaacctta ttaccggggt acccaactcc atgctcaaca gtccccaggt acagcccacc  23160
ctgcgtcgca accaggaaca gctctacagc ttcctggagc gccactcgcc ctacttccgc  23220
agccacagtg cgcagattag gagcgccact tctttttgtc acttgaaaaa catgtaaaaa  23280
taatgtacta gagacacttt caataaaggc aaatgctttt atttgtacac tctcgggtga  23340
ttatttaccc ccacccttgc cgtctgcgcc gtttaaaaat caaaggggtt ctgccgcgca  23400
tcgctatgcg ccactggcag ggacacgttg cgatactggt gtttagtgct ccacttaaac  23460
tcaggcacaa ccatccgcgg cagctcggtg aagttttcac tccacaggct gcgcaccatc  23520
accaacgcgt ttagcaggtc gggcgccgat atcttgaagt cgcagttggg gcctccgccc  23580
tgcgcgcgcg agttgcgata cacagggttg cagcactgga acactatcag cgccgggtgg  23640
tgcacgctgg ccagcacgct cttgtcggag atcagatccg cgtccaggtc ctccgcgttg  23700
ctcagggcga acggagtcaa ctttggtagc tgccttccca aaaagggcgc gtgcccaggc  23760
tttgagttgc actcgcaccg tagtggcatc aaaaggtgac cgtgcccggt ctgggcgtta  23820
ggatacagcg cctgcataaa agccttgatc tgcttaaaag ccacctgagc ctttgcgcct  23880
tcagagaaga acatgccgca agacttgccg gaaaactgat tggccggaca ggccgcgtcg  23940
tgcacgcagc accttgcgtc ggtgttggag atctgcacca catttcggcc ccaccggttc  24000
ttcacgatct tggccttgct agactgctcc ttcagcgcgc gctgcccgtt ttcgctcgtc  24060
acatccattt caatcacgtg ctccttattt atcataatgc ttccgtgtag acacttaagc  24120
tcgccttcga tctcagcgca gcggtgcagc cacaacgcgc agcccgtggg ctcgtgatgc  24180
ttgtaggtca cctctgcaaa cgactgcagg tacgcctgca ggaatcgccc catcatcgtc  24240
```

-continued

```
acaaaggtct tgttgctggt gaaggtcagc tgcaacccgc ggtgctcctc gttcagccag  24300
gtcttgcata cggccgccag agcttccact tggtcaggca gtagtttgaa gttcgccttt  24360
agatcgttat ccacgtggta cttgtccatc agcgcgcgcg cagcctccat gcccttctcc  24420
cacgcagaca cgatcggcac actcagcggg ttcatcaccg taatttcact ttccgcttcg  24480
ctgggctctt cctcttcctc ttgcgtccgc ataccacgcg ccactgggtc gtcttcattc  24540
agccgccgca ctgtgcgctt acctcctttg ccatgcttga ttagcaccgg tgggttgctg  24600
aaacccacca tttgtagcgc cacatcttct ctttcttcct cgctgtccac gattacctct  24660
ggtgatggcg ggcgctcggg cttgggagaa gggcgcttct ttttcttctt gggcgcaatg  24720
gccaaatccg ccgccgaggt cgatggccgc gggctgggtg tgcgcggcac cagcgcgtct  24780
tgtgatgagt cttcctcgtc ctcggactcg atacgccgcc tcatccgctt ttttgggggc  24840
gcccggggag gcggcggcga cggggacggg gacgacacgt cctccatggt tgggggacgt  24900
cgcgccgcac cgcgtccgcg ctcgggggtg gtttcgcgct gctcctcttc ccgactggcc  24960
atttccttct cctataggca gaaaaagatc atggagtcag tcgagaagaa ggacagccta  25020
accgcccccct ctgagttcgc caccaccgcc tccaccgatg ccgccaacgc gcctaccacc  25080
ttccccgtcg aggcaccccc gcttgaggag gaggaagtga ttatcgagca ggacccaggt  25140
tttgtaagcg aagacgacga ggaccgctca gtaccaacag aggataaaaa gcaagaccag  25200
gacaacgcag aggcaaacga ggaacaagtc gggcgggggg acgaaaggca tggcgactac  25260
ctagatgtgg gagacgacgt gctgttgaag catctgcagc gccagtgcgc cattatctgc  25320
gacgcgttgc aagagcgcag cgatgtgccc ctcgccatag cggatgtcag ccttgcctac  25380
gaacgccacc tattctcacc gcgcgtaccc cccaaacgcc aagaaaacgg cacatgcgag  25440
cccaacccgc gcctcaactt ctaccccgta tttgccgtgc cagaggtgct tgccacctat  25500
cacatctttt tccaaaactg caagataccc ctatcctgcc gtgccaaccg cagccgagcg  25560
gacaagcagc tggccttgcg gcagggcgct gtcatacctg atatcgcctc gctcaacgaa  25620
gtgccaaaaa tctttgaggg tcttggacgc gacgagaagc gcgcggcaaa cgctctgcaa  25680
caggaaaaca gcgaaaatga aagtcactct ggagtgttgg tggaactcga gggtgacaac  25740
gcgcgcctag ccgtactaaa acgcagcatc gaggtcaccc actttgccta cccggcactt  25800
aacctacccc ccaaggtcat gagcacagtc atgagtgagc tgatcgtgcg ccgtgcgcag  25860
cccctggaga gggatgcaaa tttgcaagaa caaacagagg agggcctacc cgcagttggc  25920
gacgagcagc tagcgcgctg gcttcaaacg cgcgagcctg ccgacttgga ggagcgacgc  25980
aaactaatga tggccgcagt gctcgttacc gtggagcttg agtgcatgca gcggttcttt  26040
gctgacccgg agatgcagcg caagctagag gaaacattgc actacacctt tcgacagggc  26100
tacgtacgcc aggcctgcaa gatctccaac gtggagctct gcaacctggt ctcctacctt  26160
ggaattttgc acgaaaaccg ccttgggcaa aacgtgcttc attccacgct caagggcgag  26220
gcgcgccgcg actacgtccg cgactgcgtt tacttatttc tatgctacac ctggcagacg  26280
gccatgggcg tttggcagca gtgcttggag gagtgcaacc tcaaggagct gcagaaactg  26340
ctaaagcaaa acttgaagga cctatggacg gccttcaacg agcgctccgt ggccgcgcac  26400
ctggcggaca tcattttccc cgaacgcctg cttaaaaccc tgcaacaggg tctgccagac  26460
ttcaccagtc aaagcatgtt gcagaacttt aggaacttta tcctagagcg ctcaggaatc  26520
ttgcccgcca cctgctgtgc acttcctagc gactttgtgc ccattaagta ccgcgaatgc  26580
cctccgccgc tttggggcca ctgctacctt ctgcagctag ccaactacct tgcctaccac  26640
```

```
tctgacataa tggaagacgt gagcggtgac ggtctactgg agtgtcactg tcgctgcaac  26700
ctatgcaccc cgcaccgctc cctggtttgc aattcgcagc tgcttaacga aagtcaaatt  26760
atcggtacct ttgagctgca gggtccctcg cctgacgaaa agtccgcggc tccggggttg  26820
aaactcactc cggggctgtg gacgtcggct taccttcgca aatttgtacc tgaggactac  26880
cacgcccacg agattaggtt ctacgaagac caatcccgcc cgccaaatgc ggagcttacc  26940
gcctgcgtca ttacccaggg ccacattctt ggccaattgc aagccatcaa caaagcccgc  27000
caagagtttc tgctacgaaa gggacggggg gtttacttgg acccccagtc cggcgaggag  27060
ctcaacccaa tccccccgcc gccgcagccc tatcagcagc agccgcgggc ccttgcttcc  27120
caggatggca cccaaaaaga agctgcagct gccgccgcca cccacggacg aggaggaata  27180
ctgggacagt caggcagagg aggttttgga cgaggaggag gaggacatga tggaagactg  27240
ggagagccta gacgaggaag cttccgaggt cgaagaggtg tcagacgaaa caccgtcacc  27300
ctcggtcgca ttcccctcgc cggcgcccca gaaatcggca accggttcca gcatggctac  27360
aacctccgct cctcaggcgc cgccggcact gcccgttcgc cgacccaacc gtagatggga  27420
caccactgga accagggccg gtaagtccaa gcagccgccg ccgttagccc aagagcaaca  27480
acagcgccaa ggctaccgct catggcgcgg gcacaagaac gccatagttg cttgcttgca  27540
agactgtggg ggcaacatct ccttcgcccg ccgctttctt ctctaccatc acggcgtggc  27600
cttccccgt aacatcctgc attactaccg tcatctctac agcccatact gcaccggcgg  27660
cagcggcagc ggcagcaaca gcagcggcca cacagaagca aaggcgaccg gatagcaaga  27720
ctctgacaaa gcccaagaaa tccacagcgg cggcagcagc aggaggagga gcgctgcgtc  27780
tggcgcccaa cgaacccgta tcgacccgcg agcttagaaa caggattttt cccactctgt  27840
atgctatatt tcaacagagc aggggccaag aacaagagct gaaaataaaa aacaggtctc  27900
tgcgatccct cacccgcagc tgcctgtatc acaaaagcga agatcagctt cggcgcacgc  27960
tggaagacgc ggaggctctc ttcagtaaat actgcgcgct gactcttaag gactagtttc  28020
gcgccctttc tcaaatttaa gcgcgaaaac tacgtcatct ccagcggcca cacccggcgc  28080
cagcacctgt cgtcagcgcc atttcaactt tgtatacaaa agttgtgatg agcaaggaaa  28140
ttcccacgcc ctacatgtgg agttaccagc cacaaatggg acttgcggct ggagctgccc  28200
aagactactc aacccgaata aactacatga gcgcgggacc ccacatgata tcccgggtca  28260
acggaatacg cgcccaccga aaccgaattc tcctggaaca ggcggctatt accaccacac  28320
ctcgtaataa ccttaatccc cgtagttggc ccgctgccct ggtgtaccag gaaagtcccg  28380
ctcccaccac tgtggtactt cccagagacg cccaggccga agttcagatg actaactcag  28440
gggcgcagct tgcgggcggc tttcgtcaca gggtgcggtc gcccgggcag ggtataactc  28500
acctgacaat cagagggcga ggtattcagc tcaacgacga gtcggtgagc tcctcgcttg  28560
gtctccgtcc ggacgggaca tttcagatcg gcggcgccgg ccgctcttca ttcacgcctc  28620
gtcaggcaat cctaactctg cagacctcgt cctctgagcc gcgctctgga ggcattggaa  28680
ctctgcaatt tattgaggag tttgtgccat cggtctactt taaccccttc tcgggacctc  28740
ccggccacta tccggatcaa tttattccta actttgacgc ggtaaaggac tcggcggacg  28800
gctacgactg aatgttaagt ggagaggcag agcaactgcg cctgaaacac ctggtccact  28860
gtcgccgcca caagtgcttt gcccgcgact ccggtgagtt ttgctacttt gaattgcccg  28920
aggatcatat cgagggcccg gcgcacggcg tccggcttac cgcccaggga gagcttgccc  28980
```

gtagcctgat tcgggagttt acccagcgcc ccctgctagt tgagcgggac aggggaccct 29040
gtgttctcac tgtgatttgc aactgtccta accctggatt acatcaagat ctttgttgcc 29100
atctctgtgc tgagtataat aaatacagaa attaaaatat actggggctc ctatcgccat 29160
cctgtaaacg ccaccgtctt cacccgccca agcaaaccaa ggcgaacctt acctggtact 29220
tttaacatct ctccctctgt gatttacaac agtttcaacc cagacggagt gagtctacga 29280
gagaacctct ccgagctcag ctactccatc agaaaaaaca ccacccctcct tacctgccgg 29340 gaacgtacga gtgcgtcacc ggccgctgca ccacacctac cgcctgaccg taaaccagac 29400
tttttccgga cagacctcaa taactctgtt taccagaaca ggaggtgagc ttagaaaacc 29460
cttagggtat taggccaaag gcgcagctac tgtggggttt atgaacaatt caagcaactc 29520
tacgggctat tctaattcag gtttctctag aatcggggtt ggggttattc tctgtcttgt 29580
gattctcttt attcttatac taacgcttct ctgcctaagg ctcgccgcct gctgtgtgca 29640
catttgcatt tattgtcagc tttttaaacg ctggggtcgc cacccaagat gattaggtac 29700
ataatcctag gtttactcac ccttgcgtca gcccacggta ccacccaaaa ggtggatttt 29760
aaggagccag cctgtaatgt tacattcgca gctgaagcta atgagtgcac cactcttata 29820
aaatgcacca cagaacatga aaagctgctt attcgccaca aaaacaaaat tggcaagtat 29880
gctgtttatg ctatttggca gccaggtgac actacagagt ataatgttac agttttccag 29940
ggtaaaagtc ataaaacttt tatgtatact tttccatttt atgaaatgtg cgacattacc 30000
atgtacatga gcaaacagta taagttgtgg cccccacaaa attgtgtgga aaacactggc 30060
actttctgct gcactgctat gctaattaca gtgctcgctt tggtctgtac cctactctat 30120
attaaataca aaagcagacg cagctttatt gaggaaaaga aatgccttaa atttactaag 30180
ttacaaagct aatgtcacca ctaactgctt tactcgctgc ttgcaaaaca aattcaaaaa 30240
gttagcatta taattagaat aggatttaaa ccccccggtc atttcctgct caataccatt 30300
cccctgaaca attgactcta tgtgggatat gctccagcgc tacaaccttg aagtcaggct 30360
tcctggatgt cagcatctga ctttggccag cacctgtccc gcggatttgt tccagtccaa 30420
ctacagcgac ccaccctaac agagatgacc aacacaacca acgcggccgc cgctaccgga 30480
cttacatcta ccacaaatac accccaagtt tctgcctttg tcaataactg ggataacttg 30540
ggcatgtggt ggttctccat agcgcttatg tttgtatgcc ttattattat gtggctcatc 30600
tgctgcctaa agcgcaaacg cgcccgacca cccatctata gtcccatcat tgtgctacac 30660
ccaaacaatg atggaatcca tagattggac ggactgaaac acatgttctt ttctcttaca 30720
gtatgattaa atgagacatg attcctcgag tttttatatt actgaccctt gttgcgcttt 30780
tttgtgcgtg ctccacattg gctgcggttt ctcacatcga agtagactgc attccagcct 30840
tcacagtcta tttgctttac ggatttgtca ccctcacgct catctgcagc ctcatcactg 30900
tggtcatcgc ctttatccag tgcattgact gggtctgtgt gcgctttgca tatctcagac 30960
accatcccca gtacagggac aggactatag ctgagcttct tagaattctt taattatgaa 31020
atttactgtg acttttctgc tgattatttg caccctatct gcgttttgtt ccccgacctc 31080
caagcctcaa agacatatat catgcagatt cactcgtata tggaatattc caagttgcta 31140
caatgaaaaa agcgatcttt ccgaagcctg gttatatgca atcatctctg ttatggtgtt 31200
ctgcagtacc atcttagccc tagctatata tccctacctt gacattggct ggaacgcaat 31260
agatgccatg aaccacccaa ctttccccgc gcccgctatg cttccactgc aacaagttgt 31320
tgccggcggc tttgtcccag ccaatcagcc tcgcccacct tctcccaccc ccactgaaat 31380

-continued

```
cagctacttt aatctaacag gaggagatga ctgacaccct agatctagaa atggacggaa  31440
ttattacaga gcagcgcctg ctagaaagac gcagggcagc ggccgagcaa cagcgcatga  31500
atcaagagct ccaagacatg gttaacttgc accagtgcaa aaggggtatc ttttgtctgg  31560
taaagcaggc caaagtcacc tacgacagta ataccaccgg acaccgcctt agctacaagt  31620
tgccaaccaa gcgtcagaaa ttggtggtca tggtgggaga aaagcccatt accataactc  31680
agcactcggt agaaaccgaa ggctgcattc actcaccttg tcaaggacct gaggatctct  31740
gcacccttat taagaccctg tgcggtctca aagatcttat tccctttaac taataaaaaa  31800
aaataataaa gcatcactta cttaaaatca gttagcaaat ttctgtccag tttattcagc  31860
agcacctcct tgccctcctc ccagctctgg tattgcagct tcctcctggc tgcaaacttt  31920
ctccacaatc taaatggaat gtcagtttcc tcctgttcct gtccatccgc acccactatc  31980
ttcatgttgt tgcagatgaa gcgcgcaaga ccgtctgaag ataccttcaa ccccgtgtat  32040
ccatatgaca cggaaaccgg tcctccaact gtgccttttc ttactcctcc ctttgtatcc  32100
cccaatgggt ttcaagagag tccccctggg gtactctctt tgcgcctatc cgaacctcta  32160
gttacctcca atggcatgct tgcgctcaaa atgggcaacg gcctctctct ggacgaggcc  32220
ggcaacctta cctcccaaaa tgtaaccact gtgagcccac ctctcaaaaa aaccaagtca  32280
aacataaacc tggaaatatc tgcacccctc acagttacct cagaagccct aactgtggct  32340
gccgccgcac ctctaatggt cgcgggcaac acactcacca tgcaatcaca ggccccgcta  32400
accgtgcacg actccaaact tagcattgcc acccaaggac ccctcacagt gtcagaagga  32460
aagctagccc tgcaaacatc aggcccccctc accaccaccg atagcagtac ccttactatc  32520
actgcctcac cccctctaac tactgccact ggtagcttgg gcattgactt gaaagagccc  32580
atttatacac aaaatggaaa actaggacta aagtacgggg ctcctttgca tgtaacagac  32640
gacctaaaca ctttgaccgt agcaactggt ccaggtgtga ctattaataa tacttccttg  32700
caaactaaag ttactggagc cttgggtttt gattcacaag gcaatatgca acttaatgta  32760
gcaggaggac taaggattga ttctcaaaac agacgcctta tacttgatgt tagttatccg  32820
tttgatgctc aaaaccaact aaatctaaga ctaggacagg gccctctttt tataaactca  32880
gcccacaact tggatattaa ctacaacaaa ggcctttact tgtttacagc ttcaaacaat  32940
tccaaaaagc ttgaggttaa cctaagcact gccaaggggt tgatgtttga cgctacagcc  33000
atagccatta atgcaggaga tggggcttgaa tttggttcac ctaatgcacc aaacacaaat  33060
cccctcaaaa caaaaaattgg ccatggccta gaatttgatt caaacaaggc tatggttcct  33120
aaactaggaa ctggccttag ttttgacagc acaggtgcca ttacagtagg aaacaaaaat  33180
aatgataagc taactttatg gacaggagtc aaccccaccg aagccaactg tcaaatcatg  33240
aactccagtg aatctaatga ttgcaaatta attctaacac tagttaaaac tggagcacta  33300
gtcactgcat ttgtttatgt tataggagta tctaacaatt ttaatatgct aactacacac  33360
agaaatataa attttactgc agagctgttt ttcgattcta ctggtaattt actaactaga  33420
ctctcatccc tcaaaactcc acttaatcat aaatcaggac aaaacatggc tactggtgcc  33480
attactaatg ctaaaggttt catgcccagc acgactgcct atcctttcaa tgataattct  33540
agagaaaaag aaaactacat ttacggaact tgttactaca cagctagtga tcgcactgct  33600
tttcccattg acatatctgt catgcttaac cgaagagcaa taaatgacga gacatcatat  33660
tgtattcgta taacttggtc ctggaacaca ggagatgccc cagaggtgca aacctctgct  33720
```

-continued

```
acaaccctag tcacctcccc atttaccttt tactacatca gagaagacga ctaataaaga  33780
atcgtttgtg ttatgtttca acgtgtttat ttttcaattg cagaaaattt caagtcattt  33840
ttcattcagt agtatagccc caccaccaca tagcttatac agatcaccgt acctcaactt  33900
tgtataataa agttgtaatc aaactcacag aaccctagta ttcaacctgc cacctccctc  33960
ccaacacaca gagtacacag tcctttctcc ccggctggcc ttaaaaagca tcatatcatg  34020
ggtaacagac atattcttag gtgttatatt ccacacggtt tcctgtcgag ccaaacgctc  34080
atcagtgata ttaataaact ccccgggcag ctcacttaag ttcatgtcgc tgtccagctg  34140
ctgagccaca ggctgctgtc caacttgcgg ttgcttaacg ggcggcgaag gagaagtcca  34200
cgcctacatg gggtagagt cataatcgtg catcaggata gggcggtggt gctgcagcag  34260
cgcgcgaata aactgctgcc gccgccgctc cgtcctgcag gaatacaaca tggcagtggt  34320
ctcctcagcg atgattcgca ccgcccgcag cataaggcgc cttgtcctcc gggcacagca  34380
gcgcaccctg atctcactta aatcagcaca gtaactgcag cacagcacca caatattgtt  34440
caaaatccca cagtgcaagg cgctgtatcc aaagctcatg gcggggacca cagaacccac  34500
gtggccatca taccacaagc gcaggtagat taagtggcga cccctcataa acacgctgga  34560
cataaacatt acctcttttg gcatgttgta attcaccacc tcccggtacc atataaacct  34620
ctgattaaac atggcgccat ccaccaccat cctaaaccag ctggccaaaa cctgcccgcc  34680
ggctatacac tgcagggaac cgggactgga acaatgacag tggagagccc aggactcgta  34740
accatggatc atcatgctcg tcatgatatc aatgttggca caacacaggc acacgtgcat  34800
acacttcctc aggattacaa gctcctcccg cgttagaacc atatcccagg gaacaaccca  34860
ttcctgaatc agcgtaaatc ccacactgca gggaagacct cgcacgtaac tcacgttgtg  34920
cattgtcaaa gtgttacatt cgggcagcag cggatgatcc tccagtatgg tagcgcgggt  34980
ttctgtctca aaggaggta gacgatccct actgtacgga gtgcgccgag acaaccgaga  35040
tcgtgttggt cgtagtgtca tgccaaatgg aacgccggac gtagtcatat ttcctgaagc  35100
aaaaccaggt gcgggcgtga caaacagatc tgcgtctccg gtctcgccgc ttagatcgct  35160
ctgtgtagta gttgtagtat atccactctc tcaaagcatc caggcgcccc ctggcttcgg  35220
gttctatgta aactccttca tgcgccgctg ccctgataac atccaccacc gcagaataag  35280
ccacacccag ccaacctaca cattcgttct gcgagtcaca cacgggagga gcgggaagag  35340
ctggaagaac catgtttttt tttttattcc aaaagattat ccaaaacctc aaaatgaaga  35400
tctattaagt gaacgcgctc ccctccggtg gcgtggtcaa actctacagc caaagaacag  35460
ataatggcat ttgtaagatg ttgcacaatg gcttccaaaa ggcaaacggc cctcacgtcc  35520
aagtggacgt aaaggctaaa cccttcaggg tgaatctcct ctataaacat tccagcacct  35580
tcaaccatgc ccaaataatt ctcatctcgc caccttctca atatatctct aagcaaatcc  35640
cgaatattaa gtccggccat tgtaaaaatc tgctccagag cgccctccac cttcagcctc  35700
aagcagcgaa tcatgattgc aaaaattcag gttcctcaca gacctgtata agattcaaaa  35760
gcggaacatt aacaaaaata ccgcgatccc gtaggtccct tcgcagggcc agctgaacat  35820
aatcgtgcag gtctgcacgg accagcgcgg ccacttcccc gccaggaacc atgacaaaag  35880
aacccacact gattatgaca cgcatactcg gagctatgct aaccagcgta gccccgatgt  35940
aagcttgttg catgggcggc gatataaaat gcaaggtgct gctcaaaaaa tcaggcaaag  36000
cctcgcgcaa aaaagaaagc acatcgtagt catgctcatg cagataaagg caggtaagct  36060
ccggaaccac cacagaaaaa gacaccattt ttctctcaaa catgtctgcg ggtttctgca  36120
```

taaacacaaa ataaaataac aaaaaaacat ttaaacatta gaagcctgtc ttacaacagg 36180
aaaaacaacc cttataagca taagacggac tacggccatg ccggcgtgac cgtaaaaaaa 36240
ctggtcaccg tgattaaaaa gcaccaccga cagctcctcg gtcatgtccg gagtcataat 36300
gtaagactcg gtaaacacat caggttgatt cacatcggtc agtgctaaaa agcgaccgaa 36360
atagcccggg ggaatacata cccgcaggcg tagagacaac attacagccc ccataggagg 36420
tataacaaaa ttaataggag agaaaaacac ataaacacct gaaaaaccct cctgcctagg 36480
caaaatagca ccctcccgct ccagaacaac atacagcgct tccacagcgg cagccataac 36540
agtcagcctt accagtaaaa aagaaaacct attaaaaaaa caccactcga cacggcacca 36600
gctcaatcag tcacagtgta aaaaagggcc aagtgcagag cgagtatata taggactaaa 36660
aaatgacgta acggttaaag tccacaaaaa acacccagaa aaccgcacgc gaacctacgc 36720
ccagaaacga aagccaaaaa acccacaact tcctcaaatc gtcacttccg ttttcccacg 36780
ttacgtcact tcccatttta agaaaactac aattcccaac acatacaagt tactccgccc 36840
taaaacctac gtcacccgcc ccgttcccac gccccgcgcc acgtcacaaa ctccaccccc 36900
tcattatcat attggcttca atccaaaata aggtatatta ttgatgatg 36949

<210> SEQ ID NO 5
<211> LENGTH: 36907
<212> TYPE: DNA
<213> ORGANISM: Artificial Sequence
<220> FEATURE:
<223> OTHER INFORMATION: Synthetic adenovirus construct (AdSyn-CO175)

<400> SEQUENCE: 5
catcatcaat aatatacctt attttggatt gaagccaata tgataatgag gggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattaaac cgtattaccg ccatgcattt aatggagtgc 480
ctcgtgaggc tccggtgccc gtcagtgggc agagcgcaca tcgcccacag tccccgagaa 540
gttggggga ggggtcggca attgaaccgg tgcctagaga aggtggcgcg gggtaaactg 600
ggaaagtgat gtcgtgtact ggctccgcct ttttcccgag ggtgggggag aaccgtatat 660
aagtgcagta gtcgccgtga acgttctttt tcgcaacggg tttgccgcca gaacacaggt 720
aagtgccgtg tgtggttccc gcgggcctgg cctctttacg ggttatggcc cttgcgtgcc 780
ttgaattact tccacctggc tgcagtacgt gattcttgat cccgagcttc gggttggaag 840
tgggtgggag agttcgaggc cttgcgctta aggagcccct tcgcctcgtg cttgagttga 900
ggcctggcct gggcgctggg gccgccgcgt gcgaatctgg tggcaccttc gcgcctgtct 960
cgctgctttc gataagtctc tagccattta aaatttttga tgacctgctg cgacgctttt 1020
tttctggcaa gatagtcttg taaatgcggg ccaagatctg cacactggta tttcggtttt 1080
tggggccgcg ggcggcgacg gggcccgtgc gtcccagcgc acatgttcgg cgaggcgggg 1140
cctgcgagcg cggccaccga gaatcggacg gggtagtct caagctggcc ggcctgctct 1200

-continued

```
ggtgcctggc ctcgcgccgc cgtgtatcgc cccgccctgg gcggcaaggc tggcccggtc   1260
ggcaccagtt gcgtgagcgg aaagatggcc gcttcccggc cctgctgcag ggagctcaaa   1320
atggaggacg cggcgctcgg gagagcgggc gggtgagtca cccacacaaa ggaaaagggc   1380
ctttccgtcc tcagccgtcg cttcatgtga ctccacggag taccgggcgc cgtccaggca   1440
cctcgattag ttctcgagct tttggagtac gtcgtcttta ggttgggggg aggggtttta   1500
tgcgatggag tttccccaca ctgagtgggt ggagactgaa gttaggccag cttggcactt   1560
gatgtaattc tccttggaat ttgccctttt tgagtttgga tcttggttca ttctcaagcc   1620
tcagacagtg gttcaaagtt tttttcttcc atttcaggtg tcgtgacgct agcgctaccg   1680
gactcagatc tcgagctcaa gcttcgaatt ctgcagtcga cggtaccgga tccatggaag   1740
acgccaaaaa cataaagaaa ggcccggcgc cattctatcc gctggaagat ggaaccgctg   1800
gagagcaact gcataaggct atgaagagat acgccctggt tcctggaaca attgctttta   1860
cagatgcaca tatcgaggtg gacatcactt acgctgagta cttcgaaatg tccgttcggt   1920
tggcagaagc tatgaaacga tatgggctga atacaaatca cagaatcgtc gtatgcagtg   1980
aaaactctct tcaattcttt atgccggtgt tgggcgcgtt atttatcgga gttgcagttg   2040
cgcccgcgaa cgacatttat aatgaacgtg aattgctcaa cagtatgggc atttcgcagc   2100
ctaccgtggt gttcgtttcc aaaaaggggt tgcaaaaaat tttgaacgtg caaaaaaagc   2160
tcccaatcat ccaaaaaatt attatcatgg attctaaaac ggattaccag ggatttcagt   2220
cgatgtacac gttcgtcaca tctcatctac ctcccggttt taatgaatac gattttgtgc   2280
cagagtcctt cgatagggac aagacaattg cactgatcat gaactcctct ggatctactg   2340
gtctgcctaa aggtgtcgct ctgcctcata gaactgcctg cgtgagattc tcgcatgcca   2400
gagatcctat ttttggcaat caaatcattc cggatactgc gattttaagt gttgttccat   2460
tccatcacgg ttttggaatg tttactacac tcggatattt gatatgtgga tttcgagtcg   2520
tcttaatgta tagatttgaa gaagagctgt ttctgaggag ccttcaggat tacaagattc   2580
aaagtgcgct gctggtgcca accctattct ccttcttcgc caaaagcact ctgattgaca   2640
aatacgattt atctaattta cacgaaattg cttctggtgg cgctcccctc tctaaggaag   2700
tcggggaagc ggttgccaag aggttccatc tgccaggtat caggcaagga tatgggctca   2760
ctgagactac atcagctatt ctgattacac ccgaggggga tgataaaccg ggcgcggtcg   2820
gtaaagttgt tccatttttt gaagcgaagg ttgtggatct ggataccggg aaaacgctgg   2880
gcgttaatca aagaggcgaa ctgtgtgtga gaggtcctat gattatgtcc ggttatgtaa   2940
acaatccgga agcgaccaac gccttgattg acaaggatgg atggctacat tctggagaca   3000
tagcttactg ggacgaagac gaacacttct tcatcgttga ccgcctgaag tctctgatta   3060
agtacaaagg ctatcaggtg gctcccgctg aattggaatc catcttgctc caacacccca   3120
acatcttcga cgcaggtgtc gcaggtcttc ccgacgatga cgccggtgaa cttcccgccg   3180
ccgttgttgt tttggagcac ggaaagacga tgacggaaaa agagatcgtg gattacgtcg   3240
ccagtcaagt aacaaccgcg aaaaagttgc gcggaggagt tgtgtttgtg gacgaagtac   3300
cgaaaggtct taccggaaaa ctcgacgcaa gaaaaatcag agagatcctc ataaaggcca   3360
agaagggcgg aaagatcgcc gtggcagccg cagccaccat ggtgagcaag ggcgaggagc   3420
tgttcaccgg ggtggtgccc atcctggtcg agctggacgg cgacgtaaac ggccacaagt   3480
tcagcgtgtc cggcgagggc gagggcgatg ccacctacgg caagctgacc ctgaagttca   3540
tctgcaccac cggcaagctg cccgtgccct ggcccaccct cgtgaccacc ctgacctacg   3600
```

-continued

```
gcgtgcagtg cttcagccgc taccccgacc acatgaagca gcacgacttc ttcaagtccg   3660
ccatgcccga aggctacgtc caggagcgca ccatcttctt caaggacgac ggcaactaca   3720
agacccgcgc cgaggtgaag ttcgagggcg acaccctggt gaaccgcatc gagctgaagg   3780
gcatcgactt caaggaggac ggcaacatcc tggggcacaa gctggagtac aactacaaca   3840
gccacaacgt ctatatcatg gccgacaagc agaagaacgg catcaaggtg aacttcaaga   3900
tccgccacaa catcgaggac ggcagcgtgc agctcgccga ccactaccag cagaacaccc   3960
ccatcggcga cggccccgtg ctgctgcccg acaaccacta cctgagcacc cagtccgccc   4020
tgagcaaaga ccccaacgag aagcgcgatc acatggtcct gctggagttc gtgaccgccg   4080
ccgggatcac tctcggcatg gacgagctgt acaagtaaag cgactctaga tcataatcag   4140
ccatacccaa acaccattgt cacactccaa tcgattcaaa caccattgtc acactccaac   4200
atttgtagag gttttacttg ctttaaaaaa cctcccacac ctccccctga acctgaaaca   4260
taaaatgaat gcaattgttg ttgttaactt gtttattgca gcttataatg gttacaaata   4320
aagcaatagc atcacaaatt tcacaaataa agcatttttt tcactgcatt ctagttgtgg   4380
tttgtccaaa ctcatcaatg taagtttaaa cggcgcgcct gaaatgtgtg ggcgtggctt   4440
aagggtggga aagaatatat aaggtggggg tcttatgtag ttttgtatct gttttgcagc   4500
agccgccgcc gccatgagca ccaactcgtt tgatggaagc attgtgagct catatttgac   4560
aacgcgcatg cccccatggg ccggggtgcg tcagaatgtg atgggctcca gcattgatgg   4620
tcgccccgtc ctgcccgcaa actctactac cttgacctac gagaccgtgt ctggaacgcc   4680
gttggagact gcagcctccg ccgccgcttc agccgctgca gccaccgccc gcgggattgt   4740
gactgacttt gctttcctga gcccgcttgc aagcagtgca gcttcccgtt catccgcccg   4800
cgatgacaag ttgacggctc ttttggcaca attggattct ttgacccggg aacttaatgt   4860
cgtttctcag cagctgttgg atctgcgcca gcaggtttct gccctgaagg cttcctcccc   4920
tcccaatgcg gtttaaaaca caacttttct atacaaagtt gtaaataaaa aaccagactc   4980
tgtttggatt tggatcaagc taagtgtctt gctgtcttta tttaggggtt ttgcgcgcgc   5040
ggtaggcccg ggaccagcgg tctcggtcgt tgagggtcct gtgtattttt tccaggacgt   5100
ggtaaaggtg actctggatg ttcagataca tgggcataag cccgtctctg gggtggaggt   5160
agcaccactg cagagcttca tgctgcgggg tggtgttgta gatgatccag tcgtagcagg   5220
agcgctgggc gtggtgccta aaaatgtctt tcagtagcaa gctgattgcc aggggcaggc   5280
ccttggtgta agtgtttaca aagcggttaa gctgggatgg gtgcatacgt ggggatatga   5340
gatgcatctt ggactgtatt tttaggttgg ctatgttccc agccatatcc ctccggggat   5400
tcatgttgtg cagaaccacc agcacagtgt atccggtgca cttgggaaat ttgtcatgta   5460
gcttagaagg aaatgcgtgg aagaacttgg agacgccctt gtgacctcca agattttcca   5520
tgcattcgtc cataatgatg gcaatgggcc cacgggcggc ggcctgggcg aagatatttc   5580
tgggatcact aacgtcatag ttgtgttcca ggatgagatc gtcataggcc atttttacaa   5640
agcgcgggcg gagggtgcca gactgcggta taatggttcc atccggccca ggggcgtagt   5700
taccctcaca gatttgcatt tcccacgctt tgagttcaga tggggggatc atgtctacct   5760
gcggggcgat gaagaaaacg gtttccgggg taggggagat cagctgggaa gaaagcaggt   5820
tcctgagcag ctgcgactta ccgcagccgg tgggcccgta aatcacacct attaccggct   5880
gcaactggta gttaagagag ctgcagctgc cgtcatccct gagcaggggg gccacttcgt   5940
```

```
taagcatgtc cctgactcgc atgttttccc tgaccaaatc cgccagaagg cgctcgccgc   6000
ccagcgatag cagttcttgc aaggaagcaa agtttttcaa cggtttgaga ccgtccgccg   6060
taggcatgct tttgagcgtt tgaccaagca gttccaggcg gtcccacagc tcggtcacct   6120
gctctacggc atctcgatcc agcatatctc ctcgtttcgc gggttggggc ggctttcgct   6180
gtacggcagt agtcggtgct cgtccagacg ggccagggtc atgtctttcc acgggcgcag   6240
ggtcctcgtc agcgtagtct gggtcacggt gaaggggtgc gctccgggct gcgcgctggc   6300
cagggtgcgc ttgaggctgg tcctgctggt gctgaagcgc tgccggtctt cgccctgcgc   6360
gtcggccagg tagcatttga ccatggtgtc atagtccagc ccctccgcgg cgtggccctt   6420
ggcgcgcagc ttgcccttgg aggaggcgcc gcacgagggg cagtgcagac ttttgagggc   6480
gtagagcttg ggcgcgagaa ataccgattc cggggagtag gcatccgcgc cgcaggcccc   6540
gcagacggtc tcgcattcca cgagccaggt gagctctggc cgttcggggt caaaaaccag   6600
gtttcccccca tgctttttga tgcgtttctt acctctggtt tccatgagcc ggtgtccacg   6660
ctcggtgacg aaaaggctgt ccgtgtcccc gtatacagac ttgagaggcc tgtcctcgag   6720
cggtgttccg cggtcctcct cgtatagaaa ctcggaccac tctgagacaa aggctcgcgt   6780
ccaggccagc acgaaggagg ctaagtggga ggggtagcgg tcgttgtcca ctagggggtc   6840
cactcgctcc agggtgtgaa gacacatgtc gccctcttcg gcatcaagga aggtgattgg   6900
tttgtaggtg taggccacgt gaccgggtgt tcctgaaggg gggctataaa agggggtggg   6960
ggcgcgttcg tcctcactct cttccgcatc gctgtctgcg agggccagct gttggggtga   7020
gtactccctc tgaaaagcgg gcatgacttc tgcgctaaga ttgtcagttt ccaaaaacga   7080
ggaggatttg atattcacct ggcccgcggt gatgcctttg agggtggccg catccatctg   7140
gtcagaaaag acaatctttt tgttgtcaag cttggtggca aacgacccgt agagggcgtt   7200
ggacagcaac ttggcgatgg agcgcagggt ttggtttttg tcgcgatcgg cgcgctcctt   7260
ggccgcgatg tttagctgca cgtattcgcg cgcaacgcac cgccattcgg gaaagacggt   7320
ggtgcgctcg tcgggcacca ggtgcacgcg ccaaccgcgg ttgtgcaggg tgacaaggtc   7380
aacgctggtg gctacctctc cgcgtaggcg ctcgttggtc cagcagaggc ggccgccctt   7440
gcgcgagcag aatggcggta gggggtctag ctgcgtctcg tccggggggt ctgcgtccac   7500
ggtaaagacc ccgggcagca ggcgcgcgtc gaagtagtct atcttgcatc cttgcaagtc   7560
tagcgcctgc tgccatgcgc gggcggcaag cgcgcgctcg tatgggttga gtgggggacc   7620
ccatggcatg gggtgggtga gcgcggaggc gtacatgccg caaatgtcgt aaacgtagag   7680
gggctctctg agtattccaa gatatgtagg gtagcatctt ccaccgcgga tgctggcgcg   7740
cacgtaatcg tatagttcgt gcgagggagc gaggaggtcg ggaccgaggt tgctacgggc   7800
gggctgctct gctcggaaga ctatctgcct gaagatggca tgtgagttgg atgatatggt   7860
tggacgctgg aagacgttga agctggcgtc tgtgagacct accgcgtcac gcacgaagga   7920
ggcgtaggag tcgcgcagct tgttgaccag ctcggcggtg acctgcacgt ctagggcgca   7980
gtagtccagg gtttccttga tgatgtcata cttatcctgt ccctttttttt tccacagctc   8040
gcggttgagg acaaactctt cgcggtcttt ccagtactct tggatcggaa acccgtcggc   8100
ctccgaacgg taagagccta gcatgtagaa ctggttgacg gcctggtagg cgcagcatcc   8160
cttttctacg ggtagcgcgt atgcctgcgc ggccttccgg agcgaggtgt gggtgagcgc   8220
aaaggtgtcc ctgaccatga ctttgaggta ctggtatttg aagtcagtgt cgtcgcatcc   8280
gccctgctcc cagagcaaaa agtccgtgcg ctttttggaa cgcggatttg gcagggcgaa   8340
```

```
ggtgacatcg ttgaagagta tctttcccgc gcgaggcata aagttgcgtg tgatgcggaa   8400
gggtcccggc acctcggaac ggttgttaat tacctgggcg gcgagcacga tctcgtcaaa   8460
gccgttgatg ttgtggccca caatgtaaag ttccaagaag cgcgggatgc ccttgatgga   8520
aggcaatttt ttaagttcct cgtaggtgag ctcttcaggg gagctgagcc cgtgctctga   8580
aagggcccag tctgcaagat gagggttgga agcgacgaat gagctccaca ggtcacgggc   8640
cattagcatt tgcaggtggt cgcgaaaggt cctaaactgg cgacctatgg ccattttttc   8700
tggggtgatg cagtagaagg taagcgggtc ttgttcccag cggtcccatc caaggttcgc   8760
ggctaggtct cgcgcggcag tcactagagg ctcatctccg ccgaacttca tgaccagcat   8820
gaagggcacg agctgcttcc caaaggcccc catccaagta taggtctcta catcgtaggt   8880
gacaaagaga cgctcggtgc gaggatgcga gccgatcggg aagaactgga tctcccgcca   8940
ccaattggag gagtggctat tgatgtggtg aaagtagaag tccctgcgac gggccgaaca   9000
ctcgtgctgg cttttgtaaa aacgtgcgca gtactggcag cggtgcacgg gctgtacatc   9060
ctgcacgagg ttgacctgac gaccgcgcac aaggaagcag agtgggaatt tgagcccctc   9120
gcctggcggg tttggctggt ggtcttctac ttcggctgct tgtccttgac cgtctggctg   9180
ctcgagggga gttacggtgg atcggaccac cacgccgcgc gagcccaaag tccagatgtc   9240
cgcgcgcggc ggtcggagct tgatgacaac atcgcgcaga tgggagctgt ccatggtctg   9300
gagctcccgc ggcgtcaggt caggcgggag ctcctgcagg tttacctcgc atagacgggt   9360
cagggcgcgg gctagatcca ggtgatacct aatttccagg ggctggttgg tggcggcgtc   9420
gatggcttgc aagaggccgc atccccgcgg cgcgactacg gtaccgcgcg gcgggcggtg   9480
ggccgcgggg gtgtccttgg atgatgcatc taaaagcggt gacgcgggcg agcccccgga   9540
ggtagggggg gctccggacc cgccgggaga gggggcaggg gcacgtcggc gccgcgcgcg   9600
ggcaggagct ggtgctgcgc gcgtaggttg ctggcgaacg cgacgacgcg gcggttgatc   9660
tcctgaatct ggcgcctctg cgtgaagacg acgggcccgg tgagcttgaa cctgaaagag   9720
agttcgacag aatcaatttc ggtgtcgttg acggcggcct ggcgcaaaat ctcctgcacg   9780
tctcctgagt tgtcttgata ggcgatctcg gccatgaact gctcgatctc ttcctcctgg   9840
agatctccgc gtccggctcg ctccacggtg gcggcgaggt cgttggaaat gcgggccatg   9900
agctgcgaga aggcgttgag gcctccctcg ttccagacgc ggctgtagac cacgcccccct   9960
tcggcatcgc gggcgcgcat gaccacctgc gcgagattga gctccacgtg ccgggcgaag  10020
acggcgtagt ttcgcaggcg ctgaaagagg tagttgaggg tggtggcggt gtgttctgcc  10080
acgaagaagt acataaccca gcgtcgcaac gtggattcgt tgatatcccc caaggcctca  10140
aggcgctcca tggcctcgta gaagtccacg gcgaagttga aaaactggga gttgcgcgcc  10200
gacacggtta actcctcctc cagaagacgg atgagctcgg cgacagtgtc gcgcacctcg  10260
cgctcaaagg ctacaggggc ctcttcttct tcttcaatct cctcttccat aagggcctcc  10320
ccttcttctt cttctggcgg cggtggggga gggggggacac ggcggcgacg acggcgcacc  10380
gggaggcggt cgacaaagcg ctcgatcatc tccccgcggc gacggcgcat ggtctcggtg  10440
acggcgcggc cgttctcgcg ggggcgcagt tggaagacgc cgcccgtcat gtcccggtta  10500
tgggttggcg gggggctgcc atgcggcagg gatacggcgc taacgatgca tctcaacaat  10560
tgttgtgtag gtactccgcc gccgagggac ctgagcgagt ccgcatcgac cggatcggaa  10620
aacctctcga gaaaggcgtc taaccagtca cagtcgcaag gtaggctgag caccgtggcg  10680
```

ggcggcagcg ggcggcggtc ggggttgttt ctggcggagg tgctgctgat gatgtaatta 10740
aagtaggcgg tcttgagacg gcggatggtc gacagaagca ccatgtcctt gggtccggcc 10800
tgctgaatgc gcaggcggtc ggccatgccc caggcttcgt tttgacatcg gcgcaggtct 10860
ttgtagtagt cttgcatgag cctttctacc ggcacttctt cttctccttc ctcttgtcct 10920
gcatctcttg catctatcgc tgcggcggcg gcggagtttg gccgtaggtg gcgccctctt 10980
cctcccatgc gtgtgacccc gaagcccctc atcggctgaa gcagggctag gtcggcgaca 11040
acgcgctcgg ctaatatggc ctgctgcacc tgcgtgaggg tagactggaa gtcatccatg 11100
tccacaaagc ggtggtatgc gcccgtgttg atggtgtaag tgcagttggc cataacggac 11160
cagttaacgg tctggtgacc cggctgcgag agctcggtgt acctgagacg cgagtaagcc 11220
ctcgagtcaa atacgtagtc gttgcaagtc cgcaccaggt actggtatcc caccaaaaag 11280
tgcggcggcg gctggcggta gaggggccag cgtagggtgg ccggggctcc gggggcgaga 11340
tcttccaaca taaggcgatg atatccgtag atgtacctgg acatccaggt gatgccggcg 11400
gcggtggtgg aggcgcgcgg aaagtcgcgg acgcggttcc agatgttgcg cagcggcaaa 11460
aagtgctcca tggtcgggac gctctggccg gtcaggcgcg cgcaatcgtt gacgctctag 11520
accgtgcaaa aggagagcct gtaagcgggc actcttccgt ggtctggtgg ataaattcgc 11580
aagggtatca tggcggacga ccggggttcg agccccgtat ccggccgtcc gccgtgatcc 11640
atgcggttac cgcccgcgtg tcgaacccag gtgtgcgacg tcagacaacg ggggagtgct 11700
ccttttggct tccttccagg cgcggcggct gctgcgctag ctttttggc cactggccgc 11760 gcgcagcgta agcggttagg ctggaaagcg aaagcattaa gtggctcgct ccctgtagcc 11820
ggagggttat ttccaaggg ttgagtcgcg ggacccccgg ttcgagtctc ggaccggccg 11880
gactgcggcg aacgggggtt tgcctccccg tcatgcaaga ccccgcttgc aaattcctcc 11940
ggaaacaggg acgagcccct tttttgcttt tcccagatgc atccggtgct gcggcagatg 12000
cgcccccctc ctcagcagcg gcaagagcaa gagcagcggc agacatgcag ggcaccctcc 12060
cctcctccta ccgcgtcagg aggggcgaca tccgcggttg acgcggcagc agatggtgat 12120
tacgaacccc cgcggcgccg ggcccggcac tacctggact tggaggaggg cgagggcctg 12180
gcgcggctag gagcgccctc tcctgagcgg cacccaaggg tgcagctgaa gcgtgatacg 12240
cgtgaggcgt acgtgccgcg gcagaacctg tttcgcgacc gcgagggaga ggagcccgag 12300
gagatgcggg atcgaaagtt ccacgcaggg cgcgagctgc ggcatggcct gaatcgcgag 12360
cggttgctgc gcgaggagga ctttgagccc gacgcgcgaa ccgggattag tcccgcgcgc 12420
gcacacgtgg cggccgccga cctggtaacc gcatacgagc agacggtgaa ccaggagatt 12480
aactttcaaa aaagctttaa caaccacgtg cgtacgcttg tggcgcgcga ggaggtggct 12540
ataggactga tgcatctgtg ggactttgta agcgcgctgg agcaaaaccc aaatagcaag 12600
ccgctcatgg cgcagctgtt ccttatagtg cagcacagca gggacaacga ggcattcagg 12660
gatgcgctgc taaacatagt agagcccgag ggccgctggc tgctcgattt gataaacatc 12720
ctgcagagca tagtggtgca ggagcgcagc ttgagcctgg ctgacaaggt ggccgccatc 12780
aactattcca tgcttagcct gggcaagttt tacgcccgca agatatacca taccccttac 12840
gttcccatag acaaggaggt aaagatcgag ggttctaca tgcgcatggc gctgaaggtg 12900
cttaccttga gcgacgacct gggcgtttat cgcaacgagc gcatccacaa ggccgtgagc 12960
gtgagccggc ggcgcgagct cagcgaccgc gagctgatgc acagcctgca aagggccctg 13020
gctggcacgg gcagcggcga tagagaggcc gagtcctact ttgacgcggg cgctgacctg 13080
cgctgggccc caagccgacg cgccctggag gcagctgggg ccggacctgg gctggcggtg 13140
gcacccgcgc gcgctggcaa cgtcggcggc gtggaggaat atgacgagga cgatgagtac 13200
gagccagagg acggcgagta ctaagcggtg atgtttctga tcagatgatg caagacgcaa 13260
cggacccggc ggtgcgggcg gcgctgcaga gccagccgtc cggccttaac tccacggacg 13320
actggcgcca ggtcatggac cgcatcatgt cgctgactgc gcgcaatcct gacgcgttcc 13380
ggcagcagcc gcaggccaac cggctctccg caattctgga agcggtggtc ccggcgcgcg 13440
caaaccccac gcacgagaag gtgctggcga tcgtaaacgc gctggccgaa aacagggcca 13500
tccggcccga cgaggccggc ctggtctacg acgcgctgct tcagcgcgtg gctcgttaca 13560
acagcggcaa cgtgcagacc aacctggacc ggctggtggg ggatgtgcgc gaggccgtgg 13620
cgcagcgtga gcgcgcgcag cagcagggca acctgggctc catggttgca ctaaacgcct 13680
tcctgagtac acagcccgcc aacgtgccgc ggggacagga ggactacacc aactttgtga 13740
gcgcactgcg gctaatggtg actgagacac cgcaaagtga ggtgtaccag tctgggccag 13800
actatttttt ccagaccagt agacaaggcc tgcagaccgt aaacctgagc caggctttca 13860
aaaacttgca ggggctgtgg ggggtgcggg ctcccacagg cgaccgcgcg accgtgtcta 13920
gcttgctgac gcccaactcg cgcctgttgc tgctgctaat agcgcccttc acggacagtg 13980
gcagcgtgtc ccgggacaca tacctaggtc acttgctgac actgtaccgc gaggccatag 14040
gtcaggcgca tgtggacgag catactttcc aggagattac aagtgtcagc cgcgcgctgg 14100
ggcaggagga cacgggcagc ctggaggcaa ccctaaacta cctgctgacc aaccggcggc 14160
agaagatccc ctcgttgcac agtttaaaca gcgaggagga gcgcattttg cgctacgtgc 14220
agcagagcgt gagccttaac ctgatgcgcg acggggtaac gcccagcgtg gcgctggaca 14280
tgaccgcgcg caacatggaa ccgggcatgt atgcctcaaa ccggccgttt atcaaccgcc 14340
taatggacta cttgcatcgc gcggccgccg tgaaccccga gtatttcacc aatgccatct 14400
tgaacccgca ctggctaccg ccccctggtt tctacaccgg gggattcgag gtgcccgagg 14460
gtaacgatgg attcctctgg gacgacatag acgacagcgt gttttccccg caaccgcaga 14520
ccctgctaga gttgcaacag cgcgagcagg cagaggcggc gctgcgaaag gaaagcttcc 14580
gcaggccaag cagcttgtcc gatctaggcg ctgcggcccc gcggtcagat gctagtagcc 14640
catttccaag cttgataggg tctcttacca gcactcgcac cacccgcccg cgcctgctgg 14700
gcgaggagga gtacctaaac aactcgctgc tgcagccgca gcgcgaaaaa aacctgcctc 14760
cggcatttcc caacaacggg atagagagcc tagtggacaa gatgagtaga tggaagacgt 14820
acgcgcagga gcacagggac gtgccaggcc cgcgcccgcc cacccgtcgt caaaggcacg 14880
accgtcagcg gggtctggtg tgggaggacg atgactcggc agacgacagc agcgtcctgg 14940
atttgggagg gagtggcaac ccgtttgcgc accttcgccc caggctgggg agaatgtttt 15000
aaaaaaaaaa aaaaagcatg atgcaaaata aaaaactcac caaggccatg gcaccgagcg 15060
ttggttttct tgtattcccc ttagtatgcg gcgcgcggcg atgtatgagg aaggtcctcc 15120
tccctcctac gagagtgtgg tgagcgcggc gccagtggcg gcggcgctgg gttctccctt 15180
cgatgctccc ctggacccgc cgtttgtgcc tccgcggtac ctgcggccta ccggggggag 15240
aaacagcatc cgttactctg agttggcacc cctattcgac accacccgtg tgtacctggt 15300
ggacaacaag tcaacggatg tggcatccct gaactaccag aacgaccaca gcaactttct 15360
gaccacggtc attcaaaaca atgactacag cccgggggag gcaagcacac agaccatcaa 15420

-continued

```
tcttgacgac cggtcgcact ggggcggcga cctgaaaacc atcctgcata ccaacatgcc  15480
aaatgtgaac gagttcatgt ttaccaataa gtttaaggcg cgggtgatgg tgtcgcgctt  15540
gcctactaag gacaatcagg tggagctgaa atacgagtgg gtggagttca cgctgcccga  15600
gggcaactac tccgagacca tgaccataga ccttatgaac aacgcgatcg tggagcacta  15660
cttgaaagtg ggcagacaga acggggttct ggaaagcgac atcggggtaa agtttgacac  15720
ccgcaacttc agactggggt ttgaccccgt cactggtctt gtcatgcctg ggtatatac   15780
aaacgaagcc ttccatccag acatcatttt gctgccagga tgcggggtgg acttcaccca  15840
cagccgcctg agcaacttgt tgggcatccg caagcggcaa cccttccagg agggctttag  15900
gatcacctac gatgatctgg agggtggtaa cattcccgca ctgttggatg tggacgccta  15960
ccaggcgagc ttgaaagatg acaccgaaca gggcgggggt ggcgcaggcg gcagcaacag  16020
cagtggcagc ggcgcggaag agaactccaa cgcggcagcc gcggcaatgc agccggtgga  16080
ggacatgaac gatcatgcca ttcgcggcga cacctttgcc acacgggctg aggagaagcg  16140
cgctgaggcc gaagcagcgg ccgaagctgc cgcccccgct gcgcaacccg aggtcgagaa  16200
gcctcagaag aaaccggtga tcaaacccct gacagaggac agcaagaaac gcagttacaa  16260
cctaataagc aatgacagca ccttcaccca gtaccgcagc tggtaccttg catacaacta  16320
cggcgaccct cagaccggaa tccgctcatg gaccctgctt tgcactcctg acgtaacctg  16380
cggctcggag caggtctact ggtcgttgcc agacatgatg caagaccccg tgaccttccg  16440
ctccacgcgc cagatcagca actttccggt ggtgggcgcc gagctgttgc ccgtgcactc  16500
caagagcttc tacaacgacc aggccgtcta ctcccaactc atccgccagt ttacctctct  16560
gacccacgtg ttcaatcgct ttcccgagaa ccagattttg gcgcgcccgc cagcccccac  16620
catcaccacc gtcagtgaaa acgttcctgc tctcacagat cacgggacgc taccgctgcg  16680
caacagcatc ggaggagtcc agcgagtgac cattactgac gccagacgcc gcacctgccc  16740
ctacgtttac aaggccctgg gcatagtctc gccgcgcgtc ctatcgagcc gcactttttg  16800
agcaagcatg tccatcctta tatcgcccag caataacaca ggctggggcc tgcgcttccc  16860
aagcaagatg tttggcgggg ccaagaagcg ctccgaccaa cacccagtgc gcgtgcgcgg  16920
gcactaccgc gcgccctggg gcgcgcacaa acgcggccgc actgggcgca ccaccgtcga  16980
tgacgccatc gacgcggtgg tggaggaggc gcgcaactac acgcccacgc cgccaccagt  17040
gtccacagtg gacgcggcca ttcagaccgt ggtgcgcgga gcccggcgct atgctaaaat  17100
gaagagacgg cggaggcgcg tagcacgtcg ccaccgccgc cgacccggca ctgccgccca  17160
acgcgcggcg gcggccctgc ttaaccgcgc acgtcgcacc ggccgacggg cggccatgcg  17220
ggccgctcga aggctggccg cgggtattgt cactgtgccc cccaggtcca ggcgacgagc  17280
ggccgccgca gcagccgcgg ccattagtgc tatgactcag ggtcgcaggg gcaacgtgta  17340
ttgggtgcgc gactcggtta gcggcctgcg cgtgcccgtg cgcacccgcc ccccgcgcaa  17400
ctagattgca agaaaaaact acttagactc gtactgttgt atgtatccag cggcggcggc  17460
gcgcaacgaa gctatgtcca agcgcaaaat caaagaagag atgctccagg tcatcgcgcc  17520
ggagatctat ggcccccga  agaaggaaga gcaggattac aagccccgaa agctaaagcg  17580
ggtcaaaaag aaaaagaaag atgatgatga tgaacttgac gacgaggtgg aactgctgca  17640
cgctaccgcg cccaggcgac gggtacagtg gaaaggtcga cgcgtaaaac gtgttttgcg  17700
acccggcacc accgtagtct ttacgcccgg tgagcgctcc acccgcacct acaagcgcgt  17760
gtatgatgag gtgtacggcg acgaggacct gcttgagcag gccaacgagc gcctcgggga  17820
```

gtttgcctac ggaaagcggc ataaggacat gctggcgttg ccgctggacg agggcaaccc 17880
aacacctagc ctaaagcccg taacactgca gcaggtgctg cccgcgcttg caccgtccga 17940
agaaaagcgc ggcctaaagc gcgagtctgg tgacttggca cccaccgtgc agctgatggt 18000
acccaagcgc cagcgactgg aagatgtctt ggaaaaaatg accgtggaac ctgggctgga 18060
gcccgaggtc cgcgtgcggc caatcaagca ggtggcgccg ggactgggcg tgcagaccgt 18120
ggacgttcag atacccacta ccagtagcac cagtattgcc accgccacag agggcatgga 18180
gacacaaacg tccccggttg cctcagcggt ggcggatgcc gcggtgcagg cggtcgctgc 18240
ggccgcgtcc aagacctcta cggaggtgca aacggacccg tggatgtttc gcgtttcagc 18300
cccccggcgc ccgcgccgtt cgaggaagta cggcgccgcc agcgcgctac tgcccgaata 18360
tgccctacat ccttccattg cgcctacccc cggctatcgt ggctacacct accgccccag 18420
aagacgagca actacccgac gccgaaccac cactggaacc cgccgccgcc gtcgccgtcg 18480
ccagcccgtg ctggccccga tttccgtgcg cagggtggct cgcgaaggag gcaggaccct 18540
ggtgctgcca acagcgcgct accaccccag catcgtttaa aagccggtct ttgtggttct 18600
tgcagatatg gccctcacct gccgcctccg tttcccggtg ccgggattcc gaggaagaat 18660
gcaccgtagg aggggcatgg ccggccacgg cctgacgggc ggcatgcgtc gtgcgcacca 18720
ccggcggcgg cgcgcgtcgc accgtcgcat gcgcggcggt atcctgcccc tccttattcc 18780
actgatcgcc gcggcgattg gcgccgtgcc cggaattgca tccgtggcct tgcaggcgca 18840
gagacactga ttaaaaacaa gttgcatgtg gaaaaatcaa aataaaaagt ctggactctc 18900
acgctcgctt ggtcctgtaa ctattttgta gaatggaaga catcaacttt gcgtctctgg 18960
ccccgcgaca cggctcgcgc ccgttcatgg gaaactggca agatatcggc accagcaata 19020
tgagcggtgg cgccttcagc tggggctcgc tgtggagcgg cattaaaaat ttcggttcca 19080
ccgttaagaa ctatggcagc aaggcctgga acagcagcac aggccagatg ctgagggata 19140
agttgaaaga gcaaaatttc caacaaaagg tggtagatgg cctggcctct ggcattagcg 19200
gggtggtgga cctggccaac caggcagtgc aaaataagat taacagtaag cttgatcccc 19260
gccctcccgt agaggagcct ccaccggccg tggagacagt gtctccagag gggcgtggcg 19320
aaaagcgtcc gcgccccgac agggaagaaa ctctggtgac gcaaatagac gagcctccct 19380
cgtacgagga ggcactaaag caaggcctgc ccaccacccg tcccatcgcg cccatggcta 19440
ccggagtgct gggccagcac acacccgtaa cgctggacct gcctcccccc gccgacaccc 19500
agcagaaacc tgtgctgcca ggcccgaccg ccgttgttgt aacccgtcct agccgcgcgt 19560
ccctgcgccg cgccgccagc ggtccgcgat cgttgcggcc cgtagccagt ggcaactggc 19620
aaagcacact gaacagcatc gtgggtctgg gggtgcaatc cctgaagcgc cgacgatgct 19680
tctgaatagc taacgtgtcg tatgtgtgtc atgtatgcgt ccatgtcgcc gccagaggag 19740
ctgctgagcc gccgcgcgcc cgctttccaa gatggctacc ccttcgatga tgccgcagtg 19800
gtcttacatg cacatctcgg gccaggacgc ctcggagtac ctgagccccg ggctggtgca 19860
gtttgcccgc gccaccgaga cgtacttcag cctgaataac aagtttagaa accccacggt 19920
ggcgcctacg cacgacgtga ccacagaccg gtcccagcgt ttgacgctgc ggttcatccc 19980
tgtggaccgt gaggatactg cgtactcgta caaggcgcgg ttcaccctag ctgtgggtga 20040
taaccgtgtg ctggacatgg cttccacgta ctttgacatc cgcggcgtgc tggacagggg 20100
ccctactttt aagccctact ctggcactgc ctacaacgcc ctggctccca agggtgcccc 20160
aaatccttgc gaatgggatg aagctgctac tgctcttgaa ataaacctag aagaagagga 20220
cgatgacaac gaagacgaag tagacgagca agctgagcag caaaaaactc acgtatttgg 20280
gcaggcgcct tattctggta taaatattac aaaggagggt attcaaatag gtgtcgaagg 20340
tcaaacacct aaatatgccg ataaaacatt tcaacctgaa cctcaaatag gagaatctca 20400
gtggtacgaa actgaaatta atcatgcagc tgggagagtc cttaaaaaga ctaccccaat 20460
gaaaccatgt tacggttcat atgcaaaacc cacaaatgaa aatggagggc aaggcattct 20520
tgtaaagcaa caaaatggaa agctagaaag tcaagtggaa atgcaatttt tctcaactac 20580
tgaggcgacc gcaggcaatg gtgataactt gactcctaaa gtggtattgt acagtgaaga 20640
tgtagatata gaaaccccag acactcatat ttcttacatg cccactatta aggaaggtaa 20700
ctcacgagaa ctaatgggcc aacaatctat gcccaacagg cctaattaca ttgcttttag 20760
ggacaatttt attggtctaa tgtattacaa cagcacgggt aatatgggtg ttctggcggg 20820
ccaagcatcg cagttgaatg ctgttgtaga tttgcaagac agaaacacag agctttcata 20880
ccagcttttg cttgattcca ttggtgatag aaccaggtac ttttctatgt ggaatcaggc 20940
tgttgacagc tatgatccag atgttagaat tattgaaaat catggaactg aagatgaact 21000
tccaaattac tgctttccac tgggaggtgt gattaataca gagactctta ccaaggtaaa 21060
acctaaaaca ggtcaggaaa atggatggga aaaagatgct acagaatttt cagataaaaa 21120
tcaaataaga gttggaaata attttgccat ggaaatcaat ctaaatgcca acctgtggag 21180
aaatttcctg tactccaaca tagcgctgta tttgcccgac aagctaaagt acagtccttc 21240
caacgtaaaa atttctgata acccaaacac ctacgactac atgaacaagc gagtggtggc 21300
tcccgggtta gtggactgct acattaacct tggagcacgc tggtcccttg actatatgga 21360
caacgtcaac ccatttaacc accaccgcaa tgctggcctg cgctaccgct caatgttgct 21420
gggcaatggt cgctatgtgc ccttccacat ccaggtgcct cagaagttct ttgccattaa 21480
aaacctcctt ctcctgccgg gctcatacac ctacgagtgg aacttcagga aggatgttaa 21540
catggttctg cagagctccc taggaaatga cctaagggtt gacggagcca gcattaagtt 21600
tgatagcatt tgcctttacg ccaccttctt ccccatggcc cacaacaccg cctccacgct 21660
tgaggccatg cttagaaacg acaccaacga ccagtccttt aacgactatc tctccgccgc 21720
caacatgctc taccctatac ccgccaacgc taccaacgtg cccatatcca tcccctcccg 21780
caactgggcg gctttccgcg gctgggcctt cacgcgcctt aagactaagg aaaccccatc 21840
actgggctcg ggctacgacc cttattacac ctactctggc tctataccct acctagatgg 21900
aacctttac ctcaaccaca cctttaagaa ggtggccatt acctttgact cttctgtcag 21960
ctggcctggc aatgaccgcc tgcttacccc caacgagttt gaaattaagc gctcagttga 22020
cggggagggt tacaacgttg cccagtgtaa catgaccaaa gactggttcc tggtacaaat 22080
gctagctaac tacaacattg gctaccaggg cttctatatc ccagagagct acaaggaccg 22140
catgtactcc ttctttagaa acttccagcc catgagccgt caggtggtgg atgatactaa 22200
atacaaggac taccaacagg tgggcatcct acaccaacac aacaactctg gatttgttgg 22260
ctaccttgcc cccaccatgc gcgaaggaca ggcctaccct gctaacttcc cctatccgct 22320
tataggcaag accgcagttg acagcattac ccagaaaaag tttctttgcg atcgcaccct 22380
ttggcgcatc ccattctcca gtaactttat gtccatgggc gcactcacag acctgggcca 22440
aaaccttctc tacgccaact ccgcccacgc gctagacatg acttttgagg tggatcccat 22500
ggacgagccc acccttcttt atgttttgtt tgaagtcttt gacgtggtcc gtgtgcaccg 22560

-continued

```
gccgcaccgc ggcgtcatcg aaaccgtgta cctgcgcacg cccttctcgg ccggcaacgc  22620
cacaacataa agaagcaagc aacatcaaca acagctgccg ccatgggctc cagtgagcag  22680
gaactgaaag ccattgtcaa agatcttggt tgtgggccat attttttggg cacctatgac  22740
aagcgctttc caggctttgt ttctccacac aagctcgcct gcgccatagt caatacggcc  22800
ggtcgcgaga ctgggggcgt acactggatg gcctttgcct ggaacccgca ctcaaaaaca  22860
tgctacctct ttgagccctt tggcttttct gaccagcgac tcaagcaggt ttaccagttt  22920
gagtacgagt cactcctgcg ccgtagcgcc attgcttctt cccccgaccg ctgtataacg  22980
ctggaaaagt ccacccaaag cgtacagggg cccaactcgg ccgcctgtgg actattctgc  23040
tgcatgtttc tccacgcctt tgccaactgg ccccaaactc ccatggatca caacccccacc  23100
atgaacctta ttaccggggt acccaactcc atgctcaaca gtccccaggt acagcccacc  23160
ctgcgtcgca accaggaaca gctctacagc ttcctggagc gccactcgcc ctacttccgc  23220
agccacagtg cgcagattag gagcgccact tctttttgtc acttgaaaaa catgtaaaaa  23280
taatgtacta gagacacttt caataaaggc aaatgctttt atttgtacac tctcgggtga  23340
ttatttaccc ccacccttgc cgtctgcgcc gtttaaaaat caaaggggtt ctgccgcgca  23400
tcgctatgcg ccactggcag ggacacgttg cgatactggt gtttagtgct ccacttaaac  23460
tcaggcacaa ccatccgcgg cagctcggtg aagttttcac tccacaggct gcgcaccatc  23520
accaacgcgt ttagcaggtc gggcgccgat atcttgaagt cgcagttggg gcctccgccc  23580
tgcgcgcgcg agttgcgata cacagggttg cagcactgga acactatcag cgccgggtgg  23640
tgcacgctgg ccagcacgct cttgtcggag atcagatccg cgtccaggtc ctccgcgttg  23700
ctcagggcga acggagtcaa ctttggtagc tgccttccca aaaagggcgc gtgcccaggc  23760
tttgagttgc actcgcaccg tagtggcatc aaaaggtgac cgtgcccggt ctgggcgtta  23820
ggatacagcg cctgcataaa agccttgatc tgcttaaaag ccacctgagc ctttgcgcct  23880
tcagagaaga acatgccgca agacttgccg gaaaactgat tggccggaca ggccgcgtcg  23940
tgcacgcagc accttgcgtc ggtgttggag atctgcacca catttcggcc ccaccggttc  24000
ttcacgatct tggccttgct agactgctcc ttcagcgcgc gctgcccgtt ttcgctcgtc  24060
acatccattt caatcacgtg ctccttattt atcataatgc ttccgtgtag acacttaagc  24120
tcgccttcga tctcagcgca gcggtgcagc cacaacgcgc agcccgtggg ctcgtgatgc  24180
ttgtaggtca cctctgcaaa cgactgcagg tacgcctgca ggaatcgccc catcatcgtc  24240
acaaaggtct tgttgctggt gaaggtcagc tgcaacccgc ggtgctcctc gttcagccag  24300
gtcttgcata cggccgccag agcttccact tggtcaggca gtagtttgaa gttcgccttt  24360
agatcgttat ccacgtggta cttgtccatc agcgcgcgcg cagcctccat gcccttctcc  24420
cacgcagaca cgatcggcac actcagcggg ttcatcaccg taatttcact ttccgcttcg  24480
ctgggctctt cctcttcctc ttgcgtccgc ataccacgcg ccactgggtc gtcttcattc  24540
agccgccgca ctgtgcgctt acctcctttg ccatgcttga ttagcaccgg tgggttgctg  24600
aaacccacca tttgtagcgc cacatcttct ctttcttcct cgctgtccac gattacctct  24660
ggtgatggcg ggcgctcggg cttgggagaa gggcgcttct ttttcttctt gggcgcaatg  24720
gccaaatccg ccgccgaggt cgatggccgc gggctgggtg tgcgcggcac cagcgcgtct  24780
tgtgatgagt cttcctcgtc ctcggactcg atacgccgcc tcatccgctt ttttgggggc  24840
gcccggggag gcggcggcga cggggacggg gacgacacgt cctccatggt tgggggacgt  24900
```

-continued

```
cgcgccgcac cgcgtccgcg ctcgggggtg gtttcgcgct gctcctcttc ccgactggcc  24960
atttccttct cctataggca gaaaaagatc atggagtcag tcgagaagaa ggacagccta  25020
accgccccct ctgagttcgc caccaccgcc tccaccgatg ccgccaacgc gcctaccacc  25080
ttccccgtcg aggcaccccc gcttgaggag gaggaagtga ttatcgagca ggacccaggt  25140
tttgtaagcg aagacgacga ggaccgctca gtaccaacag aggataaaaa gcaagaccag  25200
gacaacgcag aggcaaacga ggaacaagtc gggcgggggg acgaaaggca tggcgactac  25260
ctagatgtgg gagacgacgt gctgttgaag catctgcagc gccagtgcgc cattatctgc  25320
gacgcgttgc aagagcgcag cgatgtgccc ctcgccatag cggatgtcag ccttgcctac  25380
gaacgccacc tattctcacc gcgcgtaccc cccaaacgcc aagaaaacgg cacatgcgag  25440
cccaacccgc gcctcaactt ctaccccgta tttgccgtgc cagaggtgct tgccacctat  25500
cacatctttt tccaaaactg caagataccc ctatcctgcc gtgccaaccg cagccgagcg  25560
gacaagcagc tggccttgcg gcagggcgct gtcatacctg atatcgcctc gctcaacgaa  25620
gtgccaaaaa tctttgaggg tcttggacgc gacgagaagc gcgcggcaaa cgctctgcaa  25680
caggaaaaca gcgaaaatga aagtcactct ggagtgttgg tggaactcga gggtgacaac  25740
gcgcgcctag ccgtactaaa acgcagcatc gaggtcaccc actttgccta cccggcactt  25800
aacctacccc ccaaggtcat gagcacagtc atgagtgagc tgatcgtgcg ccgtgcgcag  25860
cccctggaga gggatgcaaa tttgcaagaa caaacagagg agggcctacc cgcagttggc  25920
gacgagcagc tagcgcgctg gcttcaaacg cgcgagcctg ccgacttgga ggagcgacgc  25980
aaactaatga tggccgcagt gctcgttacc gtggagcttg agtgcatgca gcggttcttt  26040
gctgacccgg agatgcagcg caagctagag gaaacattgc actacacctt tcgacagggc  26100
tacgtacgcc aggcctgcaa gatctccaac gtggagctct gcaacctggt ctcctacctt  26160
ggaattttgc acgaaaaccg ccttgggcaa aacgtgcttc attccacgct caagggcgag  26220
gcgcgccgcg actacgtccg cgactgcgtt tacttatttc tatgctacac ctggcagacg  26280
gccatgggcg tttggcagca gtgcttggag gagtgcaacc tcaaggagct gcagaaactg  26340
ctaaagcaaa acttgaagga cctatggacg gccttcaacg agcgctccgt ggccgcgcac  26400
ctggcggaca tcattttccc cgaacgcctg cttaaaaccc tgcaacaggg tctgccagac  26460
ttcaccagtc aaagcatgtt gcagaacttt aggaacttta tcctagagcg ctcaggaatc  26520
ttgcccgcca cctgctgtgc acttcctagc gactttgtgc ccattaagta ccgcgaatgc  26580
cctccgccgc tttggggcca ctgctacctt ctgcagctag ccaactacct tgcctaccac  26640
tctgacataa tggaagacgt gagcggtgac ggtctactgg agtgtcactg tcgctgcaac  26700
ctatgcaccc cgcaccgctc cctggtttgc aattcgcagc tgcttaacga aagtcaaatt  26760
atcggtacct ttgagctgca gggtccctcg cctgacgaaa agtccgcggc tccggggttg  26820
aaactcactc cggggctgtg gacgtcggct taccttcgca aatttgtacc tgaggactac  26880
cacgcccacg agattaggtt ctacgaagac caatcccgcc cgccaaatgc ggagcttacc  26940
gcctgcgtca ttacccaggg ccacattctt ggccaattgc aagccatcaa caaagcccgc  27000
caagagtttc tgctacgaaa gggacggggg gtttacttgg acccccagtc cggcgaggag  27060
ctcaacccaa tccccccgcc gccgcagccc tatcagcagc agccgcgggc ccttgcttcc  27120
caggatggca cccaaaaaga agctgcagct gccgccgcca cccacggacg aggaggaata  27180
ctgggacagt caggcagagg aggttttgga cgaggaggag gaggacatga tggaagactg  27240
ggagagccta gacgaggaag cttccgaggt cgaagaggtg tcagacgaaa caccgtcacc  27300
```

```
ctcggtcgca ttcccctcgc cggcgcccca gaaatcggca accggttcca gcatggctac  27360
aacctccgct cctcaggcgc cgccggcact gcccgttcgc cgacccaacc gtagatggga  27420
caccactgga accagggccg gtaagtccaa gcagccgccg ccgttagccc aagagcaaca  27480
acagcgccaa ggctaccgct catggcgcgg gcacaagaac gccatagttg cttgcttgca  27540
agactgtggg ggcaacatct ccttcgcccg ccgctttctt ctctaccatc acggcgtggc  27600
cttcccccgt aacatcctgc attactaccg tcatctctac agcccatact gcaccggcgg  27660
cagcggcagc ggcagcaaca gcagcggcca cacagaagca aaggcgaccg gatagcaaga  27720
ctctgacaaa gcccaagaaa tccacagcgg cggcagcagc aggaggagga gcgctgcgtc  27780
tggcgcccaa cgaacccgta tcgacccgcg agcttagaaa caggattttt cccactctgt  27840
atgctatatt tcaacagagc aggggccaag aacaagagct gaaaataaaa aacaggtctc  27900
tgcgatccct cacccgcagc tgcctgtatc acaaaagcga agatcagctt cggcgcacgc  27960
tggaagacgc ggaggctctc ttcagtaaat actgcgcgct gactcttaag gactagtttc  28020
gcgccctttc tcaaatttaa gcgcgaaaac tacgtcatct ccagcggcca cacccggcgc  28080
cagcacctgt cgtcagcgcc atttcaactt tgtatacaaa agttgtgatg agcaaggaaa  28140
ttcccacgcc ctacatgtgg agttaccagc cacaaatggg acttgcggct ggagctgccc  28200
aagactactc aacccgaata aactacatga gcgcgggacc ccacatgata tcccgggtca  28260
acggaatacg cgcccaccga aaccgaattc tcctggaaca ggcggctatt accaccacac  28320
ctcgtaataa ccttaatccc cgtagttggc ccgctgccct ggtgtaccag gaaagtcccg  28380
ctcccaccac tgtggtactt cccagagacg cccaggccga agttcagatg actaactcag  28440
gggcgcagct tgcgggcggc tttcgtcaca gggtgcggtc gcccgggcag ggtataactc  28500
acctgacaat cagagggcga ggtattcagc tcaacgacga gtcggtgagc tcctcgcttg  28560
gtctccgtcc ggacgggaca tttcagatcg gcggcgccgg ccgctcttca ttcacgcctc  28620
gtcaggcaat cctaactctg cagacctcgt cctctgagcc gcgctctgga ggcattggaa  28680
ctctgcaatt tattgaggag tttgtgccat cggtctactt taaccccttc tcgggacctc  28740
ccggccacta tccggatcaa tttattccta actttgacgc ggtaaaggac tcggcggacg  28800
gctacgactg aatgttaagt ggagaggcag agcaactgcg cctgaaacac ctggtccact  28860
gtcgccgcca caagtgcttt gcccgcgact ccggtgagtt ttgctacttt gaattgcccg  28920
aggatcatat cgagggcccg gcgcacggcg tccggcttac cgcccaggga gagcttgccc  28980
gtagcctgat tcgggagttt acccagcgcc ccctgctagt tgagcgggac aggggaccct  29040
gtgttctcac tgtgatttgc aactgtccta accctggatt acatcaagat ctttgttgcc  29100
atctctgtgc tgagtataat aaatacagaa attaaaatat actggggctc ctatcgccat  29160
cctgtaaacg ccaccgtctt cacccgccca agcaaaccaa ggcgaacctt acctggtact  29220
tttaacatct ctccctctgt gatttacaac agtttcaacc cagacggagt gagtctacga  29280
gagaacctct ccgagctcag ctactccatc agaaaaaaca ccacccctcct tacctgccgg  29340
gaacgtacga gtgcgtcacc ggccgctgca ccacacctac cgcctgaccg taaaccagac  29400
tttttccgga cagacctcaa taactctgtt taccagaaca ggaggtgagc ttagaaaacc  29460
cttagggtat taggccaaag gcgcagctac tgtggggttt atgaacaatt caagcaactc  29520
tacgggctat tctaattcag gtttctctag aatcggggtt ggggttattc tctgtcttgt  29580
gattctcttt attcttatac taacgcttct ctgcctaagg ctcgccgcct gctgtgtgca  29640
```

catttgcatt tattgtcagc tttttaaacg ctggggtcgc cacccaagat gattaggtac 29700
ataatcctag gtttactcac ccttgcgtca gcccacggta ccacccaaaa ggtggatttt 29760
aaggagccag cctgtaatgt tacattcgca gctgaagcta atgagtgcac cactcttata 29820
aaatgcacca cagaacatga aaagctgctt attcgccaca aaaacaaaat tggcaagtat 29880
gctgtttatg ctatttggca gccaggtgac actacagagt ataatgttac agttttccag 29940
ggtaaaagtc ataaaacttt tatgtatact tttccatttt atgaaatgtg cgacattacc 30000
atgtacatga gcaaacagta taagttgtgg cccccacaaa attgtgtgga aaacactggc 30060
actttctgct gcactgctat gctaattaca gtgctcgctt tggtctgtac cctactctat 30120
attaaataca aaagcagacg cagctttatt gaggaaaaga aaatgcctta atttactaag 30180
ttacaaagct aatgtcacca ctaactgctt tactcgctgc ttgcaaaaca aattcaaaaa 30240
gttagcatta taattagaat aggatttaaa ccccccggtc atttcctgct caataccatt 30300
cccctgaaca attgactcta tgtgggatat gctccagcgc tacaaccttg aagtcaggct 30360
tcctggatgt cagcatctga ctttggccag cacctgtccc gcggatttgt tccagtccaa 30420
ctacagcgac ccaccctaac agagatgacc aacacaacca acgcggccgc cgctaccgga 30480
cttacatcta ccacaaatac accccaagtt tctgcctttg tcaataactg ggataacttg 30540
ggcatgtggt ggttctccat agcgcttatg tttgtatgcc ttattattat gtggctcatc 30600
tgctgcctaa agcgcaaacg cgcccgacca cccatctata gtcccatcat tgtgctacac 30660
ccaaacaatg atggaatcca tagattggac ggactgaaac acatgttctt ttctcttaca 30720
gtatgattaa atgagacatg attcctcgag tttttatatt actgaccctt gttgcgcttt 30780
tttgtgcgtg ctccacattg gctgcggttt ctcacatcga agtagactgc attccagcct 30840
tcacagtcta tttgctttac ggatttgtca ccctcacgct catctgcagc ctcatcactg 30900
tggtcatcgc ctttatccag tgcattgact gggtctgtgt gcgctttgca tatctcagac 30960
accatcccca gtacagggac aggactatag ctgagcttct tagaattctt taattatgaa 31020
atttactgtg acttttctgc tgattatttg caccctatct gcgttttgtt ccccgacctc 31080
caagcctcaa agacatatat catgcagatt cactcgtata tggaatattc caagttgcta 31140
caatgaaaaa agcgatcttt ccgaagcctg gttatatgca atcatctctg ttatggtgtt 31200
ctgcagtacc atcttagccc tagctatata tccctacctt gacattggct ggaacgcaat 31260
agatgccatg aaccacccaa ctttccccgc gcccgctatg cttccactgc aacaagttgt 31320
tgccggcggc tttgtcccag ccaatcagcc tcgcccacct tctcccaccc ccactgaaat 31380
cagctacttt aatctaacag gaggagatga ctgacaccct agatctagaa atggacggaa 31440
ttattacaga gcagcgcctg ctagaaagac gcagggcagc ggccgagcaa cagcgcatga 31500
atcaagagct ccaagacatg gttaacttgc accagtgcaa aaggggtatc ttttgtctgg 31560
taaagcaggc caaagtcacc tacgacagta ataccaccgg acaccgcctt agctacaagt 31620
tgccaaccaa gcgtcagaaa ttggtggtca tggtgggaga aaagcccatt accataactc 31680
agcactcggt agaaaccgaa ggctgcattc actcaccttg tcaaggacct gaggatctct 31740
gcacccttat taagaccctg tgcggtctca aagatcttat tccctttaac taataaaaaa 31800
aaataataaa gcatcactta cttaaaatca gttagcaaat ttctgtccag tttattcagc 31860
agcacctcct tgccctcctc ccagctctgg tattgcagct tcctcctggc tgcaaacttt 31920
ctccacaatc taaatggaat gtcagtttcc tcctgttcct gtccatccgc acccactatc 31980
ttcatgttgt tgcagatgaa gcgcgcaaga ccgtctgaag ataccttcaa ccccgtgtat 32040
ccatatgaca cggaaaccgg tcctccaact gtgccttttc ttactcctcc ctttgtatcc 32100
cccaatgggt ttcaagagag tccccctggg gtactctctt tgcgcctatc cgaacctcta 32160
gttacctcca atggcatgct tgcgctcaaa atgggcaacg gcctctctct ggacgaggcc 32220
ggcaacctta cctcccaaaa tgtaaccact gtgagcccac ctctcaaaaa aaccaagtca 32280
aacataaacc tggaaatatc tgcacccctc acagttacct cagaagccct aactgtggct 32340
gccgccgcac ctctaatggt cgcgggcaac acactcacca tgcaatcaca ggccccgcta 32400
accgtgcacg actccaaact tagcattgcc acccaaggac ccctcacagt gtcagaagga 32460
aagctagccc tgcaaacatc aggccccctc accaccaccg atagcagtac ccttactatc 32520
actgcctcac cccctctaac tactgccact ggtagcttgg gcattgactt gaaagagccc 32580
atttatacac aaaatggaaa actaggacta aagtacgggg ctcctttgca tgtaacagac 32640
gacctaaaca ctttgaccgt agcaactggt ccaggtgtga ctattaataa tacttccttg 32700
caaactaaag ttactggagc cttgggtttt gattcacaag gcaatatgca acttaatgta 32760
gcaggaggac taaggattga ttctcaaaac agacgcctta tacttgatgt tagttatccg 32820
tttgatgctc aaaaccaact aaatctaaga ctaggacagg gccctctttt tataaactca 32880
gcccacaact tggatattaa ctacaacaaa ggcctttact tgtttacagc ttcaaacaat 32940
tccaaaaagc ttgaggttaa cctaagcact gccaaggggt tgatgtttga cgctacagcc 33000
atagccatta atgcaggaga tgggcttgaa tttggttcac ctaatgcacc aaacacaaat 33060
cccctcaaaa caaaaattgg ccatggccta gaatttgatt caaacaaggc tatggttcct 33120
aaactaggaa ctggccttag ttttgacagc acaggtgcca ttacagtagg aaacaaaaat 33180
aatgataagc taactttatg gacaactcct gacccaccac caaactgcag cctcatacaa 33240
gagctagatg caaaactcac cctgtgctta acaaaaaacg gatctattgt taatggcatt 33300
gtaagtttag tgggtgttaa gggtaatctc ctaaatatcc aaagtactac taccactgta 33360
ggagtgcatt tagtgtttga tgaacaggga agattaatca catcaacccc tactgccctg 33420
gttccccaag cttcgtgggg atatagacaa ggccaatcag tgtctaccaa tactgttacc 33480
aatggtctag gttttatgcc taatgtgagt gcttacccta gaccaaatgc cagtgaggct 33540
aaaagccaaa tggtaagtct cacgtactta cagggagata catctaaacc tataacaatg 33600
aaagttgcat ttaatggcat tacgtcgcta aatggatact ctttaacatt catgtggtca 33660
ggtctatcaa actatataaa tcagcctttc tctacaccat cctgctcctt ttcttacatt 33720
acccaagaat aataaagaat cgtttgtgtt atgtttcaac gtgtttattt ttcaattgca 33780
gaaaatttca agtcattttt cattcagtag tatagcccca ccaccacata gcttatacag 33840
atcaccgtac ctcaactttg tataataaag ttgtaatcaa actcacagaa ccctagtatt 33900
caacctgcca cctccctccc aacacacaga gtacacagtc ctttctcccc ggctggcctt 33960
aaaaagcatc atatcatggg taacagacat attcttaggt gttatattcc acacggtttc 34020
ctgtcgagcc aaacgctcat cagtgatatt aataaactcc ccgggcagct cacttaagtt 34080
catgtcgctg tccagctgct gagccacagg ctgctgtcca acttgcggtt gcttaacggg 34140
cggcgaagga gaagtccacg cctacatggg ggtagagtca taatcgtgca tcaggatagg 34200
gcggtggtgc tgcagcagcg cgcgaataaa ctgctgccgc cgccgctccg tcctgcagga 34260
atacaacatg gcagtggtct cctcagcgat gattcgcacc gcccgcagca taaggcgcct 34320
tgtcctccgg gcacagcagc gcaccctgat ctcacttaaa tcagcacagt aactgcagca 34380

-continued

```
cagcaccaca atattgttca aaatcccaca gtgcaaggcg ctgtatccaa agctcatggc  34440
ggggaccaca gaacccacgt ggccatcata ccacaagcgc aggtagatta agtggcgacc  34500
cctcataaac acgctggaca taaacattac ctcttttggc atgttgtaat tcaccacctc  34560
ccggtaccat ataaacctct gattaaacat ggcgccatcc accaccatcc taaaccagct  34620
ggccaaaacc tgcccgccgg ctatacactg cagggaaccg ggactggaac aatgacagtg  34680
gagagcccag gactcgtaac catggatcat catgctcgtc atgatatcaa tgttggcaca  34740
acacaggcac acgtgcatac acttcctcag gattacaagc tcctcccgcg ttagaaccat  34800
atcccaggga acaacccatt cctgaatcag cgtaaatccc acactgcagg gaagacctcg  34860
cacgtaactc acgttgtgca ttgtcaaagt gttacattcg ggcagcagcg gatgatcctc  34920
cagtatggta gcgcgggttt ctgtctcaaa aggaggtaga cgatccctac tgtacggagt  34980
gcgccgagac aaccgagatc gtgttggtcg tagtgtcatg ccaaatggaa cgccggacgt  35040
agtcatattt cctgaagcaa aaccaggtgc gggcgtgaca aacagatctg cgtctccggt  35100
ctcgccgctt agatcgctct gtgtagtagt tgtagtatat ccactctctc aaagcatcca  35160
ggcgcccccct ggcttcgggt tctatgtaaa ctccttcatg cgccgctgcc ctgataacat  35220
ccaccaccgc agaataagcc acacccagcc aacctacaca ttcgttctgc gagtcacaca  35280
cgggaggagc gggaagagct ggaagaacca tgtttttttt tttattccaa aagattatcc  35340
aaaacctcaa aatgaagatc tattaagtga acgcgctccc ctccggtggc gtggtcaaac  35400
tctacagcca aagaacagat aatggcattt gtaagatgtt gcacaatggc ttccaaaagg  35460
caaacggccc tcacgtccaa gtggacgtaa aggctaaacc cttcagggtg aatctcctct  35520
ataaacattc cagcaccttc aaccatgccc aaataattct catctcgcca ccttctcaat  35580
atatctctaa gcaaatcccg aatattaagt ccggccattg taaaaatctg ctccagagcg  35640
ccctccacct tcagcctcaa gcagcgaatc atgattgcaa aaattcaggt tcctcacaga  35700
cctgtataag attcaaaagc ggaacattaa caaaaatacc gcgatcccgt aggtcccttc  35760
gcagggccag ctgaacataa tcgtgcaggt ctgcacggac cagcgcggcc acttccccgc  35820
caggaaccat gacaaaagaa cccacactga ttatgacacg catactcgga gctatgctaa  35880
ccagcgtagc cccgatgtaa gcttgttgca tgggcggcga tataaaatgc aaggtgctgc  35940
tcaaaaaatc aggcaaagcc tcgcgcaaaa aagaaagcac atcgtagtca tgctcatgca  36000
gataaaggca ggtaagctcc ggaaccacca cagaaaaaga caccattttt ctctcaaaca  36060
tgtctgcggg tttctgcata aacacaaaat aaaataacaa aaaaacattt aaacattaga  36120
agcctgtctt acaacaggaa aaacaaccct tataagcata agacggacta cggccatgcc  36180
ggcgtgaccg taaaaaaact ggtcaccgtg attaaaaagc accaccgaca gctcctcggt  36240
catgtccgga gtcataatgt aagactcggt aaacacatca ggttgattca catcggtcag  36300
tgctaaaaag cgaccgaaat agcccggggg aatacatacc cgcaggcgta gagacaacat  36360
tacagccccc ataggaggta taacaaaatt aataggagag aaaaacacat aaacacctga  36420
aaaaccctcc tgcctaggca aaatagcacc ctcccgctcc agaacaacat acagcgcttc  36480
cacagcggca gccataacag tcagccttac cagtaaaaaa gaaaacctat taaaaaaaca  36540
ccactcgaca cggcaccagc tcaatcagtc acagtgtaaa aaagggccaa gtgcagagcg  36600
agtatatata ggactaaaaa atgacgtaac ggttaaagtc cacaaaaaac acccagaaaa  36660
ccgcacgcga acctacgccc agaaacgaaa gccaaaaaac ccacaacttc ctcaaatcgt  36720
cacttccgtt ttcccacgtt acgtcacttc ccattttaag aaaactacaa ttcccaacac  36780
```

atacaagtta ctccgcccta aaacctacgt cacccgcccc gttcccacgc cccgcgccac 36840
gtcacaaact ccacccccctc attatcatat tggcttcaat ccaaaataag gtatattatt 36900
gatgatg 36907

<210> SEQ ID NO 6
<211> LENGTH: 36943
<212> TYPE: DNA
<213> ORGANISM: Artificial Sequence
<220> FEATURE:
<223> OTHER INFORMATION: Synthetic adenovirus construct (AdSyn-CO176)
<220> FEATURE:
<221> NAME/KEY: misc_feature
<222> LOCATION: (4148)..(4198)
<223> OTHER INFORMATION: miR-122 binding sites

<400> SEQUENCE: 6
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattaaac cgtattaccg ccatgcattt aatggagtgc 480
ctcgtgaggc tccggtgccc gtcagtgggc agagcgcaca tcgcccacag tccccgagaa 540
gttgggggga ggggtcggca attgaaccgg tgcctagaga aggtggcgcg gggtaaactg 600
ggaaagtgat gtcgtgtact ggctccgcct ttttcccgag ggtgggggag aaccgtatat 660
aagtgcagta gtcgccgtga acgttctttt tcgcaacggg tttgccgcca gaacacaggt 720
aagtgccgtg tgtggttccc gcgggcctgg cctctttacg ggttatggcc cttgcgtgcc 780
ttgaattact tccacctggc tgcagtacgt gattcttgat cccgagcttc gggttggaag 840
tgggtgggag agttcgaggc cttgcgctta aggagcccct tcgcctcgtg cttgagttga 900
ggcctggcct gggcgctggg gccgccgcgt gcgaatctgg tggcaccttc gcgcctgtct 960
cgctgctttc gataagtctc tagccattta aaatttttga tgacctgctg cgacgctttt 1020
tttctggcaa gatagtcttg taaatgcggg ccaagatctg cacactggta tttcggtttt 1080
tggggccgcg ggcggcgacg gggcccgtgc gtcccagcgc acatgttcgg cgaggcgggg 1140
cctgcgagcg cggccaccga gaatcggacg ggggtagtct caagctggcc ggcctgctct 1200
ggtgcctggc ctcgcgccgc cgtgtatcgc cccgccctgg gcggcaaggc tggcccggtc 1260
ggcaccagtt gcgtgagcgg aaagatggcc gcttcccggc cctgctgcag ggagctcaaa 1320
atggaggacg cggcgctcgg gagagcgggc gggtgagtca cccacacaaa ggaaaagggc 1380
ctttccgtcc tcagccgtcg cttcatgtga ctccacggag taccgggcgc cgtccaggca 1440
cctcgattag ttctcgagct tttggagtac gtcgtcttta ggttgggggg aggggtttta 1500
tgcgatggag tttccccaca ctgagtgggt ggagactgaa gttaggccag cttggcactt 1560
gatgtaattc tccttggaat ttgccctttt tgagtttgga tcttggttca ttctcaagcc 1620
tcagacagtg gttcaaagtt tttttcttcc atttcaggtg tcgtgacgct agcgctaccg 1680
gactcagatc tcgagctcaa gcttcgaatt ctgcagtcga cggtaccgga tccatggaag 1740

-continued acgccaaaaa cataaagaaa ggcccggcgc cattctatcc gctggaagat ggaaccgctg 1800
gagagcaact gcataaggct atgaagagat acgccctggt tcctggaaca attgctttta 1860
cagatgcaca tatcgaggtg gacatcactt acgctgagta cttcgaaatg tccgttcggt 1920
tggcagaagc tatgaaacga tatgggctga atacaaatca cagaatcgtc gtatgcagtg 1980
aaaactctct tcaattcttt atgccggtgt tgggcgcgtt atttatcgga gttgcagttg 2040
cgcccgcgaa cgacatttat aatgaacgtg aattgctcaa cagtatgggc atttcgcagc 2100
ctaccgtggt gttcgtttcc aaaaaggggt tgcaaaaaat tttgaacgtg caaaaaaagc 2160
tcccaatcat ccaaaaaatt attatcatgg attctaaaac ggattaccag ggatttcagt 2220
cgatgtacac gttcgtcaca tctcatctac ctcccggttt taatgaatac gattttgtgc 2280
cagagtcctt cgatagggac aagacaattg cactgatcat gaactcctct ggatctactg 2340
gtctgcctaa aggtgtcgct ctgcctcata gaactgcctg cgtgagattc tcgcatgcca 2400
gagatcctat ttttggcaat caaatcattc cggatactgc gattttaagt gttgttccat 2460
tccatcacgg ttttggaatg tttactacac tcggatattt gatatgtgga tttcgagtcg 2520
tcttaatgta tagatttgaa gaagagctgt ttctgaggag ccttcaggat tacaagattc 2580
aaagtgcgct gctggtgcca accctattct ccttcttcgc caaaagcact ctgattgaca 2640
aatacgattt atctaattta cacgaaattg cttctggtgg cgctcccctc tctaaggaag 2700
tcggggaagc ggttgccaag aggttccatc tgccaggtat caggcaagga tatgggctca 2760
ctgagactac atcagctatt ctgattacac ccgaggggga tgataaaccg ggcgcggtcg 2820
gtaaagttgt tccatttttt gaagcgaagg ttgtggatct ggataccggg aaaacgctgg 2880
gcgttaatca aagaggcgaa ctgtgtgtga gaggtcctat gattatgtcc ggttatgtaa 2940
acaatccgga agcgaccaac gccttgattg acaaggatgg atggctacat tctggagaca 3000
tagcttactg ggacgaagac gaacacttct tcatcgttga ccgcctgaag tctctgatta 3060
agtacaaagg ctatcaggtg gctcccgctg aattggaatc catcttgctc caacacccca 3120
acatcttcga cgcaggtgtc gcaggtcttc ccgacgatga cgccggtgaa cttcccgccg 3180
ccgttgttgt tttggagcac ggaaagacga tgacggaaaa agagatcgtg gattacgtcg 3240
ccagtcaagt aacaaccgcg aaaaagttgc gcggaggagt tgtgtttgtg gacgaagtac 3300
cgaaaggtct taccggaaaa ctcgacgcaa gaaaaatcag agagatcctc ataaaggcca 3360
agaagggcgg aaagatcgcc gtggcagccg cagccaccat ggtgagcaag ggcgaggagc 3420
tgttcaccgg ggtggtgccc atcctggtcg agctggacgg cgacgtaaac ggccacaagt 3480
tcagcgtgtc cggcgagggc gagggcgatg ccacctacgg caagctgacc ctgaagttca 3540
tctgcaccac cggcaagctg cccgtgccct ggcccaccct cgtgaccacc ctgacctacg 3600
gcgtgcagtg cttcagccgc taccccgacc acatgaagca gcacgacttc ttcaagtccg 3660
ccatgcccga aggctacgtc caggagcgca ccatcttctt caaggacgac ggcaactaca 3720
agacccgcgc cgaggtgaag ttcgagggcg acaccctggt gaaccgcatc gagctgaagg 3780
gcatcgactt caaggaggac ggcaacatcc tggggcacaa gctggagtac aactacaaca 3840
gccacaacgt ctatatcatg gccgacaagc agaagaacgg catcaaggtg aacttcaaga 3900
tccgccacaa catcgaggac ggcagcgtgc agctcgccga ccactaccag cagaacaccc 3960
ccatcggcga cggccccgtg ctgctgcccg acaaccacta cctgagcacc cagtccgccc 4020
tgagcaaaga ccccaacgag aagcgcgatc acatggtcct gctggagttc gtgaccgccg 4080
ccgggatcac tctcggcatg gacgagctgt acaagtaaag cgactctaga tcataatcag 4140

```
ccatacccaa acaccattgt cacactccaa tcgattcaaa caccattgtc acactccaac   4200
atttgtagag gttttacttg ctttaaaaaa cctcccacac ctccccctga acctgaaaca   4260
taaaatgaat gcaattgttg ttgttaactt gtttattgca gcttataatg gttacaaata   4320
aagcaatagc atcacaaatt tcacaaataa agcatttttt tcactgcatt ctagttgtgg   4380
tttgtccaaa ctcatcaatg taagtttaaa cggcgcgcct gaaatgtgtg ggcgtggctt   4440
aagggtggga aagaatatat aaggtggggg tcttatgtag ttttgtatct gttttgcagc   4500
agccgccgcc gccatgagca ccaactcgtt tgatggaagc attgtgagct catatttgac   4560
aacgcgcatg cccccatggg ccggggtgcg tcagaatgtg atgggctcca gcattgatgg   4620
tcgccccgtc ctgcccgcaa actctactac cttgacctac gagaccgtgt ctggaacgcc   4680
gttggagact gcagcctccg ccgccgcttc agccgctgca gccaccgccc gcgggattgt   4740
gactgacttt gctttcctga gcccgcttgc aagcagtgca gcttcccgtt catccgcccg   4800
cgatgacaag ttgacggctc ttttggcaca attggattct ttgacccggg aacttaatgt   4860
cgtttctcag cagctgttgg atctgcgcca gcaggtttct gccctgaagg cttcctcccc   4920
tcccaatgcg gtttaaaaca caacttttct atacaaagtt gtaaataaaa aaccagactc   4980
tgtttggatt tggatcaagc taagtgtctt gctgtcttta tttaggggtt ttgcgcgcgc   5040
ggtaggcccg ggaccagcgg tctcggtcgt tgagggtcct gtgtattttt tccaggacgt   5100
ggtaaaggtg actctggatg ttcagataca tgggcataag cccgtctctg gggtggaggt   5160
agcaccactg cagagcttca tgctgcgggg tggtgttgta gatgatccag tcgtagcagg   5220
agcgctgggc gtggtgccta aaaatgtctt tcagtagcaa gctgattgcc aggggcaggc   5280
ccttggtgta agtgtttaca aagcggttaa gctgggatgg gtgcatacgt ggggatatga   5340
gatgcatctt ggactgtatt tttaggttgg ctatgttccc agccatatcc ctccggggat   5400
tcatgttgtg cagaaccacc agcacagtgt atccggtgca cttgggaaat ttgtcatgta   5460
gcttagaagg aaatgcgtgg aagaacttgg agacgccctt gtgacctcca agattttcca   5520
tgcattcgtc cataatgatg gcaatgggcc cacgggcggc ggcctgggcg aagatatttc   5580
tgggatcact aacgtcatag ttgtgttcca ggatgagatc gtcataggcc atttttacaa   5640
agcgcgggcg gagggtgcca gactgcggta taatggttcc atccggccca ggggcgtagt   5700
taccctcaca gatttgcatt tcccacgctt tgagttcaga tgggggggatc atgtctacct   5760
gcggggcgat gaagaaaacg gtttccgggg taggggagat cagctgggaa gaaagcaggt   5820
tcctgagcag ctgcgactta ccgcagccgg tgggcccgta aatcacacct attaccggct   5880
gcaactggta gttaagagag ctgcagctgc cgtcatccct gagcaggggg gccacttcgt   5940
taagcatgtc cctgactcgc atgttttccc tgaccaaatc cgccagaagg cgctcgccgc   6000
ccagcgatag cagttcttgc aaggaagcaa agtttttcaa cggtttgaga ccgtccgccg   6060
taggcatgct tttgagcgtt tgaccaagca gttccaggcg gtcccacagc tcggtcacct   6120
gctctacggc atctcgatcc agcatatctc ctcgtttcgc gggttggggc ggctttcgct   6180
gtacggcagt agtcggtgct cgtccagacg ggccagggtc atgtctttcc acgggcgcag   6240
ggtcctcgtc agcgtagtct gggtcacggt gaaggggtgc gctccgggct gcgcgctggc   6300
cagggtgcgc ttgaggctgg tcctgctggt gctgaagcgc tgccggtctt cgccctgcgc   6360
gtcggccagg tagcatttga ccatggtgtc atagtccagc ccctccgcgg cgtggccctt   6420
ggcgcgcagc ttgcccttgg aggaggcgcc gcacgagggg cagtgcagac ttttgagggc   6480
```

-continued gtagagcttg ggcgcgagaa ataccgattc cggggagtag gcatccgcgc cgcaggcccc 6540
gcagacggtc tcgcattcca cgagccaggt gagctctggc cgttcggggt caaaaaccag 6600 gtttcccccca tgctttttga tgcgtttctt acctctggtt tccatgagcc ggtgtccacg 6660
ctcggtgacg aaaaggctgt ccgtgtcccc gtatacagac ttgagaggcc tgtcctcgag 6720
cggtgttccg cggtcctcct cgtatagaaa ctcggaccac tctgagacaa aggctcgcgt 6780
ccaggccagc acgaaggagg ctaagtggga ggggtagcgg tcgttgtcca ctagggggtc 6840
cactcgctcc agggtgtgaa gacacatgtc gccctcttcg gcatcaagga aggtgattgg 6900
tttgtaggtg taggccacgt gaccgggtgt tcctgaaggg gggctataaa agggggtggg 6960
ggcgcgttcg tcctcactct cttccgcatc gctgtctgcg agggccagct gttggggtga 7020
gtactccctc tgaaaagcgg gcatgacttc tgcgctaaga ttgtcagttt ccaaaaacga 7080
ggaggatttg atattcacct ggcccgcggt gatgcctttg agggtggccg catccatctg 7140
gtcagaaaag acaatctttt tgttgtcaag cttggtggca aacgacccgt agagggcgtt 7200
ggacagcaac ttggcgatgg agcgcagggt ttggtttttg tcgcgatcgg cgcgctcctt 7260
ggccgcgatg tttagctgca cgtattcgcg cgcaacgcac cgccattcgg gaaagacggt 7320
ggtgcgctcg tcgggcacca ggtgcacgcg ccaaccgcgg ttgtgcaggg tgacaaggtc 7380
aacgctggtg gctacctctc cgcgtaggcg ctcgttggtc cagcagaggc ggccgccctt 7440
gcgcgagcag aatggcggta gggggtctag ctgcgtctcg tccggggggt ctgcgtccac 7500
ggtaaagacc ccgggcagca ggcgcgcgtc gaagtagtct atcttgcatc cttgcaagtc 7560
tagcgcctgc tgccatgcgc gggcggcaag cgcgcgctcg tatgggttga gtgggggacc 7620
ccatggcatg gggtgggtga gcgcggaggc gtacatgccg caaatgtcgt aaacgtagag 7680
gggctctctg agtattccaa gatatgtagg gtagcatctt ccaccgcgga tgctggcgcg 7740
cacgtaatcg tatagttcgt gcgagggagc gaggaggtcg ggaccgaggt tgctacgggc 7800
gggctgctct gctcggaaga ctatctgcct gaagatggca tgtgagttgg atgatatggt 7860
tggacgctgg aagacgttga agctggcgtc tgtgagacct accgcgtcac gcacgaagga 7920
ggcgtaggag tcgcgcagct tgttgaccag ctcggcggtg acctgcacgt ctagggcgca 7980
gtagtccagg gtttccttga tgatgtcata cttatcctgt cccttttttt tccacagctc 8040
gcggttgagg acaaactctt cgcggtcttt ccagtactct tggatcggaa acccgtcggc 8100
ctccgaacgg taagagccta gcatgtagaa ctggttgacg gcctggtagg cgcagcatcc 8160
cttttctacg ggtagcgcgt atgcctgcgc ggccttccgg agcgaggtgt gggtgagcgc 8220
aaaggtgtcc ctgaccatga ctttgaggta ctggtatttg aagtcagtgt cgtcgcatcc 8280
gccctgctcc cagagcaaaa agtccgtgcg ctttttggaa cgcggatttg gcagggcgaa 8340
ggtgacatcg ttgaagagta tctttcccgc gcgaggcata aagttgcgtg tgatgcggaa 8400
gggtcccggc acctcggaac ggttgttaat tacctgggcg gcgagcacga tctcgtcaaa 8460
gccgttgatg ttgtggccca caatgtaaag ttccaagaag cgcgggatgc ccttgatgga 8520
aggcaatttt ttaagttcct cgtaggtgag ctcttcaggg gagctgagcc cgtgctctga 8580
aagggcccag tctgcaagat gagggttgga agcgacgaat gagctccaca ggtcacgggc 8640
cattagcatt tgcaggtggt cgcgaaaggt cctaaactgg cgacctatgg ccattttttc 8700
tggggtgatg cagtagaagg taagcgggtc ttgttcccag cggtcccatc caaggttcgc 8760
ggctaggtct cgcgcggcag tcactagagg ctcatctccg ccgaacttca tgaccagcat 8820
gaagggcacg agctgcttcc caaaggcccc catccaagta taggtctcta catcgtaggt 8880

```
gacaaagaga cgctcggtgc gaggatgcga gccgatcggg aagaactgga tctcccgcca   8940
ccaattggag gagtggctat tgatgtggtg aaagtagaag tccctgcgac gggccgaaca   9000
ctcgtgctgg cttttgtaaa aacgtgcgca gtactggcag cggtgcacgg gctgtacatc   9060
ctgcacgagg ttgacctgac gaccgcgcac aaggaagcag agtgggaatt tgagcccctc   9120
gcctggcggg tttggctggt ggtcttctac ttcggctgct tgtccttgac cgtctggctg   9180
ctcgagggga gttacggtgg atcggaccac cacgccgcgc gagcccaaag tccagatgtc   9240
cgcgcgcggc ggtcggagct tgatgacaac atcgcgcaga tgggagctgt ccatggtctg   9300
gagctcccgc ggcgtcaggt caggcgggag ctcctgcagg tttacctcgc atagacgggt   9360
cagggcgcgg gctagatcca ggtgatacct aatttccagg ggctggttgg tggcggcgtc   9420
gatggcttgc aagaggccgc atccccgcgg cgcgactacg gtaccgcgcg gcgggcggtg   9480
ggccgcgggg gtgtccttgg atgatgcatc taaaagcggt gacgcgggcg agcccccgga   9540
ggtagggggg gctccggacc cgccgggaga gggggcaggg gcacgtcggc gccgcgcgcg   9600
ggcaggagct ggtgctgcgc gcgtaggttg ctggcgaacg cgacgacgcg gcggttgatc   9660
tcctgaatct ggcgcctctg cgtgaagacg acgggcccgg tgagcttgaa cctgaaagag   9720
agttcgacag aatcaatttc ggtgtcgttg acggcggcct ggcgcaaaat ctcctgcacg   9780
tctcctgagt tgtcttgata ggcgatctcg gccatgaact gctcgatctc ttcctcctgg   9840
agatctccgc gtccggctcg ctccacggtg gcggcgaggt cgttggaaat gcgggccatg   9900
agctgcgaga aggcgttgag gcctccctcg ttccagacgc ggctgtagac cacgccccct   9960
tcggcatcgc gggcgcgcat gaccacctgc gcgagattga gctccacgtg ccgggcgaag  10020
acggcgtagt ttcgcaggcg ctgaaagagg tagttgaggg tggtggcggt gtgttctgcc  10080
acgaagaagt acataaccca gcgtcgcaac gtggattcgt tgatatcccc caaggcctca  10140
aggcgctcca tggcctcgta gaagtccacg gcgaagttga aaaactggga gttgcgcgcc  10200
gacacggtta actcctcctc cagaagacgg atgagctcgg cgacagtgtc gcgcacctcg  10260
cgctcaaagg ctacaggggc ctcttcttct tcttcaatct cctcttccat aagggcctcc  10320
ccttcttctt cttctggcgg cggtggggga ggggggacac ggcggcgacg acggcgcacc  10380
gggaggcggt cgacaaagcg ctcgatcatc tccccgcggc gacggcgcat ggtctcggtg  10440
acggcgcggc cgttctcgcg gggggcgcagt tggaagacgc cgcccgtcat gtcccggtta  10500
tgggttggcg gggggctgcc atgcggcagg gatacggcgc taacgatgca tctcaacaat  10560
tgttgtgtag gtactccgcc gccgagggac ctgagcgagt ccgcatcgac cggatcggaa  10620
aacctctcga gaaaggcgtc taaccagtca cagtcgcaag gtaggctgag caccgtggcg  10680
ggcggcagcg ggcggcggtc ggggttgttt ctggcggagg tgctgctgat gatgtaatta  10740
aagtaggcgg tcttgagacg gcggatggtc gacagaagca ccatgtcctt gggtccggcc  10800
tgctgaatgc gcaggcggtc ggccatgccc caggcttcgt tttgacatcg gcgcaggtct  10860
ttgtagtagt cttgcatgag cctttctacc ggcacttctt cttctccttc ctcttgtcct  10920
gcatctcttg catctatcgc tgcggcggcg gcggagtttg gccgtaggtg gcgccctctt  10980
cctcccatgc gtgtgacccc gaagcccctc atcggctgaa gcagggctag gtcggcgaca  11040
acgcgctcgg ctaatatggc ctgctgcacc tgcgtgaggg tagactggaa gtcatccatg  11100
tccacaaagc ggtggtatgc gcccgtgttg atggtgtaag tgcagttggc cataacggac  11160
cagttaacgg tctggtgacc cggctgcgag agctcggtgt acctgagacg cgagtaagcc  11220
```

```
ctcgagtcaa atacgtagtc gttgcaagtc cgcaccaggt actggtatcc caccaaaaag  11280
tgcggcggcg gctggcggta gaggggccag cgtagggtgg ccggggctcc gggggcgaga  11340
tcttccaaca taaggcgatg atatccgtag atgtacctgg acatccaggt gatgccggcg  11400
gcggtggtgg aggcgcgcgg aaagtcgcgg acgcggttcc agatgttgcg cagcggcaaa  11460
aagtgctcca tggtcgggac gctctggccg gtcaggcgcg cgcaatcgtt gacgctctag  11520
accgtgcaaa aggagagcct gtaagcgggc actcttccgt ggtctggtgg ataaattcgc  11580
aagggtatca tggcggacga ccggggttcg agccccgtat ccggccgtcc gccgtgatcc  11640
atgcggttac cgcccgcgtg tcgaacccag gtgtgcgacg tcagacaacg ggggagtgct  11700
ccttttggct tccttccagg cgcggcggct gctgcgctag ctttttggc cactggccgc  11760
gcgcagcgta agcggttagg ctggaaagcg aaagcattaa gtggctcgct ccctgtagcc  11820
ggagggttat tttccaaggg ttgagtcgcg ggacccccgg ttcgagtctc ggaccggccg  11880
gactgcggcg aacgggggtt tgcctccccg tcatgcaaga ccccgcttgc aaattcctcc  11940
ggaaacaggg acgagcccct tttttgcttt tcccagatgc atccggtgct gcggcagatg  12000
cgcccccctc ctcagcagcg gcaagagcaa gagcagcggc agacatgcag ggcaccctcc  12060
cctcctccta ccgcgtcagg aggggcgaca tccgcggttg acgcggcagc agatggtgat  12120
tacgaacccc cgcggcgccg ggcccggcac tacctggact tggaggaggg cgagggcctg  12180
gcgcggctag gagcgccctc tcctgagcgg cacccaaggg tgcagctgaa gcgtgatacg  12240
cgtgaggcgt acgtgccgcg gcagaacctg tttcgcgacc gcgagggaga ggagcccgag  12300
gagatgcggg atcgaaagtt ccacgcaggg cgcgagctgc ggcatggcct gaatcgcgag  12360
cggttgctgc gcgaggagga ctttgagccc gacgcgcgaa ccgggattag tcccgcgcgc  12420
gcacacgtgg cggccgccga cctggtaacc gcatacgagc agacggtgaa ccaggagatt  12480
aactttcaaa aaagctttaa caaccacgtg cgtacgcttg tggcgcgcga ggaggtggct  12540
ataggactga tgcatctgtg ggactttgta agcgcgctgg agcaaaaccc aaatagcaag  12600
ccgctcatgg cgcagctgtt ccttatagtg cagcacagca gggacaacga ggcattcagg  12660
gatgcgctgc taaacatagt agagcccgag ggccgctggc tgctcgattt gataaacatc  12720
ctgcagagca tagtggtgca ggagcgcagc ttgagcctgg ctgacaaggt ggccgccatc  12780
aactattcca tgcttagcct gggcaagttt tacgcccgca agatatacca taccccttac  12840
gttcccatag acaaggaggt aaagatcgag gggttctaca tgcgcatggc gctgaaggtg  12900
cttaccttga gcgacgacct gggcgtttat cgcaacgagc gcatccacaa ggccgtgagc  12960
gtgagccggc ggcgcgagct cagcgaccgc gagctgatgc acagcctgca aagggccctg  13020
gctggcacgg gcagcggcga tagagaggcc gagtcctact ttgacgcggg cgctgacctg  13080
cgctgggccc caagccgacg cgccctggag gcagctgggg ccggacctgg gctggcggtg  13140
gcacccgcgc gcgctggcaa cgtcggcggc gtggaggaat atgacgagga cgatgagtac  13200
gagccagagg acggcgagta ctaagcggtg atgtttctga tcagatgatg caagacgcaa  13260
cggacccggc ggtgcgggcg gcgctgcaga gccagccgtc cggccttaac tccacggacg  13320
actggcgcca ggtcatggac cgcatcatgt cgctgactgc gcgcaatcct gacgcgttcc  13380
ggcagcagcc gcaggccaac cggctctccg caattctgga agcggtggtc ccggcgcgcg  13440
caaaccccac gcacgagaag gtgctggcga tcgtaaacgc gctggccgaa aacagggcca  13500
tccggcccga cgaggccggc ctggtctacg acgcgctgct tcagcgcgtg gctcgttaca  13560
acagcggcaa cgtgcagacc aacctggacc ggctggtggg ggatgtgcgc gaggccgtgg  13620
```

cgcagcgtga gcgcgcgcag cagcagggca acctgggctc catggttgca ctaaacgcct 13680
tcctgagtac acagcccgcc aacgtgccgc ggggacagga ggactacacc aactttgtga 13740
gcgcactgcg gctaatggtg actgagacac cgcaaagtga ggtgtaccag tctgggccag 13800
actatttttt ccagaccagt agacaaggcc tgcagaccgt aaacctgagc caggctttca 13860
aaaacttgca ggggctgtgg ggggtgcggg ctcccacagg cgaccgcgcg accgtgtcta 13920
gcttgctgac gcccaactcg cgcctgttgc tgctgctaat agcgcccttc acggacagtg 13980
gcagcgtgtc ccgggacaca tacctaggtc acttgctgac actgtaccgc gaggccatag 14040
gtcaggcgca tgtggacgag catactttcc aggagattac aagtgtcagc cgcgcgctgg 14100
ggcaggagga cacgggcagc ctggaggcaa ccctaaacta cctgctgacc aaccggcggc 14160
agaagatccc ctcgttgcac agtttaaaca gcgaggagga gcgcattttg cgctacgtgc 14220
agcagagcgt gagccttaac ctgatgcgcg acggggtaac gcccagcgtg gcgctggaca 14280
tgaccgcgcg caacatggaa ccgggcatgt atgcctcaaa ccggccgttt atcaaccgcc 14340
taatggacta cttgcatcgc gcggccgccg tgaaccccga gtatttcacc aatgccatct 14400
tgaacccgca ctggctaccg cccccctggtt tctacaccgg gggattcgag gtgcccgagg 14460
gtaacgatgg attcctctgg gacgacatag acgacagcgt gttttccccg caaccgcaga 14520
ccctgctaga gttgcaacag cgcgagcagg cagaggcggc gctgcgaaag gaaagcttcc 14580
gcaggccaag cagcttgtcc gatctaggcg ctgcggcccc gcggtcagat gctagtagcc 14640
catttccaag cttgataggg tctcttacca gcactcgcac cacccgcccg cgcctgctgg 14700
gcgaggagga gtacctaaac aactcgctgc tgcagccgca gcgcgaaaaa aacctgcctc 14760
cggcatttcc caacaacggg atagagagcc tagtggacaa gatgagtaga tggaagacgt 14820
acgcgcagga gcacagggac gtgccaggcc cgcgcccgcc cacccgtcgt caaaggcacg 14880
accgtcagcg gggtctggtg tgggaggacg atgactcggc agacgacagc agcgtcctgg 14940
atttgggagg gagtggcaac ccgtttgcgc accttcgccc caggctgggg agaatgtttt 15000
aaaaaaaaaa aaaaagcatg atgcaaaata aaaaactcac caaggccatg gcaccgagcg 15060
ttggttttct tgtattcccc ttagtatgcg gcgcgcggcg atgtatgagg aaggtcctcc 15120
tccctcctac gagagtgtgg tgagcgcggc gccagtggcg gcggcgctgg gttctccctt 15180
cgatgctccc ctggacccgc cgtttgtgcc tccgcggtac ctgcggccta ccggggggag 15240
aaacagcatc cgttactctg agttggcacc cctattcgac accacccgtg tgtacctggt 15300
ggacaacaag tcaacggatg tggcatccct gaactaccag aacgaccaca gcaactttct 15360
gaccacggtc attcaaaaca atgactacag cccgggggag gcaagcacac agaccatcaa 15420
tcttgacgac cggtcgcact ggggcggcga cctgaaaacc atcctgcata ccaacatgcc 15480
aaatgtgaac gagttcatgt ttaccaataa gtttaaggcg cgggtgatgg tgtcgcgctt 15540
gcctactaag gacaatcagg tggagctgaa atacgagtgg gtggagttca cgctgcccga 15600
gggcaactac tccgagacca tgaccataga ccttatgaac aacgcgatcg tggagcacta 15660
cttgaaagtg ggcagacaga acggggttct ggaaagcgac atcggggtaa agtttgacac 15720
ccgcaacttc agactggggt ttgaccccgt cactggtctt gtcatgcctg ggtatatac 15780
aaacgaagcc ttccatccag acatcatttt gctgccagga tgcggggtgg acttcaccca 15840
cagccgcctg agcaacttgt tgggcatccg caagcggcaa cccttccagg agggctttag 15900
gatcacctac gatgatctgg agggtggtaa cattcccgca ctgttggatg tggacgccta 15960

-continued

```
ccaggcgagc ttgaaagatg acaccgaaca gggcgggggt ggcgcaggcg gcagcaacag  16020
cagtggcagc ggcgcggaag agaactccaa cgcggcagcc gcggcaatgc agccggtgga  16080
ggacatgaac gatcatgcca ttcgcggcga cacctttgcc acacgggctg aggagaagcg  16140
cgctgaggcc gaagcagcgg ccgaagctgc cgccccccgct gcgcaacccg aggtcgagaa  16200
gcctcagaag aaaccggtga tcaaacccct gacagaggac agcaagaaac gcagttacaa  16260
cctaataagc aatgacagca ccttcaccca gtaccgcagc tggtaccttg catacaacta  16320
cggcgaccct cagaccggaa tccgctcatg gaccctgctt tgcactcctg acgtaacctg  16380
cggctcggag caggtctact ggtcgttgcc agacatgatg caagaccccg tgaccttccg  16440
ctccacgcgc cagatcagca actttccggt ggtgggcgcc gagctgttgc ccgtgcactc  16500
caagagcttc tacaacgacc aggccgtcta ctcccaactc atccgccagt ttacctctct  16560
gacccacgtg ttcaatcgct ttcccgagaa ccagattttg gcgcgcccgc cagcccccac  16620
catcaccacc gtcagtgaaa acgttcctgc tctcacagat cacgggacgc taccgctgcg  16680
caacagcatc ggaggagtcc agcgagtgac cattactgac gccagacgcc gcacctgccc  16740
ctacgtttac aaggccctgg gcatagtctc gccgcgcgtc ctatcgagcc gcactttttg  16800
agcaagcatg tccatcctta tatcgcccag caataacaca ggctggggcc tgcgcttccc  16860
aagcaagatg tttggcgggg ccaagaagcg ctccgaccaa cacccagtgc gcgtgcgcgg  16920
gcactaccgc gcgccctggg gcgcgcacaa acgcggccgc actgggcgca ccaccgtcga  16980
tgacgccatc gacgcggtgg tggaggaggc gcgcaactac acgcccacgc cgccaccagt  17040
gtccacagtg gacgcggcca ttcagaccgt ggtgcgcgga gcccggcgct atgctaaaat  17100
gaagagacgg cggaggcgcg tagcacgtcg ccaccgccgc cgacccggca ctgccgccca  17160
acgcgcggcg gcggccctgc ttaaccgcgc acgtcgcacc ggccgacggg cggccatgcg  17220
ggccgctcga aggctggccg cgggtattgt cactgtgccc cccaggtcca ggcgacgagc  17280
ggccgccgca gcagccgcgg ccattagtgc tatgactcag ggtcgcaggg gcaacgtgta  17340
ttgggtgcgc gactcggtta gcggcctgcg cgtgcccgtg cgcacccgcc ccccgcgcaa  17400
ctagattgca agaaaaaact acttagactc gtactgttgt atgtatccag cggcggcggc  17460
gcgcaacgaa gctatgtcca agcgcaaaat caaagaagag atgctccagg tcatcgcgcc  17520
ggagatctat ggcccccccga agaaggaaga gcaggattac aagccccgaa agctaaagcg  17580
ggtcaaaaag aaaaagaaag atgatgatga tgaacttgac gacgaggtgg aactgctgca  17640
cgctaccgcg cccaggcgac gggtacagtg gaaaggtcga cgcgtaaaac gtgttttgcg  17700
acccggcacc accgtagtct ttacgcccgg tgagcgctcc acccgcacct acaagcgcgt  17760
gtatgatgag gtgtacggcg acgaggacct gcttgagcag gccaacgagc gcctcgggga  17820
gtttgcctac ggaaagcggc ataaggacat gctggcgttg ccgctggacg agggcaaccc  17880
aacacctagc ctaaagcccg taacactgca gcaggtgctg cccgcgcttg caccgtccga  17940
agaaaagcgc ggcctaaagc gcgagtctgg tgacttggca cccaccgtgc agctgatggt  18000
acccaagcgc cagcgactgg aagatgtctt ggaaaaaatg accgtggaac ctgggctgga  18060
gcccgaggtc cgcgtgcggc caatcaagca ggtggcgccg ggactgggcg tgcagaccgt  18120
ggacgttcag atacccacta ccagtagcac cagtattgcc accgccacag agggcatgga  18180
gacacaaacg tccccggttg cctcagcggt ggcggatgcc gcggtgcagg cggtcgctgc  18240
ggccgcgtcc aagacctcta cggaggtgca aacggacccg tggatgtttc gcgtttcagc  18300
cccccggcgc ccgcgccgtt cgaggaagta cggcgccgcc agcgcgctac tgcccgaata  18360
```

-continued

```
tgccctacat ccttccattg cgcctacccc cggctatcgt ggctacacct accgccccag  18420
aagacgagca actacccgac gccgaaccac cactggaacc cgccgccgcc gtcgccgtcg  18480
ccagcccgtg ctggccccga tttccgtgcg cagggtggct cgcgaaggag gcaggaccct  18540
ggtgctgcca acagcgcgct accaccccag catcgtttaa aagccggtct ttgtggttct  18600
tgcagatatg gccctcacct gccgcctccg tttcccggtg ccgggattcc gaggaagaat  18660
gcaccgtagg aggggcatgg ccggccacgg cctgacgggc ggcatgcgtc gtgcgcacca  18720
ccggcggcgg cgcgcgtcgc accgtcgcat gcgcggcggt atcctgcccc tccttattcc  18780
actgatcgcc gcggcgattg gcgccgtgcc cggaattgca tccgtggcct tgcaggcgca  18840
gagacactga ttaaaaacaa gttgcatgtg gaaaaatcaa aataaaaagt ctggactctc  18900
acgctcgctt ggtcctgtaa ctattttgta gaatggaaga catcaacttt gcgtctctgg  18960
ccccgcgaca cggctcgcgc ccgttcatgg gaaactggca agatatcggc accagcaata  19020
tgagcggtgg cgccttcagc tggggctcgc tgtggagcgg cattaaaaat ttcggttcca  19080
ccgttaagaa ctatggcagc aaggcctgga acagcagcac aggccagatg ctgagggata  19140
agttgaaaga gcaaaatttc caacaaaagg tggtagatgg cctggcctct ggcattagcg  19200
gggtggtgga cctggccaac caggcagtgc aaaataagat taacagtaag cttgatcccc  19260
gccctcccgt agaggagcct ccaccggccg tggagacagt gtctccagag gggcgtggcg  19320
aaaagcgtcc gcgccccgac agggaagaaa ctctggtgac gcaaatagac gagcctccct  19380
cgtacgagga ggcactaaag caaggcctgc ccaccacccg tcccatcgcg cccatggcta  19440
ccggagtgct gggccagcac acacccgtaa cgctggacct gcctcccccc gccgacaccc  19500
agcagaaacc tgtgctgcca ggcccgaccg ccgttgttgt aacccgtcct agccgcgcgt  19560
ccctgcgccg cgccgccagc ggtccgcgat cgttgcggcc cgtagccagt ggcaactggc  19620
aaagcacact gaacagcatc gtgggtctgg gggtgcaatc cctgaagcgc cgacgatgct  19680
tctgaatagc taacgtgtcg tatgtgtgtc atgtatgcgt ccatgtcgcc gccagaggag  19740
ctgctgagcc gccgcgcgcc cgctttccaa gatggctacc ccttcgatga tgccgcagtg  19800
gtcttacatg cacatctcgg gccaggacgc ctcggagtac ctgagccccg ggctggtgca  19860
gtttgcccgc gccaccgaga cgtacttcag cctgaataac aagtttagaa accccacggt  19920
ggcgcctacg cacgacgtga ccacagaccg gtcccagcgt ttgacgctgc ggttcatccc  19980
tgtggaccgt gaggatactg cgtactcgta caaggcgcgg ttcaccctag ctgtgggtga  20040
taaccgtgtg ctggacatgg cttccacgta ctttgacatc cgcggcgtgc tggacagggg  20100
ccctactttt aagccctact ctggcactgc ctacaacgcc ctggctccca agggtgcccc  20160
aaatccttgc gaatgggatg aagctgctac tgctcttgaa ataaacctag aagaagagga  20220
cgatgacaac gaagacgaag tagacgagca agctgagcag caaaaaactc acgtatttgg  20280
gcaggcgcct tattctggta taaatattac aaaggagggt attcaaatag gtgtcgaagg  20340
tcaaacacct aaatatgccg ataaaacatt tcaacctgaa cctcaaatag gagaatctca  20400
gtggtacgaa actgaaatta atcatgcagc tgggagagtc cttaaaaaga ctaccccaat  20460
gaaaccatgt tacggttcat atgcaaaacc cacaaatgaa aatggagggc aaggcattct  20520
tgtaaagcaa caaaatggaa agctagaaag tcaagtggaa atgcaatttt tctcaactac  20580
tgaggcgacc gcaggcaatg gtgataactt gactcctaaa gtggtattgt acagtgaaga  20640
tgtagatata gaaaccccag acactcatat ttcttacatg cccactatta aggaaggtaa  20700
```

-continued

```
ctcacgagaa ctaatgggcc aacaatctat gcccaacagg cctaattaca ttgcttttag 20760
ggacaatttt attggtctaa tgtattacaa cagcacgggt aatatgggtg ttctggcggg 20820
ccaagcatcg cagttgaatg ctgttgtaga tttgcaagac agaaacacag agctttcata 20880
ccagcttttg cttgattcca ttggtgatag aaccaggtac ttttctatgt ggaatcaggc 20940
tgttgacagc tatgatccag atgttagaat tattgaaaat catggaactg aagatgaact 21000
tccaaattac tgctttccac tgggaggtgt gattaataca gagactctta ccaaggtaaa 21060
acctaaaaca ggtcaggaaa atggatggga aaaagatgct acagaatttt cagataaaaa 21120
tcaaataaga gttggaaata attttgccat ggaaatcaat ctaaatgcca acctgtggag 21180
aaatttcctg tactccaaca tagcgctgta tttgcccgac aagctaaagt acagtccttc 21240
caacgtaaaa atttctgata acccaaacac ctacgactac atgaacaagc gagtggtggc 21300
tcccgggtta gtggactgct acattaacct tggagcacgc tggtcccttg actatatgga 21360
caacgtcaac ccatttaacc accaccgcaa tgctggcctg cgctaccgct caatgttgct 21420
gggcaatggt cgctatgtgc ccttccacat ccaggtgcct cagaagttct ttgccattaa 21480
aaacctcctt ctcctgccgg gctcatacac ctacgagtgg aacttcagga aggatgttaa 21540
catggttctg cagagctccc taggaaatga cctaagggtt gacggagcca gcattaagtt 21600
tgatagcatt tgcctttacg ccaccttctt ccccatggcc cacaacaccg cctccacgct 21660
tgaggccatg cttagaaacg acaccaacga ccagtccttt aacgactatc tctccgccgc 21720
caacatgctc taccctatac ccgccaacgc taccaacgtg cccatatcca tcccctcccg 21780
caactgggcg gctttccgcg gctgggcctt cacgcgcctt aagactaagg aaaccccatc 21840
actgggctcg ggctacgacc cttattacac ctactctggc tctataccct acctagatgg 21900
aaccttttac ctcaaccaca cctttaagaa ggtggccatt acctttgact cttctgtcag 21960
ctggcctggc aatgaccgcc tgcttacccc caacgagttt gaaattaagc gctcagttga 22020
cggggagggt tacaacgttg cccagtgtaa catgaccaaa gactggttcc tggtacaaat 22080
gctagctaac tacaacattg gctaccaggg cttctatatc ccagagagct acaaggaccg 22140
catgtactcc ttctttagaa acttccagcc catgagccgt caggtggtgg atgatactaa 22200
atacaaggac taccaacagg tgggcatcct acaccaacac aacaactctg gatttgttgg 22260
ctaccttgcc cccaccatgc gcgaaggaca ggcctaccct gctaacttcc cctatccgct 22320
tataggcaag accgcagttg acagcattac ccagaaaaag tttctttgcg atcgcaccct 22380
ttggcgcatc ccattctcca gtaactttat gtccatgggc gcactcacag acctgggcca 22440
aaaccttctc tacgccaact ccgcccacgc gctagacatg acttttgagg tggatcccat 22500
ggacgagccc acccttcttt atgttttgtt tgaagtcttt gacgtggtcc gtgtgcaccg 22560
gccgcaccgc ggcgtcatcg aaaccgtgta cctgcgcacg cccttctcgg ccggcaacgc 22620
cacaacataa agaagcaagc aacatcaaca acagctgccg ccatgggctc cagtgagcag 22680
gaactgaaag ccattgtcaa agatcttggt tgtgggccat atttttttggg cacctatgac 22740
aagcgctttc caggctttgt ttctccacac aagctcgcct gcgccatagt caatacggcc 22800
ggtcgcgaga ctgggggcgt acactggatg gcctttgcct ggaacccgca ctcaaaaaca 22860
tgctacctct ttgagccctt tggcttttct gaccagcgac tcaagcaggt ttaccagttt 22920
gagtacgagt cactcctgcg ccgtagcgcc attgcttctt cccccgaccg ctgtataacg 22980
ctggaaaagt ccacccaaag cgtacagggg cccaactcgg ccgcctgtgg actattctgc 23040
tgcatgtttc tccacgcctt tgccaactgg ccccaaactc ccatggatca caaccccacc 23100
```

atgaacctta ttaccggggt acccaactcc atgctcaaca gtccccaggt acagcccacc 23160
ctgcgtcgca accaggaaca gctctacagc ttcctggagc gccactcgcc ctacttccgc 23220
agccacagtg cgcagattag gagcgccact tctttttgtc acttgaaaaa catgtaaaaa 23280
taatgtacta gagacacttt caataaaggc aaatgctttt atttgtacac tctcgggtga 23340
ttatttaccc ccacccttgc cgtctgcgcc gtttaaaaat caaaggggtt ctgccgcgca 23400
tcgctatgcg ccactggcag ggacacgttg cgatactggt gtttagtgct ccacttaaac 23460
tcaggcacaa ccatccgcgg cagctcggtg aagttttcac tccacaggct gcgcaccatc 23520
accaacgcgt ttagcaggtc gggcgccgat atcttgaagt cgcagttggg gcctccgccc 23580
tgcgcgcgcg agttgcgata cacagggttg cagcactgga acactatcag cgccgggtgg 23640
tgcacgctgg ccagcacgct cttgtcggag atcagatccg cgtccaggtc ctccgcgttg 23700
ctcagggcga acggagtcaa ctttggtagc tgccttccca aaaagggcgc gtgcccaggc 23760
tttgagttgc actcgcaccg tagtggcatc aaaaggtgac cgtgcccggt ctgggcgtta 23820
ggatacagcg cctgcataaa agccttgatc tgcttaaaag ccacctgagc ctttgcgcct 23880
tcagagaaga acatgccgca agacttgccg gaaaactgat tggccggaca ggccgcgtcg 23940
tgcacgcagc accttgcgtc ggtgttggag atctgcacca catttcggcc ccaccggttc 24000
ttcacgatct tggccttgct agactgctcc ttcagcgcgc gctgcccgtt ttcgctcgtc 24060
acatccattt caatcacgtg ctccttattt atcataatgc ttccgtgtag acacttaagc 24120
tcgccttcga tctcagcgca gcggtgcagc cacaacgcgc agcccgtggg ctcgtgatgc 24180
ttgtaggtca cctctgcaaa cgactgcagg tacgcctgca ggaatcgccc catcatcgtc 24240
acaaaggtct tgttgctggt gaaggtcagc tgcaacccgc ggtgctcctc gttcagccag 24300
gtcttgcata cggccgccag agcttccact tggtcaggca gtagtttgaa gttcgccttt 24360
agatcgttat ccacgtggta cttgtccatc agcgcgcgcg cagcctccat gcccttctcc 24420
cacgcagaca cgatcggcac actcagcggg ttcatcaccg taatttcact ttccgcttcg 24480
ctgggctctt cctcttcctc ttgcgtccgc ataccacgcg ccactgggtc gtcttcattc 24540
agccgccgca ctgtgcgctt acctcctttg ccatgcttga ttagcaccgg tgggttgctg 24600
aaacccacca tttgtagcgc cacatcttct ctttcttcct cgctgtccac gattacctct 24660
ggtgatggcg ggcgctcggg cttgggagaa gggcgcttct ttttcttctt gggcgcaatg 24720
gccaaatccg ccgccgaggt cgatggccgc gggctgggtg tgcgcggcac cagcgcgtct 24780
tgtgatgagt cttcctcgtc ctcggactcg atacgccgcc tcatccgctt ttttgggggc 24840
gcccggggag gcggcggcga cggggacggg gacgacacgt cctccatggt tgggggacgt 24900
cgcgccgcac cgcgtccgcg ctcgggggtg gtttcgcgct gctcctcttc ccgactggcc 24960
atttccttct cctataggca gaaaaagatc atggagtcag tcgagaagaa ggacagccta 25020
accgcccccct ctgagttcgc caccaccgcc tccaccgatg ccgccaacgc gcctaccacc 25080
ttccccgtcg aggcaccccc gcttgaggag gaggaagtga ttatcgagca ggacccaggt 25140
tttgtaagcg aagacgacga ggaccgctca gtaccaacag aggataaaaa gcaagaccag 25200
gacaacgcag aggcaaacga ggaacaagtc gggcgggggg acgaaaggca tggcgactac 25260
ctagatgtgg gagacgacgt gctgttgaag catctgcagc gccagtgcgc cattatctgc 25320
gacgcgttgc aagagcgcag cgatgtgccc ctcgccatag cggatgtcag ccttgcctac 25380
gaacgccacc tattctcacc gcgcgtaccc cccaaacgcc aagaaaacgg cacatgcgag 25440
cccaacccgc gcctcaactt ctaccccgta tttgccgtgc cagaggtgct tgccacctat 25500
cacatctttt tccaaaactg caagataccc ctatcctgcc gtgccaaccg cagccgagcg 25560
gacaagcagc tggccttgcg gcagggcgct gtcatacctg atatcgcctc gctcaacgaa 25620
gtgccaaaaa tctttgaggg tcttggacgc gacgagaagc gcgcggcaaa cgctctgcaa 25680
caggaaaaca gcgaaaatga aagtcactct ggagtgttgg tggaactcga gggtgacaac 25740
gcgcgcctag ccgtactaaa acgcagcatc gaggtcaccc actttgccta cccggcactt 25800
aacctacccc ccaaggtcat gagcacagtc atgagtgagc tgatcgtgcg ccgtgcgcag 25860
cccctggaga gggatgcaaa tttgcaagaa caaacagagg agggcctacc cgcagttggc 25920
gacgagcagc tagcgcgctg gcttcaaacg cgcgagcctg ccgacttgga ggagcgacgc 25980
aaactaatga tggccgcagt gctcgttacc gtggagcttg agtgcatgca gcggttcttt 26040
gctgacccgg agatgcagcg caagctagag gaaacattgc actacacctt tcgacagggc 26100
tacgtacgcc aggcctgcaa gatctccaac gtggagctct gcaacctggt ctcctacctt 26160
ggaattttgc acgaaaaccg ccttgggcaa aacgtgcttc attccacgct caagggcgag 26220
gcgcgccgcg actacgtccg cgactgcgtt tacttatttc tatgctacac ctggcagacg 26280
gccatgggcg tttggcagca gtgcttggag gagtgcaacc tcaaggagct gcagaaactg 26340
ctaaagcaaa acttgaagga cctatggacg gccttcaacg agcgctccgt ggccgcgcac 26400
ctggcggaca tcattttccc cgaacgcctg cttaaaaccc tgcaacaggg tctgccagac 26460
ttcaccagtc aaagcatgtt gcagaacttt aggaacttta tcctagagcg ctcaggaatc 26520
ttgcccgcca cctgctgtgc acttcctagc gactttgtgc ccattaagta ccgcgaatgc 26580
cctccgccgc tttggggcca ctgctacctt ctgcagctag ccaactacct tgcctaccac 26640
tctgacataa tggaagacgt gagcggtgac ggtctactgg agtgtcactg tcgctgcaac 26700
ctatgcaccc cgcaccgctc cctggtttgc aattcgcagc tgcttaacga aagtcaaatt 26760
atcggtacct ttgagctgca gggtccctcg cctgacgaaa agtccgcggc tccggggttg 26820
aaactcactc cggggctgtg gacgtcggct taccttcgca aatttgtacc tgaggactac 26880
cacgcccacg agattaggtt ctacgaagac caatcccgcc cgccaaatgc ggagcttacc 26940
gcctgcgtca ttacccaggg ccacattctt ggccaattgc aagccatcaa caaagcccgc 27000
caagagtttc tgctacgaaa gggacggggg gtttacttgg acccccagtc cggcgaggag 27060
ctcaacccaa tcccccgcc gccgcagccc tatcagcagc agccgcgggc ccttgcttcc 27120
caggatggca cccaaaaaga agctgcagct gccgccgcca cccacggacg aggaggaata 27180
ctgggacagt caggcagagg aggttttgga cgaggaggag gaggacatga tggaagactg 27240
ggagagccta gacgaggaag cttccgaggt cgaagaggtg tcagacgaaa caccgtcacc 27300
ctcggtcgca ttcccctcgc cggcgcccca gaaatcggca accggttcca gcatggctac 27360
aacctccgct cctcaggcgc cgccggcact gcccgttcgc cgacccaacc gtagatggga 27420
caccactgga accagggccg gtaagtccaa gcagccgccg ccgttagccc aagagcaaca 27480
acagcgccaa ggctaccgct catggcgcgg gcacaagaac gccatagttg cttgcttgca 27540
agactgtggg ggcaacatct ccttcgcccg ccgctttctt ctctaccatc acggcgtggc 27600
cttcccccgt aacatcctgc attactaccg tcatctctac agcccatact gcaccggcgg 27660
cagcggcagc ggcagcaaca gcagcggcca cacagaagca aaggcgaccg gatagcaaga 27720
ctctgacaaa gcccaagaaa tccacagcgg cggcagcagc aggaggagga gcgctgcgtc 27780
tggcgcccaa cgaacccgta tcgacccgcg agcttagaaa caggattttt cccactctgt 27840
atgctatatt tcaacagagc aggggccaag aacaagagct gaaaataaaa aacaggtctc 27900
tgcgatccct cacccgcagc tgcctgtatc acaaaagcga agatcagctt cggcgcacgc 27960
tggaagacgc ggaggctctc ttcagtaaat actgcgcgct gactcttaag gactagtttc 28020
gcgccctttc tcaaatttaa gcgcgaaaac tacgtcatct ccagcggcca cacccggcgc 28080
cagcacctgt cgtcagcgcc atttcaactt tgtatacaaa agttgtgatg agcaaggaaa 28140
ttcccacgcc ctacatgtgg agttaccagc cacaaatggg acttgcggct ggagctgccc 28200
aagactactc aacccgaata aactacatga gcgcgggacc ccacatgata tcccgggtca 28260
acggaatacg cgcccaccga aaccgaattc tcctggaaca ggcggctatt accaccacac 28320
ctcgtaataa ccttaatccc cgtagttggc ccgctgccct ggtgtaccag gaaagtcccg 28380
ctcccaccac tgtggtactt cccagagacg cccaggccga agttcagatg actaactcag 28440
gggcgcagct tgcgggcggc tttcgtcaca gggtgcggtc gcccgggcag ggtataactc 28500
acctgacaat cagagggcga ggtattcagc tcaacgacga gtcggtgagc tcctcgcttg 28560
gtctccgtcc ggacgggaca tttcagatcg gcggcgccgg ccgctcttca ttcacgcctc 28620
gtcaggcaat cctaactctg cagacctcgt cctctgagcc gcgctctgga ggcattggaa 28680
ctctgcaatt tattgaggag tttgtgccat cggtctactt taacccettc tcgggacctc 28740
ccggccacta tccggatcaa tttattccta actttgacgc ggtaaaggac tcggcggacg 28800
gctacgactg aatgttaagt ggagaggcag agcaactgcg cctgaaacac ctggtccact 28860
gtcgccgcca caagtgcttt gcccgcgact ccggtgagtt ttgctacttt gaattgcccg 28920
aggatcatat cgagggcccg gcgcacggcg tccggcttac cgcccaggga gagcttgccc 28980
gtagcctgat tcgggagttt acccagcgcc ccctgctagt tgagcgggac aggggaccct 29040
gtgttctcac tgtgatttgc aactgtccta accctggatt acatcaagat ctttgttgcc 29100
atctctgtgc tgagtataat aaatacagaa attaaaatat actggggctc ctatcgccat 29160
cctgtaaacg ccaccgtctt cacccgccca agcaaaccaa ggcgaacctt acctggtact 29220
tttaacatct ctccctctgt gatttacaac agtttcaacc cagacggagt gagtctacga 29280
gagaacctct ccgagctcag ctactccatc agaaaaaaca ccaccctcct tacctgccgg 29340
gaacgtacga gtgcgtcacc ggccgctgca ccacacctac cgcctgaccg taaaccagac 29400
tttttccgga cagacctcaa taactctgtt taccagaaca ggaggtgagc ttagaaaacc 29460
cttagggtat taggccaaag gcgcagctac tgtggggttt atgaacaatt caagcaactc 29520
tacgggctat tctaattcag gtttctctag aatcggggtt ggggttattc tctgtcttgt 29580
gattctcttt attcttatac taacgcttct ctgcctaagg ctcgccgcct gctgtgtgca 29640
catttgcatt tattgtcagc tttttaaacg ctggggtcgc cacccaagat gattaggtac 29700
ataatcctag gtttactcac ccttgcgtca gcccacggta ccacccaaaa ggtggatttt 29760
aaggagccag cctgtaatgt tacattcgca gctgaagcta atgagtgcac cactcttata 29820
aaatgcacca cagaacatga aaagctgctt attcgccaca aaaacaaaat tggcaagtat 29880
gctgtttatg ctatttggca gccaggtgac actacagagt ataatgttac agttttccag 29940
ggtaaaagtc ataaaacttt tatgtatact tttccatttt atgaaatgtg cgacattacc 30000
atgtacatga gcaaacagta taagttgtgg cccccacaaa attgtgtgga aaacactggc 30060
actttctgct gcactgctat gctaattaca gtgctcgctt tggtctgtac cctactctat 30120
attaaataca aaagcagacg cagctttatt gaggaaaaga aaatgcctta atttactaag 30180

```
ttacaaagct aatgtcacca ctaactgctt tactcgctgc ttgcaaaaca aattcaaaaa  30240
gttagcatta taattagaat aggatttaaa ccccccggtc atttcctgct caataccatt  30300
cccctgaaca attgactcta tgtgggatat gctccagcgc tacaaccttg aagtcaggct  30360
tcctggatgt cagcatctga ctttggccag cacctgtccc gcggatttgt tccagtccaa  30420
ctacagcgac ccaccctaac agagatgacc aacacaacca acgcggccgc cgctaccgga  30480
cttacatcta ccacaaatac accccaagtt tctgcctttg tcaataactg ggataacttg  30540
ggcatgtggt ggttctccat agcgcttatg tttgtatgcc ttattattat gtggctcatc  30600
tgctgcctaa agcgcaaacg cgcccgacca cccatctata gtcccatcat tgtgctacac  30660
ccaaacaatg atggaatcca tagattggac ggactgaaac acatgttctt ttctcttaca  30720
gtatgattaa atgagacatg attcctcgag tttttatatt actgaccctt gttgcgcttt  30780
tttgtgcgtg ctccacattg gctgcggttt ctcacatcga agtagactgc attccagcct  30840
tcacagtcta tttgctttac ggatttgtca ccctcacgct catctgcagc ctcatcactg  30900
tggtcatcgc ctttatccag tgcattgact gggtctgtgt gcgctttgca tatctcagac  30960
accatcccca gtacagggac aggactatag ctgagcttct tagaattctt taattatgaa  31020
atttactgtg acttttctgc tgattatttg caccctatct gcgttttgtt ccccgacctc  31080
caagcctcaa agacatatat catgcagatt cactcgtata tggaatattc caagttgcta  31140
caatgaaaaa agcgatcttt ccgaagcctg gttatatgca atcatctctg ttatggtgtt  31200
ctgcagtacc atcttagccc tagctatata tccctacctt gacattggct ggaacgcaat  31260
agatgccatg aaccacccaa ctttccccgc gcccgctatg cttccactgc aacaagttgt  31320
tgccggcggc tttgtcccag ccaatcagcc tcgcccacct tctcccaccc ccactgaaat  31380
cagctacttt aatctaacag gaggagatga ctgacaccct agatctagaa atggacggaa  31440
ttattacaga gcagcgcctg ctagaaagac gcagggcagc ggccgagcaa cagcgcatga  31500
atcaagagct ccaagacatg gttaacttgc accagtgcaa aaggggtatc ttttgtctgg  31560
taaagcaggc caaagtcacc tacgacagta ataccaccgg acaccgcctt agctacaagt  31620
tgccaaccaa gcgtcagaaa ttggtggtca tggtgggaga aaagcccatt accataactc  31680
agcactcggt agaaaccgaa ggctgcattc actcaccttg tcaaggacct gaggatctct  31740
gcacccttat taagaccctg tgcggtctca aagatcttat tccctttaac taataaaaaa  31800
aaataataaa gcatcactta cttaaaatca gttagcaaat ttctgtccag tttattcagc  31860
agcacctcct tgccctcctc ccagctctgg tattgcagct tcctcctggc tgcaaacttt  31920
ctccacaatc taaatggaat gtcagtttcc tcctgttcct gtccatccgc acccactatc  31980
ttcatgttgt tgcagatgaa gcgcgcaaga ccgtctgaag ataccttcaa ccccgtgtat  32040
ccatatgaca cggaaaccgg tcctccaact gtgccttttc ttactcctcc ctttgtatcc  32100
cccaatgggt ttcaagagag tccccctggg gtactctctt tgcgcctatc cgaacctcta  32160
gttacctcca atggcatgct tgcgctcaaa atgggcaacg gcctctctct ggacgaggcc  32220
ggcaacctta cctcccaaaa tgtaaccact gtgagcccac ctctcaaaaa aaccaagtca  32280
aacataaacc tggaaatatc tgcacccctc acagttacct cagaagccct aactgtggct  32340
gccgccgcac ctctaatggt cgcgggcaac acactcacca tgcaatcaca ggccccgcta  32400
accgtgcacg actccaaact tagcattgcc acccaaggac ccctcacagt gtcagaagga  32460
aagctagccc tgcaaacatc aggcccccctc accaccaccg atagcagtac ccttactatc  32520
actgcctcac cccctctaac tactgccact ggtagcttgg gcattgactt gaaagagccc  32580
```

```
atttatacac aaaatggaaa actaggacta aagtacgggg ctcctttgca tgtaacagac  32640
gacctaaaca ctttgaccgt agcaactggt ccaggtgtga ctattaataa tacttccttg  32700
caaactaaag ttactggagc cttgggtttt gattcacaag gcaatatgca acttaatgta  32760
gcaggaggac taaggattga ttctcaaaac agacgcctta tacttgatgt tagttatccg  32820
tttgatgctc aaaaccaact aaatctaaga ctaggacagg gccctctttt tataaactca  32880
gcccacaact tggatattaa ctacaacaaa ggcctttact tgtttacagc ttcaaacaat  32940
tccaaaaagc ttgaggttaa cctaagcact gccaaggggt tgatgtttga cgctacagcc  33000
atagccatta atgcaggaga tgggcttgaa tttggttcac ctaatgcacc aaacacaaat  33060
cccctcaaaa caaaaattgg ccatggccta gaatttgatt caaacaaggc tatggttcct  33120
aaactaggaa ctggccttag ttttgacagc acaggtgcca ttacagtagg aaacaaaaat  33180
aatgataagc taactttatg gactggaata aaccctccac ctaactgtca aattgtggaa  33240
aacactaata caaatgatgg caaacttact ttagtattag taaaaaacgg agggcttgtt  33300
aatggctacg tgtctctagt tggtgtatca gacactgtga accaaatgtt cacacaaaag  33360
acagcaaaca tccaattaag attatatttt gactcttctg gaaatctatt aactgatgaa  33420
tcagacttaa aaattccact taaaaataaa tcttctacag cgaccagtga aactgtagcc  33480
agcagcaaag cctttatgcc aagtactaca gcttatccct tcaacaccac tactagggat  33540
agtgaaaact acattcatgg aatatgttac tacatgacta gttatgatag aagtctattt  33600
cccttgaaca tttctataat gctaaacagc cgtatgattt cttccaatgt tgcctatgcc  33660
atacaatttg aatggaatct aaatgcaagt gaatctccag aaagcaacat agctacgctg  33720
accacatccc cctttttctt ttcttacatt acagaagacg acaactaata aagaatcgtt  33780
tgtgttatgt ttcaacgtgt ttatttttca attgcagaaa atttcaagtc atttttcatt  33840
cagtagtata gccccaccac cacatagctt atacagatca ccgtacctca actttgtata  33900
ataaagttgt aatcaaactc acagaaccct agtattcaac ctgccacctc cctcccaaca  33960
cacagagtac acagtccttt ctccccggct ggccttaaaa agcatcatat catgggtaac  34020
agacatattc ttaggtgtta tattccacac ggtttcctgt cgagccaaac gctcatcagt  34080
gatattaata aactccccgg gcagctcact taagttcatg tcgctgtcca gctgctgagc  34140
cacaggctgc tgtccaactt gcggttgctt aacgggcggc gaaggagaag tccacgccta  34200
catgggggta gagtcataat cgtgcatcag gatagggcgg tggtgctgca gcagcgcgcg  34260
aataaactgc tgccgccgcc gctccgtcct gcaggaatac aacatggcag tggtctcctc  34320
agcgatgatt cgcaccgccc gcagcataag gcgccttgtc ctccgggcac agcagcgcac  34380
cctgatctca cttaaatcag cacagtaact gcagcacagc accacaatat tgttcaaaat  34440
cccacagtgc aaggcgctgt atccaaagct catggcgggg accacagaac ccacgtggcc  34500
atcataccac aagcgcaggt agattaagtg gcgacccctc ataaacacgc tggacataaa  34560
cattacctct tttggcatgt tgtaattcac cacctcccgg taccatataa acctctgatt  34620
aaacatggcg ccatccacca ccatcctaaa ccagctggcc aaaacctgcc cgccggctat  34680
acactgcagg gaaccgggac tggaacaatg acagtggaga gcccaggact cgtaaccatg  34740
gatcatcatg ctcgtcatga tatcaatgtt ggcacaacac aggcacacgt gcatacactt  34800
cctcaggatt acaagctcct cccgcgttag aaccatatcc cagggaacaa cccattcctg  34860
aatcagcgta aatcccacac tgcagggaag acctcgcacg taactcacgt tgtgcattgt  34920
```

-continued

```
caaagtgtta cattcgggca gcagcggatg atcctccagt atggtagcgc gggtttctgt  34980
ctcaaaagga ggtagacgat ccctactgta cggagtgcgc cgagacaacc gagatcgtgt  35040
tggtcgtagt gtcatgccaa atggaacgcc ggacgtagtc atatttcctg aagcaaaacc  35100
aggtgcgggc gtgacaaaca gatctgcgtc tccggtctcg ccgcttagat cgctctgtgt  35160
agtagttgta gtatatccac tctctcaaag catccaggcg ccccctggct tcgggttcta  35220
tgtaaactcc ttcatgcgcc gctgccctga taacatccac caccgcagaa taagccacac  35280
ccagccaacc tacacattcg ttctgcgagt cacacacggg aggagcggga agagctggaa  35340
gaaccatgtt ttttttttta ttccaaaaga ttatccaaaa cctcaaaatg aagatctatt  35400
aagtgaacgc gctcccctcc ggtggcgtgg tcaaactcta cagccaaaga acagataatg  35460
gcatttgtaa gatgttgcac aatggcttcc aaaaggcaaa cggccctcac gtccaagtgg  35520
acgtaaaggc taaacccttc agggtgaatc tcctctataa acattccagc accttcaacc  35580
atgcccaaat aattctcatc tcgccacctt ctcaatatat ctctaagcaa atcccgaata  35640
ttaagtccgg ccattgtaaa aatctgctcc agagcgccct ccaccttcag cctcaagcag  35700
cgaatcatga ttgcaaaaat tcaggttcct cacagacctg tataagattc aaaagcggaa  35760
cattaacaaa aataccgcga tcccgtaggt cccttcgcag ggccagctga acataatcgt  35820
gcaggtctgc acggaccagc gcggccactt ccccgccagg aaccatgaca aaagaaccca  35880
cactgattat gacacgcata ctcggagcta tgctaaccag cgtagccccg atgtaagctt  35940
gttgcatggg cggcgatata aaatgcaagg tgctgctcaa aaaatcaggc aaagcctcgc  36000
gcaaaaaaga aagcacatcg tagtcatgct catgcagata aaggcaggta agctccggaa  36060
ccaccacaga aaaagacacc atttttctct caaacatgtc tgcgggtttc tgcataaaca  36120
caaaataaaa taacaaaaaa acatttaaac attagaagcc tgtcttacaa caggaaaaac  36180
aacccttata agcataagac ggactacggc catgccggcg tgaccgtaaa aaaactggtc  36240
accgtgatta aaaagcacca ccgacagctc ctcggtcatg tccggagtca taatgtaaga  36300
ctcggtaaac acatcaggtt gattcacatc ggtcagtgct aaaaagcgac cgaaatagcc  36360
cgggggaata catacccgca ggcgtagaga caacattaca gcccccatag gaggtataac  36420
aaaattaata ggagagaaaa acacataaac acctgaaaaa ccctcctgcc taggcaaaat  36480
agcaccctcc cgctccagaa caacatacag cgcttccaca gcggcagcca taacagtcag  36540
ccttaccagt aaaaaagaaa acctattaaa aaaacaccac tcgacacggc accagctcaa  36600
tcagtcacag tgtaaaaaag ggccaagtgc agagcgagta tatataggac taaaaaatga  36660
cgtaacggtt aaagtccaca aaaaacaccc agaaaaccgc acgcgaacct acgcccagaa  36720
acgaaagcca aaaaacccac aacttcctca aatcgtcact tccgttttcc cacgttacgt  36780
cacttcccat tttaagaaaa ctacaattcc caacacatac aagttactcc gccctaaaac  36840
ctacgtcacc cgccccgttc ccacgccccg cgccacgtca caaactccac cccctcatta  36900
tcatattggc ttcaatccaa aataaggtat attattgatg atg                    36943
```

<210> SEQ ID NO 7
<211> LENGTH: 36900
<212> TYPE: DNA
<213> ORGANISM: Artificial Sequence
<220> FEATURE:
<223> OTHER INFORMATION: Synthetic adenovirus construct (AdSyn-CO199)

<400> SEQUENCE: 7

```
catcatcaat aatatacctt attttggatt gaagccaata tgataatgag ggggtggagt     60
```

```
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattaaac cgtattaccg ccatgcatta gttattaata    480
gtaatcaatt acggggtcat tagttcttaa tggagtgcct cgtgaggctc cggtgcccgt    540
cagtgggcag agcgcacatc gcccacagtc cccgagaagt tggggggagg ggtcggcaat    600
tgaaccggtg cctagagaag gtggcgcggg gtaaactggg aaagtgatgt cgtgtactgg    660
ctccgccttt ttcccgaggg tgggggagaa ccgtatataa gtgcagtagt cgccgtgaac    720
gttctttttc gcaacgggtt tgccgccaga acacaggtaa gtgccgtgtg tggttcccgc    780
gggcctggcc tctttacggg ttatggccct tgcgtgcctt gaattacttc cacctggctg    840
cagtacgtga ttcttgatcc cgagcttcgg gttggaagtg ggtgggagag ttcgaggcct    900
tgcgcttaag gagccccttc gcctcgtgct tgagttgagg cctggcctgg gcgctggggc    960
cgccgcgtgc gaatctggtg gcaccttcgc gcctgtctcg ctgctttcga taagtctcta   1020
gccatttaaa atttttgatg acctgctgcg acgctttttt tctggcaaga tagtcttgta   1080
aatgcgggcc aagatctgca cactggtatt tcggtttttg gggccgcggg cggcgacggg   1140
gcccgtgcgt cccagcgcac atgttcggcg aggcggggcc tgcgagcgcg gccaccgaga   1200
atcggacggg ggtagtctca agctggccgg cctgctctgg tgcctggcct cgcgccgccg   1260
tgtatcgccc cgccctgggc ggcaaggctg gcccggtcgg caccagttgc gtgagcggaa   1320
agatggccgc ttcccggccc tgctgcaggg agctcaaaat ggaggacgcg gcgctcggga   1380
gagcgggcgg gtgagtcacc cacacaaagg aaaagggcct ttccgtcctc agccgtcgct   1440
tcatgtgact ccacggagta ccgggcgccg tccaggcacc tcgattagtt ctcgagcttt   1500
tggagtacgt cgtctttagg ttggggggag gggttttatg cgatggagtt tccccacact   1560
gagtgggtgg agactgaagt taggccagct tggcacttga tgtaattctc cttggaattt   1620
gccctttttg agtttggatc ttggttcatt ctcaagcctc agacagtggt tcaaagtttt   1680
tttcttccat ttcaggtgtc gtgacgctag cgctaccgga ctcagatctc gagctcaagc   1740
ttcgaattct gcagtcgacg gtaccggatc catggaagac gccaaaaaca taaagaaagg   1800
cccggcgcca ttctatccgc tggaagatgg aaccgctgga gagcaactgc ataaggctat   1860
gaagagatac gccctggttc ctggaacaat tgcttttaca gatgcacata tcgaggtgga   1920
catcacttac gctgagtact tcgaaatgtc cgttcggttg gcagaagcta tgaaacgata   1980
tgggctgaat acaaatcaca gaatcgtcgt atgcagtgaa aactctcttc aattctttat   2040
gccggtgttg ggcgcgttat ttatcggagt tgcagttgcg cccgcgaacg acatttataa   2100
tgaacgtgaa ttgctcaaca gtatgggcat ttcgcagcct accgtggtgt tcgtttccaa   2160
aaaggggttg caaaaaattt tgaacgtgca aaaaaagctc ccaatcatcc aaaaaattat   2220
tatcatggat tctaaaacgg attaccaggg atttcagtcg atgtacacgt tcgtcacatc   2280
tcatctacct cccggtttta atgaatacga ttttgtgcca gagtccttcg atagggacaa   2340
gacaattgca ctgatcatga actcctctgg atctactggt ctgcctaaag gtgtcgctct   2400
```

-continued gcctcataga actgcctgcg tgagattctc gcatgccaga gatcctattt ttggcaatca 2460
aatcattccg gatactgcga ttttaagtgt tgttccattc catcacggtt ttggaatgtt 2520
tactacactc ggatatttga tatgtggatt tcgagtcgtc ttaatgtata gatttgaaga 2580
agagctgttt ctgaggagcc ttcaggatta caagattcaa agtgcgctgc tggtgccaac 2640
cctattctcc ttcttcgcca aaagcactct gattgacaaa tacgatttat ctaatttaca 2700
cgaaattgct tctggtggcg ctcccctctc taaggaagtc ggggaagcgg ttgccaagag 2760
gttccatctg ccaggtatca ggcaaggata tgggctcact gagactacat cagctattct 2820
gattacaccc gagggggatg ataaaccggg cgcggtcggt aaagttgttc cattttttga 2880
agcgaaggtt gtggatctgg ataccgggaa aacgctgggc gttaatcaaa gaggcgaact 2940
gtgtgtgaga ggtcctatga ttatgtccgg ttatgtaaac aatccggaag cgaccaacgc 3000
cttgattgac aaggatggat ggctacattc tggagacata gcttactggg acgaagacga 3060
acacttcttc atcgttgacc gcctgaagtc tctgattaag tacaaaggct atcaggtggc 3120
tcccgctgaa ttggaatcca tcttgctcca acaccccaac atcttcgacg caggtgtcgc 3180
aggtcttccc gacgatgacg ccggtgaact tcccgccgcc gttgttgttt tggagcacgg 3240
aaagacgatg acggaaaaag agatcgtgga ttacgtcgcc agtcaagtaa caaccgcgaa 3300
aaagttgcgc ggaggagttg tgtttgtgga cgaagtaccg aaaggtctta ccggaaaact 3360
cgacgcaaga aaaatcagag agatcctcat aaaggccaag aagggcggaa agatcgccgt 3420
ggcagccgca gccaccatgg tgagcaaggg cgaggagctg ttcaccgggg tggtgcccat 3480
cctggtcgag ctggacggcg acgtaaacgg ccacaagttc agcgtgtccg gcgagggcga 3540
gggcgatgcc acctacggca agctgaccct gaagttcatc tgcaccaccg gcaagctgcc 3600
cgtgccctgg cccaccctcg tgaccaccct gacctacggc gtgcagtgct tcagccgcta 3660
ccccgaccac atgaagcagc acgacttctt caagtccgcc atgcccgaag gctacgtcca 3720
ggagcgcacc atcttcttca aggacgacgg caactacaag acccgcgccg aggtgaagtt 3780
cgagggcgac accctggtga accgcatcga gctgaagggc atcgacttca aggaggacgg 3840
caacatcctg gggcacaagc tggagtacaa ctacaacagc cacaacgtct atatcatggc 3900
cgacaagcag aagaacggca tcaaggtgaa cttcaagatc cgccacaaca tcgaggacgg 3960
cagcgtgcag ctcgccgacc actaccagca gaacaccccc atcggcgacg gccccgtgct 4020
gctgcccgac aaccactacc tgagcaccca gtccgccctg agcaaagacc ccaacgagaa 4080
gcgcgatcac atggtcctgc tggagttcgt gaccgccgcc gggatcactc tcggcatgga 4140
cgagctgtac aagtaaagcg actctagatc ataatcagcc ataccacatt tgtagaggtt 4200
ttacttgctt taaaaaacct cccacacctc cccctgaacc tgaaacataa aatgaatgca 4260
attgttgttg ttaacttgtt tattgcagct tataatggtt acaaataaag caatagcatc 4320
acaaatttca caaataaagc atttttttca ctgcattcta gttgtggttt gtccaaactc 4380
atcaatgtaa gtttaaacgg cgcgcctgaa atgtgtgggc gtggcttaag ggtgggaaag 4440
aatatataag gtgggggtct tatgtagttt tgtatctgtt ttgcagcagc cgccgccgcc 4500
atgagcacca actcgtttga tggaagcatt gtgagctcat atttgacaac gcgcatgccc 4560
ccatgggccg gggtgcgtca gaatgtgatg ggctccagca ttgatggtcg ccccgtcctg 4620
cccgcaaact ctactacctt gacctacgag accgtgtctg gaacgccgtt ggagactgca 4680
gcctccgccg ccgcttcagc cgctgcagcc accgcccgcg ggattgtgac tgactttgct 4740
ttcctgagcc cgcttgcaag cagtgcagct tcccgttcat ccgcccgcga tgacaagttg 4800
acggctcttt tggcacaatt ggattctttg acccgggaac ttaatgtcgt ttctcagcag 4860
ctgttggatc tgcgccagca ggtttctgcc ctgaaggctt cctcccctcc caatgcggtt 4920
taaaacacaa cttttctata caaagttgta aataaaaaac cagactctgt ttggatttgg 4980
atcaagctaa gtgtcttgct gtctttattt aggggttttg cgcgcgcggt aggcccggga 5040
ccagcggtct cggtcgttga gggtcctgtg tattttttcc aggacgtggt aaaggtgact 5100
ctggatgttc agatacatgg gcataagccc gtctctgggg tggaggtagc accactgcag 5160
agcttcatgc tgcggggtgg tgttgtagat gatccagtcg tagcaggagc gctgggcgtg 5220
gtgcctaaaa atgtctttca gtagcaagct gattgccagg ggcaggccct tggtgtaagt 5280
gtttacaaag cggttaagct gggatgggtg catacgtggg gatatgagat gcatcttgga 5340
ctgtattttt aggttggcta tgttcccagc catatccctc cggggattca tgttgtgcag 5400
aaccaccagc acagtgtatc cggtgcactt gggaaatttg tcatgtagct tagaaggaaa 5460
tgcgtggaag aacttggaga cgcccttgtg acctccaaga ttttccatgc attcgtccat 5520
aatgatggca atgggcccac gggcggcggc ctgggcgaag atatttctgg gatcactaac 5580
gtcatagttg tgttccagga tgagatcgtc ataggccatt tttacaaagc gcgggcggag 5640
ggtgccagac tgcggtataa tggttccatc cggcccaggg gcgtagttac cctcacagat 5700
ttgcatttcc cacgctttga gttcagatgg ggggatcatg tctacctgcg gggcgatgaa 5760
gaaaacggtt tccggggtag gggagatcag ctgggaagaa agcaggttcc tgagcagctg 5820
cgacttaccg cagccggtgg gcccgtaaat cacacctatt accggctgca actggtagtt 5880
aagagagctg cagctgccgt catccctgag caggggggcc acttcgttaa gcatgtccct 5940
gactcgcatg ttttccctga ccaaatccgc cagaaggcgc tcgccgccca gcgatagcag 6000
ttcttgcaag gaagcaaagt ttttcaacgg tttgagaccg tccgccgtag gcatgctttt 6060
gagcgtttga ccaagcagtt ccaggcggtc ccacagctcg gtcacctgct ctacggcatc 6120
tcgatccagc atatctcctc gtttcgcggg ttggggcggc tttcgctgta cggcagtagt 6180
cggtgctcgt ccagacgggc cagggtcatg tctttccacg ggcgcagggt cctcgtcagc 6240
gtagtctggg tcacggtgaa ggggtgcgct ccgggctgcg cgctggccag ggtgcgcttg 6300
aggctggtcc tgctggtgct gaagcgctgc cggtcttcgc cctgcgcgtc ggccaggtag 6360
catttgacca tggtgtcata gtccagcccc tccgcggcgt ggcccttggc gcgcagcttg 6420
cccttggagg aggcgccgca cgaggggcag tgcagacttt tgagggcgta gagcttgggc 6480
gcgagaaata ccgattccgg ggagtaggca tccgcgccgc aggccccgca gacggtctcg 6540
cattccacga gccaggtgag ctctggccgt tcggggtcaa aaaccaggtt tcccccatgc 6600
tttttgatgc gtttcttacc tctggtttcc atgagccggt gtccacgctc ggtgacgaaa 6660
aggctgtccg tgtccccgta tacagacttg agaggcctgt cctcgagcgg tgttccgcgg 6720
tcctcctcgt atagaaactc ggaccactct gagacaaagg ctcgcgtcca ggccagcacg 6780
aaggaggcta agtgggaggg gtagcggtcg ttgtccacta gggggtccac tcgctccagg 6840
gtgtgaagac acatgtcgcc ctcttcggca tcaaggaagg tgattggttt gtaggtgtag 6900
gccacgtgac cgggtgttcc tgaagggggg ctataaaagg gggtgggggc gcgttcgtcc 6960
tcactctctt ccgcatcgct gtctgcgagg gccagctgtt ggggtgagta ctccctctga 7020
aaagcgggca tgacttctgc gctaagattg tcagtttcca aaaacgagga ggatttgata 7080
ttcacctggc ccgcggtgat gcctttgagg gtggccgcat ccatctggtc agaaaagaca 7140

```
atctttttgt tgtcaagctt ggtggcaaac gacccgtaga gggcgttgga cagcaacttg   7200
gcgatggagc gcagggtttg gtttttgtcg cgatcggcgc gctccttggc cgcgatgttt   7260
agctgcacgt attcgcgcgc aacgcaccgc cattcgggaa agacggtggt gcgctcgtcg   7320
ggcaccaggt gcacgcgcca accgcggttg tgcagggtga caaggtcaac gctggtggct   7380
acctctccgc gtaggcgctc gttggtccag cagaggcggc cgcccttgcg cgagcagaat   7440
ggcggtaggg ggtctagctg cgtctcgtcc ggggggtctg cgtccacggt aaagaccccg   7500
ggcagcaggc gcgcgtcgaa gtagtctatc ttgcatcctt gcaagtctag cgcctgctgc   7560
catgcgcggg cggcaagcgc gcgctcgtat gggttgagtg ggggacccca tggcatgggg   7620
tgggtgagcg cggaggcgta catgccgcaa atgtcgtaaa cgtagagggg ctctctgagt   7680
attccaagat atgtagggta gcatcttcca ccgcggatgc tggcgcgcac gtaatcgtat   7740
agttcgtgcg agggagcgag gaggtcggga ccgaggttgc tacgggcggg ctgctctgct   7800
cggaagacta tctgcctgaa gatggcatgt gagttggatg atatggttgg acgctggaag   7860
acgttgaagc tggcgtctgt gagacctacc gcgtcacgca cgaaggaggc gtaggagtcg   7920
cgcagcttgt tgaccagctc ggcggtgacc tgcacgtcta gggcgcagta gtccagggtt   7980
tccttgatga tgtcatactt atcctgtccc ttttttttcc acagctcgcg gttgaggaca   8040
aactcttcgc ggtctttcca gtactcttgg atcggaaacc cgtcggcctc cgaacggtaa   8100
gagcctagca tgtagaactg gttgacggcc tggtaggcgc agcatccctt ttctacgggt   8160
agcgcgtatg cctgcgcggc cttccggagc gaggtgtggg tgagcgcaaa ggtgtccctg   8220
accatgactt tgaggtactg gtatttgaag tcagtgtcgt cgcatccgcc ctgctcccag   8280
agcaaaaagt ccgtgcgctt tttggaacgc ggatttggca gggcgaaggt gacatcgttg   8340
aagagtatct ttcccgcgcg aggcataaag ttgcgtgtga tgcggaaggg tcccggcacc   8400
tcggaacggt tgttaattac ctgggcggcg agcacgatct cgtcaaagcc gttgatgttg   8460
tggcccacaa tgtaaagttc caagaagcgc gggatgccct tgatggaagg caatttttta   8520
agttcctcgt aggtgagctc ttcaggggag ctgagcccgt gctctgaaag ggcccagtct   8580
gcaagatgag ggttggaagc gacgaatgag ctccacaggt cacgggccat tagcatttgc   8640
aggtggtcgc gaaaggtcct aaactggcga cctatggcca tttttctgg ggtgatgcag    8700
tagaaggtaa gcgggtcttg ttcccagcgg tcccatccaa ggttcgcggc taggtctcgc   8760
gcggcagtca ctagaggctc atctccgccg aacttcatga ccagcatgaa gggcacgagc   8820
tgcttcccaa aggcccccat ccaagtatag gtctctacat cgtaggtgac aaagagacgc   8880
tcggtgcgag gatgcgagcc gatcgggaag aactggatct cccgccacca attggaggag   8940
tggctattga tgtggtgaaa gtagaagtcc ctgcgacggg ccgaacactc gtgctggctt   9000
ttgtaaaaac gtgcgcagta ctggcagcgg tgcacgggct gtacatcctg cacgaggttg   9060
acctgacgac cgcgcacaag gaagcagagt gggaatttga gcccctcgcc tggcgggttt   9120
ggctggtggt cttctacttc ggctgcttgt ccttgaccgt ctggctgctc gaggggagtt   9180
acggtggatc ggaccaccac gccgcgcgag cccaaagtcc agatgtccgc gcgcggcggt   9240
cggagcttga tgacaacatc gcgcagatgg gagctgtcca tggtctggag ctcccgcggc   9300
gtcaggtcag gcgggagctc ctgcaggttt acctcgcata gacgggtcag ggcgcgggct   9360
agatccaggt gatacctaat ttccaggggc tggttggtgg cggcgtcgat ggcttgcaag   9420
aggccgcatc cccgcggcgc gactacggta ccgcgcggcg ggcggtgggc cgcgggggtg   9480
tccttggatg atgcatctaa aagcggtgac gcgggcgagc ccccggaggt agggggggct   9540
```

```
ccggacccgc cgggagaggg ggcaggggca cgtcggcgcc gcgcgcgggc aggagctggt   9600
gctgcgcgcg taggttgctg gcgaacgcga cgacgcggcg gttgatctcc tgaatctggc   9660
gcctctgcgt gaagacgacg ggcccggtga gcttgaacct gaaagagagt tcgacagaat   9720
caatttcggt gtcgttgacg gcggcctggc gcaaaatctc ctgcacgtct cctgagttgt   9780
cttgataggc gatctcggcc atgaactgct cgatctcttc ctcctggaga tctccgcgtc   9840
cggctcgctc cacggtggcg gcgaggtcgt tggaaatgcg ggccatgagc tgcgagaagg   9900
cgttgaggcc tccctcgttc cagacgcggc tgtagaccac gccccttcg gcatcgcggg   9960
cgcgcatgac cacctgcgcg agattgagct ccacgtgccg ggcgaagacg gcgtagtttc  10020
gcaggcgctg aaagaggtag ttgagggtgg tggcggtgtg ttctgccacg aagaagtaca  10080
taacccagcg tcgcaacgtg gattcgttga tatcccccaa ggcctcaagg cgctccatgg  10140
cctcgtagaa gtccacggcg aagttgaaaa actgggagtt gcgcgccgac acggttaact  10200
cctcctccag aagacggatg agctcggcga cagtgtcgcg cacctcgcgc tcaaaggcta  10260
caggggcctc ttcttcttct tcaatctcct cttccataag ggcctcccct tcttcttctt  10320
ctggcggcgg tgggggaggg gggacacggc ggcgacgacg gcgcaccggg aggcggtcga  10380
caaagcgctc gatcatctcc ccgcggcgac ggcgcatggt ctcggtgacg gcgcggccgt  10440
tctcgcgggg gcgcagttgg aagacgccgc ccgtcatgtc ccggttatgg gttggcgggg  10500
ggctgccatg cggcagggat acggcgctaa cgatgcatct caacaattgt tgtgtaggta  10560
ctccgccgcc gagggacctg agcgagtccg catcgaccgg atcggaaaac ctctcgagaa  10620
aggcgtctaa ccagtcacag tcgcaaggta ggctgagcac cgtggcgggc ggcagcgggc  10680
ggcggtcggg gttgtttctg gcggaggtgc tgctgatgat gtaattaaag taggcggtct  10740
tgagacggcg gatggtcgac agaagcacca tgtccttggg tccggcctgc tgaatgcgca  10800
ggcggtcggc catgccccag gcttcgtttt gacatcggcg caggtctttg tagtagtctt  10860
gcatgagcct ttctaccggc acttcttctt ctccttcctc ttgtcctgca tctcttgcat  10920
ctatcgctgc ggcggcggcg gagtttggcc gtaggtggcg ccctcttcct cccatgcgtg  10980
tgaccccgaa gcccctcatc ggctgaagca gggctaggtc ggcgacaacg cgctcggcta  11040
atatggcctg ctgcacctgc gtgagggtag actggaagtc atccatgtcc acaaagcggt  11100
ggtatgcgcc cgtgttgatg gtgtaagtgc agttggccat aacggaccag ttaacggtct  11160
ggtgacccgg ctgcgagagc tcggtgtacc tgagacgcga gtaagccctc gagtcaaata  11220
cgtagtcgtt gcaagtccgc accaggtact ggtatcccac caaaaagtgc ggcggcggct  11280
ggcggtagag gggccagcgt agggtggccg gggctccggg ggcgagatct tccaacataa  11340
ggcgatgata tccgtagatg tacctggaca tccaggtgat gccggcggcg gtggtggagg  11400
cgcgcggaaa gtcgcggacg cggttccaga tgttgcgcag cggcaaaaag tgctccatgg  11460
tcgggacgct ctggccggtc aggcgcgcgc aatcgttgac gctctagacc gtgcaaaagg  11520
agagcctgta agcgggcact cttccgtggt ctggtggata aattcgcaag ggtatcatgg  11580
cggacgaccg gggttcgagc cccgtatccg gccgtccgcc gtgatccatg cggttaccgc  11640
ccgcgtgtcg aacccaggtg tgcgacgtca gacaacgggg gagtgctcct tttggcttcc  11700
ttccaggcgc ggcggctgct gcgctagctt ttttggccac tggccgcgcg cagcgtaagc  11760
ggttaggctg gaaagcgaaa gcattaagtg gctcgctccc tgtagccgga gggttatttt  11820
ccaagggttg agtcgcggga cccccggttc gagtctcgga ccggccggac tgcggcgaac  11880
```

gggggtttgc ctccccgtca tgcaagaccc cgcttgcaaa ttcctccgga aacagggacg 11940
agccccttt ttgcttttcc cagatgcatc cggtgctgcg gcagatgcgc ccccctcctc 12000
agcagcggca agagcaagag cagcggcaga catgcagggc accctcccct cctcctaccg 12060
cgtcaggagg ggcgacatcc gcggttgacg cggcagcaga tggtgattac gaacccccgc 12120
ggcgccgggc ccggcactac ctggacttgg aggagggcga gggcctggcg cggctaggag 12180
cgccctctcc tgagcggcac ccaagggtgc agctgaagcg tgatacgcgt gaggcgtacg 12240
tgccgcggca gaacctgttt cgcgaccgcg agggagagga gcccgaggag atgcgggatc 12300
gaaagttcca cgcagggcgc gagctgcggc atggcctgaa tcgcgagcgg ttgctgcgcg 12360
aggaggactt tgagcccgac gcgcgaaccg ggattagtcc cgcgcgcgca cacgtggcgg 12420
ccgccgacct ggtaaccgca tacgagcaga cggtgaacca ggagattaac tttcaaaaaa 12480
gctttaacaa ccacgtgcgt acgcttgtgg cgcgcgagga ggtggctata ggactgatgc 12540
atctgtggga ctttgtaagc gcgctggagc aaaacccaaa tagcaagccg ctcatggcgc 12600
agctgttcct tatagtgcag cacagcaggg acaacgaggc attcagggat gcgctgctaa 12660
acatagtaga gcccgagggc cgctggctgc tcgatttgat aaacatcctg cagagcatag 12720
tggtgcagga gcgcagcttg agcctggctg acaaggtggc cgccatcaac tattccatgc 12780
ttagcctggg caagttttac gcccgcaaga tataccatac cccttacgtt cccatagaca 12840
aggaggtaaa gatcgagggg ttctacatgc gcatggcgct gaaggtgctt accttgagcg 12900
acgacctggg cgtttatcgc aacgagcgca tccacaaggc cgtgagcgtg agccggcggc 12960
gcgagctcag cgaccgcgag ctgatgcaca gcctgcaaag ggccctggct ggcacgggca 13020
gcggcgatag agaggccgag tcctactttg acgcgggcgc tgacctgcgc tgggccccaa 13080
gccgacgcgc cctggaggca gctggggccg gacctgggct ggcggtggca cccgcgcgcg 13140
ctggcaacgt cggcggcgtg gaggaatatg acgaggacga tgagtacgag ccagaggacg 13200
gcgagtacta agcggtgatg tttctgatca gatgatgcaa gacgcaacgg acccggcggt 13260
gcgggcggcg ctgcagagcc agccgtccgg ccttaactcc acggacgact ggcgccaggt 13320
catggaccgc atcatgtcgc tgactgcgcg caatcctgac gcgttccggc agcagccgca 13380
ggccaaccgg ctctccgcaa ttctggaagc ggtggtcccg gcgcgcgcaa accccacgca 13440
cgagaaggtg ctggcgatcg taaacgcgct ggccgaaaac agggccatcc ggcccgacga 13500
ggccggcctg gtctacgacg cgctgcttca gcgcgtggct cgttacaaca gcggcaacgt 13560
gcagaccaac ctggaccggc tggtggggga tgtgcgcgag gccgtggcgc agcgtgagcg 13620
cgcgcagcag cagggcaacc tgggctccat ggttgcacta aacgccttcc tgagtacaca 13680
gcccgccaac gtgccgcggg gacaggagga ctacaccaac tttgtgagcg cactgcggct 13740
aatggtgact gagacaccgc aaagtgaggt gtaccagtct gggccagact atttttttcca 13800
gaccagtaga caaggcctgc agaccgtaaa cctgagccag gctttcaaaa acttgcaggg 13860
gctgtggggg gtgcgggctc ccacaggcga ccgcgcgacc gtgtctagct tgctgacgcc 13920
caactcgcgc ctgttgctgc tgctaatagc gcccttcacg gacagtggca gcgtgtcccg 13980
ggacacatac ctaggtcact tgctgacact gtaccgcgag gccataggtc aggcgcatgt 14040
ggacgagcat actttccagg agattacaag tgtcagccgc gcgctggggc aggaggacac 14100
gggcagcctg gaggcaaccc taaactacct gctgaccaac cggcggcaga agatcccctc 14160
gttgcacagt ttaaacagcg aggaggagcg cattttgcgc tacgtgcagc agagcgtgag 14220
ccttaacctg atgcgcgacg gggtaacgcc cagcgtggcg ctggacatga ccgcgcgcaa 14280

```
catggaaccg ggcatgtatg cctcaaaccg gccgtttatc aaccgcctaa tggactactt  14340
gcatcgcgcg gccgccgtga accccgagta tttcaccaat gccatcttga acccgcactg  14400
gctaccgccc cctggtttct acaccggggg attcgaggtg cccgagggta acgatggatt  14460
cctctgggac gacatagacg acagcgtgtt ttccccgcaa ccgcagaccc tgctagagtt  14520
gcaacagcgc gagcaggcag aggcggcgct gcgaaaggaa agcttccgca ggccaagcag  14580
cttgtccgat ctaggcgctg cggccccgcg gtcagatgct agtagcccat ttccaagctt  14640
gatagggtct cttaccagca ctcgcaccac ccgcccgcgc ctgctgggcg aggaggagta  14700
cctaaacaac tcgctgctgc agccgcagcg cgaaaaaaac ctgcctccgg catttcccaa  14760
caacgggata gagagcctag tggacaagat gagtagatgg aagacgtacg cgcaggagca  14820
cagggacgtg ccaggcccgc gcccgcccac ccgtcgtcaa aggcacgacc gtcagcgggg  14880
tctggtgtgg gaggacgatg actcggcaga cgacagcagc gtcctggatt tgggagggag  14940
tggcaacccg tttgcgcacc ttcgccccag gctggggaga atgttttaaa aaaaaaaaaa  15000
aagcatgatg caaaataaaa aactcaccaa ggccatggca ccgagcgttg gttttcttgt  15060
attcccctta gtatgcggcg cgcggcgatg tatgaggaag gtcctcctcc ctcctacgag  15120
agtgtggtga gcgcggcgcc agtggcggcg gcgctgggtt ctcccttcga tgctcccctg  15180
gacccgccgt ttgtgcctcc gcggtacctg cggcctaccg gggggagaaa cagcatccgt  15240
tactctgagt tggcacccct attcgacacc acccgtgtgt acctggtgga caacaagtca  15300
acggatgtgg catccctgaa ctaccagaac gaccacagca actttctgac cacggtcatt  15360
caaaacaatg actacagccc gggggaggca agcacacaga ccatcaatct tgacgaccgg  15420
tcgcactggg gcggcgacct gaaaaccatc ctgcatacca acatgccaaa tgtgaacgag  15480
ttcatgttta ccaataagtt taaggcgcgg gtgatggtgt cgcgcttgcc tactaaggac  15540
aatcaggtgg agctgaaata cgagtgggtg gagttcacgc tgcccgaggg caactactcc  15600
gagaccatga ccatagacct tatgaacaac gcgatcgtgg agcactactt gaaagtgggc  15660
agacagaacg gggttctgga aagcgacatc ggggtaaagt ttgacacccg caacttcaga  15720
ctggggtttg accccgtcac tggtcttgtc atgcctgggg tatatacaaa cgaagccttc  15780
catccagaca tcattttgct gccaggatgc ggggtggact tcacccacag ccgcctgagc  15840
aacttgttgg gcatccgcaa gcggcaaccc ttccaggagg gctttaggat cacctacgat  15900
gatctggagg gtggtaacat tcccgcactg ttggatgtgg acgcctacca ggcgagcttg  15960
aaagatgaca ccgaacaggg cgggggtggc gcaggcggca gcaacagcag tggcagcggc  16020
gcggaagaga actccaacgc ggcagccgcg gcaatgcagc cggtggagga catgaacgat  16080
catgccattc gcggcgacac ctttgccaca cgggctgagg agaagcgcgc tgaggccgaa  16140
gcagcggccg aagctgccgc ccccgctgcg caacccgagg tcgagaagcc tcagaagaaa  16200
ccggtgatca aacccctgac agaggacagc aagaaacgca gttacaacct aataagcaat  16260
gacagcacct tcacccagta ccgcagctgg taccttgcat acaactacgg cgaccctcag  16320
accggaatcc gctcatggac cctgctttgc actcctgacg taacctgcgg ctcggagcag  16380
gtctactggt cgttgccaga catgatgcaa gaccccgtga ccttccgctc cacgcgccag  16440
atcagcaact ttccggtggt gggcgccgag ctgttgcccg tgcactccaa gagcttctac  16500
aacgaccagg ccgtctactc ccaactcatc cgccagttta cctctctgac ccacgtgttc  16560
aatcgctttc ccgagaacca gattttggcg cgcccgccag cccccaccat caccaccgtc  16620
```

agtgaaaacg ttcctgctct cacagatcac gggacgctac cgctgcgcaa cagcatcgga 16680
ggagtccagc gagtgaccat tactgacgcc agacgccgca cctgccccta cgtttacaag 16740
gccctgggca tagtctcgcc gcgcgtccta tcgagccgca ctttttgagc aagcatgtcc 16800
atccttatat cgcccagcaa taacacaggc tggggcctgc gcttcccaag caagatgttt 16860
ggcggggcca agaagcgctc cgaccaacac ccagtgcgcg tgcgcgggca ctaccgcgcg 16920
ccctggggcg cgcacaaacg cggccgcact gggcgcacca ccgtcgatga cgccatcgac 16980
gcggtggtgg aggaggcgcg caactacacg cccacgccgc caccagtgtc cacagtggac 17040
gcggccattc agaccgtggt gcgcggagcc cggcgctatg ctaaaatgaa gagacggcgg 17100
aggcgcgtag cacgtcgcca ccgccgccga cccggcactg ccgcccaacg cgcggcggcg 17160
gccctgctta accgcgcacg tcgcaccggc cgacgggcgg ccatgcgggc cgctcgaagg 17220
ctggccgcgg gtattgtcac tgtgcccccc aggtccaggc gacgagcggc cgccgcagca 17280
gccgcggcca ttagtgctat gactcagggt cgcaggggca acgtgtattg ggtgcgcgac 17340
tcggttagcg gcctgcgcgt gcccgtgcgc acccgccccc cgcgcaacta gattgcaaga 17400
aaaaactact tagactcgta ctgttgtatg tatccagcgg cggcggcgcg caacgaagct 17460
atgtccaagc gcaaaatcaa agaagagatg ctccaggtca tcgcgccgga gatctatggc 17520
cccccgaaga aggaagagca ggattacaag ccccgaaagc taaagcgggt caaaaagaaa 17580
aagaaagatg atgatgatga acttgacgac gaggtggaac tgctgcacgc taccgcgccc 17640
aggcgacggg tacagtggaa aggtcgacgc gtaaaacgtg ttttgcgacc cggcaccacc 17700
gtagtcttta cgcccggtga gcgctccacc cgcacctaca agcgcgtgta tgatgaggtg 17760
tacggcgacg aggacctgct tgagcaggcc aacgagcgcc tcggggagtt tgcctacgga 17820
aagcggcata aggacatgct ggcgttgccg ctggacgagg gcaacccaac acctagccta 17880
aagcccgtaa cactgcagca ggtgctgccc gcgcttgcac cgtccgaaga aaagcgcggc 17940
ctaaagcgcg agtctggtga cttggcaccc accgtgcagc tgatggtacc caagcgccag 18000
cgactggaag atgtcttgga aaaaatgacc gtggaacctg ggctggagcc cgaggtccgc 18060
gtgcggccaa tcaagcaggt ggcgccggga ctgggcgtgc agaccgtgga cgttcagata 18120
cccactacca gtagcaccag tattgccacc gccacagagg gcatggagac acaaacgtcc 18180
ccggttgcct cagcggtggc ggatgccgcg gtgcaggcgg tcgctgcggc cgcgtccaag 18240
acctctacgg aggtgcaaac ggacccgtgg atgtttcgcg tttcagcccc ccggcgcccg 18300
cgccgttcga ggaagtacgg cgccgccagc gcgctactgc ccgaatatgc cctacatcct 18360
tccattgcgc ctacccccgg ctatcgtggc tacacctacc gccccagaag acgagcaact 18420
acccgacgcc gaaccaccac tggaacccgc cgccgccgtc gccgtcgcca gcccgtgctg 18480
gccccgattt ccgtgcgcag ggtggctcgc gaaggaggca ggaccctggt gctgccaaca 18540
gcgcgctacc accccagcat cgtttaaaag ccggtctttg tggttcttgc agatatggcc 18600
ctcacctgcc gcctccgttt cccggtgccg ggattccgag gaagaatgca ccgtaggagg 18660
ggcatggccg gccacggcct gacgggcggc atgcgtcgtg cgcaccaccg gcggcggcgc 18720
gcgtcgcacc gtcgcatgcg cggcggtatc ctgcccctcc ttattccact gatcgccgcg 18780
gcgattggcg ccgtgcccgg aattgcatcc gtggccttgc aggcgcagag acactgatta 18840
aaaacaagtt gcatgtggaa aaatcaaaat aaaaagtctg gactctcacg ctcgcttggt 18900
cctgtaacta ttttgtagaa tggaagacat caactttgcg tctctggccc cgcgacacgg 18960
ctcgcgcccg ttcatgggaa actggcaaga tatcggcacc agcaatatga gcggtggcgc 19020

```
cttcagctgg ggctcgctgt ggagcggcat taaaaatttc ggttccaccg ttaagaacta  19080
tggcagcaag gcctggaaca gcagcacagg ccagatgctg agggataagt tgaaagagca  19140
aaatttccaa caaaaggtgg tagatggcct ggcctctggc attagcgggg tggtggacct  19200
ggccaaccag gcagtgcaaa ataagattaa cagtaagctt gatccccgcc ctcccgtaga  19260
ggagcctcca ccggccgtgg agacagtgtc tccagagggg cgtggcgaaa agcgtccgcg  19320
ccccgacagg gaagaaactc tggtgacgca aatagacgag cctccctcgt acgaggaggc  19380
actaaagcaa ggcctgccca ccacccgtcc catcgcgccc atggctaccg gagtgctggg  19440
ccagcacaca cccgtaacgc tggacctgcc tccccccgcc gacacccagc agaaacctgt  19500
gctgccaggc ccgaccgccg ttgttgtaac ccgtcctagc cgcgcgtccc tgcgccgcgc  19560
cgccagcggt ccgcgatcgt tgcggcccgt agccagtggc aactggcaaa gcacactgaa  19620
cagcatcgtg ggtctggggg tgcaatccct gaagcgccga cgatgcttct gaatagctaa  19680
cgtgtcgtat gtgtgtcatg tatgcgtcca tgtcgccgcc agaggagctg ctgagccgcc  19740
gcgcgcccgc tttccaagat ggctacccct tcgatgatgc cgcagtggtc ttacatgcac  19800
atctcgggcc aggacgcctc ggagtacctg agccccgggc tggtgcagtt tgcccgcgcc  19860
accgagacgt acttcagcct gaataacaag tttagaaacc ccacggtggc gcctacgcac  19920
gacgtgacca cagaccggtc ccagcgtttg acgctgcggt tcatccctgt ggaccgtgag  19980
gatactgcgt actcgtacaa ggcgcggttc accctagctg tgggtgataa ccgtgtgctg  20040
gacatggctt ccacgtactt tgacatccgc ggcgtgctgg acaggggccc tacttttaag  20100
ccctactctg gcactgccta caacgccctg gctcccaagg gtgccccaaa tccttgcgaa  20160
tgggatgaag ctgctactgc tcttgaaata aacctagaag aagaggacga tgacaacgaa  20220
gacgaagtag acgagcaagc tgagcagcaa aaaactcacg tatttgggca ggcgccttat  20280
tctggtataa atattacaaa ggagggtatt caaataggtg tcgaaggtca aacacctaaa  20340
tatgccgata aaacatttca acctgaacct caaataggag aatctcagtg gtacgaaact  20400
gaaattaatc atgcagctgg gagagtcctt aaaaagacta ccccaatgaa accatgttac  20460
ggttcatatg caaaacccac aaatgaaaat ggagggcaag gcattcttgt aaagcaacaa  20520
aatggaaagc tagaaagtca agtggaaatg caatttttct caactactga ggcgaccgca  20580
ggcaatggtg ataacttgac tcctaaagtg gtattgtaca gtgaagatgt agatatagaa  20640
accccagaca ctcatatttc ttacatgccc actattaagg aaggtaactc acgagaacta  20700
atgggccaac aatctatgcc caacaggcct aattacattg cttttaggga caattttatt  20760
ggtctaatgt attacaacag cacgggtaat atgggtgttc tggcgggcca agcatcgcag  20820
ttgaatgctg ttgtagattt gcaagacaga aacacagagc tttcatacca gcttttgctt  20880
gattccattg gtgatagaac caggtacttt tctatgtgga atcaggctgt tgacagctat  20940
gatccagatg ttagaattat tgaaaatcat ggaactgaag atgaacttcc aaattactgc  21000
tttccactgg gaggtgtgat taatacagag actcttacca aggtaaaacc taaaacaggt  21060
caggaaaatg gatgggaaaa agatgctaca gaattttcag ataaaaatga aataagagtt  21120
ggaaataatt ttgccatgga aatcaatcta aatgccaacc tgtggagaaa tttcctgtac  21180
tccaacatag cgctgtattt gcccgacaag ctaaagtaca gtccttccaa cgtaaaaatt  21240
tctgataacc caaacaccta cgactacatg aacaagcgag tggtggctcc cgggttagtg  21300
gactgctaca ttaaccttgg agcacgctgg tcccttgact atatggacaa cgtcaaccca  21360
```

-continued

```
tttaaccacc accgcaatgc tggcctgcgc taccgctcaa tgttgctggg caatggtcgc  21420
tatgtgccct tccacatcca ggtgcctcag aagttctttg ccattaaaaa cctccttctc  21480
ctgccgggct catacaccta cgagtggaac ttcaggaagg atgttaacat ggttctgcag  21540
agctccctag gaaatgacct aagggttgac ggagccagca ttaagtttga tagcatttgc  21600
ctttacgcca ccttcttccc catggcccac aacaccgcct ccacgcttga ggccatgctt  21660
agaaacgaca ccaacgacca gtcctttaac gactatctct ccgccgccaa catgctctac  21720
cctatacccg ccaacgctac caacgtgccc atatccatcc cctcccgcaa ctgggcggct  21780
ttccgcggct gggccttcac gcgccttaag actaaggaaa ccccatcact gggctcgggc  21840
tacgaccctt attacaccta ctctggctct ataccctacc tagatggaac cttttacctc  21900
aaccacacct ttaagaaggt ggccattacc tttgactctt ctgtcagctg gcctggcaat  21960
gaccgcctgc ttacccccaa cgagtttgaa attaagcgct cagttgacgg ggagggttac  22020
aacgttgccc agtgtaacat gaccaaagac tggttcctgg tacaaatgct agctaactac  22080
aacattggct accagggctt ctatatccca gagagctaca aggaccgcat gtactccttc  22140
tttagaaact tccagcccat gagccgtcag gtggtggatg atactaaata caaggactac  22200
caacaggtgg gcatcctaca ccaacacaac aactctggat ttgttggcta ccttgccccc  22260
accatgcgcg aaggacaggc ctaccctgct aacttcccct atccgcttat aggcaagacc  22320
gcagttgaca gcattaccca gaaaaagttt ctttgcgatc gcaccctttg gcgcatccca  22380
ttctccagta actttatgtc catgggcgca ctcacagacc tgggccaaaa ccttctctac  22440
gccaactccg cccacgcgct agacatgact tttgaggtgg atcccatgga cgagcccacc  22500
cttctttatg ttttgtttga agtctttgac gtggtccgtg tgcaccggcc gcaccgcggc  22560
gtcatcgaaa ccgtgtacct gcgcacgccc ttctcggccg gcaacgccac aacataaaga  22620
agcaagcaac atcaacaaca gctgccgcca tgggctccag tgagcaggaa ctgaaagcca  22680
ttgtcaaaga tcttggttgt gggccatatt ttttgggcac ctatgacaag cgctttccag  22740
gctttgtttc tccacacaag ctcgcctgcg ccatagtcaa tacggccggt cgcgagactg  22800
ggggcgtaca ctggatggcc tttgcctgga acccgcactc aaaaacatgc tacctctttg  22860
agccctttgg cttttctgac cagcgactca agcaggttta ccagtttgag tacgagtcac  22920
tcctgcgccg tagcgccatt gcttcttccc ccgaccgctg tataacgctg gaaaagtcca  22980
cccaaagcgt acaggggccc aactcggccg cctgtggact attctgctgc atgtttctcc  23040
acgcctttgc caactggccc caaactccca tggatcacaa ccccaccatg aaccttatta  23100
ccggggtacc caactccatg ctcaacagtc cccaggtaca gcccaccctg cgtcgcaacc  23160
aggaacagct ctacagcttc ctggagcgcc actcgcccta cttccgcagc cacagtgcgc  23220
agattaggag cgccacttct ttttgtcact tgaaaaacat gtaaaaataa tgtactagag  23280
acactttcaa taaaggcaaa tgcttttatt tgtacactct cgggtgatta tttaccccca  23340
cccttgccgt ctgcgccgtt taaaaatcaa aggggttctg ccgcgcatcg ctatgcgcca  23400
ctggcaggga cacgttgcga tactggtgtt tagtgctcca cttaaactca ggcacaacca  23460
tccgcggcag ctcggtgaag ttttcactcc acaggctgcg caccatcacc aacgcgttta  23520
gcaggtcggg cgccgatatc ttgaagtcgc agttggggcc tccgccctgc gcgcgcgagt  23580
tgcgatacac agggttgcag cactggaaca ctatcagcgc cgggtggtgc acgctggcca  23640
gcacgctctt gtcggagatc agatccgcgt ccaggtcctc cgcgttgctc agggcgaacg  23700
gagtcaactt tggtagctgc cttcccaaaa agggcgcgtg cccaggcttt gagttgcact  23760
```

```
cgcaccgtag tggcatcaaa aggtgaccgt gcccggtctg ggcgttagga tacagcgcct  23820
gcataaaagc cttgatctgc ttaaaagcca cctgagcctt tgcgccttca gagaagaaca  23880
tgccgcaaga cttgccggaa aactgattgg ccggacaggc cgcgtcgtgc acgcagcacc  23940
ttgcgtcggt gttggagatc tgcaccacat ttcggcccca ccggttcttc acgatcttgg  24000
ccttgctaga ctgctccttc agcgcgcgct gcccgttttc gctcgtcaca tccatttcaa  24060
tcacgtgctc cttatttatc ataatgcttc cgtgtagaca cttaagctcg ccttcgatct  24120
cagcgcagcg gtgcagccac aacgcgcagc ccgtgggctc gtgatgcttg taggtcacct  24180
ctgcaaacga ctgcaggtac gcctgcagga atcgccccat catcgtcaca aaggtcttgt  24240
tgctggtgaa ggtcagctgc aacccgcggt gctcctcgtt cagccaggtc ttgcatacgg  24300
ccgccagagc ttccacttgg tcaggcagta gtttgaagtt cgcctttaga tcgttatcca  24360
cgtggtactt gtccatcagc gcgcgcgcag cctccatgcc cttctcccac gcagacacga  24420
tcggcacact cagcgggttc atcaccgtaa tttcactttc cgcttcgctg ggctcttcct  24480
cttcctcttg cgtccgcata ccacgcgcca ctgggtcgtc ttcattcagc cgccgcactg  24540
tgcgcttacc tcctttgcca tgcttgatta gcaccggtgg gttgctgaaa cccaccattt  24600
gtagcgccac atcttctctt tcttcctcgc tgtccacgat tacctctggt gatggcgggc  24660
gctcgggctt gggagaaggg cgcttctttt tcttcttggg cgcaatggcc aaatccgccg  24720
ccgaggtcga tggccgcggg ctgggtgtgc gcggcaccag cgcgtcttgt gatgagtctt  24780
cctcgtcctc ggactcgata cgccgcctca tccgcttttt tgggggcgcc cggggaggcg  24840
gcggcgacgg ggacggggac gacacgtcct ccatggttgg gggacgtcgc gccgcaccgc  24900
gtccgcgctc gggggtggtt tcgcgctgct cctcttcccg actggccatt tccttctcct  24960
ataggcagaa aaagatcatg gagtcagtcg agaagaagga cagcctaacc gccccctctg  25020
agttcgccac caccgcctcc accgatgccg ccaacgcgcc taccaccttc cccgtcgagg  25080
caccccccgct tgaggaggag gaagtgatta tcgagcagga cccaggtttt gtaagcgaag  25140
acgacgagga ccgctcagta ccaacagagg ataaaaagca agaccaggac aacgcagagg  25200
caaacgagga acaagtcggg cggggggacg aaaggcatgg cgactaccta gatgtgggag  25260
acgacgtgct gttgaagcat ctgcagcgcc agtgcgccat tatctgcgac gcgttgcaag  25320
agcgcagcga tgtgcccctc gccatagcgg atgtcagcct tgcctacgaa cgccacctat  25380
tctcaccgcg cgtacccccc aaacgccaag aaaacggcac atgcgagccc aacccgcgcc  25440
tcaacttcta ccccgtattt gccgtgccag aggtgcttgc cacctatcac atctttttcc  25500
aaaactgcaa gatacccccta tcctgccgtg ccaaccgcag ccgagcggac aagcagctgg  25560
ccttgcggca gggcgctgtc atacctgata tcgcctcgct caacgaagtg ccaaaaatct  25620
ttgagggtct tggacgcgac gagaagcgcg cggcaaacgc tctgcaacag gaaaacagcg  25680
aaaatgaaag tcactctgga gtgttggtgg aactcgaggg tgacaacgcg cgcctagccg  25740
tactaaaacg cagcatcgag gtcacccact ttgcctaccc ggcacttaac ctacccccca  25800
aggtcatgag cacagtcatg agtgagctga tcgtgcgccg tgcgcagccc ctggagaggg  25860
atgcaaattt gcaagaacaa acagaggagg gcctacccgc agttggcgac gagcagctag  25920
cgcgctggct tcaaacgcgc gagcctgccg acttggagga gcgacgcaaa ctaatgatgg  25980
ccgcagtgct cgttaccgtg gagcttgagt gcatgcagcg gttctttgct gacccggaga  26040
tgcagcgcaa gctagaggaa acattgcact acacctttcg acagggctac gtacgccagg  26100
```

```
cctgcaagat ctccaacgtg gagctctgca acctggtctc ctaccttgga attttgcacg  26160
aaaaccgcct tgggcaaaac gtgcttcatt ccacgctcaa gggcgaggcg cgccgcgact  26220
acgtccgcga ctgcgtttac ttatttctat gctacacctg gcagacggcc atgggcgttt  26280
ggcagcagtg cttggaggag tgcaacctca aggagctgca gaaactgcta aagcaaaact  26340
tgaaggacct atggacggcc ttcaacgagc gctccgtggc cgcgcacctg gcggacatca  26400
ttttccccga acgcctgctt aaaaccctgc aacagggtct gccagacttc accagtcaaa  26460
gcatgttgca gaactttagg aactttatcc tagagcgctc aggaatcttg cccgccacct  26520
gctgtgcact tcctagcgac tttgtgccca ttaagtaccg cgaatgccct ccgccgcttt  26580
ggggccactg ctaccttctg cagctagcca actaccttgc ctaccactct gacataatgg  26640
aagacgtgag cggtgacggt ctactggagt gtcactgtcg ctgcaaccta tgcaccccgc  26700
accgctccct ggtttgcaat tcgcagctgc ttaacgaaag tcaaattatc ggtacctttg  26760
agctgcaggg tccctcgcct gacgaaaagt ccgcggctcc ggggttgaaa ctcactccgg  26820
ggctgtggac gtcggcttac cttcgcaaat ttgtacctga ggactaccac gcccacgaga  26880
ttaggttcta cgaagaccaa tcccgcccgc caaatgcgga gcttaccgcc tgcgtcatta  26940
cccagggcca cattcttggc caattgcaag ccatcaacaa agcccgccaa gagtttctgc  27000
tacgaaaggg acgggggtt tacttggacc cccagtccgg cgaggagctc aacccaatcc  27060
ccccgccgcc gcagccctat cagcagcagc cgcgggccct tgcttcccag gatggcaccc  27120
aaaaagaagc tgcagctgcc gccgccaccc acggacgagg aggaatactg ggacagtcag  27180
gcagaggagg ttttggacga ggaggaggag gacatgatgg aagactggga gagcctagac  27240
gaggaagctt ccgaggtcga agaggtgtca gacgaaacac cgtcaccctc ggtcgcattc  27300
ccctcgccgg cgccccagaa atcggcaacc ggttccagca tggctacaac ctccgctcct  27360
caggcgccgc cggcactgcc cgttcgccga cccaaccgta gatgggacac cactggaacc  27420
agggccggta agtccaagca gccgccgccg ttagcccaag agcaacaaca gcgccaaggc  27480
taccgctcat ggcgcgggca caagaacgcc atagttgctt gcttgcaaga ctgtgggggc  27540
aacatctcct tcgcccgccg ctttcttctc taccatcacg gcgtggcctt cccccgtaac  27600
atcctgcatt actaccgtca tctctacagc ccatactgca ccggcggcag cggcagcggc  27660
agcaacagca gcggccacac agaagcaaag gcgaccggat agcaagactc tgacaaagcc  27720
caagaaatcc acagcggcgg cagcagcagg aggaggagcg ctgcgtctgg cgcccaacga  27780
acccgtatcg acccgcgagc ttagaaacag gatttttccc actctgtatg ctatatttca  27840
acagagcagg ggccaagaac aagagctgaa aataaaaaac aggtctctgc gatccctcac  27900
ccgcagctgc ctgtatcaca aaagcgaaga tcagcttcgg cgcacgctgg aagacgcgga  27960
ggctctcttc agtaaatact gcgcgctgac tcttaaggac tagtttcgcg ccctttctca  28020
aatttaagcg cgaaaactac gtcatctcca gcggccacac ccggcgccag cacctgtcgt  28080
cagcgccatt tcaactttgt atacaaaagt tgtgatgagc aaggaaattc ccacgcccta  28140
catgtggagt taccagccac aaatgggact tgcggctgga gctgcccaag actactcaac  28200
ccgaataaac tacatgagcg cgggacccca catgatatcc cgggtcaacg gaatacgcgc  28260
ccaccgaaac cgaattctcc tggaacaggc ggctattacc accacacctc gtaataacct  28320
taatccccgt agttggcccg ctgccctggt gtaccaggaa agtcccgctc ccaccactgt  28380
ggtacttccc agagacgccc aggccgaagt tcagatgact aactcagggg cgcagcttgc  28440
gggcggcttt cgtcacaggg tgcggtcgcc cgggcagggt ataactcacc tgacaatcag  28500
```

```
agggcgaggt attcagctca acgacgagtc ggtgagctcc tcgcttggtc tccgtccgga  28560
cgggacattt cagatcggcg gcgccggccg ctcttcattc acgcctcgtc aggcaatcct  28620
aactctgcag acctcgtcct ctgagccgcg ctctggaggc attggaactc tgcaatttat  28680
tgaggagttt gtgccatcgg tctactttaa ccccttctcg ggacctcccg gccactatcc  28740
ggatcaattt attcctaact ttgacgcggt aaaggactcg gcggacggct acgactgaat  28800
gttaagtgga gaggcagagc aactgcgcct gaaacacctg gtccactgtc gccgccacaa  28860
gtgctttgcc cgcgactccg gtgagttttg ctactttgaa ttgcccgagg atcatatcga  28920
gggcccggcg cacggcgtcc ggcttaccgc ccagggagag cttgcccgta gcctgattcg  28980
ggagtttacc cagcgccccc tgctagttga gcgggacagg ggaccctgtg ttctcactgt  29040
gatttgcaac tgtcctaacc ctggattaca tcaagatctt tgttgccatc tctgtgctga  29100
gtataataaa tacagaaatt aaaatatact ggggctccta tcgccatcct gtaaacgcca  29160
ccgtcttcac ccgcccaagc aaaccaaggc gaaccttacc tggtactttt aacatctctc  29220
cctctgtgat ttacaacagt ttcaacccag acggagtgag tctacgagag aacctctccg  29280
agctcagcta ctccatcaga aaaaacacca ccctccttac ctgccgggaa cgtacgagtg  29340
cgtcaccggc cgctgcacca cacctaccgc ctgaccgtaa accagacttt ttccggacag  29400
acctcaataa ctctgtttac cagaacagga ggtgagctta gaaaaccctt agggtattag  29460
gccaaaggcg cagctactgt ggggtttatg aacaattcaa gcaactctac gggctattct  29520
aattcaggtt tctctagaat cggggttggg gttattctct gtcttgtgat tctctttatt  29580
cttatactaa cgcttctctg cctaaggctc gccgcctgct gtgtgcacat ttgcatttat  29640
tgtcagcttt ttaaacgctg ggtcgccac ccaagatgat taggtacata atcctaggtt  29700
tactcaccct tgcgtcagcc cacggtacca cccaaaaggt ggattttaag gagccagcct  29760
gtaatgttac attcgcagct gaagctaatg agtgcaccac tcttataaaa tgcaccacag  29820
aacatgaaaa gctgcttatt cgccacaaaa acaaaattgg caagtatgct gtttatgcta  29880
tttggcagcc aggtgacact acagagtata atgttacagt tttccagggt aaaagtcata  29940
aaacttttat gtatactttt ccattttatg aaatgtgcga cattaccatg tacatgagca  30000
aacagtataa gttgtggccc ccacaaaatt gtgtggaaaa cactggcact ttctgctgca  30060
ctgctatgct aattacagtg ctcgctttgg tctgtaccct actctatatt aaatacaaaa  30120
gcagacgcag ctttattgag gaaaagaaaa tgccttaatt tactaagtta caaagctaat  30180
gtcaccacta actgctttac tcgctgcttg caaaacaaat tcaaaaagtt agcattataa  30240
ttagaatagg atttaaaccc cccggtcatt tcctgctcaa taccattccc ctgaacaatt  30300
gactctatgt gggatatgct ccagcgctac aaccttgaag tcaggcttcc tggatgtcag  30360
catctgactt tggccagcac ctgtcccgcg gatttgttcc agtccaacta cagcgaccca  30420
ccctaacaga gatgaccaac acaaccaacg cggccgccgc taccggactt acatctacca  30480
caaatacacc ccaagtttct gcctttgtca ataactggga taacttgggc atgtggtggt  30540
tctccatagc gcttatgttt gtatgcctta ttattatgtg gctcatctgc tgcctaaagc  30600
gcaaacgcgc ccgaccaccc atctatagtc ccatcattgt gctacaccca aacaatgatg  30660
gaatccatag attggacgga ctgaaacaca tgttcttttc tcttacagta tgattaaatg  30720
agacatgatt cctcgagttt ttatattact gacccttgtt gcgctttttt gtgcgtgctc  30780
cacattggct gcggtttctc acatcgaagt agactgcatt ccagccttca cagtctattt  30840
```

-continued gctttacgga tttgtcaccc tcacgctcat ctgcagcctc atcactgtgg tcatcgcctt 30900
tatccagtgc attgactggg tctgtgtgcg ctttgcatat ctcagacacc atccccagta 30960
cagggacagg actatagctg agcttcttag aattctttaa ttatgaaatt tactgtgact 31020
tttctgctga ttatttgcac cctatctgcg ttttgttccc cgacctccaa gcctcaaaga 31080
catatatcat gcagattcac tcgtatatgg aatattccaa gttgctacaa tgaaaaaagc 31140
gatctttccg aagcctggtt atatgcaatc atctctgtta tggtgttctg cagtaccatc 31200
ttagccctag ctatatatcc ctaccttgac attggctgga acgcaataga tgccatgaac 31260
cacccaactt tccccgcgcc cgctatgctt ccactgcaac aagttgttgc cggcggcttt 31320
gtcccagcca atcagcctcg cccaccttct cccacccccca ctgaaatcag ctactttaat 31380
ctaacaggag gagatgactg acaccctaga tctagaaatg gacggaatta ttacagagca 31440
gcgcctgcta gaaagacgca gggcagcggc cgagcaacag cgcatgaatc aagagctcca 31500
agacatggtt aacttgcacc agtgcaaaag ggtatcttt tgtctggtaa agcaggccaa 31560
agtcacctac gacagtaata ccaccggaca ccgccttagc tacaagttgc caaccaagcg 31620
tcagaaattg gtggtcatgg tgggagaaaa gcccattacc ataactcagc actcggtaga 31680
aaccgaaggc tgcattcact caccttgtca aggacctgag gatctctgca cccttattaa 31740
gaccctgtgc ggtctcaaag atcttattcc ctttaactaa taaaaaaaaa taataaagca 31800
tcacttactt aaaatcagtt agcaaatttc tgtccagttt attcagcagc acctccttgc 31860
cctcctccca gctctggtat tgcagcttcc tcctggctgc aaactttctc cacaatctaa 31920
atggaatgtc agtttcctcc tgttcctgtc catccgcacc cactatcttc atgttgttgc 31980
agatgaagcg cgcaagaccg tctgaagata ccttcaaccc cgtgtatcca tatgacacgg 32040
aaaccggtcc tccaactgtg ccttttctta ctcctccctt tgtatccccc aatgggtttc 32100
aagagagtcc ccctggggta ctctctttgc gcctatccga acctctagtt acctccaatg 32160
gcatgcttgc gctcaaaatg ggcaacggcc tctctctgga cgaggccggc aaccttacct 32220
cccaaaatgt aaccactgtg agcccacctc tcaaaaaaac caagtcaaac ataaacctgg 32280
aaatatctgc acccctcaca gttacctcag aagccctaac tgtggctgcc gccgcacctc 32340
taatggtcgc gggcaacaca ctcaccatgc aatcacaggc cccgctaacc gtgcacgact 32400
ccaaacttag cattgccacc caaggacccc tcacagtgtc agaaggaaag ctagccctgc 32460
aaacatcagg ccccctcacc accaccgata gcagtaccct tactatcact gcctcacccc 32520
ctctaactac tgccactggt agcttgggca ttgacttgaa agagcccatt tatacacaaa 32580
atggaaaact aggactaaag tacggggctc ctttgcatgt aacagacgac ctaaacactt 32640
tgaccgtagc aactggtcca ggtgtgacta ttaataatac ttccttgcaa actaaagtta 32700
ctggagcctt gggttttgat tcacaaggca atatgcaact taatgtagca ggaggactaa 32760
ggattgattc tcaaaacaga cgccttatac ttgatgttag ttatccgttt gatgctcaaa 32820
accaactaaa tctaagacta ggacagggcc ctctttttat aaactcagcc cacaacttgg 32880
atattaacta caacaaaggc ctttacttgt ttacagcttc aaacaattcc aaaaagcttg 32940
aggttaacct aagcactgcc aaggggttga tgtttgacgc tacagccata gccattaatg 33000
caggagatgg gcttgaattt ggttcaccta atgcaccaaa cacaaatccc ctcaaaacaa 33060
aaattggcca tggcctagaa tttgattcaa acaaggctat ggttcctaaa ctaggaactg 33120
gccttagttt tgacagcaca ggtgccatta cagtaggaaa caaaaataat gataagctaa 33180
ctttgtggac cacaccagct ccatctccta actgtagact aaatgcagag aaagatgcta 33240

```
aactcacttt ggtcttaaca aaatgtggca gtcaaatact tgctacagtt tcagttttgg  33300
ctgttaaagg cagtttggct ccaatatctg gaacagttca aagtgctcat cttattataa  33360
gatttgacga aaatggagtg ctactaaaca attccttcct ggacccagaa tattggaact  33420
ttagaaatgg agatcttact gaaggcacag cctatacaaa cgctgttgga tttatgccta  33480
acctatcagc ttatccaaaa tctcacggta aaactgccaa aagtaacatt gtcagtcaag  33540
tttacttaaa cggagacaaa actaaacctg taacactaac cattacacta aacggtacac  33600
aggaaacagg agacacaact ccaagtgcat actctatgtc attttcatgg gactggtctg  33660
gccacaacta cattaatgaa atatttgcca catcctctta cactttttca tacattgccc  33720
aagaataaag aatcgtttgt gttatgtttc aacgtgttta tttttcaatt gcagaaaatt  33780
tcaagtcatt tttcattcag tagtatagcc ccaccaccac atagcttata cagatcaccg  33840
tacctcaact ttgtataata aagttgtaat caaactcaca gaaccctagt attcaacctg  33900
ccacctccct cccaacacac agagtacaca gtcctttctc cccggctggc cttaaaaagc  33960
atcatatcat gggtaacaga catattctta ggtgttatat tccacacggt ttcctgtcga  34020
gccaaacgct catcagtgat attaataaac tccccgggca gctcacttaa gttcatgtcg  34080
ctgtccagct gctgagccac aggctgctgt ccaacttgcg gttgcttaac gggcggcgaa  34140
ggagaagtcc acgcctacat gggggtagag tcataatcgt gcatcaggat agggcggtgg  34200
tgctgcagca gcgcgcgaat aaactgctgc cgccgccgct ccgtcctgca ggaatacaac  34260
atggcagtgg tctcctcagc gatgattcgc accgcccgca gcataaggcg ccttgtcctc  34320
cgggcacagc agcgcaccct gatctcactt aaatcagcac agtaactgca gcacagcacc  34380
acaatattgt tcaaaatccc acagtgcaag gcgctgtatc caaagctcat ggcggggacc  34440
acagaaccca cgtggccatc ataccacaag cgcaggtaga ttaagtggcg acccctcata  34500
aacacgctgg acataaacat tacctctttt ggcatgttgt aattcaccac ctcccggtac  34560
catataaacc tctgattaaa catggcgcca tccaccacca tcctaaacca gctggccaaa  34620
acctgcccgc cggctataca ctgcagggaa ccgggactgg aacaatgaca gtggagagcc  34680
caggactcgt aaccatggat catcatgctc gtcatgatat caatgttggc acaacacagg  34740
cacacgtgca tacacttcct caggattaca agctcctccc gcgttagaac catatcccag  34800
ggaacaaccc attcctgaat cagcgtaaat cccacactgc agggaagacc tcgcacgtaa  34860
ctcacgttgt gcattgtcaa agtgttacat tcgggcagca gcggatgatc ctccagtatg  34920
gtagcgcggg tttctgtctc aaaaggaggt agacgatccc tactgtacgg agtgcgccga  34980
gacaaccgag atcgtgttgg tcgtagtgtc atgccaaatg gaacgccgga cgtagtcata  35040
tttcctgaag caaaaccagg tgcgggcgtg acaaacagat ctgcgtctcc ggtctcgccg  35100
cttagatcgc tctgtgtagt agttgtagta tatccactct ctcaaagcat ccaggcgccc  35160
cctggcttcg ggttctatgt aaactccttc atgcgccgct gccctgataa catccaccac  35220
cgcagaataa gccacaccca gccaacctac acattcgttc tgcgagtcac acacgggagg  35280
agcgggaaga gctggaagaa ccatgttttt ttttttattc caaaagatta tccaaaacct  35340
caaaatgaag atctattaag tgaacgcgct cccctccggt ggcgtggtca aactctacag  35400
ccaaagaaca gataatggca tttgtaagat gttgcacaat ggcttccaaa aggcaaacgg  35460
ccctcacgtc caagtggacg taaaggctaa acccttcagg gtgaatctcc tctataaaca  35520
ttccagcacc ttcaaccatg cccaaataat tctcatctcg ccaccttctc aatatatctc  35580
```

```
taagcaaatc ccgaatatta agtccggcca ttgtaaaaat ctgctccaga gcgccctcca  35640

ccttcagcct caagcagcga atcatgattg caaaaattca ggttcctcac agacctgtat  35700

aagattcaaa agcggaacat taacaaaaat accgcgatcc cgtaggtccc ttcgcagggc  35760

cagctgaaca taatcgtgca ggtctgcacg gaccagcgcg gccacttccc cgccaggaac  35820

catgacaaaa gaacccacac tgattatgac acgcatactc ggagctatgc taaccagcgt  35880

agccccgatg taagcttgtt gcatgggcgg cgatataaaa tgcaaggtgc tgctcaaaaa  35940

atcaggcaaa gcctcgcgca aaaaagaaag cacatcgtag tcatgctcat gcagataaag  36000

gcaggtaagc tccggaacca ccacagaaaa agacaccatt tttctctcaa acatgtctgc  36060

gggtttctgc ataaacacaa aataaaataa caaaaaaaca tttaaacatt agaagcctgt  36120

cttacaacag gaaaaacaac ccttataagc ataagacgga ctacggccat gccggcgtga  36180

ccgtaaaaaa actggtcacc gtgattaaaa agcaccaccg acagctcctc ggtcatgtcc  36240

ggagtcataa tgtaagactc ggtaaacaca tcaggttgat tcacatcggt cagtgctaaa  36300

aagcgaccga aatagcccgg gggaatacat acccgcaggc gtagagacaa cattacagcc  36360

cccataggag gtataacaaa attaatagga gagaaaaaca cataaacacc tgaaaaaccc  36420

tcctgcctag gcaaaatagc accctcccgc tccagaacaa catacagcgc ttccacagcg  36480

gcagccataa cagtcagcct taccagtaaa aaagaaaacc tattaaaaaa acaccactcg  36540

acacggcacc agctcaatca gtcacagtgt aaaaaagggc caagtgcaga gcgagtatat  36600

ataggactaa aaaatgacgt aacggttaaa gtccacaaaa aacacccaga aaaccgcacg  36660

cgaacctacg cccagaaacg aaagccaaaa aacccacaac ttcctcaaat cgtcacttcc  36720

gttttcccac gttacgtcac ttcccatttt aagaaaacta caattcccaa cacatacaag  36780

ttactccgcc ctaaaaccta cgtcacccgc cccgttccca cgccccgcgc cacgtcacaa  36840

actccacccc ctcattatca tattggcttc aatccaaaat aaggtatatt attgatgatg  36900
```

<210> SEQ ID NO 8
<211> LENGTH: 952
<212> TYPE: PRT
<213> ORGANISM: Adenovirus type 5

<400> SEQUENCE: 8

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Ala Ala Thr Ala Leu Glu Ile
    130                 135                 140
```

-continued

```
Asn Leu Glu Glu Glu Asp Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
    210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255

Lys Leu Glu Ser Gln Val Glu Met Gln Phe Phe Ser Thr Thr Glu Ala
            260                 265                 270

Thr Ala Gly Asn Gly Asp Asn Leu Thr Pro Lys Val Val Leu Tyr Ser
        275                 280                 285

Glu Asp Val Asp Ile Glu Thr Pro Asp Thr His Ile Ser Tyr Met Pro
    290                 295                 300

Thr Ile Lys Glu Gly Asn Ser Arg Glu Leu Met Gly Gln Gln Ser Met
305                 310                 315                 320

Pro Asn Arg Pro Asn Tyr Ile Ala Phe Arg Asp Asn Phe Ile Gly Leu
                325                 330                 335

Met Tyr Tyr Asn Ser Thr Gly Asn Met Gly Val Leu Ala Gly Gln Ala
            340                 345                 350

Ser Gln Leu Asn Ala Val Val Asp Leu Gln Asp Arg Asn Thr Glu Leu
        355                 360                 365

Ser Tyr Gln Leu Leu Leu Asp Ser Ile Gly Asp Arg Thr Arg Tyr Phe
    370                 375                 380

Ser Met Trp Asn Gln Ala Val Asp Ser Tyr Asp Pro Asp Val Arg Ile
385                 390                 395                 400

Ile Glu Asn His Gly Thr Glu Asp Glu Leu Pro Asn Tyr Cys Phe Pro
                405                 410                 415

Leu Gly Gly Val Ile Asn Thr Glu Thr Leu Thr Lys Val Lys Pro Lys
            420                 425                 430

Thr Gly Gln Glu Asn Gly Trp Glu Lys Asp Ala Thr Glu Phe Ser Asp
        435                 440                 445

Lys Asn Glu Ile Arg Val Gly Asn Asn Phe Ala Met Glu Ile Asn Leu
    450                 455                 460

Asn Ala Asn Leu Trp Arg Asn Phe Leu Tyr Ser Asn Ile Ala Leu Tyr
465                 470                 475                 480

Leu Pro Asp Lys Leu Lys Tyr Ser Pro Ser Asn Val Lys Ile Ser Asp
                485                 490                 495

Asn Pro Asn Thr Tyr Asp Tyr Met Asn Lys Arg Val Val Ala Pro Gly
            500                 505                 510

Leu Val Asp Cys Tyr Ile Asn Leu Gly Ala Arg Trp Ser Leu Asp Tyr
        515                 520                 525

Met Asp Asn Val Asn Pro Phe Asn His His Arg Asn Ala Gly Leu Arg
    530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Leu Pro
```

-continued

```
                565                 570                 575

Gly Ser Tyr Thr Tyr Glu Trp Asn Phe Arg Lys Asp Val Asn Met Val
            580                 585                 590

Leu Gln Ser Ser Leu Gly Asn Asp Leu Arg Val Asp Gly Ala Ser Ile
        595                 600                 605

Lys Phe Asp Ser Ile Cys Leu Tyr Ala Thr Phe Phe Pro Met Ala His
    610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
                645                 650                 655

Pro Ala Asn Ala Thr Asn Val Pro Ile Ser Ile Pro Ser Arg Asn Trp
            660                 665                 670

Ala Ala Phe Arg Gly Trp Ala Phe Thr Arg Leu Lys Thr Lys Glu Thr
        675                 680                 685

Pro Ser Leu Gly Ser Gly Tyr Asp Pro Tyr Tyr Thr Tyr Ser Gly Ser
    690                 695                 700

Ile Pro Tyr Leu Asp Gly Thr Phe Tyr Leu Asn His Thr Phe Lys Lys
705                 710                 715                 720

Val Ala Ile Thr Phe Asp Ser Ser Val Ser Trp Pro Gly Asn Asp Arg
                725                 730                 735

Leu Leu Thr Pro Asn Glu Phe Glu Ile Lys Arg Ser Val Asp Gly Glu
            740                 745                 750

Gly Tyr Asn Val Ala Gln Cys Asn Met Thr Lys Asp Trp Phe Leu Val
        755                 760                 765

Gln Met Leu Ala Asn Tyr Asn Ile Gly Tyr Gln Gly Phe Tyr Ile Pro
    770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
                805                 810                 815

Val Gly Ile Leu His Gln His Asn Asn Ser Gly Phe Val Gly Tyr Leu
            820                 825                 830

Ala Pro Thr Met Arg Glu Gly Gln Ala Tyr Pro Ala Asn Phe Pro Tyr
        835                 840                 845

Pro Leu Ile Gly Lys Thr Ala Val Asp Ser Ile Thr Gln Lys Lys Phe
    850                 855                 860

Leu Cys Asp Arg Thr Leu Trp Arg Ile Pro Phe Ser Ser Asn Phe Met
865                 870                 875                 880

Ser Met Gly Ala Leu Thr Asp Leu Gly Gln Asn Leu Leu Tyr Ala Asn
                885                 890                 895

Ser Ala His Ala Leu Asp Met Thr Phe Glu Val Asp Pro Met Asp Glu
            900                 905                 910

Pro Thr Leu Leu Tyr Val Leu Phe Glu Val Phe Asp Val Val Arg Val
        915                 920                 925

His Arg Pro His Arg Gly Val Ile Glu Thr Val Tyr Leu Arg Thr Pro
    930                 935                 940

Phe Ser Ala Gly Asn Ala Thr Thr
945                 950
```

<210> SEQ ID NO 9
<211> LENGTH: 952
<212> TYPE: PRT
<213> ORGANISM: Artificial Sequence
<220> FEATURE:
<223> OTHER INFORMATION: Modified adenovirus hexon protein

<400> SEQUENCE: 9

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Ala Ala Thr Ala Leu Glu Ile
    130                 135                 140

Asn Leu Glu Glu Glu Asp Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
    210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255

Lys Leu Glu Ser Gln Val Glu Met Gln Phe Phe Ser Thr Thr Glu Ala
            260                 265                 270

Thr Ala Gly Asn Gly Asp Asn Leu Thr Pro Lys Val Val Leu Tyr Ser
        275                 280                 285

Glu Asp Val Asp Ile Glu Thr Pro Asp Thr His Ile Ser Tyr Met Pro
    290                 295                 300

Thr Ile Lys Glu Gly Asn Ser Arg Glu Leu Met Gly Gln Gln Ser Met
305                 310                 315                 320

Pro Asn Arg Pro Asn Tyr Ile Ala Phe Arg Asp Asn Phe Ile Gly Leu
                325                 330                 335

Met Tyr Tyr Asn Ser Thr Gly Asn Met Gly Val Leu Ala Gly Gln Ala
            340                 345                 350

Ser Gln Leu Asn Ala Val Val Asp Leu Gln Asp Arg Asn Thr Glu Leu
        355                 360                 365

Ser Tyr Gln Leu Leu Leu Asp Ser Ile Gly Asp Arg Thr Arg Tyr Phe
    370                 375                 380

Ser Met Trp Asn Gln Ala Val Asp Ser Tyr Asp Pro Asp Val Arg Ile
385                 390                 395                 400
```

-continued

```
Ile Glu Asn His Gly Thr Glu Asp Glu Leu Pro Asn Tyr Cys Phe Pro
                405                 410                 415

Leu Gly Gly Val Ile Asn Thr Glu Thr Leu Thr Lys Val Lys Pro Lys
            420                 425                 430

Thr Gly Gln Glu Asn Gly Trp Glu Lys Asp Ala Thr Glu Phe Ser Asp
        435                 440                 445

Lys Asn Gln Ile Arg Val Gly Asn Asn Phe Ala Met Glu Ile Asn Leu
    450                 455                 460

Asn Ala Asn Leu Trp Arg Asn Phe Leu Tyr Ser Asn Ile Ala Leu Tyr
465                 470                 475                 480

Leu Pro Asp Lys Leu Lys Tyr Ser Pro Ser Asn Val Lys Ile Ser Asp
                485                 490                 495

Asn Pro Asn Thr Tyr Asp Tyr Met Asn Lys Arg Val Val Ala Pro Gly
            500                 505                 510

Leu Val Asp Cys Tyr Ile Asn Leu Gly Ala Arg Trp Ser Leu Asp Tyr
        515                 520                 525

Met Asp Asn Val Asn Pro Phe Asn His His Arg Asn Ala Gly Leu Arg
    530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Leu Pro
                565                 570                 575

Gly Ser Tyr Thr Tyr Glu Trp Asn Phe Arg Lys Asp Val Asn Met Val
            580                 585                 590

Leu Gln Ser Ser Leu Gly Asn Asp Leu Arg Val Asp Gly Ala Ser Ile
        595                 600                 605

Lys Phe Asp Ser Ile Cys Leu Tyr Ala Thr Phe Phe Pro Met Ala His
    610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
                645                 650                 655

Pro Ala Asn Ala Thr Asn Val Pro Ile Ser Ile Pro Ser Arg Asn Trp
            660                 665                 670

Ala Ala Phe Arg Gly Trp Ala Phe Thr Arg Leu Lys Thr Lys Glu Thr
        675                 680                 685

Pro Ser Leu Gly Ser Gly Tyr Asp Pro Tyr Tyr Thr Tyr Ser Gly Ser
    690                 695                 700

Ile Pro Tyr Leu Asp Gly Thr Phe Tyr Leu Asn His Thr Phe Lys Lys
705                 710                 715                 720

Val Ala Ile Thr Phe Asp Ser Ser Val Ser Trp Pro Gly Asn Asp Arg
                725                 730                 735

Leu Leu Thr Pro Asn Glu Phe Glu Ile Lys Arg Ser Val Asp Gly Glu
            740                 745                 750

Gly Tyr Asn Val Ala Gln Cys Asn Met Thr Lys Asp Trp Phe Leu Val
        755                 760                 765

Gln Met Leu Ala Asn Tyr Asn Ile Gly Tyr Gln Gly Phe Tyr Ile Pro
    770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
                805                 810                 815
```

```
Val Gly Ile Leu His Gln His Asn Asn Ser Gly Phe Val Gly Tyr Leu
            820                 825                 830

Ala Pro Thr Met Arg Glu Gly Gln Ala Tyr Pro Ala Asn Phe Pro Tyr
        835                 840                 845

Pro Leu Ile Gly Lys Thr Ala Val Asp Ser Ile Thr Gln Lys Lys Phe
    850                 855                 860

Leu Cys Asp Arg Thr Leu Trp Arg Ile Pro Phe Ser Ser Asn Phe Met
865                 870                 875                 880

Ser Met Gly Ala Leu Thr Asp Leu Gly Gln Asn Leu Leu Tyr Ala Asn
                885                 890                 895

Ser Ala His Ala Leu Asp Met Thr Phe Glu Val Asp Pro Met Asp Glu
            900                 905                 910

Pro Thr Leu Leu Tyr Val Leu Phe Glu Val Phe Asp Val Val Arg Val
        915                 920                 925

His Arg Pro His Arg Gly Val Ile Glu Thr Val Tyr Leu Arg Thr Pro
    930                 935                 940

Phe Ser Ala Gly Asn Ala Thr Thr
945                 950
```

<210> SEQ ID NO 10
<211> LENGTH: 41638
<212> TYPE: DNA
<213> ORGANISM: Artificial Sequence
<220> FEATURE:
<223> OTHER INFORMATION: Synthetic adenovirus construct (AdSyn-CO877)

<400> SEQUENCE: 10

```
gttccactga gcgtcagacc ccttaataag atgatcttct tgagatcgtt ttggtctgcg     60

cgtaatctct tgctctgaaa acgaaaaaac cgccttgcag ggcggttttt cgaaggttct    120

ctgagctacc aactctttga accgaggtaa ctggcttgga ggagcgcagt caccaaaact    180

tgtcctttca gtttagcctt aaccggcgca tgacttcaag actaactcct ctaaatcaat    240

taccagtggc tgctgccagt ggtgcttttg catgtctttc cgggttggac tcaagacgat    300

agttaccgga taaggcgcag cggtcggact gaacgggggg ttcgtgcata cagtccagct    360

tggagcgaac tgcctacccg gaactgagtg tcaggcgtgg aatgagacaa acgcggccat    420

aacagcggaa tgacaccggt aaaccgaaag gcaggaacag gagagcgcac gagggagccg    480

ccaggggaaa cgcctggtat ctttatagtc ctgtcgggtt tcgccaccac tgatttgagc    540

gtcagatttc gtgatgcttg tcaggggggc ggagcctatg gaaaaacggc tttgccgcgg    600

ccctctcact tccctgttaa gtatcttcct ggcatcttcc aggaaatctc cgccccgttc    660

gtaagccatt tccgctcgcc gcagtcgaac gaccgagcgt agcgagtcag tgagcgagga    720

agcggaatat atcctgtatc acatattctg ctgacgcacc ggtgcagcct tttttctcct    780

gccacatgaa gcacttcact gacaccctca tcagtgccaa catagtaagc cagtatacac    840

tccgctagcg ctgaggtctg cctcgtgaag aaggtgttgc tgactcatac caggcctgaa    900

tcgccccatc atccagccag aaagtgaggg agccacggtt gatgagagct ttgttgtagg    960

tggaccagtt ggtgattttg aacttttgct ttgccacgga acggtctgcg ttgtcgggaa   1020

gatgcgtgat ctgatccttc aactcagcaa aagttcgatt tattcaacaa agccacgttg   1080

tgtctcaaaa tctctgatgt tacattgcac aagataaaaa tatatcatca tgaacaataa   1140

aactgtctgc ttacataaac agtaatacaa ggggtgttga tactctcagt acaatctgct   1200

ctgatgccgc atagttaagc cagtatctgc tccctgcttg tgtgttggag gtcgctgagt   1260
```

agtgcgcgag caaaatttaa gctacaacaa ggcaaggctt gaccgacaat tgcatgaaga 1320
atctgcttag ggttaggcgt tttgcgctgc ttcgcgatgt acgggccaga tatacgcgta 1380
tctgagggga ctagggtgtg tttaggcgaa aagcggggct tcggttgtac gcggttagga 1440
gtcccctcag gatatagtag tttcgctttt gcatagggag ggggaaatgt agtcttatgc 1500
aatactcttg tagtcttgca acatggtaac gatgagttag caacatgcct tacaaggaga 1560
gaaaaagcac cgtgcatgcc gattggtgga agtaaggtgg tacgatcgtg ccttattagg 1620
aaggcaacag acgggtctga catggattgg acgaaccact gaattccgca ttgcagagat 1680
attgtattta agtgcctagc tcgatacaat aaacgccatt tgaccattca ccacattggt 1740
gtgcacctcc aagctgggta cggatccggc cttgccggcc tcgagcggcc gctagcgccg 1800
ccactatggg atcaagatcg ccaaaaaaga agagaaaggt gccgaagaag catgcagcac 1860
caccaaaaaa aaaacgaaaa gtagaagacc cacgatttat gtacccatac gatgttcctg 1920
actatgcggg tatgaaaaac atcaaaaaaa accaggtaat gaacctgggt ccgaactcta 1980
aactgctgaa agaatacaaa tcccagctga tcgaactgaa catcgaacag ttcgaagcag 2040
gtatcggtct gatcctgggt gatgcttaca tccgttctcg tgatgaaggt aaaacctact 2100
gtatgcagtt cgagtggaaa aacaaagcat acatggacca cgtatgtctg ctgtacgatc 2160
agtgggtact gtccccgccg cacaaaaaag aacgtgttaa ccacctgggt aacctggtaa 2220
tcacctgggg cgcccagact ttcaaacacc aagctttcaa caaactggct aacctgttca 2280
tcgttaacaa caaaaaaacc atcccgaaca acctggttga aaactacctg accccgatgt 2340
ctctggcata ctggttcatg gatgatggtg gtaaatggga ttacaacaaa aactctacca 2400
acaaatcgat cgtactgaac acccagtctt tcactttcga agaagtagaa tacctggtta 2460
agggtctgcg taacaaattc caactgaact gttacgtaaa aatcaacaaa aacaaaccga 2520
tcatctacat cgattctatg tcttacctga tcttctacaa cctgatcaaa ccgtacctga 2580
tcccgcagat gatgtacaaa ctgccgaaca ctatctcctc cgaaactttc ctgaaataag 2640
gtaccgatcc agacatgata agatacattg atgagtttgg acaaaccaca actagaatgc 2700
agtgaaaaaa atgctttatt tgtgaaattt gtgatgctat tgctttattt gtaaccatta 2760
taagctgcaa taaacaagtt aacaacaaca attgcattca ttttatgttt caggttcagg 2820
gggaggtgtg ggaggttttt taaagcaagt aaaacctcta caaatgtggt atggctgatt 2880
atgatcatcg taaacttggt ctgacagtta ccaatgctta atcagtgagg cacctatctc 2940
agcgatctgt ctatttcgtt catccatagt tgcctgactc cccgtcgtgt agataactac 3000
gatacgggag ggcttaccat ctggccccag tgctgcaatg ataccgcgag acccacgctc 3060
accggctcca gatttatcag caataaacca gccagccgga agggccgagc gcagaagtgg 3120
tcctgcaact ttatccgcct ccatccagtc tattaattgt tgccgggaag ctagagtaag 3180
tagttcgcca gttaatagtt tgcgcaacgt tgttgccatt gctacaggca tcgtggtgtc 3240
acgctcgtcg tttggtatgg cttcattcag ctccggttcc caacgatcaa ggcgagttac 3300
atgatccccc atgttgtgca aaaaagcggt tagctccttc ggtcctccga tcgttgtcag 3360
aagtaagttg gccgcagtgt tatcactcat ggttatggca gcactgcata attctcttac 3420
tgtcatgcca tccgtaagat gcttttctgt gactggtgag tactcaacca agtcattctg 3480
agaatagtgt atgcggcgac cgagttgctc ttgcccggcg tcaatacggg ataataccgc 3540
gccacatagc agaactttaa aagtgctcat cattggaaaa cgttcttcgg ggcgaaaact 3600
ctcaaggatc ttaccgctgt tgagatccag ttcgatgtaa cccactcgtg cacccaactg 3660

-continued atcttcagca tcttttactt tcaccagcgt ttctgggtga gcaaaaacag gaaggcaaaa 3720
tgccgcaaaa aagggaataa gggcgacacg gaaatgttga atactcatac tcttcctttt 3780
tcaatattat tgaagcattt atcagggtta ttgtctcatg agcggataca tatttgaatg 3840
tatttagaaa aataaacaaa taggggttcc gcgcacattt ccccgaaaag tgccacctga 3900
cgtctaagaa accattatta tcatgacatt aacctataaa aataggcgta tcacgaggcc 3960
ctttcgtctc gcgcgtttcg gtgatgacgg tgaaaacctc tgacacatgc agctcccgga 4020
gacggtcaca gcttgtctgt aagcggatgc cgggagcaga caagcccgtc agggcgcgtc 4080
agcgggtgtt ggcgggtgtc ggggctggct taactatgcg gcatcagagc agattgtact 4140
gagagtgcac catatgcggt gtgaaatacc gcacagatgc gtaaggagaa aataccgcat 4200
caggcgccat tcgccattca ggctgcgcaa ctgttgggaa gggcgatcgg tgcgggcctc 4260
ttcgctatta cgccagctgg cgaaaggggg atgtgctgca aggcgattaa gttgggtaac 4320
gccagggttt tcccagtcac gacgttgtaa aacgacggcc agtgaattac aactttgtac 4380
aaaaaagcag attaccctgt tatccctaca tcatcaataa tataccttat tttggattga 4440
agccaatatg ataatgaggg ggtggagttt gtgacgtggc gcggggcgtg ggaacggggc 4500
gggtgacgta gtagtgtggc ggaagtgtga tgttgcaagt gtggcggaac acatgtaagc 4560
gacggatgtg gcaaaagtga cgtttttggt gtgcgccggt gtacacagga agtgacaatt 4620
ttcgcgcggt tttaggcgga tgttgtagta aatttgggcg taaccgagta agatttggcc 4680
attttcgcgg gaaaactgaa taagaggaag tgaaatctga ataattttgt gttactcata 4740
gcgcgtaata tttgtctagg gccgcgggga ctttgaccgt ttacgtggag actcgcccag 4800
gtgtttttct caggtgtttt ccgcgttccg ggtcaaagtt ggcgttttat tattaaaccg 4860
tattaccgcc atgcatttaa tggagtgcct cgtgaggctc cggtgcccgt cagtgggcag 4920
agcgcacatc gcccacagtc cccgagaagt tggggggagg ggtcggcaat tgaaccggtg 4980
cctagagaag gtggcgcggg gtaaactggg aaagtgatgt cgtgtactgg ctccgccttt 5040
ttcccgaggg tgggggagaa ccgtatataa gtgcagtagt cgccgtgaac gttctttttc 5100
gcaacgggtt tgccgccaga acacaggtaa gtgccgtgtg tggttcccgc gggcctggcc 5160
tctttacggg ttatggccct tgcgtgcctt gaattacttc cacctggctg cagtacgtga 5220
ttcttgatcc cgagcttcgg gttggaagtg ggtgggagag ttcgaggcct tgcgcttaag 5280
gagccccttc gcctcgtgct tgagttgagg cctggcctgg gcgctggggc cgccgcgtgc 5340
gaatctggtg gcaccttcgc gcctgtctcg ctgctttcga taagtctcta gccatttaaa 5400
atttttgatg acctgctgcg acgctttttt tctggcaaga tagtcttgta aatgcgggcc 5460
aagatctgca cactggtatt tcggtttttg gggccgcggg cggcgacggg gcccgtgcgt 5520
cccagcgcac atgttcggcg aggcggggcc tgcgagcgcg gccaccgaga atcggacggg 5580
ggtagtctca agctggccgg cctgctctgg tgcctggcct cgcgccgccg tgtatcgccc 5640
cgccctgggc ggcaaggctg gcccggtcgg caccagttgc gtgagcggaa agatggccgc 5700
ttcccggccc tgctgcaggg agctcaaaat ggaggacgcg gcgctcggga gagcgggcgg 5760
gtgagtcacc cacacaaagg aaaagggcct ttccgtcctc agccgtcgct tcatgtgact 5820
ccacggagta ccgggcgccg tccaggcacc tcgattagtt ctcgagcttt tggagtacgt 5880
cgtctttagg ttggggggag gggttttatg cgatggagtt tccccacact gagtgggtgg 5940
agactgaagt taggccagct tggcacttga tgtaattctc cttggaattt gccctttttg 6000

-continued

```
agtttggatc ttggttcatt ctcaagcctc agacagtggt tcaaagtttt tttcttccat   6060
ttcaggtgtc gtgacgctag cgctaccgga ctcagatctc gagctcaagc ttcgaattct   6120
gcagtcgacg gtaccggatc catgaatcgc tgctgggcgc tcttcctgtc tctctgctgc   6180
tacctgcgtc tggtcagcgc cgagggggac cccattcccg aggagcttta tgagatgctg   6240
agtgaccact cgatccgctc ctttgatgat ctccaacgcc tgctgcacgg agaccccgga   6300
gaggaagatg gggccgagtt ggacctgaac atgacccgct cccactctgg aggcgagctg   6360
gagagcttgg ctcgtggaag aaggagcctg ggttccctga ccattgctga gccggccatg   6420
atcgccgagt gcaagacgcg caccgaggtg ttcgagatct cccggcgcct catagaccgc   6480
accaacgcca acttcctggt gtggccgccc tgtgtggagg tgcagcgctg ctccggctgc   6540
tgcaacaacc gcaacgtgca gtgccgcccc acccaggtgc agctgcgacc tgtccaggtg   6600
agaaagatcg agattgtgcg gaagaagcca atctttaaga aggccacggt gacgctggaa   6660
gaccacctgg catgcaagtg tgagacagtg gcagctgcac ggcctgtgac ccgaagcccg   6720
gggggttccc aggagcagcg agccaaaacg ccccaaactc gggtgaccat tcggacggtg   6780
cgagtccgcc ggcccccaa gggcaagcac cggaaattca agcacacgca tgacaagacg   6840
gcactgaagg agacccttgg agccggctct gggtccggat cgggctctgg gtccggaagc   6900
ggagctacta acttcagcct gctgaagcag gctggtgacg tcgaggagaa tcctggccca   6960
atggaagacg ccaaaaacat aaagaaaggc ccggcgccat tctatccgct ggaagatgga   7020
accgctggag agcaactgca taaggctatg aagagatacg ccctggttcc tggaacaatt   7080
gcttttacag atgcacatat cgaggtggac atcacttacg ctgagtactt cgaaatgtcc   7140
gttcggttgg cagaagctat gaaacgatat gggctgaata caaatcacag aatcgtcgta   7200
tgcagtgaaa actctcttca attctttatg ccggtgttgg gcgcgttatt tatcggagtt   7260
gcagttgcgc ccgcgaacga catttataat gaacgtgaat tgctcaacag tatgggcatt   7320
tcgcagccta ccgtggtgtt cgtttccaaa aaggggttgc aaaaaatttt gaacgtgcaa   7380
aaaaagctcc caatcatcca aaaaattatt atcatggatt ctaaaacgga ttaccaggga   7440
tttcagtcga tgtacacgtt cgtcacatct catctacctc ccggttttaa tgaatacgat   7500
tttgtgccag agtccttcga tagggacaag acaattgcac tgatcatgaa ctcctctgga   7560
tctactggtc tgcctaaagg tgtcgctctg cctcatagaa ctgcctgcgt gagattctcg   7620
catgccagag atcctatttt tggcaatcaa atcattccgg atactgcgat tttaagtgtt   7680
gttccattcc atcacggttt tggaatgttt actacactcg gatatttgat atgtggattt   7740
cgagtcgtct taatgtatag atttgaagaa gagctgtttc tgaggagcct tcaggattac   7800
aagattcaaa gtgcgctgct ggtgccaacc ctattctcct tcttcgccaa aagcactctg   7860
attgacaaat acgatttatc taatttacac gaaattgctt ctggtggcgc tcccctctct   7920
aaggaagtcg gggaagcggt tgccaagagg ttccatctgc caggtatcag gcaaggatat   7980
gggctcactg agactacatc agctattctg attacacccg agggggatga taaaccgggc   8040
gcggtcggta aagttgttcc atttttgaa gcgaaggttg tggatctgga taccgggaaa   8100
acgctgggcg ttaatcaaag aggcgaactg tgtgtgagag gtcctatgat tatgtccggt   8160
tatgtaaaca atccggaagc gaccaacgcc ttgattgaca aggatggatg gctacattct   8220
ggagacatag cttactggga cgaagacgaa cacttcttca tcgttgaccg cctgaagtct   8280
ctgattaagt acaaaggcta tcaggtggct cccgctgaat tggaatccat cttgctccaa   8340
caccccaaca tcttcgacgc aggtgtcgca ggtcttcccg acgatgacgc cggtgaactt   8400
```

-continued

```
cccgccgccg ttgttgtttt ggagcacgga aagacgatga cggaaaaaga gatcgtggat   8460
tacgtcgcca gtcaagtaac aaccgcgaaa aagttgcgcg gaggagttgt gtttgtggac   8520
gaagtaccga aaggtcttac cggaaaactc gacgcaagaa aaatcagaga gatcctcata   8580
aaggccaaga agggcggaaa gatcgccgtg taaagcgact ctagatcata atcagccata   8640
cccaaacacc attgtcacac tccaatcgat tcaaacacca ttgtcacact ccaacatttg   8700
tagaggtttt acttgcttta aaaaacctcc cacacctccc cctgaacctg aaacataaaa   8760
tgaatgcaat tgttgttgtt aacttgttta ttgcagctta taatggttac aaataaagca   8820
atagcatcac aaatttcaca aataaagcat ttttttcact gcattctagt tgtggtttgt   8880
ccaaactcat caatgtaagt ttaaacggcg cgcctgaaat gtgtgggcgt ggcttaaggg   8940
tgggaaagaa tatataaggt gggggtctta tgtagttttg tatctgtttt gcagcagccg   9000
ccgccgccat gagcaccaac tcgtttgatg gaagcattgt gagctcatat ttgacaacgc   9060
gcatgccccc atgggccggg gtgcgtcaga atgtgatggg ctccagcatt gatggtcgcc   9120
ccgtcctgcc cgcaaactct actaccttga cctacgagac cgtgtctgga acgccgttgg   9180
agactgcagc ctccgccgcc gcttcagccg ctgcagccac cgcccgcggg attgtgactg   9240
actttgcttt cctgagcccg cttgcaagca gtgcagcttc ccgttcatcc gcccgcgatg   9300
acaagttgac ggctcttttg gcacaattgg attctttgac ccgggaactt aatgtcgttt   9360
ctcagcagct gttggatctg cgccagcagg tttctgccct gaaggcttcc tcccctccca   9420
atgcggttta aaacacaact tttctataca aagttgtaaa taaaaaacca gactctgttt   9480
ggatttggat caagctaagt gtcttgctgt ctttatttag ggttttgcg  cgcgcggtag   9540
gcccgggacc agcggtctcg gtcgttgagg gtcctgtgta tttttccag  gacgtggtaa   9600
aggtgactct ggatgttcag atacatgggc ataagcccgt ctctggggtg gaggtagcac   9660
cactgcagag cttcatgctg cggggtggtg ttgtagatga tccagtcgta gcaggagcgc   9720
tgggcgtggt gcctaaaaat gtctttcagt agcaagctga ttgccagggg caggcccttg   9780
gtgtaagtgt ttacaaagcg gttaagctgg gatgggtgca tacgtgggga tatgagatgc   9840
atcttggact gtatttttag gttggctatg ttcccagcca tatccctccg gggattcatg   9900
ttgtgcagaa ccaccagcac agtgtatccg gtgcacttgg gaaatttgtc atgtagctta   9960
gaaggaaatg cgtggaagaa cttggagacg cccttgtgac ctccaagatt ttccatgcat  10020
tcgtccataa tgatggcaat gggcccacgg gcggcggcct gggcgaagat atttctggga  10080
tcactaacgt catagttgtg ttccaggatg agatcgtcat aggccatttt tacaaagcgc  10140
gggcggaggg tgccagactg cggtataatg gttccatccg gcccaggggc gtagttaccc  10200
tcacagattt gcatttccca cgctttgagt tcagatgggg ggatcatgtc tacctgcggg  10260
gcgatgaaga aaacggtttc cggggtaggg gagatcagct gggaagaaag caggttcctg  10320
agcagctgcg acttaccgca gccggtgggc ccgtaaatca cacctattac cggctgcaac  10380
tggtagttaa gagagctgca gctgccgtca tccctgagca ggggggccac ttcgttaagc  10440
atgtccctga ctcgcatgtt ttccctgacc aaatccgcca gaaggcgctc gccgcccagc  10500
gatagcagtt cttgcaagga agcaaagttt ttcaacggtt tgagaccgtc cgccgtaggc  10560
atgcttttga gcgtttgacc aagcagttcc aggcggtccc acagctcggt cacctgctct  10620
acggcatctc gatccagcat atctcctcgt ttcgcgggtt ggggcggctt tcgctgtacg  10680
gcagtagtcg gtgctcgtcc agacgggcca gggtcatgtc tttccacggg cgcaggtcc   10740
```

-continued

```
tcgtcagcgt agtctgggtc acggtgaagg ggtgcgctcc gggctgcgcg ctggccaggg 10800
tgcgcttgag gctggtcctg ctggtgctga agcgctgccg gtcttcgccc tgcgcgtcgg 10860
ccaggtagca tttgaccatg gtgtcatagt ccagcccctc cgcggcgtgg cccttggcgc 10920
gcagcttgcc cttggaggag gcgccgcacg aggggcagtg cagacttttg agggcgtaga 10980
gcttgggcgc gagaaatacc gattccgggg agtaggcatc cgcgccgcag gccccgcaga 11040
cggtctcgca ttccacgagc caggtgagct ctggccgttc ggggtcaaaa accaggtttc 11100
ccccatgctt tttgatgcgt ttcttacctc tggtttccat gagccggtgt ccacgctcgg 11160
tgacgaaaag gctgtccgtg tccccgtata cagacttgag aggcctgtcc tcgagcggtg 11220
ttccgcggtc ctcctcgtat agaaactcgg accactctga gacaaaggct cgcgtccagg 11280
ccagcacgaa ggaggctaag tgggaggggt agcggtcgtt gtccactagg gggtccactc 11340
gctccagggt gtgaagacac atgtcgccct cttcggcatc aaggaaggtg attggtttgt 11400
aggtgtaggc cacgtgaccg ggtgttcctg aaggggggct ataaaagggg gtgggggcgc 11460
gttcgtcctc actctcttcc gcatcgctgt ctgcgagggc cagctgttgg ggtgagtact 11520
ccctctgaaa agcgggcatg acttctgcgc taagattgtc agtttccaaa aacgaggagg 11580
atttgatatt cacctggccc gcggtgatgc ctttgagggt ggccgcatcc atctggtcag 11640
aaaagacaat ctttttgttg tcaagcttgg tggcaaacga cccgtagagg gcgttggaca 11700
gcaacttggc gatggagcgc agggtttggt ttttgtcgcg atcggcgcgc tccttggccg 11760
cgatgtttag ctgcacgtat tcgcgcgcaa cgcaccgcca ttcgggaaag acggtggtgc 11820
gctcgtcggg caccaggtgc acgcgccaac cgcggttgtg cagggtgaca aggtcaacgc 11880
tggtggctac ctctccgcgt aggcgctcgt tggtccagca gaggcggccg cccttgcgcg 11940
agcagaatgg cggtaggggg tctagctgcg tctcgtccgg ggggtctgcg tccacggtaa 12000
agaccccggg cagcaggcgc gcgtcgaagt agtctatctt gcatccttgc aagtctagcg 12060
cctgctgcca tgcgcgggcg gcaagcgcgc gctcgtatgg gttgagtggg ggaccccatg 12120
gcatggggtg ggtgagcgcg gaggcgtaca tgccgcaaat gtcgtaaacg tagaggggct 12180
ctctgagtat tccaagatat gtagggtagc atcttccacc gcggatgctg gcgcgcacgt 12240
aatcgtatag ttcgtgcgag ggagcgagga ggtcgggacc gaggttgcta cgggcgggct 12300
gctctgctcg gaagactatc tgcctgaaga tggcatgtga gttggatgat atggttggac 12360
gctggaagac gttgaagctg gcgtctgtga gacctaccgc gtcacgcacg aaggaggcgt 12420
aggagtcgcg cagcttgttg accagctcgg cggtgacctg cacgtctagg gcgcagtagt 12480
ccagggtttc cttgatgatg tcatacttat cctgtccctt tttttccac agctcgcggt 12540
tgaggacaaa ctcttcgcgg tctttccagt actcttggat cggaaacccg tcggcctccg 12600
aacggtaaga gcctagcatg tagaactggt tgacggcctg gtaggcgcag catccctttt 12660
ctacgggtag cgcgtatgcc tgcgcggcct tccggagcga ggtgtgggtg agcgcaaagg 12720
tgtccctgac catgactttg aggtactggt atttgaagtc agtgtcgtcg catccgccct 12780
gctcccagag caaaaagtcc gtgcgctttt tggaacgcgg atttggcagg gcgaaggtga 12840
catcgttgaa gagtatcttt cccgcgcgag gcataaagtt gcgtgtgatg cggaagggtc 12900
ccggcacctc ggaacggttg ttaattacct gggcggcgag cacgatctcg tcaaagccgt 12960
tgatgttgtg gcccacaatg taaagttcca agaagcgcgg gatgcccttg atggaaggca 13020
attttttaag ttcctcgtag gtgagctctt caggggagct gagcccgtgc tctgaaaggg 13080
cccagtctgc aagatgaggg ttggaagcga cgaatgagct ccacaggtca cgggccatta 13140
```

```
gcatttgcag gtggtcgcga aaggtcctaa actggcgacc tatggccatt ttttctgggg  13200
tgatgcagta gaaggtaagc gggtcttgtt cccagcggtc ccatccaagg ttcgcggcta  13260
ggtctcgcgc ggcagtcact agaggctcat ctccgccgaa cttcatgacc agcatgaagg  13320
gcacgagctg cttcccaaag gcccccatcc aagtataggt ctctacatcg taggtgacaa  13380
agagacgctc ggtgcgagga tgcgagccga tcgggaagaa ctggatctcc cgccaccaat  13440
tggaggagtg gctattgatg tggtgaaagt agaagtccct gcgacgggcc gaacactcgt  13500
gctggctttt gtaaaaacgt gcgcagtact ggcagcggtg cacgggctgt acatcctgca  13560
cgaggttgac ctgacgaccg cgcacaagga agcagagtgg gaatttgagc ccctcgcctg  13620
gcgggtttgg ctggtggtct tctacttcgg ctgcttgtcc ttgaccgtct ggctgctcga  13680
ggggagttac ggtggatcgg accaccacgc cgcgcgagcc caaagtccag atgtccgcgc  13740
gcggcggtcg gagcttgatg acaacatcgc gcagatggga gctgtccatg gtctggagct  13800
cccgcggcgt caggtcaggc gggagctcct gcaggtttac ctcgcataga cgggtcaggg  13860
cgcgggctag atccaggtga tacctaattt ccaggggctg gttggtggcg gcgtcgatgg  13920
cttgcaagag gccgcatccc cgcggcgcga ctacggtacc gcgcggcggg cggtgggccg  13980
cgggggtgtc cttggatgat gcatctaaaa gcggtgacgc gggcgagccc ccggaggtag  14040
ggggggctcc ggacccgccg ggagaggggg caggggcacg tcggcgccgc gcgcgggcag  14100
gagctggtgc tgcgcgcgta ggttgctggc gaacgcgacg acgcggcggt tgatctcctg  14160
aatctggcgc ctctgcgtga agacgacggg cccggtgagc ttgaacctga aagagagttc  14220
gacagaatca atttcggtgt cgttgacggc ggcctggcgc aaaatctcct gcacgtctcc  14280
tgagttgtct tgataggcga tctcggccat gaactgctcg atctcttcct cctggagatc  14340
tccgcgtccg gctcgctcca cggtggcggc gaggtcgttg gaaatgcggg ccatgagctg  14400
cgagaaggcg ttgaggcctc cctcgttcca gacgcggctg tagaccacgc ccccttcggc  14460
atcgcgggcg cgcatgacca cctgcgcgag attgagctcc acgtgccggg cgaagacggc  14520
gtagtttcgc aggcgctgaa agaggtagtt gagggtggtg gcggtgtgtt ctgccacgaa  14580
gaagtacata acccagcgtc gcaacgtgga ttcgttgata tcccccaagg cctcaaggcg  14640
ctccatggcc tcgtagaagt ccacggcgaa gttgaaaaac tgggagttgc gcgccgacac  14700
ggttaactcc tcctccagaa gacggatgag ctcggcgaca gtgtcgcgca cctcgcgctc  14760
aaaggctaca ggggcctctt cttcttcttc aatctcctct tccataaggg cctccccttc  14820
ttcttcttct ggcggcggtg gggggagggg gacacggcgg cgacgacggc gcaccgggag  14880
gcggtcgaca aagcgctcga tcatctcccc gcggcgacgg cgcatggtct cggtgacggc  14940
gcggccgttc tcgcgggggc gcagttggaa gacgccgccc gtcatgtccc ggttatgggt  15000
tggcgggggg ctgccatgcg gcagggatac ggcgctaacg atgcatctca acaattgttg  15060
tgtaggtact ccgccgccga gggacctgag cgagtccgca tcgaccggat cggaaaacct  15120
ctcgagaaag gcgtctaacc agtcacagtc gcaaggtagg ctgagcaccg tggcgggcgg  15180
cagcgggcgg cggtcggggt tgtttctggc ggaggtgctg ctgatgatgt aattaaagta  15240
ggcggtcttg agacggcgga tggtcgacag aagcaccatg tccttgggtc cggcctgctg  15300
aatgcgcagg cggtcggcca tgccccaggc ttcgttttga catcggcgca ggtctttgta  15360
gtagtcttgc atgagccttt ctaccggcac ttcttcttct ccttcctctt gtcctgcatc  15420
tcttgcatct atcgctgcgg cggcggcgga gtttggccgt aggtggcgcc ctcttcctcc  15480
```

-continued

```
catgcgtgtg accccgaagc ccctcatcgg ctgaagcagg gctaggtcgg cgacaacgcg  15540
ctcggctaat atggcctgct gcacctgcgt gagggtagac tggaagtcat ccatgtccac  15600
aaagcggtgg tatgcgcccg tgttgatggt gtaagtgcag ttggccataa cggaccagtt  15660
aacggtctgg tgacccggct gcgagagctc ggtgtacctg agacgcgagt aagccctcga  15720
gtcaaatacg tagtcgttgc aagtccgcac caggtactgg tatcccacca aaaagtgcgg  15780
cggcggctgg cggtagaggg gccagcgtag ggtggccggg gctccggggg cgagatcttc  15840
caacataagg cgatgatatc cgtagatgta cctggacatc caggtgatgc cggcggcggt  15900
ggtggaggcg cgcggaaagt cgcggacgcg gttccagatg ttgcgcagcg gcaaaaagtg  15960
ctccatggtc gggacgctct ggccggtcag gcgcgcgcaa tcgttgacgc tctagaccgt  16020
gcaaaaggag agcctgtaag cgggcactct tccgtggtct ggtggataaa ttcgcaaggg  16080
tatcatggcg gacgaccggg gttcgagccc cgtatccggc cgtccgccgt gatccatgcg  16140
gttaccgccc gcgtgtcgaa cccaggtgtg cgacgtcaga caacgggga gtgctccttt  16200
tggcttcctt ccaggcgcgg cggctgctgc gctagctttt ttggccactg gccgcgcgca  16260
gcgtaagcgg ttaggctgga aagcgaaagc attaagtggc tcgctccctg tagccggagg  16320
gttattttcc aagggttgag tcgcgggacc cccggttcga gtctcggacc ggccggactg  16380
cggcgaacgg gggtttgcct ccccgtcatg caagaccccg cttgcaaatt cctccggaaa  16440
cagggacgag cccctttttt gcttttccca gatgcatccg gtgctgcggc agatgcgccc  16500
ccctcctcag cagcggcaag agcaagagca gcggcagaca tgcagggcac cctcccctcc  16560
tcctaccgcg tcaggagggg cgacatccgc ggttgacgcg gcagcagatg gtgattacga  16620
acccccgcgg cgccgggccc ggcactacct ggacttggag gagggcgagg gcctggcgcg  16680
gctaggagcg ccctctcctg agcggcaccc aagggtgcag ctgaagcgtg atacgcgtga  16740
ggcgtacgtg ccgcggcaga acctgtttcg cgaccgcgag ggagaggagc ccgaggagat  16800
gcgggatcga aagttccacg cagggcgcga gctgcggcat ggcctgaatc gcgagcggtt  16860
gctgcgcgag gaggactttg agcccgacgc gcgaaccggg attagtcccg cgcgcgcaca  16920
cgtggcggcc gccgacctgg taaccgcata cgagcagacg gtgaaccagg agattaactt  16980
tcaaaaaagc tttaacaacc acgtgcgtac gcttgtggcg cgcgaggagg tggctatagg  17040
actgatgcat ctgtgggact ttgtaagcgc gctggagcaa aacccaaata gcaagccgct  17100
catggcgcag ctgttcctta tagtgcagca cagcagggac aacgaggcat tcagggatgc  17160
gctgctaaac atagtagagc ccgagggccg ctggctgctc gatttgataa acatcctgca  17220
gagcatagtg gtgcaggagc gcagcttgag cctggctgac aaggtggccg ccatcaacta  17280
ttccatgctt agcctgggca agttttacgc ccgcaagata taccataccc cttacgttcc  17340
catagacaag gaggtaaaga tcgaggggtt ctacatgcgc atggcgctga aggtgcttac  17400
cttgagcgac gacctgggcg tttatcgcaa cgagcgcatc cacaaggccg tgagcgtgag  17460
ccggcggcgc gagctcagcg accgcgagct gatgcacagc ctgcaaaggg ccctggctgg  17520
cacgggcagc ggcgatagag aggccgagtc ctactttgac gcgggcgctg acctgcgctg  17580
ggccccaagc cgacgcgccc tggaggcagc tggggccgga cctgggctgg cggtggcacc  17640
cgcgcgcgct ggcaacgtcg gcggcgtgga ggaatatgac gaggacgatg agtacgagcc  17700
agaggacggc gagtactaag cggtgatgtt tctgatcaga tgatgcaaga cgcaacggac  17760
ccggcggtgc gggcggcgct gcagagccag ccgtccggcc ttaactccac ggacgactgg  17820
cgccaggtca tggaccgcat catgtcgctg actgcgcgca atcctgacgc gttccggcag  17880
```

```
cagccgcagg ccaaccggct ctccgcaatt ctggaagcgg tggtcccggc gcgcgcaaac  17940
cccacgcacg agaaggtgct ggcgatcgta aacgcgctgg ccgaaaacag ggccatccgg  18000
cccgacgagg ccggcctggt ctacgacgcg ctgcttcagc gcgtggctcg ttacaacagc  18060
ggcaacgtgc agaccaacct ggaccggctg gtgggggatg tgcgcgaggc cgtggcgcag  18120
cgtgagcgcg cgcagcagca gggcaacctg ggctccatgg ttgcactaaa cgccttcctg  18180
agtacacagc ccgccaacgt gccgcgggga caggaggact acaccaactt tgtgagcgca  18240
ctgcggctaa tggtgactga gacaccgcaa agtgaggtgt accagtctgg gccagactat  18300
tttttccaga ccagtagaca aggcctgcag accgtaaacc tgagccaggc tttcaaaaac  18360
ttgcaggggc tgtggggggt gcgggctccc acaggcgacc gcgcgaccgt gtctagcttg  18420
ctgacgccca actcgcgcct gttgctgctg ctaatagcgc ccttcacgga cagtggcagc  18480
gtgtcccggg acacatacct aggtcacttg ctgacactgt accgcgaggc cataggtcag  18540
gcgcatgtgg acgagcatac tttccaggag attacaagtg tcagccgcgc gctggggcag  18600
gaggacacgg gcagcctgga ggcaacccta aactacctgc tgaccaaccg gcggcagaag  18660
atcccctcgt tgcacagttt aaacagcgag gaggagcgca ttttgcgcta cgtgcagcag  18720
agcgtgagcc ttaacctgat gcgcgacggg gtaacgccca gcgtggcgct ggacatgacc  18780
gcgcgcaaca tggaaccggg catgtatgcc tcaaaccggc cgtttatcaa ccgcctaatg  18840
gactacttgc atcgcgcggc cgccgtgaac cccgagtatt tcaccaatgc catcttgaac  18900
ccgcactggc taccgccccc tggtttctac accgggggat tcgaggtgcc cgagggtaac  18960
gatggattcc tctgggacga catagacgac agcgtgtttt ccccgcaacc gcagaccctg  19020
ctagagttgc aacagcgcga gcaggcagag gcggcgctgc gaaaggaaag cttccgcagg  19080
ccaagcagct tgtccgatct aggcgctgcg gccccgcggt cagatgctag tagcccattt  19140
ccaagcttga tagggtctct taccagcact cgcaccaccc gcccgcgcct gctgggcgag  19200
gaggagtacc taaacaactc gctgctgcag ccgcagcgcg aaaaaaacct gcctccggca  19260
tttcccaaca acgggataga gagcctagtg gacaagatga gtagatggaa gacgtacgcg  19320
caggagcaca gggacgtgcc aggcccgcgc ccgcccaccc gtcgtcaaag gcacgaccgt  19380
cagcggggtc tggtgtggga ggacgatgac tcggcagacg acagcagcgt cctggatttg  19440
ggagggagtg gcaacccgtt tgcgcacctt cgccccaggc tggggagaat gttttaaaaa  19500
aaaaaaaaaa gcatgatgca aaataaaaaa ctcaccaagg ccatggcacc gagcgttggt  19560
tttcttgtat tccccttagt atgcggcgcg cggcgatgta tgaggaaggt cctcctccct  19620
cctacgagag tgtggtgagc gcggcgccag tggcggcggc gctgggttct cccttcgatg  19680
ctcccctgga cccgccgttt gtgcctccgc ggtacctgcg gcctaccggg gggagaaaca  19740
gcatccgtta ctctgagttg gcacccctat tcgacaccac ccgtgtgtac ctggtggaca  19800
acaagtcaac ggatgtggca tccctgaact accagaacga ccacagcaac tttctgacca  19860
cggtcattca aaacaatgac tacagcccgg gggaggcaag cacacagacc atcaatcttg  19920
acgaccggtc gcactggggc ggcgacctga aaaccatcct gcataccaac atgccaaatg  19980
tgaacgagtt catgtttacc aataagttta aggcgcgggt gatggtgtcg cgcttgccta  20040
ctaaggacaa tcaggtggag ctgaaatacg agtgggtgga gttcacgctg cccgagggca  20100
actactccga gaccatgacc atagacctta tgaacaacgc gatcgtggag cactacttga  20160
aagtgggcag acagaacggg gttctggaaa gcgacatcgg ggtaaagttt gacacccgca  20220
```

-continued

```
acttcagact ggggtttgac cccgtcactg gtcttgtcat gcctggggta tatacaaacg  20280
aagccttcca tccagacatc attttgctgc caggatgcgg ggtggacttc acccacagcc  20340
gcctgagcaa cttgttgggc atccgcaagc ggcaaccctt ccaggagggc tttaggatca  20400
cctacgatga tctggagggt ggtaacattc ccgcactgtt ggatgtggac gcctaccagg  20460
cgagcttgaa agatgacacc gaacagggcg ggggtggcgc aggcggcagc aacagcagtg  20520
gcagcggcgc ggaagagaac tccaacgcgg cagccgcggc aatgcagccg gtggaggaca  20580
tgaacgatca tgccattcgc ggcgacacct ttgccacacg ggctgaggag aagcgcgctg  20640
aggccgaagc agcggccgaa gctgccgccc ccgctgcgca acccgaggtc gagaagcctc  20700
agaagaaacc ggtgatcaaa cccctgacag aggacagcaa gaaacgcagt tacaacctaa  20760
taagcaatga cagcaccttc acccagtacc gcagctggta ccttgcatac aactacggcg  20820
accctcagac cggaatccgc tcatggaccc tgctttgcac tcctgacgta acctgcggct  20880
cggagcaggt ctactggtcg ttgccagaca tgatgcaaga ccccgtgacc ttccgctcca  20940
cgcgccagat cagcaacttt ccggtggtgg gcgccgagct gttgcccgtg cactccaaga  21000
gcttctacaa cgaccaggcc gtctactccc aactcatccg ccagtttacc tctctgaccc  21060
acgtgttcaa tcgctttccc gagaaccaga ttttggcgcg cccgccagcc cccaccatca  21120
ccaccgtcag tgaaaacgtt cctgctctca cagatcacgg gacgctaccg ctgcgcaaca  21180
gcatcggagg agtccagcga gtgaccatta ctgacgccag acgccgcacc tgcccctacg  21240
tttacaaggc cctgggcata gtctcgccgc gcgtcctatc gagccgcact ttttgagcaa  21300
gcatgtccat ccttatatcg cccagcaata acacaggctg gggcctgcgc ttcccaagca  21360
agatgtttgg cggggccaag aagcgctccg accaacaccc agtgcgcgtg cgcgggcact  21420
accgcgcgcc ctggggcgcg cacaaacgcg gccgcactgg gcgcaccacc gtcgatgacg  21480
ccatcgacgc ggtggtggag gaggcgcgca actacacgcc cacgccgcca ccagtgtcca  21540
cagtggacgc ggccattcag accgtggtgc gcggagcccg gcgctatgct aaaatgaaga  21600
gacggcggag gcgcgtagca cgtcgccacc gccgccgacc cggcactgcc gcccaacgcg  21660
cggcggcggc cctgcttaac cgcgcacgtc gcaccggccg acgggcggcc atgcgggccg  21720
ctcgaaggct ggccgcgggt attgtcactg tgcccccccag gtccaggcga cgagcggccg  21780
ccgcagcagc cgcggccatt agtgctatga ctcagggtcg caggggcaac gtgtattggg  21840
tgcgcgactc ggttagcggc ctgcgcgtgc ccgtgcgcac ccgcccccccg cgcaactaga  21900
ttgcaagaaa aaactactta gactcgtact gttgtatgta tccagcggcg gcggcgcgca  21960
acgaagctat gtccaagcgc aaaatcaaag aagagatgct ccaggtcatc gcgccggaga  22020
tctatggccc cccgaagaag gaagagcagg attacaagcc ccgaaagcta aagcgggtca  22080
aaaagaaaaa gaaagatgat gatgatgaac ttgacgacga ggtggaactg ctgcacgcta  22140
ccgcgcccag gcgacgggta cagtggaaag gtcgacgcgt aaaacgtgtt ttgcgacccg  22200
gcaccaccgt agtctttacg cccggtgagc gctccacccg cacctacaag cgcgtgtatg  22260
atgaggtgta cggcgacgag gacctgcttg agcaggccaa cgagcgcctc ggggagtttg  22320
cctacggaaa gcggcataag gacatgctgg cgttgccgct ggacgagggc aacccaacac  22380
ctagcctaaa gcccgtaaca ctgcagcagg tgctgcccgc gcttgcaccg tccgaagaaa  22440
agcgcggcct aaagcgcgag tctggtgact tggcacccac cgtgcagctg atggtaccca  22500
agcgccagcg actggaagat gtcttggaaa aaatgaccgt ggaacctggg ctggagcccg  22560
aggtccgcgt gcggccaatc aagcaggtgg cgccgggact gggcgtgcag accgtggacg  22620
```

-continued

```
ttcagatacc cactaccagt agcaccagta ttgccaccgc cacagagggc atggagacac  22680
aaacgtcccc ggttgcctca gcggtggcgg atgccgcggt gcaggcggtc gctgcggccg  22740
cgtccaagac ctctacggag gtgcaaacgg acccgtggat gtttcgcgtt tcagcccccc  22800
ggcgcccgcg ccgttcgagg aagtacggcg ccgccagcgc gctactgccc gaatatgccc  22860
tacatccttc cattgcgcct acccccggct atcgtggcta cacctaccgc cccagaagac  22920
gagcaactac ccgacgccga accaccactg gaacccgccg ccgccgtcgc cgtcgccagc  22980
ccgtgctggc cccgatttcc gtgcgcaggg tggctcgcga aggaggcagg accctggtgc  23040
tgccaacagc gcgctaccac cccagcatcg tttaaaagcc ggtctttgtg gttcttgcag  23100
atatggccct cacctgccgc ctccgtttcc cggtgccggg attccgagga agaatgcacc  23160
gtaggagggg catggccggc cacggcctga cgggcggcat gcgtcgtgcg caccaccggc  23220
ggcggcgcgc gtcgcaccgt cgcatgcgcg gcggtatcct gcccctcctt attccactga  23280
tcgccgcggc gattggcgcc gtgcccggaa ttgcatccgt ggccttgcag gcgcagagac  23340
actgattaaa aacaagttgc atgtggaaaa atcaaaataa aaagtctgga ctctcacgct  23400
cgcttggtcc tgtaactatt ttgtagaatg gaagacatca actttgcgtc tctggccccg  23460
cgacacggct cgcgcccgtt catgggaaac tggcaagata tcggcaccag caatatgagc  23520
ggtggcgcct tcagctgggg ctcgctgtgg agcggcatta aaaatttcgg ttccaccgtt  23580
aagaactatg gcagcaaggc ctggaacagc agcacaggcc agatgctgag ggataagttg  23640
aaagagcaaa atttccaaca aaaggtggta gatggcctgg cctctggcat tagcggggtg  23700
gtggacctgg ccaaccaggc agtgcaaaat aagattaaca gtaagcttga tccccgccct  23760
cccgtagagg agcctccacc ggccgtggag acagtgtctc cagaggggcg tggcgaaaag  23820
cgtccgcgcc ccgacaggga agaaactctg gtgacgcaaa tagacgagcc tccctcgtac  23880
gaggaggcac taaagcaagg cctgcccacc acccgtccca tcgcgcccat ggctaccgga  23940
gtgctgggcc agcacacacc cgtaacgctg gacctgcctc cccccgccga cacccagcag  24000
aaacctgtgc tgccaggccc gaccgccgtt gttgtaaccc gtcctagccg cgcgtccctg  24060
cgccgcgccg ccagcggtcc gcgatcgttg cggcccgtag ccagtggcaa ctggcaaagc  24120
acactgaaca gcatcgtggg tctgggggtg caatccctga agcgccgacg atgcttctga  24180
atagctaacg tgtcgtatgt gtgtcatgta tgcgtccatg tcgccgccag aggagctgct  24240
gagccgccgc gcgcccgctt tccaagatgg ctaccccttc gatgatgccg cagtggtctt  24300
acatgcacat ctcgggccag gacgcctcgg agtacctgag ccccgggctg gtgcagtttg  24360
cccgcgccac cgagacgtac ttcagcctga ataacaagtt tagaaacccc acggtggcgc  24420
ctacgcacga cgtgaccaca gaccggtccc agcgtttgac gctgcggttc atccctgtgg  24480
accgtgagga tactgcgtac tcgtacaagg cgcggttcac cctagctgtg ggtgataacc  24540
gtgtgctgga catggcttcc acgtactttg acatccgcgg cgtgctggac aggggcccta  24600
cttttaagcc ctactctggc actgcctaca acgccctggc tcccaagggt gccccaaatc  24660
cttgcgaatg ggatgaagct gctactgctc ttgaaataaa cctagaagaa gaggacgatg  24720
acaacgaaga cgaagtagac gagcaagctg agcagcaaaa aactcacgta tttgggcagg  24780
cgccttattc tggtataaat attacaaagg agggtattca aataggtgtc gaaggtcaaa  24840
cacctaaata tgccgataaa acatttcaac ctgaacctca aataggagaa tctcagtggt  24900
acgaaactga aattaatcat gcagctggga gagtccttaa aaagactacc ccaatgaaac  24960
```

catgttacgg ttcatatgca aaacccacaa atgaaaatgg agggcaaggc attcttgtaa 25020
agcaacaaaa tggaaagcta gaaagtcaag tggaaatgca atttttctca actactgagg 25080
cgaccgcagg caatggtgat aacttgactc ctaaagtggt attgtacagt gaagatgtag 25140
atatagaaac cccagacact catatttctt acatgcccac tattaaggaa ggtaactcac 25200
gagaactaat gggccaacaa tctatgccca acaggcctaa ttacattgct tttagggaca 25260
attttattgg tctaatgtat tacaacagca cgggtaatat gggtgttctg gcgggccaag 25320
catcgcagtt gaatgctgtt gtagatttgc aagacagaaa cacagagctt tcataccagc 25380
ttttgcttga ttccattggt gatagaacca ggtacttttc tatgtggaat caggctgttg 25440
acagctatga tccagatgtt agaattattg aaaatcatgg aactgaagat gaacttccaa 25500
attactgctt tccactggga ggtgtgatta atacagagac tcttaccaag gtaaaaccta 25560
aaacaggtca ggaaaatgga tgggaaaaag atgctacaga attttcagat aaaaatcaaa 25620
taagagttgg aaataatttt gccatggaaa tcaatctaaa tgccaacctg tggagaaatt 25680
tcctgtactc caacatagcg ctgtatttgc ccgacaagct aaagtacagt ccttccaacg 25740
taaaaatttc tgataaccca aacacctacg actacatgaa caagcgagtg gtggctcccg 25800
ggttagtgga ctgctacatt aaccttggag cacgctggtc ccttgactat atggacaacg 25860
tcaacccatt taaccaccac cgcaatgctg gcctgcgcta ccgctcaatg ttgctgggca 25920
atggtcgcta tgtgcccttc cacatccagg tgcctcagaa gttctttgcc attaaaaacc 25980
tccttctcct gccgggctca tacacctacg agtggaactt caggaaggat gttaacatgg 26040
ttctgcagag ctccctagga aatgacctaa gggttgacgg agccagcatt aagtttgata 26100
gcatttgcct ttacgccacc ttcttcccca tggcccacaa caccgcctcc acgcttgagg 26160
ccatgcttag aaacgacacc aacgaccagt cctttaacga ctatctctcc gccgccaaca 26220
tgctctaccc tatacccgcc aacgctacca acgtgcccat atccatcccc tcccgcaact 26280
gggcggcttt ccgcggctgg gccttcacgc gccttaagac taaggaaacc ccatcactgg 26340
gctcgggcta cgacccttat tacacctact ctggctctat accctaccta gatggaacct 26400
tttacctcaa ccacaccttt aagaaggtgg ccattacctt tgactcttct gtcagctggc 26460
ctggcaatga ccgcctgctt acccccaacg agtttgaaat taagcgctca gttgacgggg 26520
agggttacaa cgttgcccag tgtaacatga ccaaagactg gttcctggta caaatgctag 26580
ctaactacaa cattggctac cagggcttct atatcccaga gagctacaag gaccgcatgt 26640
actccttctt tagaaacttc cagcccatga gccgtcaggt ggtggatgat actaaataca 26700
aggactacca acaggtgggc atcctacacc aacacaacaa ctctggattt gttggctacc 26760
ttgcccccac catgcgcgaa ggacaggcct accctgctaa cttcccctat ccgcttatag 26820
gcaagaccgc agttgacagc attacccaga aaaagtttct ttgcgatcgc accctttggc 26880
gcatcccatt ctccagtaac tttatgtcca tgggcgcact cacagacctg ggccaaaacc 26940
ttctctacgc caactccgcc cacgcgctag acatgacttt tgaggtggat cccatggacg 27000
agcccaccct tctttatgtt ttgtttgaag tctttgacgt ggtccgtgtg caccggccgc 27060
accgcggcgt catcgaaacc gtgtacctgc gcacgccctt ctcggccggc aacgccacaa 27120
cataaagaag caagcaacat caacaacagc tgccgccatg ggctccagtg agcaggaact 27180
gaaagccatt gtcaaagatc ttggttgtgg gccatatttt ttgggcacct atgacaagcg 27240
ctttccaggc tttgtttctc cacacaagct cgcctgcgcc atagtcaata cggccggtcg 27300
cgagactggg ggcgtacact ggatggcctt tgcctggaac ccgcactcaa aaacatgcta 27360
cctctttgag ccctttggct tttctgacca gcgactcaag caggtttacc agtttgagta 27420
cgagtcactc ctgcgccgta gcgccattgc ttcttccccc gaccgctgta taacgctgga 27480
aaagtccacc caaagcgtac aggggcccaa ctcggccgcc tgtggactat tctgctgcat 27540
gtttctccac gcctttgcca actggcccca aactcccatg gatcacaacc ccaccatgaa 27600
ccttattacc ggggtaccca actccatgct caacagtccc caggtacagc ccaccctgcg 27660
tcgcaaccag gaacagctct acagcttcct ggagcgccac tcgccctact tccgcagcca 27720
cagtgcgcag attaggagcg ccacttcttt ttgtcacttg aaaaacatgt aaaaataatg 27780
tactagagac actttcaata aaggcaaatg cttttatttg tacactctcg ggtgattatt 27840
tacccccacc cttgccgtct gcgccgttta aaaatcaaag ggttctgccg cgcatcgct 27900
atgcgccact ggcagggaca cgttgcgata ctggtgttta gtgctccact taaactcagg 27960
cacaaccatc cgcggcagct cggtgaagtt ttcactccac aggctgcgca ccatcaccaa 28020
cgcgtttagc aggtcgggcg ccgatatctt gaagtcgcag ttggggcctc cgccctgcgc 28080
gcgcgagttg cgatacacag ggttgcagca ctggaacact atcagcgccg ggtggtgcac 28140
gctggccagc acgctcttgt cggagatcag atccgcgtcc aggtcctccg cgttgctcag 28200
ggcgaacgga gtcaactttg gtagctgcct tcccaaaaag ggcgcgtgcc caggctttga 28260
gttgcactcg caccgtagtg gcatcaaaag gtgaccgtgc ccggtctggg cgttaggata 28320
cagcgcctgc ataaaagcct tgatctgctt aaaagccacc tgagcctttg cgccttcaga 28380
gaagaacatg ccgcaagact tgccggaaaa ctgattggcc ggacaggccg cgtcgtgcac 28440
gcagcacctt gcgtcggtgt tggagatctg caccacattt cggccccacc ggttcttcac 28500
gatcttggcc ttgctagact gctccttcag cgcgcgctgc ccgttttcgc tcgtcacatc 28560
catttcaatc acgtgctcct tatttatcat aatgcttccg tgtagacact taagctcgcc 28620
ttcgatctca gcgcagcggt gcagccacaa cgcgcagccc gtgggctcgt gatgcttgta 28680
ggtcacctct gcaaacgact gcaggtacgc ctgcaggaat cgccccatca tcgtcacaaa 28740
ggtcttgttg ctggtgaagg tcagctgcaa cccgcggtgc tcctcgttca gccaggtctt 28800
gcatacggcc gccagagctt ccacttggtc aggcagtagt ttgaagttcg cctttagatc 28860
gttatccacg tggtacttgt ccatcagcgc gcgcgcagcc tccatgccct tctcccacgc 28920
agacacgatc ggcacactca gcgggttcat caccgtaatt tcactttccg cttcgctggg 28980
ctcttcctct tcctcttgcg tccgcatacc acgcgccact gggtcgtctt cattcagccg 29040
ccgcactgtg cgcttacctc ctttgccatg cttgattagc accggtgggt tgctgaaacc 29100
caccatttgt agcgccacat cttctctttc ttcctcgctg tccacgatta cctctggtga 29160
tggcgggcgc tcgggcttgg gagaagggcg cttctttttc ttcttgggcg caatggccaa 29220
atccgccgcc gaggtcgatg gccgcgggct gggtgtgcgc ggcaccagcg cgtcttgtga 29280
tgagtcttcc tcgtcctcgg actcgatacg ccgcctcatc cgcttttttg ggggcgcccg 29340
gggaggcggc ggcgacgggg acggggacga cacgtcctcc atggttgggg gacgtcgcgc 29400
cgcaccgcgt ccgcgctcgg gggtggtttc gcgctgctcc tcttcccgac tggccatttc 29460
cttctcctat aggcagaaaa agatcatgga gtcagtcgag aagaaggaca gcctaaccgc 29520
cccctctgag ttcgccacca ccgcctccac cgatgccgcc aacgcgccta ccaccttccc 29580
cgtcgaggca cccccgcttg aggaggagga agtgattatc gagcaggacc caggttttgt 29640
aagcgaagac gacgaggacc gctcagtacc aacagaggat aaaaagcaag accaggacaa 29700

```
cgcagaggca aacgaggaac aagtcgggcg gggggacgaa aggcatggcg actacctaga  29760
tgtgggagac gacgtgctgt tgaagcatct gcagcgccag tgcgccatta tctgcgacgc  29820
gttgcaagag cgcagcgatg tgcccctcgc catagcggat gtcagccttg cctacgaacg  29880
ccacctattc tcaccgcgcg taccccccaa acgccaagaa aacggcacat gcgagcccaa  29940
cccgcgcctc aacttctacc ccgtatttgc cgtgccagag gtgcttgcca cctatcacat  30000
ctttttccaa aactgcaaga tacccctatc ctgccgtgcc aaccgcagcc gagcggacaa  30060
gcagctggcc ttgcggcagg gcgctgtcat acctgatatc gcctcgctca acgaagtgcc  30120
aaaaatcttt gagggtcttg gacgcgacga gaagcgcgcg gcaaacgctc tgcaacagga  30180
aaacagcgaa aatgaaagtc actctggagt gttggtggaa ctcgagggtg acaacgcgcg  30240
cctagccgta ctaaaacgca gcatcgaggt cacccacttt gcctacccgg cacttaacct  30300
accccccaag gtcatgagca cagtcatgag tgagctgatc gtgcgccgtg cgcagcccct  30360
ggagagggat gcaaatttgc aagaacaaac agaggagggc ctacccgcag ttggcgacga  30420
gcagctagcg cgctggcttc aaacgcgcga gcctgccgac ttggaggagc gacgcaaact  30480
aatgatggcc gcagtgctcg ttaccgtgga gcttgagtgc atgcagcggt tctttgctga  30540
cccggagatg cagcgcaagc tagaggaaac attgcactac acctttcgac agggctacgt  30600
acgccaggcc tgcaagatct ccaacgtgga gctctgcaac ctggtctcct accttggaat  30660
tttgcacgaa aaccgccttg ggcaaaacgt gcttcattcc acgctcaagg gcgaggcgcg  30720
ccgcgactac gtccgcgact gcgtttactt atttctatgc tacacctggc agacggccat  30780
gggcgtttgg cagcagtgct tggaggagtg caacctcaag gagctgcaga aactgctaaa  30840
gcaaaacttg aaggacctat ggacggcctt caacgagcgc tccgtggccg cgcacctggc  30900
ggacatcatt ttccccgaac gcctgcttaa aaccctgcaa cagggtctgc cagacttcac  30960
cagtcaaagc atgttgcaga actttaggaa ctttatccta gagcgctcag gaatcttgcc  31020
cgccacctgc tgtgcacttc ctagcgactt tgtgcccatt aagtaccgcg aatgccctcc  31080
gccgctttgg ggccactgct accttctgca gctagccaac taccttgcct accactctga  31140
cataatggaa gacgtgagcg gtgacggtct actggagtgt cactgtcgct gcaacctatg  31200
caccccgcac cgctccctgg tttgcaattc gcagctgctt aacgaaagtc aaattatcgg  31260
tacctttgag ctgcagggtc cctcgcctga cgaaaagtcc gcggctccgg ggttgaaact  31320
cactccgggg ctgtggacgt cggcttacct tcgcaaattt gtacctgagg actaccacgc  31380
ccacgagatt aggttctacg aagaccaatc ccgcccgcca aatgcggagc ttaccgcctg  31440
cgtcattacc cagggccaca ttcttggcca attgcaagcc atcaacaaag cccgccaaga  31500
gtttctgcta cgaaagggac ggggggttta cttggacccc cagtccggcg aggagctcaa  31560
cccaatcccc ccgccgccgc agccctatca gcagcagccg cgggcccttg cttcccagga  31620
tggcacccaa aaagaagctg cagctgccgc cgccacccac ggacgaggag gaatactggg  31680
acagtcaggc agaggaggtt ttggacgagg aggaggagga catgatggaa gactgggaga  31740
gcctagacga ggaagcttcc gaggtcgaag aggtgtcaga cgaaacaccg tcaccctcgg  31800
tcgcattccc ctcgccggcg ccccagaaat cggcaaccgg ttccagcatg gctacaacct  31860
ccgctcctca ggcgccgccg gcactgcccg ttcgccgacc caaccgtaga tgggacacca  31920
ctggaaccag ggccggtaag tccaagcagc cgccgccgtt agcccaagag caacaacagc  31980
gccaaggcta ccgctcatgg cgcgggcaca agaacgccat agttgcttgc ttgcaagact  32040
gtgggggcaa catctccttc gcccgccgct ttcttctcta ccatcacggc gtggccttcc  32100
```

-continued cccgtaacat cctgcattac taccgtcatc tctacagccc atactgcacc ggcggcagcg 32160
gcagcggcag caacagcagc ggccacacag aagcaaaggc gaccggatag caagactctg 32220
acaaagccca agaaatccac agcggcggca gcagcaggag gaggagcgct gcgtctggcg 32280
cccaacgaac ccgtatcgac ccgcgagctt agaaacagga tttttcccac tctgtatgct 32340
atatttcaac agagcagggg ccaagaacaa gagctgaaaa taaaaaacag gtctctgcga 32400
tccctcaccc gcagctgcct gtatcacaaa agcgaagatc agcttcggcg cacgctggaa 32460
gacgcggagg ctctcttcag taaatactgc gcgctgactc ttaaggacta gtttcgcgcc 32520
ctttctcaaa tttaagcgcg aaaactacgt catctccagc ggccacaccc ggcgccagca 32580
cctgtcgtca gcgccatttc aactttgtat acaaaagttg tgatgagcaa ggaaattccc 32640
acgccctaca tgtggagtta ccagccacaa atgggacttg cggctggagc tgcccaagac 32700
tactcaaccc gaataaacta catgagcgcg ggaccccaca tgatatcccg ggtcaacgga 32760
atacgcgccc accgaaaccg aattctcctg gaacaggcgg ctattaccac cacacctcgt 32820
aataacctta atccccgtag ttggcccgct gccctggtgt accaggaaag tcccgctccc 32880
accactgtgg tacttcccag agacgcccag gccgaagttc agatgactaa ctcaggggcg 32940
cagcttgcgg gcggctttcg tcacagggtg cggtcgcccg ggcagggtat aactcacctg 33000
acaatcagag ggcgaggtat tcagctcaac gacgagtcgg tgagctcctc gcttggtctc 33060
cgtccggacg ggacatttca gatcggcggc gccggccgct cttcattcac gcctcgtcag 33120
gcaatcctaa ctctgcagac ctcgtcctct gagccgcgct ctggaggcat tggaactctg 33180
caatttattg aggagtttgt gccatcggtc tactttaacc ccttctcggg acctcccggc 33240
cactatccgg atcaatttat tcctaacttt gacgcggtaa aggactcggc ggacggctac 33300
gactgaatgt taagtggaga ggcagagcaa ctgcgcctga aacacctggt ccactgtcgc 33360
cgccacaagt gctttgcccg cgactccggt gagttttgct actttgaatt gcccgaggat 33420
catatcgagg gcccggcgca cggcgtccgg cttaccgccc agggagagct tgcccgtagc 33480
ctgattcggg agtttaccca gcgccccctg ctagttgagc gggacagggg accctgtgtt 33540
ctcactgtga tttgcaactg tcctaaccct ggattacatc aagatctttg ttgccatctc 33600
tgtgctgagt ataataaata cagaaattaa aatatactgg ggctcctatc gccatcctgt 33660
aaacgccacc gtcttcaccc gcccaagcaa accaaggcga accttacctg gtacttttaa 33720
catctctccc tctgtgattt acaacagttt caacccagac ggagtgagtc tacgagagaa 33780
cctctccgag ctcagctact ccatcagaaa aaacaccacc ctccttacct gccgggaacg 33840
tacgagtgcg tcaccggccg ctgcaccaca cctaccgcct gaccgtaaac cagacttttt 33900
ccggacagac ctcaataact ctgtttacca gaacaggagg tgagcttaga aaaccccttag 33960
ggtattaggc caaaggcgca gctactgtgg ggtttatgaa caattcaagc aactctacgg 34020
gctattctaa ttcaggtttc tctagaatcg gggttggggt tattctctgt cttgtgattc 34080
tctttattct tatactaacg cttctctgcc taaggctcgc cgcctgctgt gtgcacattt 34140
gcatttattg tcagcttttt aaacgctggg gtcgccaccc aagatgatta ggtacataat 34200
cctaggttta ctcacccttg cgtcagccca cggtaccacc caaaaggtgg attttaagga 34260
gccagcctgt aatgttacat tcgcagctga agctaatgag tgcaccactc ttataaaatg 34320
caccacagaa catgaaaagc tgcttattcg ccacaaaaac aaaattggca agtatgctgt 34380
ttatgctatt tggcagccag gtgacactac agagtataat gttacagttt tccagggtaa 34440
aagtcataaa acttttatgt atacttttcc attttatgaa atgtgcgaca ttaccatgta 34500
catgagcaaa cagtataagt tgtggccccc acaaaattgt gtggaaaaca ctggcacttt 34560
ctgctgcact gctatgctaa ttacagtgct cgctttggtc tgtaccctac tctatattaa 34620
atacaaaagc agacgcagct ttattgagga aaagaaaatg ccttaattta ctaagttaca 34680
aagctaatgt caccactaac tgctttactc gctgcttgca aaacaaattc aaaaagttag 34740
cattataatt agaataggat ttaaaccccc cggtcatttc ctgctcaata ccattcccct 34800
gaacaattga ctctatgtgg gatatgctcc agcgctacaa ccttgaagtc aggcttcctg 34860
gatgtcagca tctgactttg gccagcacct gtcccgcgga tttgttccag tccaactaca 34920
gcgacccacc ctaacagaga tgaccaacac aaccaacgcg gccgccgcta ccggacttac 34980
atctaccaca aatacacccc aagtttctgc ctttgtcaat aactgggata acttgggcat 35040
gtggtggttc tccatagcgc ttatgtttgt atgccttatt attatgtggc tcatctgctg 35100
cctaaagcgc aaacgcgccc gaccacccat ctatagtccc atcattgtgc tacacccaaa 35160
caatgatgga atccatagat tggacggact gaaacacatg ttcttttctc ttacagtatg 35220
attaaatgag acatgattcc tcgagttttt atattactga cccttgttgc gctttttttgt 35280 gcgtgctcca cattggctgc ggtttctcac atcgaagtag actgcattcc agccttcaca 35340
gtctatttgc tttacggatt tgtcaccctc acgctcatct gcagcctcat cactgtggtc 35400
atcgccttta tccagtgcat tgactgggtc tgtgtgcgct ttgcatatct cagacaccat 35460
ccccagtaca gggacaggac tatagctgag cttcttagaa ttctttaatt atgaaattta 35520
ctgtgacttt tctgctgatt atttgcaccc tatctgcgtt ttgttccccg acctccaagc 35580
ctcaaagaca tatatcatgc agattcactc gtatatggaa tattccaagt tgctacaatg 35640
aaaaaagcga tctttccgaa gcctggttat atgcaatcat ctctgttatg gtgttctgca 35700
gtaccatctt agccctagct atatatccct accttgacat tggctggaac gcaatagatg 35760
ccatgaacca cccaactttc cccgcgcccg ctatgcttcc actgcaacaa gttgttgccg 35820
gcggctttgt cccagccaat cagcctcgcc caccttctcc cacccccact gaaatcagct 35880
actttaatct aacaggagga gatgactgac accctagatc tagaaatgga cggaattatt 35940
acagagcagc gcctgctaga aagacgcagg gcagcggccg agcaacagcg catgaatcaa 36000
gagctccaag acatggttaa cttgcaccag tgcaaaaggg gtatcttttg tctggtaaag 36060
caggccaaag tcacctacga cagtaatacc accggacacc gccttagcta caagttgcca 36120
accaagcgtc agaaattggt ggtcatggtg ggagaaaagc ccattaccat aactcagcac 36180
tcggtagaaa ccgaaggctg cattcactca ccttgtcaag gacctgagga tctctgcacc 36240
cttattaaga ccctgtgcgg tctcaaagat cttattccct ttaactaata aaaaaaaata 36300
ataaagcatc acttacttaa aatcagttag caaatttctg tccagtttat tcagcagcac 36360
ctccttgccc tcctcccagc tctggtattg cagcttcctc ctggctgcaa actttctcca 36420
caatctaaat ggaatgtcag tttcctcctg ttcctgtcca tccgcaccca ctatcttcat 36480
gttgttgcag atgaagcgcg caagaccgtc tgaagatacc ttcaaccccg tgtatccata 36540
tgacacggaa accggtcctc caactgtgcc ttttcttact cctccctttg tatcccccaa 36600
tgggtttcaa gagagtcccc ctggggtact ctctttgcgc ctatccgaac ctctagttac 36660
ctccaatggc atgcttgcgc tcaaaatggg caacggcctc tctctggacg aggccggcaa 36720
ccttacctcc caaaatgtaa ccactgtgag cccacctctc aaaaaaacca agtcaaacat 36780
aaacctggaa atatctgcac ccctcacagt tacctcagaa gccctaactg tggctgccgc 36840

```
cgcacctcta atggtcgcgg gcaacacact caccatgcaa tcacaggccc cgctaaccgt  36900
gcacgactcc aaacttagca ttgccaccca aggacccctc acagtgtcag aaggaaagct  36960
agccctgcaa acatcaggcc ccctcaccac caccgatagc agtaccctta ctatcactgc  37020
ctcaccccct ctaactactg ccactggtag cttgggcatt gacttgaaag agcccattta  37080
tacacaaaat ggaaaactag gactaaagta cggggctcct ttgcatgtaa cagacgacct  37140
aaacactttg accgtagcaa ctggtccagg tgtgactatt aataatactt ccttgcaaac  37200
taaagttact ggagccttgg gttttgattc acaaggcaat atgcaactta atgtagcagg  37260
aggactaagg attgattctc aaaacagacg ccttatactt gatgttagtt atccgtttga  37320
tgctcaaaac caactaaatc taagactagg acagggccct ctttttataa actcagccca  37380
caacttggat attaactaca acaaaggcct ttacttgttt acagcttcaa acaattccaa  37440
aaagcttgag gttaacctaa gcactgccaa ggggttgatg tttgacgcta cagccatagc  37500
cattaatgca ggagatgggc ttgaatttgg ttcacctaat gcaccaaaca caaatcccct  37560
caaaacaaaa attggccatg gcctagaatt tgattcaaac aaggctatgg ttcctaaact  37620
aggaactggc cttagttttg acagcacagg tgccattaca gtaggaaaca aaaataatga  37680
taagctaact ttatggactg gaataaaccc tccacctaac tgtcaaattg tggaaaacac  37740
taatacaaat gatggcaaac ttactttagt attagtaaaa aacggagggc ttgttaatgg  37800
ctacgtgtct ctagttggtg tatcagacac tgtgaaccaa atgttcacac aaaagacagc  37860
aaacatccaa ttaagattat attttgactc ttctggaaat ctattaactg atgaatcaga  37920
cttaaaaatt ccacttaaaa ataaatcttc tacagcgacc agtgaaactg tagccagcag  37980
caaagccttt atgccaagta ctacagctta tcccttcaac accactacta gggatagtga  38040
aaactacatt catggaatat gttactacat gactagttat gatagaagtc tatttccctt  38100
gaacatttct ataatgctaa acagccgtat gatttcttcc aatgttgcct atgccataca  38160
atttgaatgg aatctaaatg caagtgaatc tccagaaagc aacatagcta cgctgaccac  38220
atccccccttt ttcttttctt acattacaga agacgacaac taataaagaa tcgtttgtgt  38280
tatgtttcaa cgtgtttatt tttcaattgc agaaaatttc aagtcatttt tcattcagta  38340
gtatagcccc accaccacat agcttataca gatcaccgta cctcaacttt gtataataaa  38400
gttgtaatca aactcacaga accctagtat tcaacctgcc acctccctcc caacacacag  38460
agtacacagt cctttctccc cggctggcct taaaaagcat catatcatgg gtaacagaca  38520
tattcttagg tgttatattc cacacggttt cctgtcgagc caaacgctca tcagtgatat  38580
taataaactc cccgggcagc tcacttaagt tcatgtcgct gtccagctgc tgagccacag  38640
gctgctgtcc aacttgcggt tgcttaacgg gcggcgaagg agaagtccac gcctacatgg  38700
gggtagagtc ataatcgtgc atcaggatag ggcggtggtg ctgcagcagc gcgcgaataa  38760
actgctgccg ccgccgctcc gtcctgcagg aatacaacat ggcagtggtc tcctcagcga  38820
tgattcgcac cgcccgcagc ataaggcgcc ttgtcctccg ggcacagcag cgcaccctga  38880
tctcacttaa atcagcacag taactgcagc acagcaccac aatattgttc aaaatcccac  38940
agtgcaaggc gctgtatcca aagctcatgg cggggaccac agaacccacg tggccatcat  39000
accacaagcg caggtagatt aagtggcgac ccctcataaa cacgctggac ataaacatta  39060
cctcttttgg catgttgtaa ttcaccacct cccggtacca tataaacctc tgattaaaca  39120
tggcgccatc caccaccatc ctaaaccagc tggccaaaac ctgcccgccg gctatacact  39180
```

-continued gcagggaacc gggactggaa caatgacagt ggagagccca ggactcgtaa ccatggatca 39240
tcatgctcgt catgatatca atgttggcac aacacaggca cacgtgcata cacttcctca 39300
ggattacaag ctcctcccgc gttagaacca tatcccaggg aacaacccat tcctgaatca 39360
gcgtaaatcc cacactgcag ggaagacctc gcacgtaact cacgttgtgc attgtcaaag 39420
tgttacattc gggcagcagc ggatgatcct ccagtatggt agcgcgggtt tctgtctcaa 39480
aaggaggtag acgatcccta ctgtacggag tgcgccgaga caaccgagat cgtgttggtc 39540
gtagtgtcat gccaaatgga acgccggacg tagtcatatt tcctgaagca aaaccaggtg 39600
cgggcgtgac aaacagatct gcgtctccgg tctcgccgct tagatcgctc tgtgtagtag 39660
ttgtagtata tccactctct caaagcatcc aggcgccccc tggcttcggg ttctatgtaa 39720
actccttcat gcgccgctgc cctgataaca tccaccaccg cagaataagc cacacccagc 39780
caacctacac attcgttctg cgagtcacac acgggaggag cgggaagagc tggaagaacc 39840
atgttttttt ttttattcca aaagattatc caaaacctca aaatgaagat ctattaagtg 39900
aacgcgctcc cctccggtgg cgtggtcaaa ctctacagcc aaagaacaga taatggcatt 39960
tgtaagatgt tgcacaatgg cttccaaaag gcaaacggcc ctcacgtcca agtggacgta 40020
aaggctaaac ccttcagggt gaatctcctc tataaacatt ccagcacctt caaccatgcc 40080
caaataattc tcatctcgcc accttctcaa tatatctcta agcaaatccc gaatattaag 40140
tccggccatt gtaaaaatct gctccagagc gccctccacc ttcagcctca agcagcgaat 40200
catgattgca aaaattcagg ttcctcacag acctgtataa gattcaaaag cggaacatta 40260
acaaaaatac cgcgatcccg taggtccctt cgcagggcca gctgaacata atcgtgcagg 40320
tctgcacgga ccagcgcggc cacttccccg ccaggaacca tgacaaaaga acccacactg 40380
attatgacac gcatactcgg agctatgcta accagcgtag ccccgatgta agcttgttgc 40440
atgggcggcg atataaaatg caaggtgctg ctcaaaaaat caggcaaagc ctcgcgcaaa 40500
aaagaaagca catcgtagtc atgctcatgc agataaaggc aggtaagctc cggaaccacc 40560
acagaaaaag acaccatttt tctctcaaac atgtctgcgg gtttctgcat aaacacaaaa 40620
taaaataaca aaaaaacatt taaacattag aagcctgtct tacaacagga aaaacaaccc 40680
ttataagcat aagacggact acggccatgc cggcgtgacc gtaaaaaaac tggtcaccgt 40740
gattaaaaag caccaccgac agctcctcgg tcatgtccgg agtcataatg taagactcgg 40800
taaacacatc aggttgattc acatcggtca gtgctaaaaa gcgaccgaaa tagcccgggg 40860
gaatacatac ccgcaggcgt agagacaaca ttacagcccc cataggaggt ataacaaaat 40920
taataggaga gaaaaacaca taaacacctg aaaaaccctc ctgcctaggc aaaatagcac 40980
cctcccgctc cagaacaaca tacagcgctt ccacagcggc agccataaca gtcagcctta 41040
ccagtaaaaa agaaaaccta ttaaaaaaac accactcgac acggcaccag ctcaatcagt 41100
cacagtgtaa aaaagggcca agtgcagagc gagtatatat aggactaaaa aatgacgtaa 41160
cggttaaagt ccacaaaaaa cacccagaaa accgcacgcg aacctacgcc cagaaacgaa 41220
agccaaaaaa cccacaactt cctcaaatcg tcacttccgt tttcccacgt tacgtcactt 41280
cccattttaa gaaaactaca attcccaaca catacaagtt actccgccct aaaacctacg 41340
tcacccgccc cgttcccacg ccccgcgcca cgtcacaaac tccacccccct cattatcata 41400
ttggcttcaa tccaaaataa ggtatattat tgatgatgta gggataacag ggtaatcagc 41460
tttcttgtac aaagttgaaa tccggggatc ctctagagtc gacctgcagg catgcaagct 41520
tggcgtaatc atggtcatag ctgtttcctg tgtgaaattg ttatccgctc acaattccac 41580
acaacatacg agccggaagc ataaagtgta aagcctgggg tgcctaatga gtgagcta 41638

<210> SEQ ID NO 11
<211> LENGTH: 39474
<212> TYPE: DNA
<213> ORGANISM: Artificial Sequence
<220> FEATURE:
<223> OTHER INFORMATION: Synthetic adenovirus construct (AdSyn-CO338)
<220> FEATURE:
<221> NAME/KEY: misc_feature
<222> LOCATION: (9137)..(9239)
<223> OTHER INFORMATION: miR142-3p binding sites

<400> SEQUENCE: 11
gttccactga gcgtcagacc ccttaataag atgatcttct tgagatcgtt ttggtctgcg 60
cgtaatctct tgctctgaaa acgaaaaaac cgccttgcag ggcggttttt cgaaggttct 120
ctgagctacc aactctttga accgaggtaa ctggcttgga ggagcgcagt caccaaaact 180
tgtcctttca gtttagcctt aaccggcgca tgacttcaag actaactcct ctaaatcaat 240
taccagtggc tgctgccagt ggtgcttttg catgtctttc cgggttggac tcaagacgat 300
agttaccgga taaggcgcag cggtcggact gaacgggggg ttcgtgcata cagtccagct 360
tggagcgaac tgcctacccg gaactgagtg tcaggcgtgg aatgagacaa acgcggccat 420
aacagcggaa tgacaccggt aaaccgaaag gcaggaacag gagagcgcac gagggagccg 480
ccaggggaaa cgcctggtat ctttatagtc ctgtcgggtt tcgccaccac tgatttgagc 540
gtcagatttc gtgatgcttg tcaggggggc ggagcctatg gaaaaacggc tttgccgcgg 600
ccctctcact tccctgttaa gtatcttcct ggcatcttcc aggaaatctc cgccccgttc 660
gtaagccatt tccgctcgcc gcagtcgaac gaccgagcgt agcgagtcag tgagcgagga 720
agcggaatat atcctgtatc acatattctg ctgacgcacc ggtgcagcct tttttctcct 780
gccacatgaa gcacttcact gacaccctca tcagtgccaa catagtaagc cagtatacac 840
tccgctagcg ctgaggtctg cctcgtgaag aaggtgttgc tgactcatac caggcctgaa 900
tcgccccatc atccagccag aaagtgaggg agccacggtt gatgagagct ttgttgtagg 960
tggaccagtt ggtgattttg aacttttgct ttgccacgga acggtctgcg ttgtcgggaa 1020
gatgcgtgat ctgatccttc aactcagcaa aagttcgatt tattcaacaa agccacgttg 1080
tgtctcaaaa tctctgatgt tacattgcac aagataaaaa tatatcatca tgaacaataa 1140
aactgtctgc ttacataaac agtaatacaa ggggtgttga tactctcagt acaatctgct 1200
ctgatgccgc atagttaagc cagtatctgc tccctgcttg tgtgttggag gtcgctgagt 1260
agtgcgcgag caaaatttaa gctacaacaa ggcaaggctt gaccgacaat tgcatgaaga 1320
atctgcttag ggttaggcgt tttgcgctgc ttcgcgatgt acgggccaga tatacgcgta 1380
tctgagggga ctagggtgtg tttaggcgaa aagcggggct tcggttgtac gcggttagga 1440
gtcccctcag gatatagtag tttcgctttt gcatagggag ggggaaatgt agtcttatgc 1500
aatactcttg tagtcttgca acatggtaac gatgagttag caacatgcct tacaaggaga 1560
gaaaaagcac cgtgcatgcc gattggtgga agtaaggtgg tacgatcgtg ccttattagg 1620
aaggcaacag acgggtctga catggattgg acgaaccact gaattccgca ttgcagagat 1680
attgtattta agtgcctagc tcgatacaat aaacgccatt tgaccattca ccacattggt 1740
gtgcacctcc aagctgggta cggatccggc cttgccggcc tcgagcggcc gctagcgccg 1800
ccactatggg atcaagatcg ccaaaaaaga agagaaaggt gccgaagaag catgcagcac 1860
caccaaaaaa aaaacgaaaa gtagaagacc cacgatttat gtacccatac gatgttcctg 1920
actatgcggg tatgaaaaac atcaaaaaaa accaggtaat gaacctgggt ccgaactcta 1980
aactgctgaa agaatacaaa tcccagctga tcgaactgaa catcgaacag ttcgaagcag 2040
gtatcggtct gatcctgggt gatgcttaca tccgttctcg tgatgaaggt aaaacctact 2100
gtatgcagtt cgagtggaaa aacaaagcat acatggacca cgtatgtctg ctgtacgatc 2160
agtgggtact gtccccgccg cacaaaaaag aacgtgttaa ccacctgggt aacctggtaa 2220
tcacctgggg cgcccagact ttcaaacacc aagctttcaa caaactggct aacctgttca 2280
tcgttaacaa caaaaaaacc atcccgaaca acctggttga aaactacctg accccgatgt 2340
ctctggcata ctggttcatg gatgatggtg gtaaatggga ttacaacaaa aactctacca 2400
acaaatcgat cgtactgaac acccagtctt tcactttcga agaagtagaa tacctggtta 2460
agggtctgcg taacaaattc caactgaact gttacgtaaa aatcaacaaa aacaaaccga 2520
tcatctacat cgattctatg tcttacctga tcttctacaa cctgatcaaa ccgtacctga 2580
tcccgcagat gatgtacaaa ctgccgaaca ctatctcctc cgaaactttc ctgaaataag 2640
gtaccgatcc agacatgata agatacattg atgagtttgg acaaaccaca actagaatgc 2700
agtgaaaaaa atgctttatt tgtgaaattt gtgatgctat tgctttattt gtaaccatta 2760
taagctgcaa taaacaagtt aacaacaaca attgcattca ttttatgttt caggttcagg 2820
gggaggtgtg ggaggttttt taaagcaagt aaaacctcta caaatgtggt atggctgatt 2880
atgatcatcg taaacttggt ctgacagtta ccaatgctta atcagtgagg cacctatctc 2940
agcgatctgt ctatttcgtt catccatagt tgcctgactc cccgtcgtgt agataactac 3000
gatacgggag ggcttaccat ctggccccag tgctgcaatg ataccgcgag acccacgctc 3060
accggctcca gatttatcag caataaacca gccagccgga agggccgagc gcagaagtgg 3120
tcctgcaact ttatccgcct ccatccagtc tattaattgt tgccgggaag ctagagtaag 3180
tagttcgcca gttaatagtt tgcgcaacgt tgttgccatt gctacaggca tcgtggtgtc 3240
acgctcgtcg tttggtatgg cttcattcag ctccggttcc caacgatcaa ggcgagttac 3300
atgatccccc atgttgtgca aaaaagcggt tagctccttc ggtcctccga tcgttgtcag 3360
aagtaagttg gccgcagtgt tatcactcat ggttatggca gcactgcata attctcttac 3420
tgtcatgcca tccgtaagat gcttttctgt gactggtgag tactcaacca agtcattctg 3480
agaatagtgt atgcggcgac cgagttgctc ttgcccggcg tcaatacggg ataataccgc 3540
gccacatagc agaactttaa aagtgctcat cattggaaaa cgttcttcgg ggcgaaaact 3600
ctcaaggatc ttaccgctgt tgagatccag ttcgatgtaa cccactcgtg cacccaactg 3660
atcttcagca tcttttactt tcaccagcgt ttctgggtga gcaaaaacag gaaggcaaaa 3720
tgccgcaaaa aagggaataa gggcgacacg gaaatgttga atactcatac tcttcctttt 3780
tcaatattat tgaagcattt atcagggtta ttgtctcatg agcggataca tatttgaatg 3840
tatttagaaa aataaacaaa taggggttcc gcgcacattt ccccgaaaag tgccacctga 3900
cgtctaagaa accattatta tcatgacatt aacctataaa aataggcgta tcacgaggcc 3960
ctttcgtctc gcgcgtttcg gtgatgacgg tgaaaacctc tgacacatgc agctcccgga 4020
gacggtcaca gcttgtctgt aagcggatgc cgggagcaga caagcccgtc agggcgcgtc 4080
agcgggtgtt ggcgggtgtc ggggctggct taactatgcg gcatcagagc agattgtact 4140
gagagtgcac catatgcggt gtgaaatacc gcacagatgc gtaaggagaa aataccgcat 4200
caggcgccat tcgccattca ggctgcgcaa ctgttgggaa gggcgatcgg tgcgggcctc 4260
ttcgctatta cgccagctgg cgaaaggggg atgtgctgca aggcgattaa gttgggtaac 4320
gccagggttt tcccagtcac gacgttgtaa aacgacggcc agtgaattac aactttgtac 4380
aaaaaagcag attaccctgt tatccctaca tcatcaataa tataccttat tttggattga 4440
agccaatatg ataatgaggg ggtggagttt gtgacgtggc gcggggcgtg ggaacggggc 4500
gggtgacgta gtagtgtggc ggaagtgtga tgttgcaagt gtggcggaac acatgtaagc 4560
gacggatgtg gcaaaagtga cgtttttggt gtgcgccggt gtacacagga agtgacaatt 4620
ttcgcgcggt tttaggcgga tgttgtagta aatttgggcg taaccgagta agatttggcc 4680
attttcgcgg gaaaactgaa taagaggaag tgaaatctga ataattttgt gttactcata 4740
gcgcgtaata tttgtctagg gccgcgggga ctttgaccgt ttacgtggag actcgcccag 4800
gtgtttttct caggtgtttt ccgcgttccg ggtcaaagtt ggcgttttat tattaaaccg 4860
tattaccgcc atgcattagt tattaatagt aatttaatgg agtgcctcgt gaggctccgg 4920
tgcccgtcag tgggcagagc gcacatcgcc cacagtcccc gagaagttgg ggggaggggt 4980
cggcaattga accggtgcct agagaaggtg gcgcggggta aactgggaaa gtgatgtcgt 5040
gtactggctc cgcctttttc ccgagggtgg gggagaaccg tatataagtg cagtagtcgc 5100
cgtgaacgtt ctttttcgca acgggtttgc cgccagaaca caggtaagtg ccgtgtgtgg 5160
ttcccgcggg cctggcctct ttacgggtta tggcccttgc gtgccttgaa ttacttccac 5220
ctggctgcag tacgtgattc ttgatcccga gcttcgggtt ggaagtgggt gggagagttc 5280
gaggccttgc gcttaaggag ccccttcgcc tcgtgcttga gttgaggcct ggcctgggcg 5340
ctggggccgc cgcgtgcgaa tctggtggca ccttcgcgcc tgtctcgctg ctttcgataa 5400
gtctctagcc atttaaaatt tttgatgacc tgctgcgacg ctttttttct ggcaagatag 5460
tcttgtaaat gcgggccaag atctgcacac tggtatttcg gtttttgggg ccgcgggcgg 5520
cgacggggcc cgtgcgtccc agcgcacatg ttcggcgagg cggggcctgc gagcgcggcc 5580
accgagaatc ggacgggggt agtctcaagc tggccggcct gctctggtgc ctggcctcgc 5640
gccgccgtgt atcgccccgc cctgggcggc aaggctggcc cggtcggcac cagttgcgtg 5700
agcggaaaga tggccgcttc ccggccctgc tgcagggagc tcaaaatgga ggacgcggcg 5760
ctcgggagag cgggcgggtg agtcacccac acaaaggaaa agggcctttc cgtcctcagc 5820
cgtcgcttca tgtgactcca cggagtaccg ggcgccgtcc aggcacctcg attagttctc 5880
gagcttttgg agtacgtcgt ctttaggttg gggggagggg ttttatgcga tggagtttcc 5940
ccacactgag tgggtggaga ctgaagttag gccagcttgg cacttgatgt aattctcctt 6000
ggaatttgcc ctttttgagt ttggatcttg gttcattctc aagcctcaga cagtggttca 6060
aagttttttt cttccatttc aggtgtcgtg atcagatctc gagctcaagc ttcgaattct 6120
gcagtcgacg gtaccggatc catggaagac gccaaaaaca taaagaaagg cccggcgcca 6180
ttctatccgc tggaagatgg aaccgctgga gagcaactgc ataaggctat gaagagatac 6240
gccctggttc ctggaacaat tgcttttaca gatgcacata tcgaggtgga catcacttac 6300
gctgagtact tcgaaatgtc cgttcggttg gcagaagcta tgaaacgata tgggctgaat 6360
acaaatcaca gaatcgtcgt atgcagtgaa aactctcttc aattctttat gccggtgttg 6420
ggcgcgttat ttatcggagt tgcagttgcg cccgcgaacg acatttataa tgaacgtgaa 6480
ttgctcaaca gtatgggcat ttcgcagcct accgtggtgt tcgtttccaa aaaggggttg 6540
caaaaaattt tgaacgtgca aaaaaagctc ccaatcatcc aaaaaattat tatcatggat 6600

-continued

```
tctaaaacgg attaccaggg atttcagtcg atgtacacgt tcgtcacatc tcatctacct   6660
cccggtttta atgaatacga ttttgtgcca gagtccttcg atagggacaa gacaattgca   6720
ctgatcatga actcctctgg atctactggt ctgcctaaag gtgtcgctct gcctcataga   6780
actgcctgcg tgagattctc gcatgccaga gatcctattt ttggcaatca aatcattccg   6840
gatactgcga ttttaagtgt tgttccattc catcacggtt ttggaatgtt tactacactc   6900
ggatatttga tatgtggatt tcgagtcgtc ttaatgtata gatttgaaga agagctgttt   6960
ctgaggagcc ttcaggatta caagattcaa agtgcgctgc tggtgccaac cctattctcc   7020
ttcttcgcca aaagcactct gattgacaaa tacgatttat ctaatttaca cgaaattgct   7080
tctggtggcg ctcccctctc taaggaagtc ggggaagcgg ttgccaagag gttccatctg   7140
ccaggtatca ggcaaggata tgggctcact gagactacat cagctattct gattacaccc   7200
gagggggatg ataaaccggg cgcggtcggt aaagttgttc cattttttga agcgaaggtt   7260
gtggatctgg ataccgggaa aacgctgggc gttaatcaaa gaggcgaact gtgtgtgaga   7320
ggtcctatga ttatgtccgg ttatgtaaac aatccggaag cgaccaacgc cttgattgac   7380
aaggatggat ggctacattc tggagacata gcttactggg acgaagacga acacttcttc   7440
atcgttgacc gcctgaagtc tctgattaag tacaaaggct atcaggtggc tcccgctgaa   7500
ttggaatcca tcttgctcca acaccccaac atcttcgacg caggtgtcgc aggtcttccc   7560
gacgatgacg ccggtgaact tcccgccgcc gttgttgttt tggagcacgg aaagacgatg   7620
acggaaaaag agatcgtgga ttacgtcgcc agtcaagtaa caaccgcgaa aaagttgcgc   7680
ggaggagttg tgtttgtgga cgaagtaccg aaaggtctta ccggaaaact cgacgcaaga   7740
aaaatcagag agatcctcat aaaggccaag aagggcggaa agatcgccgt ggcagccgca   7800
gccaccatgg tgagcaaggg cgaggagctg ttcaccgggg tggtgcccat cctggtcgag   7860
ctggacggcg acgtaaacgg ccacaagttc agcgtgtccg gcgagggcga gggcgatgcc   7920
acctacggca agctgaccct gaagttcatc tgcaccaccg gcaagctgcc cgtgccctgg   7980
cccaccctcg tgaccaccct gacctacggc gtgcagtgct tcagccgcta ccccgaccac   8040
atgaagcagc acgacttctt caagtccgcc atgcccgaag gctacgtcca ggagcgcacc   8100
atcttcttca aggacgacgg caactacaag acccgcgccg aggtgaagtt cgagggcgac   8160
accctggtga accgcatcga gctgaagggc atcgacttca aggaggacgg caacatcctg   8220
gggcacaagc tggagtacaa ctacaacagc cacaacgtct atatcatggc cgacaagcag   8280
aagaacggca tcaaggtgaa cttcaagatc cgccacaaca tcgaggacgg cagcgtgcag   8340
ctcgccgacc actaccagca gaacaccccc atcggcgacg gccccgtgct gctgcccgac   8400
aaccactacc tgagcaccca gtccgccctg agcaaagacc ccaacgagaa gcgcgatcac   8460
atggtcctgc tggagttcgt gaccgccgcc gggatcactc tcggcatgga cgagctgtac   8520
aagtaaagcg actctagatc ataatcagct caacctctgg attacaaaat ttgtgaaaga   8580
ttgactggta ttcttaacta tgttgctcct tttacgctat gtggatacgc tgctttaatg   8640
cctttgtatc atgctattgc ttcccgtatg gctttcattt tctcctcctt gtataaatcc   8700
tggttgctgt ctctttatga ggagttgtgg cccgttgtca ggcaacgtgg cgtggtgtgc   8760
actgtgtttg ctgacgcaac ccccactggt tggggcattg ccaccacctg tcagctcctt   8820
tccgggactt tcgctttccc cctccctatt gccacggcgg aactcatcgc cgcctgcctt   8880
gcccgctgct ggacaggggc tcggctgttg ggcactgaca attccgtggt gttgtcgggg   8940
aagctgacgt cctttccatg gctgctcgcc tgtgttgcca cctggattct gcgcgggacg   9000
```

-continued

```
tccttctgct acgtcccttc ggccctcaat ccagcggacc ttccttcccg cggcctgctg   9060
ccggctctgc ggcctcttcc gcgtcttcgc cttcgccctc agacgagtcg gatctccctt   9120
tgggccatac cacatttcca taaagtagga aacactacat ctatccataa agtaggaaac   9180
actacatttt ccataaagta ggaaacacta catctatcca taaagtagga aacactacaa   9240
aatgtagagg ttttacttgc tttaaaaaac ctcccacacc tccccctgaa cctgaaacat   9300
aaaatgaatg caattgttgt tgttaacttg tttattgcag cttataatgg ttacaaataa   9360
agcaatagca tcacaaattt cacaaataaa gcattttttt cactgcattc tagttgtggt   9420
ttgtccaaac tcatcaatgt aagtttaaac ggcgcgcctg aaatgtgtgg gcgtggctta   9480
agggtgggaa agaatatata aggtgggggt cttatgtagt tttgtatctg ttttgcagca   9540
gccgccgccg ccatgagcac caactcgttt gatggaagca ttgtgagctc atatttgaca   9600
acgcgcatgc ccccatgggc cggggtgcgt cagaatgtga tgggctccag cattgatggt   9660
cgccccgtcc tgcccgcaaa ctctactacc ttgacctacg agaccgtgtc tggaacgccg   9720
ttggagactg cagcctccgc cgccgcttca gccgctgcag ccaccgcccg cgggattgtg   9780
actgactttg ctttcctgag cccgcttgca agcagtgcag cttcccgttc atccgcccgc   9840
gatgacaagt tgacggctct tttggcacaa ttggattctt tgacccggga acttaatgtc   9900
gtttctcagc agctgttgga tctgcgccag caggtttctg ccctgaaggc ttcctcccct   9960
cccaatgcgg tttaaaacac aactttttcta tacaaagttg taaataaaaa accagactct  10020
gtttggattt ggatcaagct aagtgtcttg ctgtctttat ttaggggttt tgcgcgcgcg  10080
gtaggcccgg gaccagcggt ctcggtcgtt gagggtcctg tgtatttttt ccaggacgtg  10140
gtaaaggtga ctctggatgt tcagatacat gggcataagc ccgtctctgg ggtggaggta  10200
gcaccactgc agagcttcat gctgcggggt ggtgttgtag atgatccagt cgtagcagga  10260
gcgctgggcg tggtgcctaa aaatgtcttt cagtagcaag ctgattgcca ggggcaggcc  10320
cttggtgtaa gtgtttacaa agcggttaag ctgggatggg tgcatacgtg gggatatgag  10380
atgcatcttg gactgtattt ttaggttggc tatgttccca gccatatccc tccggggatt  10440
catgttgtgc agaaccacca gcacagtgta tccggtgcac ttgggaaatt tgtcatgtag  10500
cttagaagga aatgcgtgga agaacttgga gacgcccttg tgacctccaa gattttccat  10560
gcattcgtcc ataatgatgg caatgggccc acgggcggcg gcctgggcga agatatttct  10620
gggatcacta acgtcatagt tgtgttccag gatgagatcg tcataggcca tttttacaaa  10680
gcgcgggcgg agggtgccag actgcggtat aatggttcca tccggcccag gggcgtagtt  10740
accctcacag atttgcattt cccacgcttt gagttcagat ggggggatca tgtctacctg  10800
cggggcgatg aagaaaacgg tttccggggt aggggagatc agctgggaag aaagcaggtt  10860
cctgagcagc tgcgacttac cgcagccggt gggcccgtaa atcacaccta ttaccggctg  10920
caactggtag ttaagagagc tgcagctgcc gtcatccctg agcagggggg ccacttcgtt  10980
aagcatgtcc ctgactcgca tgttttccct gaccaaatcc gccagaaggc gctcgccgcc  11040
cagcgatagc agttcttgca aggaagcaaa gtttttcaac ggtttgagac cgtccgccgt  11100
aggcatgctt ttgagcgttt gaccaagcag ttccaggcgg tcccacagct cggtcacctg  11160
ctctacggca tctcgatcca gcatatctcc tcgtttcgcg ggttggggcg gctttcgctg  11220
tacggcagta gtcggtgctc gtccagacgg gccagggtca tgtctttcca cgggcgcagg  11280
gtcctcgtca gcgtagtctg ggtcacggtg aaggggtgcg ctccgggctg cgcgctggcc  11340
```

-continued

```
agggtgcgct tgaggctggt cctgctggtg ctgaagcgct gccggtcttc gccctgcgcg  11400
tcggccaggt agcatttgac catggtgtca tagtccagcc cctccgcggc gtggcccttg  11460
gcgcgcagct tgcccttgga ggaggcgccg cacgaggggc agtgcagact tttgagggcg  11520
tagagcttgg gcgcgagaaa taccgattcc ggggagtagg catccgcgcc gcaggccccg  11580
cagacggtct cgcattccac gagccaggtg agctctggcc gttcggggtc aaaaaccagg  11640
tttcccccat gctttttgat gcgtttctta cctctggttt ccatgagccg gtgtccacgc  11700
tcggtgacga aaaggctgtc cgtgtccccg tatacagact tgagaggcct gtcctcgagc  11760
ggtgttccgc ggtcctcctc gtatagaaac tcggaccact ctgagacaaa ggctcgcgtc  11820
caggccagca cgaaggaggc taagtgggag gggtagcggt cgttgtccac tagggggtcc  11880
actcgctcca gggtgtgaag acacatgtcg ccctcttcgg catcaaggaa ggtgattggt  11940
ttgtaggtgt aggccacgtg accgggtgtt cctgaagggg ggctataaaa gggggtgggg  12000
gcgcgttcgt cctcactctc ttccgcatcg ctgtctgcga gggccagctg ttggggtgag  12060
tactccctct gaaaagcggg catgacttct gcgctaagat tgtcagtttc caaaaacgag  12120
gaggatttga tattcacctg gcccgcggtg atgcctttga gggtggccgc atccatctgg  12180
tcagaaaaga caatcttttt gttgtcaagc ttggtggcaa acgacccgta gagggcgttg  12240
gacagcaact tggcgatgga gcgcagggtt tggtttttgt cgcgatcggc gcgctccttg  12300
gccgcgatgt ttagctgcac gtattcgcgc gcaacgcacc gccattcggg aaagacggtg  12360
gtgcgctcgt cgggcaccag gtgcacgcgc caaccgcggt tgtgcagggt gacaaggtca  12420
acgctggtgg ctacctctcc gcgtaggcgc tcgttggtcc agcagaggcg gccgcccttg  12480
cgcgagcaga atggcggtag gggtctagc tgcgtctcgt ccgggggggtc tgcgtccacg  12540
gtaaagaccc cgggcagcag gcgcgcgtcg aagtagtcta tcttgcatcc ttgcaagtct  12600
agcgcctgct gccatgcgcg ggcggcaagc gcgcgctcgt atgggttgag tgggggaccc  12660
catggcatgg ggtgggtgag cgcggaggcg tacatgccgc aaatgtcgta aacgtagagg  12720
ggctctctga gtattccaag atatgtaggg tagcatcttc caccgcggat gctggcgcgc  12780
acgtaatcgt atagttcgtg cgagggagcg aggaggtcgg gaccgaggtt gctacgggcg  12840
ggctgctctg ctcggaagac tatctgcctg aagatggcat gtgagttgga tgatatggtt  12900
ggacgctgga agacgttgaa gctggcgtct gtgagaccta ccgcgtcacg cacgaaggag  12960
gcgtaggagt cgcgcagctt gttgaccagc tcggcggtga cctgcacgtc tagggcgcag  13020
tagtccaggg tttccttgat gatgtcatac ttatcctgtc cctttttttt ccacagctcg  13080
cggttgagga caaactcttc gcggtctttc cagtactctt ggatcggaaa cccgtcggcc  13140
tccgaacggt aagagcctag catgtagaac tggttgacgg cctggtaggc gcagcatccc  13200
ttttctacgg gtagcgcgta tgcctgcgcg gccttccgga gcgaggtgtg ggtgagcgca  13260
aaggtgtccc tgaccatgac tttgaggtac tggtatttga agtcagtgtc gtcgcatccg  13320
ccctgctccc agagcaaaaa gtccgtgcgc tttttggaac gcggatttgg cagggcgaag  13380
gtgacatcgt tgaagagtat ctttcccgcg cgaggcataa agttgcgtgt gatgcggaag  13440
ggtcccggca cctcggaacg gttgttaatt acctgggcgg cgagcacgat ctcgtcaaag  13500
ccgttgatgt tgtggcccac aatgtaaagt tccaagaagc gcgggatgcc cttgatggaa  13560
ggcaattttt taagttcctc gtaggtgagc tcttcagggg agctgagccc gtgctctgaa  13620
agggcccagt ctgcaagatg agggttggaa gcgacgaatg agctccacag gtcacgggcc  13680
attagcattt gcaggtggtc gcgaaaggtc ctaaactggc gacctatggc catttttct  13740
```

```
ggggtgatgc agtagaaggt aagcgggtct tgttcccagc ggtcccatcc aaggttcgcg  13800
gctaggtctc gcgcggcagt cactagaggc tcatctccgc cgaacttcat gaccagcatg  13860
aagggcacga gctgcttccc aaaggccccc atccaagtat aggtctctac atcgtaggtg  13920
acaaagagac gctcggtgcg aggatgcgag ccgatcggga agaactggat ctcccgccac  13980
caattggagg agtggctatt gatgtggtga aagtagaagt ccctgcgacg ggccgaacac  14040
tcgtgctggc ttttgtaaaa acgtgcgcag tactggcagc ggtgcacggg ctgtacatcc  14100
tgcacgaggt tgacctgacg accgcgcaca aggaagcaga gtgggaattt gagcccctcg  14160
cctggcgggt ttggctggtg gtcttctact tcggctgctt gtccttgacc gtctggctgc  14220
tcgaggggag ttacggtgga tcggaccacc acgccgcgcg agcccaaagt ccagatgtcc  14280
gcgcgcggcg gtcggagctt gatgacaaca tcgcgcagat gggagctgtc catggtctgg  14340
agctcccgcg gcgtcaggtc aggcgggagc tcctgcaggt ttacctcgca tagacgggtc  14400
agggcgcggg ctagatccag gtgataccta atttccaggg gctggttggt ggcggcgtcg  14460
atggcttgca agaggccgca tccccgcggc gcgactacgg taccgcgcgg cgggcggtgg  14520
gccgcggggg tgtccttgga tgatgcatct aaaagcggtg acgcgggcga gcccccggag  14580
gtaggggggg ctccggaccc gccgggagag ggggcagggg cacgtcggcg ccgcgcgcgg  14640
gcaggagctg gtgctgcgcg cgtaggttgc tggcgaacgc gacgacgcgg cggttgatct  14700
cctgaatctg gcgcctctgc gtgaagacga cgggcccggt gagcttgaac ctgaaagaga  14760
gttcgacaga atcaatttcg gtgtcgttga cggcggcctg gcgcaaaatc tcctgcacgt  14820
ctcctgagtt gtcttgatag gcgatctcgg ccatgaactg ctcgatctct tcctcctgga  14880
gatctccgcg tccggctcgc tccacggtgg cggcgaggtc gttggaaatg cgggccatga  14940
gctgcgagaa ggcgttgagg cctccctcgt tccagacgcg gctgtagacc acgccccctt  15000
cggcatcgcg ggcgcgcatg accacctgcg cgagattgag ctccacgtgc cgggcgaaga  15060
cggcgtagtt tcgcaggcgc tgaaagaggt agttgagggt ggtggcggtg tgttctgcca  15120
cgaagaagta cataacccag cgtcgcaacg tggattcgtt gatatccccc aaggcctcaa  15180
ggcgctccat ggcctcgtag aagtccacgg cgaagttgaa aaactgggag ttgcgcgccg  15240
acacggttaa ctcctcctcc agaagacgga tgagctcggc gacagtgtcg cgcacctcgc  15300
gctcaaaggc tacaggggcc tcttcttctt cttcaatctc ctcttccata agggcctccc  15360
cttcttcttc ttctggcggc ggtgggggag gggggacacg gcggcgacga cggcgcaccg  15420
ggaggcggtc gacaaagcgc tcgatcatct ccccgcggcg acggcgcatg gtctcggtga  15480
cggcgcggcc gttctcgcgg gggcgcagtt ggaagacgcc gcccgtcatg tcccggttat  15540
gggttggcgg ggggctgcca tgcggcaggg atacggcgct aacgatgcat ctcaacaatt  15600
gttgtgtagg tactccgccg ccgagggacc tgagcgagtc cgcatcgacc ggatcggaaa  15660
acctctcgag aaaggcgtct aaccagtcac agtcgcaagg taggctgagc accgtggcgg  15720
gcggcagcgg gcggcggtcg gggttgtttc tggcggaggt gctgctgatg atgtaattaa  15780
agtaggcggt cttgagacgg cggatggtcg acagaagcac catgtccttg ggtccggcct  15840
gctgaatgcg caggcggtcg gccatgcccc aggcttcgtt ttgacatcgg cgcaggtctt  15900
tgtagtagtc ttgcatgagc ctttctaccg gcacttcttc ttctccttcc tcttgtcctg  15960
catctcttgc atctatcgct gcggcggcgg cggagtttgg ccgtaggtgg cgccctcttc  16020
ctcccatgcg tgtgaccccg aagcccctca tcggctgaag cagggctagg tcggcgacaa  16080
```

-continued

```
cgcgctcggc taatatggcc tgctgcacct gcgtgagggt agactggaag tcatccatgt  16140
ccacaaagcg gtggtatgcg cccgtgttga tggtgtaagt gcagttggcc ataacggacc  16200
agttaacggt ctggtgaccc ggctgcgaga gctcggtgta cctgagacgc gagtaagccc  16260
tcgagtcaaa tacgtagtcg ttgcaagtcc gcaccaggta ctggtatccc accaaaaagt  16320
gcggcggcgg ctggcggtag aggggccagc gtagggtggc cggggctccg ggggcgagat  16380
cttccaacat aaggcgatga tatccgtaga tgtacctgga catccaggtg atgccggcgg  16440
cggtggtgga ggcgcgcgga aagtcgcgga cgcggttcca gatgttgcgc agcggcaaaa  16500
agtgctccat ggtcgggacg ctctggccgg tcaggcgcgc gcaatcgttg acgctctaga  16560
ccgtgcaaaa ggagagcctg taagcgggca ctcttccgtg gtctggtgga taaattcgca  16620
agggtatcat ggcggacgac cggggttcga gccccgtatc cggccgtccg ccgtgatcca  16680
tgcggttacc gcccgcgtgt cgaacccagg tgtgcgacgt cagacaacgg gggagtgctc  16740
cttttggctt ccttccaggc gcggcggctg ctgcgctagc ttttttggcc actggccgcg  16800
cgcagcgtaa gcggttaggc tggaaagcga aagcattaag tggctcgctc cctgtagccg  16860
gagggttatt ttccaagggt tgagtcgcgg gacccccggt tcgagtctcg gaccggccgg  16920
actgcggcga acgggggttt gcctccccgt catgcaagac cccgcttgca aattcctccg  16980
gaaacaggga cgagcccctt ttttgctttt cccagatgca tccggtgctg cggcagatgc  17040
gcccccctcc tcagcagcgg caagagcaag agcagcggca gacatgcagg gcaccctccc  17100
ctcctcctac cgcgtcagga ggggcgacat ccgcggttga cgcggcagca gatggtgatt  17160
acgaaccccc gcggcgccgg gcccggcact acctggactt ggaggagggc gagggcctgg  17220
cgcggctagg agcgccctct cctgagcggc acccaagggt gcagctgaag cgtgatacgc  17280
gtgaggcgta cgtgccgcgg cagaacctgt ttcgcgaccg cgagggagag gagcccgagg  17340
agatgcggga tcgaaagttc cacgcagggc gcgagctgcg gcatggcctg aatcgcgagc  17400
ggttgctgcg cgaggaggac tttgagcccg acgcgcgaac cgggattagt cccgcgcgcg  17460
cacacgtggc ggccgccgac ctggtaaccg catacgagca gacggtgaac caggagatta  17520
actttcaaaa aagctttaac aaccacgtgc gtacgcttgt ggcgcgcgag gaggtggcta  17580
taggactgat gcatctgtgg gactttgtaa gcgcgctgga gcaaaaccca aatagcaagc  17640
cgctcatggc gcagctgttc cttatagtgc agcacagcag ggacaacgag gcattcaggg  17700
atgcgctgct aaacatagta gagcccgagg gccgctggct gctcgatttg ataaacatcc  17760
tgcagagcat agtggtgcag gagcgcagct tgagcctggc tgacaaggtg gccgccatca  17820
actattccat gcttagcctg ggcaagtttt acgcccgcaa gatataccat accccttacg  17880
ttcccataga caaggaggta aagatcgagg ggttctacat gcgcatggcg ctgaaggtgc  17940
ttaccttgag cgacgacctg ggcgtttatc gcaacgagcg catccacaag gccgtgagcg  18000
tgagccggcg gcgcgagctc agcgaccgcg agctgatgca cagcctgcaa agggccctgg  18060
ctggcacggg cagcggcgat agagaggccg agtcctactt tgacgcgggc gctgacctgc  18120
gctgggcccc aagccgacgc gccctggagg cagctggggc cggacctggg ctggcggtgg  18180
cacccgcgcg cgctggcaac gtcggcggcg tggaggaata tgacgaggac gatgagtacg  18240
agccagagga cggcgagtac taagcggtga tgtttctgat cagatgatgc aagacgcaac  18300
ggacccggcg gtgcgggcgg cgctgcagag ccagccgtcc ggccttaact ccacggacga  18360
ctggcgccag gtcatggacc gcatcatgtc gctgactgcg cgcaatcctg acgcgttccg  18420
gcagcagccg caggccaacc ggctctccgc aattctggaa gcggtggtcc cggcgcgcgc  18480
```

aaaccccacg cacgagaagg tgctggcgat cgtaaacgcg ctggccgaaa acagggccat 18540
ccggcccgac gaggccggcc tggtctacga cgcgctgctt cagcgcgtgg ctcgttacaa 18600
cagcggcaac gtgcagacca acctggaccg gctggtgggg gatgtgcgcg aggccgtggc 18660
gcagcgtgag cgcgcgcagc agcagggcaa cctgggctcc atggttgcac taaacgcctt 18720
cctgagtaca cagcccgcca acgtgccgcg ggacaggag gactacacca actttgtgag 18780
cgcactgcgg ctaatggtga ctgagacacc gcaaagtgag gtgtaccagt ctgggccaga 18840
ctatttttc cagaccagta gacaaggcct gcagaccgta aacctgagcc aggctttcaa 18900
aaacttgcag gggctgtggg gggtgcgggc tcccacaggc gaccgcgcga ccgtgtctag 18960
cttgctgacg cccaactcgc gcctgttgct gctgctaata gcgcccttca cggacagtgg 19020
cagcgtgtcc cgggacacat acctaggtca cttgctgaca ctgtaccgcg aggccatagg 19080
tcaggcgcat gtggacgagc atactttcca ggagattaca agtgtcagcc gcgcgctggg 19140
gcaggaggac acgggcagcc tggaggcaac cctaaactac ctgctgacca accggcggca 19200
gaagatcccc tcgttgcaca gtttaaacag cgaggaggag cgcattttgc gctacgtgca 19260
gcagagcgtg agccttaacc tgatgcgcga cggggtaacg cccagcgtgg cgctggacat 19320
gaccgcgcgc aacatggaac cggcatgta tgcctcaaac cggccgttta tcaaccgcct 19380
aatggactac ttgcatcgcg cggccgccgt gaaccccgag tatttcacca atgccatctt 19440
gaacccgcac tggctaccgc cccctggttt ctacaccggg ggattcgagg tgcccgaggg 19500
taacgatgga ttcctctggg acgacataga cgacagcgtg ttttccccgc aaccgcagac 19560
cctgctagag ttgcaacagc gcgagcaggc agaggcggcg ctgcgaaagg aaagcttccg 19620
caggccaagc agcttgtccg atctaggcgc tgcggccccg cggtcagatg ctagtagccc 19680
atttccaagc ttgatagggt ctcttaccag cactcgcacc acccgcccgc gcctgctggg 19740
cgaggaggag tacctaaaca actcgctgct gcagccgcag cgcgaaaaaa acctgcctcc 19800
ggcatttccc aacaacggga tagagagcct agtggacaag atgagtagat ggaagacgta 19860
cgcgcaggag cacagggacg tgccaggccc gcgcccgccc acccgtcgtc aaaggcacga 19920
ccgtcagcgg ggtctggtgt gggaggacga tgactcggca gacgacagca gcgtcctgga 19980
tttgggaggg agtggcaacc cgtttgcgca ccttcgcccc aggctgggga gaatgtttta 20040
aaaaaaaaaa aaaagcatga tgcaaaataa aaaactcacc aaggccatgg caccgagcgt 20100
tggttttctt gtattcccct tagtatgcgg cgcgcggcga tgtatgagga aggtcctcct 20160
ccctcctacg agagtgtggt gagcgcggcg ccagtggcgg cggcgctggg ttctcccttc 20220
gatgctcccc tggacccgcc gtttgtgcct ccgcggtacc tgcggcctac cggggggaga 20280
aacagcatcc gttactctga gttggcaccc ctattcgaca ccacccgtgt gtacctggtg 20340
gacaacaagt caacggatgt ggcatccctg aactaccaga acgaccacag caactttctg 20400
accacggtca ttcaaaacaa tgactacagc ccgggggagg caagcacaca gaccatcaat 20460
cttgacgacc ggtcgcactg ggcggcgac ctgaaaacca tcctgcatac caacatgcca 20520
aatgtgaacg agttcatgtt taccaataag tttaaggcgc gggtgatggt gtcgcgcttg 20580
cctactaagg acaatcaggt ggagctgaaa tacgagtggg tggagttcac gctgcccgag 20640
ggcaactact ccgagaccat gaccatagac cttatgaaca acgcgatcgt ggagcactac 20700
ttgaaagtgg gcagacagaa cggggttctg gaaagcgaca tcggggtaaa gtttgacacc 20760
cgcaacttca gactggggtt tgaccccgtc actggtcttg tcatgcctgg ggtatataca 20820

-continued

```
aacgaagcct tccatccaga catcattttg ctgccaggat gcggggtgga cttcacccac  20880
agccgcctga gcaacttgtt gggcatccgc aagcggcaac ccttccagga gggctttagg  20940
atcacctacg atgatctgga gggtggtaac attcccgcac tgttggatgt ggacgcctac  21000
caggcgagct tgaaagatga caccgaacag ggcgggggtg gcgcaggcgg cagcaacagc  21060
agtggcagcg gcgcggaaga gaactccaac gcggcagccg cggcaatgca gccggtggag  21120
gacatgaacg atcatgccat tcgcggcgac acctttgcca cacgggctga ggagaagcgc  21180
gctgaggccg aagcagcggc cgaagctgcc gcccccgctg cgcaacccga ggtcgagaag  21240
cctcagaaga aaccggtgat caaacccctg acagaggaca gcaagaaacg cagttacaac  21300
ctaataagca atgacagcac cttcacccag taccgcagct ggtaccttgc atacaactac  21360
ggcgaccctc agaccggaat ccgctcatgg accctgcttt gcactcctga cgtaacctgc  21420
ggctcggagc aggtctactg gtcgttgcca gacatgatgc aagaccccgt gaccttccgc  21480
tccacgcgcc agatcagcaa ctttccggtg gtgggcgccg agctgttgcc cgtgcactcc  21540
aagagcttct acaacgacca ggccgtctac tcccaactca tccgccagtt tacctctctg  21600
acccacgtgt tcaatcgctt tcccgagaac cagattttgg cgcgcccgcc agcccccacc  21660
atcaccaccg tcagtgaaaa cgttcctgct ctcacagatc acgggacgct accgctgcgc  21720
aacagcatcg gaggagtcca gcgagtgacc attactgacg ccagacgccg cacctgcccc  21780
tacgtttaca aggccctggg catagtctcg ccgcgcgtcc tatcgagccg cactttttga  21840
gcaagcatgt ccatccttat atcgcccagc aataacacag gctggggcct gcgcttccca  21900
agcaagatgt ttggcggggc caagaagcgc tccgaccaac acccagtgcg cgtgcgcggg  21960
cactaccgcg cgccctgggg cgcgcacaaa cgcggccgca ctgggcgcac caccgtcgat  22020
gacgccatcg acgcggtggt ggaggaggcg cgcaactaca cgcccacgcc gccaccagtg  22080
tccacagtgg acgcggccat tcagaccgtg gtgcgcggag cccggcgcta tgctaaaatg  22140
aagagacggc ggaggcgcgt agcacgtcgc caccgccgcc gacccggcac tgccgcccaa  22200
cgcgcggcgg cggccctgct taaccgcgca cgtcgcaccg gccgacgggc ggccatgcgg  22260
gccgctcgaa ggctggccgc gggtattgtc actgtgcccc ccaggtccag gcgacgagcg  22320
gccgccgcag cagccgcggc cattagtgct atgactcagg gtcgcagggg caacgtgtat  22380
tgggtgcgcg actcggttag cggcctgcgc gtgcccgtgc gcacccgccc cccgcgcaac  22440
tagattgcaa gaaaaaacta cttagactcg tactgttgta tgtatccagc ggcggcggcg  22500
cgcaacgaag ctatgtccaa gcgcaaaatc aaagaagaga tgctccaggt catcgcgccg  22560
gagatctatg gccccccgaa gaaggaagag caggattaca agccccgaaa gctaaagcgg  22620
gtcaaaaaga aaaagaaaga tgatgatgat gaacttgacg acgaggtgga actgctgcac  22680
gctaccgcgc ccaggcgacg ggtacagtgg aaaggtcgac gcgtaaaacg tgttttgcga  22740
cccggcacca ccgtagtctt tacgcccggt gagcgctcca cccgcaccta caagcgcgtg  22800
tatgatgagg tgtacggcga cgaggacctg cttgagcagg ccaacgagcg cctcggggag  22860
tttgcctacg gaaagcggca taaggacatg ctggcgttgc cgctggacga gggcaaccca  22920
acacctagcc taaagcccgt aacactgcag caggtgctgc ccgcgcttgc accgtccgaa  22980
gaaaagcgcg gcctaaagcg cgagtctggt gacttggcac ccaccgtgca gctgatggta  23040
cccaagcgcc agcgactgga agatgtcttg gaaaaaatga ccgtggaacc tgggctggag  23100
cccgaggtcc gcgtgcggcc aatcaagcag gtggcgccgg gactgggcgt gcagaccgtg  23160
gacgttcaga tacccactac cagtagcacc agtattgcca ccgccacaga gggcatggag  23220
```

```
acacaaacgt ccccggttgc ctcagcggtg gcggatgccg cggtgcaggc ggtcgctgcg  23280
gccgcgtcca agacctctac ggaggtgcaa acggacccgt ggatgtttcg cgtttcagcc  23340
ccccggcgcc cgcgccgttc gaggaagtac ggcgccgcca gcgcgctact gcccgaatat  23400
gccctacatc cttccattgc gcctaccccc ggctatcgtg gctacaccta ccgccccaga  23460
agacgagcaa ctacccgacg ccgaaccacc actggaaccc gccgccgccg tcgccgtcgc  23520
cagcccgtgc tggccccgat ttccgtgcgc agggtggctc gcgaaggagg caggaccctg  23580
gtgctgccaa cagcgcgcta ccaccccagc atcgtttaaa agccggtctt tgtggttctt  23640
gcagatatgg ccctcacctg ccgcctccgt ttcccggtgc cgggattccg aggaagaatg  23700
caccgtagga ggggcatggc cggccacggc ctgacgggcg gcatgcgtcg tgcgcaccac  23760
cggcggcggc gcgcgtcgca ccgtcgcatg cgcggcggta tcctgcccct ccttattcca  23820
ctgatcgccg cggcgattgg cgccgtgccc ggaattgcat ccgtggcctt gcaggcgcag  23880
agacactgat taaaaacaag ttgcatgtgg aaaaatcaaa ataaaaagtc tggactctca  23940
cgctcgcttg gtcctgtaac tattttgtag aatggaagac atcaactttg cgtctctggc  24000
cccgcgacac ggctcgcgcc cgttcatggg aaactggcaa gatatcggca ccagcaatat  24060
gagcggtggc gccttcagct ggggctcgct gtggagcggc attaaaaatt tcggttccac  24120
cgttaagaac tatggcagca aggcctggaa cagcagcaca ggccagatgc tgagggataa  24180
gttgaaagag caaaatttcc aacaaaaggt ggtagatggc ctggcctctg gcattagcgg  24240
ggtggtggac ctggccaacc aggcagtgca aaataagatt aacagtaagc ttgatccccg  24300
ccctcccgta gaggagcctc caccggccgt ggagacagtg tctccagagg ggcgtggcga  24360
aaagcgtccg cgccccgaca gggaagaaac tctggtgacg caaatagacg agcctccctc  24420
gtacgaggag gcactaaagc aaggcctgcc caccacccgt cccatcgcgc ccatggctac  24480
cggagtgctg ggccagcaca cacccgtaac gctggacctg cctcccccccg ccgacaccca  24540
gcagaaacct gtgctgccag gcccgaccgc cgttgttgta acccgtccta gccgcgcgtc  24600
cctgcgccgc gccgccagcg gtccgcgatc gttgcggccc gtagccagtg gcaactggca  24660
aagcacactg aacagcatcg tgggtctggg ggtgcaatcc ctgaagcgcc gacgatgctt  24720
ctgatagcta acgtgtcgta tgtgtgtcat gtatgcgtcc atgtcgccgc cagaggagct  24780
gctgagccgc cgcgcgcccg ctttccaaga tggctacccc ttcgatgatg ccgcagtggt  24840
cttacatgca catctcgggc caggacgcct cggagtacct gagccccggg ctggtgcagt  24900
ttgcccgcgc caccgagacg tacttcagcc tgaataacaa gtttagaaac cccacggtgg  24960
cgcctacgca cgacgtgacc acagaccggt cccagcgttt gacgctgcgg ttcatccctg  25020
tggaccgtga ggatactgcg tactcgtaca aggcgcggtt caccctagct gtgggtgata  25080
accgtgtgct ggacatggct tccacgtact ttgacatccg cggcgtgctg gacaggggcc  25140
ctacttttaa gccctactct ggcactgcct acaacgccct ggctcccaag ggtgccccaa  25200
atccttgcga atgggatgaa gctgctactg ctcttgaaat aaacctagaa gaagaggacg  25260
atgacaacga agacgaagta gacgagcaag ctgagcagca aaaaactcac gtatttgggc  25320
aggcgcctta ttctggtata aatattacaa aggagggtat tcaaataggt gtcgaaggtc  25380
aaacacctaa atatgccgat aaaacatttc aacctgaacc tcaaatagga gaatctcagt  25440
ggtacgaaac agaaattaat catgcagctg ggagagtcct aaaaaagact accccaatga  25500
aaccatgtta cggttcatat gcaaaaccca caaatgaaaa tggagggcaa ggcattcttg  25560
```

-continued

```
taaagcaaca aaatggaaag ctagaaagtc aagtggaaat gcaatttttc tcaactactg  25620
aggcagccgc aggcaatggt gataacttga ctcctaaagt ggtattgtac agtgaagatg  25680
tagatataga aaccccagac actcatattt cttacatgcc cactattaag gaaggtaact  25740
cacgagaact aatgggccaa caatctatgc ccaacaggcc taattacatt gcttttaggg  25800
acaattttat tggtctaatg tattacaaca gcacgggtaa tatgggtgtt ctggcgggcc  25860
aagcatcgca gttgaatgct gttgtagatt tgcaagacag aaacacagag ctttcatacc  25920
agcttttgct tgattccatt ggtgatagaa ccaggtactt ttctatgtgg aatcaggctg  25980
ttgacagcta tgatccagat gttagaatta ttgaaaatca tggaactgaa gatgaacttc  26040
caaattactg ctttccactg ggaggtgtga ttaatacaga gactcttacc aaggtaaaac  26100
ctaaaacagg tcaggaaaat ggatgggaaa aagatgctac agaattttca gataaaaatc  26160
aaataagagt tggaaataat tttgccatgg aaatcaatct aaatgccaac ctgtggagaa  26220
atttcctgta ctccaacata gcgctgtatt tgcccgacaa gctaaagtac agtccttcca  26280
acgtaaaaat ttctgataac ccaaacacct acgactacat gaacaagcga gtggtggctc  26340
ccgggctagt ggactgctac attaaccttg gagcacgctg gtcccttgac tatatggaca  26400
acgtcaaccc atttaaccac caccgcaatg ctggcctgcg ctaccgctca atgttgctgg  26460
gcaatggtcg ctatgtgccc ttccacatcc aggtgcctca gaagttcttt gccattaaaa  26520
acctccttct cctgccgggc tcatacacct acgagtggaa cttcaggaag gatgttaaca  26580
tggttctgca gagctcccta ggaaatgacc taagggttga cggagccagc attaagtttg  26640
atagcatttg cctttacgcc accttcttcc ccatggccca caacaccgcc tccacgcttg  26700
aggccatgct tagaaacgac accaacgacc agtcctttaa cgactatctc tccgccgcca  26760
acatgctcta ccctataccc gccaacgcta ccaacgtgcc catatccatc cctcccgca  26820
actgggcggc tttccgcggc tggggccttca cgcgccttaa gactaaggaa accccatcac  26880
tgggctcggg ctacgaccct tattacacct actctggctc tataccctac ctagatggaa  26940
ccttttacct caaccacacc tttaagaagg tggccattac ctttgactct tctgtcagct  27000
ggcctggcaa tgaccgcctg cttacccca acgagtttga aattaagcgc tcagttgacg  27060
gggagggtta caacgttgcc cagtgtaaca tgaccaaaga ctggttcctg gtacaaatgc  27120
tagctaacta taacattggc taccagggct tctatatccc agagagctac aaggaccgca  27180
tgtactcctt ctttagaaac ttccagccca tgagccgtca ggtggtggat gatactaaat  27240
acaaggacta ccaacaggtg ggcatcctac accaacacaa caactctgga tttgttggct  27300
accttgcccc caccatgcgc gaaggacagg cctaccctgc taacttcccc tatccgctta  27360
taggcaagac cgcagttgac agcattaccc agaaaaagtt tctttgcgat cgcacccttt  27420
ggcgcatccc attctccagt aactttatgt ccatgggcgc actcacagac ctgggccaaa  27480
accttctcta cgccaactcc gcccacgcgc tagacatgac ttttgaggtg gatcccatgg  27540
acgagcccac ccttctttat gttttgtttg aagtctttga cgtggtccgt gtgcaccagc  27600
cgcaccgcgg cgtcatcgaa accgtgtacc tgcgcacgcc cttctcggcc ggcaacgcca  27660
caacataaag aagcaagcaa catcaacaac agctgccgcc atgggctcca gtgagcagga  27720
actgaaagcc attgtcaaag atcttggttg tgggccatat tttttgggca cctatgacaa  27780
gcgctttcca ggctttgttt ctccacacaa gctcgcctgc gccatagtca atacggccgg  27840
tcgcgagact gggggcgtac actggatggc ctttgcctgg aacccgcact caaaaacatg  27900
ctacctcttt gagccctttg gcttttctga ccagcgactc aagcaggttt accagtttga  27960
```

gtacgagtca ctcctgcgcc gtagcgccat tgcttcttcc cccgaccgct gtataacgct 28020
ggaaaagtcc acccaaagcg tacaggggcc caactcggcc gcctgtggac tattctgctg 28080
catgtttctc cacgcctttg ccaactggcc ccaaactccc atggatcaca accccaccat 28140
gaaccttatt accggggtac ccaactccat gctcaacagt ccccaggtac agcccaccct 28200
gcgtcgcaac caggaacagc tctacagctt cctggagcgc cactcgccct acttccgcag 28260
ccacagtgcg cagattagga gcgccacttc tttttgtcac ttgaaaaaca tgtaaaaata 28320
atgtactaga gacactttca ataaaggcaa atgcttttat ttgtacactc tcgggtgatt 28380
atttaccccc acccttgccg tctgcgccgt ttaaaaatca aaggggttct gccgcgcatc 28440
gctatgcgcc actggcaggg acacgttgcg atactggtgt ttagtgctcc acttaaactc 28500
aggcacaacc atccgcggca gctcggtgaa gttttcactc cacaggctgc gcaccatcac 28560
caacgcgttt agcaggtcgg gcgccgatat cttgaagtcg cagttggggc ctccgccctg 28620
cgcgcgcgag ttgcgataca cagggttgca gcactggaac actatcagcg ccgggtggtg 28680
cacgctggcc agcacgctct tgtcggagat cagatccgcg tccaggtcct ccgcgttgct 28740
cagggcgaac ggagtcaact ttggtagctg ccttcccaaa aagggcgcgt gcccaggctt 28800
tgagttgcac tcgcaccgta gtggcatcaa aaggtgaccg tgcccggtct gggcgttagg 28860
atacagcgcc tgcataaaag ccttgatctg cttaaaagcc acctgagcct ttgcgccttc 28920
agagaagaac atgccgcaag acttgccgga aaactgattg gccggacagg ccgcgtcgtg 28980
cacgcagcac cttgcgtcgg tgttggagat ctgcaccaca tttcggcccc accggttctt 29040
cacgatcttg gccttgctag actgctcctt cagcgcgcgc tgcccgtttt cgctcgtcac 29100
atccatttca atcacgtgct ccttatttat cataatgctt ccgtgtagac acttaagctc 29160
gccttcgatc tcagcgcagc ggtgcagcca caacgcgcag cccgtgggct cgtgatgctt 29220
gtaggtcacc tctgcaaacg actgcaggta cgcctgcagg aatcgcccca tcatcgtcac 29280
aaaggtcttg ttgctggtga aggtcagctg caacccgcgg tgctcctcgt tcagccaggt 29340
cttgcatacg gccgccagag cttccacttg gtcaggcagt agtttgaagt tcgcctttag 29400
atcgttatcc acgtggtact tgtccatcag cgcgcgcgca gcctccatgc ccttctccca 29460
cgcagacacg atcggcacac tcagcgggtt catcaccgta atttcacttt ccgcttcgct 29520
gggctcttcc tcttcctctt gcgtccgcat accacgcgcc actgggtcgt cttcattcag 29580
ccgccgcact gtgcgcttac ctcctttgcc atgcttgatt agcaccggtg ggttgctgaa 29640
acccaccatt tgtagcgcca catcttctct ttcttcctcg ctgtccacga ttacctctgg 29700
tgatggcggg cgctcgggct tgggagaagg gcgcttcttt ttcttcttgg gcgcaatggc 29760
caaatccgcc gccgaggtcg atggccgcgg gctgggtgtg cgcggcacca gcgcgtcttg 29820
tgatgagtct tcctcgtcct cggactcgat acgccgcctc atccgctttt ttgggggcgc 29880
ccggggaggc ggcggcgacg gggacgggga cgacacgtcc tccatggttg ggggacgtcg 29940
cgccgcaccg cgtccgcgct cgggggtggt ttcgcgctgc tcctcttccc gactggccat 30000
ttccttctcc tataggcaga aaaagatcat ggagtcagtc gagaagaagg acagcctaac 30060
cgccccctct gagttcgcca ccaccgcctc caccgatgcc gccaacgcgc ctaccacctt 30120
ccccgtcgag gcacccccgc ttgaggagga ggaagtgatt atcgagcagg acccaggttt 30180
tgtaagcgaa gacgacgagg accgctcagt accaacagag gataaaaagc aagaccagga 30240
caacgcagag gcaaacgagg aacaagtcgg gcggggggac gaaaggcatg gcgactacct 30300

-continued

```
agatgtggga gacgacgtgc tgttgaagca tctgcagcgc cagtgcgcca ttatctgcga  30360
cgcgttgcaa gagcgcagcg atgtgcccct cgccatagcg gatgtcagcc ttgcctacga  30420
acgccaccta ttctcaccgc gcgtaccccc caaacgccaa gaaaacggca catgcgagcc  30480
caacccgcgc ctcaacttct accccgtatt tgccgtgcca gaggtgcttg ccacctatca  30540
catctttttc caaaactgca agatacccct atcctgccgt gccaaccgca gccgagcgga  30600
caagcagctg gccttgcggc agggcgctgt catacctgat atcgcctcgc tcaacgaagt  30660
gccaaaaatc tttgagggtc ttggacgcga cgagaagcgc gcggcaaacg ctctgcaaca  30720
ggaaaacagc gaaaatgaaa gtcactctgg agtgttggtg gaactcgagg gtgacaacgc  30780
gcgcctagcc gtactaaaac gcagcatcga ggtcacccac tttgcctacc cggcacttaa  30840
cctacccccc aaggtcatga gcacagtcat gagtgagctg atcgtgcgcc gtgcgcagcc  30900
cctggagagg gatgcaaatt tgcaagaaca aacagaggag ggcctacccg cagttggcga  30960
cgagcagcta gcgcgctggc ttcaaacgcg cgagcctgcc gacttggagg agcgacgcaa  31020
actaatgatg gccgcagtgc tcgttaccgt ggagcttgag tgcatgcagc ggttctttgc  31080
tgacccggag atgcagcgca agctagagga aacattgcac tacacctttc gacagggcta  31140
cgtacgccag gcctgcaaga tctccaacgt ggagctctgc aacctggtct cctaccttgg  31200
aattttgcac gaaaaccgcc ttgggcaaaa cgtgcttcat tccacgctca agggcgaggc  31260
gcgccgcgac tacgtccgcg actgcgttta cttatttcta tgctacacct ggcagacggc  31320
catgggcgtt tggcagcagt gcttggagga gtgcaacctc aaggagctgc agaaactgct  31380
aaagcaaaac ttgaaggacc tatggacggc cttcaacgag cgctccgtgg ccgcgcacct  31440
ggcggacatc attttccccg aacgcctgct taaaaccctg caacagggtc tgccagactt  31500
caccagtcaa agcatgttgc agaactttag gaactttatc ctagagcgct caggaatctt  31560
gcccgccacc tgctgtgcac ttcctagcga ctttgtgccc attaagtacc gcgaatgccc  31620
tccgccgctt tggggccact gctaccttct gcagctagcc aactaccttg cctaccactc  31680
tgacataatg gaagacgtga gcggtgacgg tctactggag tgtcactgtc gctgcaacct  31740
atgcaccccg caccgctccc tggtttgcaa ttcgcagctg cttaacgaaa gtcaaattat  31800
cggtaccttt gagctgcagg gtccctcgcc tgacgaaaag tccgcggctc cggggttgaa  31860
actcactccg gggctgtgga cgtcggctta ccttcgcaaa tttgtacctg aggactacca  31920
cgcccacgag attaggttct acgaagacca atcccgcccg cctaatgcgg agcttaccgc  31980
ctgcgtcatt acccagggcc acattcttgg ccaattgcaa gccatcaaca aagcccgcca  32040
agagtttctg ctacgaaagg gacggggggt ttacttggac ccccagtccg gcgaggagct  32100
caacccaatc cccccgccgc cgcagcccta tcagcagcag ccgcgggccc ttgcttccca  32160
ggatggcacc caaaaagaag ctgcagctgc cgccgccacc cacggacgag gaggaatact  32220
gggacagtca ggcagaggag gttttggacg aggaggagga ggacatgatg gaagactggg  32280
agagcctaga cgaggaagct tccgaggtcg aagaggtgtc agacgaaaca ccgtcaccct  32340
cggtcgcatt cccctcgccg gcgccccaga aatcggcaac cggttccagc atggctacaa  32400
cctccgctcc tcaggcgccg ccggcactgc ccgttcgccg acccaaccgt agatgggaca  32460
ccactggaac cagggccggt aagtccaagc agccgccgcc gttagcccaa gagcaacaac  32520
agcgccaagg ctaccgctca tggcgcgggc acaagaacgc catagttgct tgcttgcaag  32580
actgtggggg caacatctcc ttcgcccgcc gctttcttct ctaccatcac ggcgtggcct  32640
tcccccgtaa catcctgcat tactaccgtc atctctacag cccatactgc accggcggca  32700
```

```
gcggcagcaa cagcagcggc cacacagaag caaaggcgac cggatagcaa gactctgaca  32760
aagcccaaga aatccacagc ggcggcagca gcaggaggag gagcgctgcg tctggcgccc  32820
aacgaacccg tatcgacccg cgagcttaga aacaggattt ttcccactct gtatgctata  32880
tttcaacaga gcaggggcca agaacaagag ctgaaaataa aaaacaggtc tctgcgatcc  32940
ctcacccgca gctgcctgta tcacaaaagc gaagatcagc ttcggcgcac gctggaagac  33000
gcggaggctc tcttcagtaa atactgcgcg ctgactctta aggactagtt tcgcgccctt  33060
tctcaaattt aagcgcgaaa actacgtcat ctccagcggc cacacccggc gccagcacct  33120
gtcgtcagcg ccatttcaac tttgtataca aaagttgtga tgagcaagga aattcccacg  33180
ccctacatgt ggagttacca gccacaaatg ggacttgcgg ctggagctgc ccaagactac  33240
tcaacccgaa taaactacat gagcgcggga ccccacatga tatcccgggt caacggaata  33300
cgcgcccacc gaaaccgaat tctcctggaa caggcggcta ttaccaccac acctcgtaat  33360
aaccttaatc cccgtagttg gcccgctgcc ctggtgtacc aggaaagtcc cgctcccacc  33420
actgtggtac ttcccagaga cgcccaggcc gaagttcaga tgactaactc aggggcgcag  33480
cttgcgggcg gctttcgtca cagggtgcgg tcgcccgggc agggtataac tcacctgaca  33540
atcagagggc gaggtattca gctcaacgac gagtcggtga gctcctcgct tggtctccgt  33600
ccggacggga catttcagat cggcggcgcc ggccgctctt cattcacgcc tcgtcaggca  33660
atcctaactc tgcagacctc gtcctctgag ccgcgctctg gaggcattgg aactctgcaa  33720
tttattgagg agtttgtgcc atcggtctac tttaacccct tctcgggacc tcccggccac  33780
tatccggatc aatttattcc taactttgac gcggtaaagg actcggcgga cggctacgac  33840
tgaatgttaa gtggagaggc agagcaactg cgcctgaaac acctggtcca ctgtcgccgc  33900
cacaagtgct ttgcccgcga ctccggtgag ttttgctact ttgaattgcc cgaggatcat  33960
atcgagggcc cggcgcacgg cgtccggctt accgcccagg gagagcttgc ccgtagcctg  34020
attcgggagt ttacccagcg ccccctgcta gttgagcggg acaggggacc ctgtgttctc  34080
actgtgattt gcaactgtcc taaccctgga ttacatttaa atgcggtctc aaagatctta  34140
ttccctttaa ctaataaaaa aaaataataa agcatcactt acttaaaatc agttagcaaa  34200
tttctgtcca gtttattcag cagcacctcc ttgccctcct cccagctctg gtattgcagc  34260
ttcctcctgg ctgcaaactt tctccacaat ctaaatggaa tgtcagtttc ctcctgttcc  34320
tgtccatccg cacccactat cttcatgttg ttgcagatga agcgcgcaag accgtctgaa  34380
gataccttca accccgtgta tccatatgac acggaaaccg gtcctccaac tgtgcctttt  34440
cttactcctc cctttgtatc ccccaatggg tttcaagaga gtccccctgg ggtactctct  34500
ttgcgcctat ccgaacctct agttacctcc aatggcatgc ttgcgctcaa aatgggcaac  34560
ggcctctctc tggacgaggc cggcaacctt acctcccaaa atgtaaccac tgtgagccca  34620
cctctcaaaa aaaccaagtc aaacataaac ctggaaatat ctgcacccct cacagttacc  34680
tcagaagccc taactgtggc tgccgccgca cctctaatgg tcgcgggcaa cacactcacc  34740
atgcaatcac aggccccgct aaccgtgcac gactccaaac ttagcattgc cacccaagga  34800
cccctcacag tgtcagaagg aaagctagcc ctgcaaacat caggccccct caccaccacc  34860
gatagcagta cccttactat cactgcctca ccccctctaa ctactgccac tggtagcttg  34920
ggcattgact tgaaagagcc catttataca caaaatggaa aactaggact aaagtacggg  34980
gctcctttgc atgtaacaga cgacctaaac actttgaccg tagcaactgg tccaggtgtg  35040
```

-continued actattaata atacttcctt gcaaactaaa gttactggag ccttgggttt tgattcacaa 35100
ggcaatatgc aacttaatgt agcaggagga ctaaggattg attctcaaaa cagacgcctt 35160
atacttgatg ttagttatcc gtttgatgct caaaaccaac taaatctaag actaggacag 35220
ggccctcttt ttataaactc agcccacaac ttggatatta actacaacaa aggcctttac 35280
ttgtttacag cttcaaacaa ttccaaaaag cttgaggtta acctaagcac tgccaagggg 35340
ttgatgtttg acgctacagc catagccatt aatgcaggag atgggcttga atttggttca 35400
cctaatgcac caaacacaaa tcccctcaaa acaaaaattg gccatggcct agaatttgat 35460
tcaaacaagg ctatggttcc taaactagga actggcctta gttttgacag cacaggtgcc 35520
attacagtag gaaacaaaaa taatgataag ctaactttgt ggaccacacc agctccatct 35580
cctaactgta gactaaatgc agagaaagat gctaaactca ctttggtctt aacaaaatgt 35640
ggcagtcaaa tacttgctac agtttcagtt ttggctgtta aaggcagttt ggctccaata 35700
tctggaacag ttcaaagtgc tcatcttatt ataagatttg acgaaaatgg agtgctacta 35760
aacaattcct tcctggaccc agaatattgg aactttagaa atggagatct tactgaaggc 35820
acagcctata caaacgctgt tggatttatg cctaacctat cagcttatcc aaaatctcac 35880
ggtaaaactg ccaaaagtaa cattgtcagt caagtttact taaacggaga caaaactaaa 35940
cctgtaacac taaccattac actaaacggt acacaggaaa caggagacac aactccaagt 36000
gcatactcta tgtcattttc atgggactgg tctggccaca actacattaa tgaaatattt 36060
gccacatcct cttacacttt ttcatacatt gcccaagaat aaagaatcgt ttgtgttatg 36120
tttcaacgtg tttatttttc aattgcagaa aatttcgaat catttttcat tcagtagtat 36180
agccccacca ccacatagct tatacagatc accgtacctc aactttgtat aataaagttg 36240
taatcaaact cacagaaccc tagtattcaa cctgccacct ccctcccaac acacagagta 36300
cacagtcctt tctccccggc tggccttaaa aagcatcata tcatgggtaa cagacatatt 36360
cttaggtgtt atattccaca cggtttcctg tcgagccaaa cgctcatcag tgatattaat 36420
aaactccccg ggcagctcac ttaagttcat gtcgctgtcc agctgctgag ccacaggctg 36480
ctgtccaact tgcggttgct taacgggcgg cgaaggagaa gtccacgcct acatgggggt 36540
agagtcataa tcgtgcatca ggatagggcg gtggtgctgc agcagcgcgc gaataaactg 36600
ctgccgccgc cgctccgtcc tgcaggaata caacatggca gtggtctcct cagcgatgat 36660
tcgcaccgcc cgcagcataa ggcgccttgt cctccgggca cagcagcgca ccctgatctc 36720
acttaaatca gcacagtaac tgcagcacag caccacaata ttgttcaaaa tcccacagtg 36780
caaggcgctg tatccaaagc tcatggcggg gaccacagaa cccacgtggc catcatacca 36840
caagcgcagg tagattaagt ggcgacccct cataaacacg ctggacataa acattacctc 36900
ttttggcatg ttgtaattca ccacctcccg gtaccatata aacctctgat taaacatggc 36960
gccatccacc accatcctaa accagctggc caaaacctgc ccgccggcta tacactgcag 37020
ggaaccggga ctggaacaat gacagtggag agcccaggac tcgtaaccat ggatcatcat 37080
gctcgtcatg atatcaatgt tggcacaaca caggcacacg tgcatacact tcctcaggat 37140
tacaagctcc tcccgcgtta gaaccatatc ccagggaaca acccattcct gaatcagcgt 37200
aaatcccaca ctgcagggaa gacctcgcac gtaactcacg ttgtgcattg tcaaagtgtt 37260
acattcgggc agcagcggat gatcctccag tatggtagcg cgggtttctg tctcaaaagg 37320
aggtagacga tccctactgt acggagtgcg ccgagacaac cgagatcgtg ttggtcgtag 37380
tgtcatgcca aatggaacgc cggacgtagt catatttcct gaagcaaaac caggtgcggg 37440

-continued

```
cgtgacaaac agatctgcgt ctccggtctc gccgcttaga tcgctctgtg tagtagttgt  37500
agtatatcca ctctctcaaa gcatccaggc gccccctggc ttcgggttct atgtaaactc  37560
cttcatgcgc cgctgccctg ataacatcca ccaccgcaga ataagccaca cccagccaac  37620
ctacacattc gttctgcgag tcacacacgg gaggagcggg aagagctgga agaaccatgt  37680
ttttttttt attccaaaag attatccaaa acctcaaaat gaagatctat taagtgaacg  37740
cgctcccctc cggtggcgtg gtcaaactct acagccaaag aacagataat ggcatttgta  37800
agatgttgca caatggcttc caaaaggcaa acggccctca cgtccaagtg gacgtaaagg  37860
ctaaaccctt cagggtgaat ctcctctata aacattccag caccttcaac catgcccaaa  37920
taattctcat ctcgccacct tctcaatata tctctaagca aatcccgaat attaagtccg  37980
gccattgtaa aaatctgctc cagagcgccc tccaccttca gcctcaagca gcgaatcatg  38040
attgcaaaaa ttcaggttcc tcacagacct gtataagatt caaaagcgga acattaacaa  38100
aaataccgcg atcccgtagg tcccttcgca gggccagctg aacataatcg tgcaggtctg  38160
cacggaccag cgcggccact tccccgccag gaaccatgac aaaagaaccc acactgatta  38220
tgacacgcat actcggagct atgctaacca gcgtagcccc gatgtaagct tgttgcatgg  38280
gcggcgatat aaaatgcaag gtgctgctca aaaaatcagg caaagcctcg cgcaaaaaag  38340
aaagcacatc gtagtcatgc tcatgcagat aaaggcaggt aagctccgga accaccacag  38400
aaaaagacac catttttctc tcaaacatgt ctgcgggttt ctgcataaac acaaaataaa  38460
ataacaaaaa aacatttaaa cattagaagc ctgtcttaca acaggaaaaa caacccttat  38520
aagcataaga cggactacgg ccatgccggc gtgaccgtaa aaaaactggt caccgtgatt  38580
aaaaagcacc accgacagct cctcggtcat gtccggagtc ataatgtaag actcggtaaa  38640
cacatcaggt tgattcacat cggtcagtgc taaaaagcga ccgaaatagc ccgggggaat  38700
acatacccgc aggcgtagag acaacattac agcccccata ggaggtataa caaaattaat  38760
aggagagaaa aacacataaa cacctgaaaa accctcctgc ctaggcaaaa tagcaccctc  38820
ccgctccaga acaacataca gcgcttccac agcggcagcc ataacagtca gccttaccag  38880
taaaaaagaa aacctattaa aaaaacacca ctcgacacgg caccagctca atcagtcaca  38940
gtgtaaaaaa gggccaagtg cagagcgagt atatatagga ctaaaaaatg acgtaacggt  39000
taaagtccac aaaaaacacc cagaaaaccg cacgcgaacc tacgcccaga aacgaaagcc  39060
aaaaaaccca caacttcctc aaatcgtcac ttccgttttc ccacgttacg tcacttccca  39120
ttttaagaaa actacaattc ccaacacata caagttactc cgccctaaaa cctacgtcac  39180
ccgccccgtt cccacgcccc gcgccacgtc acaaactcca ccccctcatt atcatattgg  39240
cttcaatcca aaataaggta tattattgat gatgtaggga taacagggta atcagctttc  39300
ttgtacaaag ttgaaatccg gggatcctct agagtcgacc tgcaggcatg caagcttggc  39360
gtaatcatgg tcatagctgt ttcctgtgtg aaattgttat ccgctcacaa ttccacacaa  39420
catacgagcc ggaagcataa agtgtaaagc ctggggtgcc taatgagtga gcta        39474
```